(12) United States Patent
Heffernan et al.

(10) Patent No.: US 10,722,487 B2
(45) Date of Patent: Jul. 28, 2020

(54) GLUTAMINASE INHIBITOR THERAPY

(71) Applicant: Board of Regents, The University of Texas System, Austin, TX (US)

(72) Inventors: Timothy Heffernan, Sugar Land, TX (US); Jeffrey Kovacs, Pearland, TX (US); Nakia Spencer, Houston, TX (US); Christopher Bristow, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/164,581

(22) Filed: Oct. 18, 2018

(65) Prior Publication Data

US 2019/0274993 A1    Sep. 12, 2019

Related U.S. Application Data

(60) Provisional application No. 62/573,906, filed on Oct. 18, 2017.

(51) Int. Cl.
| | | |
|---|---|---|
| *A61K 31/50* | (2006.01) |
| *A61K 31/282* | (2006.01) |
| *A61P 35/00* | (2006.01) |
| *A61K 31/337* | (2006.01) |
| *G01N 33/574* | (2006.01) |
| *A61K 31/501* | (2006.01) |
| *A61K 31/55* | (2006.01) |
| *A61K 33/243* | (2019.01) |
| *A61K 31/433* | (2006.01) |
| *A61K 31/4196* | (2006.01) |
| *A61K 45/06* | (2006.01) |
| *A61K 51/04* | (2006.01) |

(52) U.S. Cl.
CPC .......... *A61K 31/282* (2013.01); *A61K 31/337* (2013.01); *A61K 31/4196* (2013.01); *A61K 31/433* (2013.01); *A61K 31/501* (2013.01); *A61K 31/55* (2013.01); *A61K 33/243* (2019.01); *A61K 45/06* (2013.01); *A61P 35/00* (2018.01); *G01N 33/57449* (2013.01); *A61K 51/0408* (2013.01)

(58) Field of Classification Search
CPC .................................................. A61K 31/50
USPC .......... 514/252.02, 252.03, 252.05
See application file for complete search history.

(56) References Cited

U.S. PATENT DOCUMENTS

| | | | |
|---|---|---|---|
| 4,399,140 A | 8/1983 | Gacek |
| 4,720,447 A | 1/1988 | De Keyzer |
| 6,153,628 A | 11/2000 | Jin |
| 6,239,137 B1 | 5/2001 | Karmali |
| 7,956,070 B2 | 6/2011 | Alcaraz |
| 9,809,588 B2 | 11/2017 | Di Francesco |
| 10,125,128 B2 | 11/2018 | Lewis |
| 10,344,025 B2 | 7/2019 | Di Francesco |
| 2002/0115698 A1 | 8/2002 | Newcomb |
| 2009/0215750 A1 | 8/2009 | Bamberg |
| 2010/0255117 A1 | 10/2010 | Biswal |
| 2011/0229984 A1 | 9/2011 | Lorenzi |
| 2012/0202776 A1 | 8/2012 | Wang |
| 2013/0157998 A1 | 6/2013 | Li |
| 2014/0050699 A1 | 2/2014 | Li |
| 2014/0142081 A1 | 5/2014 | Lemieux |
| 2015/0344466 A1 | 12/2015 | Mitsudera |
| 2015/0368240 A1 | 12/2015 | Bleisch |
| 2016/0002204 A1 | 1/2016 | Di Francesco |
| 2016/0002248 A1 | 1/2016 | Di Francesco |
| 2016/0009704 A1 | 1/2016 | Di Francesco |
| 2016/0058759 A1 | 3/2016 | Heffernan |
| 2017/0174661 A1 | 6/2017 | Jones |
| 2019/0031651 A1 | 1/2019 | Lewis |
| 2019/0134032 A1 | 5/2019 | Heffernan |
| 2019/0144425 A1 | 5/2019 | Jones |
| 2019/0270736 A1 | 9/2019 | Di Francesco |

FOREIGN PATENT DOCUMENTS

| | | |
|---|---|---|
| CN | 105102458 A | 11/2015 |
| WO | 1991009848 A1 | 7/1991 |
| WO | 1998043962 | 10/1998 |
| WO | 1999026945 | 6/1999 |
| WO | 2008083238 | 7/2008 |
| WO | 2010023946 A1 | 3/2010 |
| WO | 2010099527 A1 | 9/2010 |
| WO | 2010111504 | 9/2010 |
| WO | 2011089995 | 7/2011 |
| WO | 2011143160 A2 | 11/2011 |

(Continued)

OTHER PUBLICATIONS

Aurora Fine Chemicals, 1-[3-(3-aminopyrazol-1-yl)propyl]pyrazole-4-carboxamide, Cat. No. A04.256.259 http://online.aurorafinechemicals.com/StrSearch.asp, Jul. 1, 2015.
Balasubramanian, M. et al., "Asparagine Synthetase: Regulation by Cell Stress and Involvement in Tumor Biology", Am J Physiol Endocrinol Metab., 304(8):E789-99, (2013).
Blair, S. et al., "Glutathione Metabolism in Patients with Non-Small Cell Lung Cancers", Cancer Res., 57(1):152-5, (1997).
Brunton, L. et al., "Chemotherapy of Neoplastic Disease", Goodman and Gilman's, The Pharmacological Basis for Therapeutics, eds., 11:853-903, (2008).
CAPLUS Accession No. 2011:590393.
CAS Indexed Compounds, 2(1H)-Pyridinone, 1-[3-(1-phenyl-1H-tetrazol-5-yl)propyl]-5(trifluoromethyl), Registry No. 1311902-55-2, Jul. 7, 2011.

(Continued)

*Primary Examiner* — Raymond J Henley, III
(74) *Attorney, Agent, or Firm* — Dennis A. Bennett; Cynthia Hathaway; John Desper

(57) ABSTRACT

Disclosed herein are methods of treating a tumor or cancer in a subject whose tumor or cancer cells express low levels of asparagine synthetase (ASNS), and compounds and compositions useful in such treatment. Also disclosed herein are methods of evaluating whether to administer a compound that inhibits glutathione production or a glutaminase inhibitor to a subject with a tumor or cancer.

35 Claims, 25 Drawing Sheets

(56) References Cited

FOREIGN PATENT DOCUMENTS

| WO | 2013078123 A1 | 5/2013 |
|---|---|---|
| WO | 2014078645 A1 | 5/2014 |
| WO | 2014079150 | 5/2014 |
| WO | 2014081925 | 5/2014 |
| WO | 2014089048 A1 | 6/2014 |
| WO | 2014119696 | 8/2014 |
| WO | 2015101957 | 7/2015 |
| WO | 2016004404 | 1/2016 |
| WO | 2016004413 | 1/2016 |
| WO | 2016004417 | 1/2016 |
| WO | 2016004418 | 1/2016 |
| WO | 2017004359 A1 | 1/2017 |
| WO | 2017112831 A1 | 6/2017 |
| WO | 2019079632 | 4/2019 |

OTHER PUBLICATIONS

CAS Indexed Compounds, 2(1H)-Pyridinone, 1-[3-(3-amino-1H-pyrazol-1-yl)propyl]-4-methyl, Registry No. 1284137-43-4, Apr. 22, 2011.
CAS Indexed Compounds, 2(1H)-Pyridinone, 1-[3-(3-amino-1H-pyrazol-1-yl)propyl]-5-bromo, Registry No. 1272932-30-5, Mar. 31, 2011.
CAS Indexed Compounds, 2(1H)-Pyridinone, 1-[3-(3-amino-1H-pyrazol-1-yl)propyl]-5(trifluoromethyl), Registry No. 1406035-29-7, Nov. 25, 2012.
CAS Indexed Compounds, 2(1H)-Pyridinone, 1-[3-(3-amino-1H-pyrazol-1-yl)propyl], Registry No. 1341730-05-9, Nov. 6, 2011.
CAS Indexed Compounds, 2(1H)-Pyridinone, 1-[3-[3-(3-fluoro-4-methylphenyl)-1,2,4-oxadiazol-5yl]propyl]-5-(trifluoromethyl), Registry No. 1387392-92-8, Aug. 7, 2012.
CAS Indexed Compounds, 2(1H)-Pyridinone, 1-[3-[4-(chloromethyl)-2-thiazolyl]propyl]-4-methyl, Registry No. 1408458-49-0, Nov. 30, 2012.
CAS Indexed Compounds, 2(1H)-Pyridinone, 1-[3-[4-(chloromethyl)-2-thiazolyl]propyl]-5(trifluoromethyl), Registry No. 1484369-40-5, Dec. 1, 2013.
CAS Indexed Compounds, 2(1H)-Pyridinone, 1-[3-[4-(chloromethyl)-2-thiazolyl]propyl], Registry No. 1094436-44-8, Jan. 20, 2009.
CAS Indexed Compounds, 2(1H)-Pyridinone, 1-[4-[4-(chloromethyl)-2-thiazolyl]butyl]-4-methyl, Registry No. 1284050-00-5, Apr. 22, 2011.
CAS Indexed Compounds, 2(1H)-Pyridinone, 1-[4-[4-(chloromethyl)-2-thiazolyl]butyl], Registry No. 1272826-97-7, Mar. 31, 2011.
CAS Indexed Compounds, 2(1H)-Pyridinone, 1-[4-oxo-4-(2-thienyl)butyl]-5-(trifluoromethyl), Registry No. 1456227-69-2, Oct. 6, 2013.
CAS Indexed Compounds, 2(1H)-Pyridinone, 1-[4-oxo-4-(2-thienyl)butyl], Registry No. 1456935-71-9, Oct. 11, 2013.
CAS Indexed Compounds, 2(1H)-Pyridinone, 5-(trifluoromethyl)-1-[3-[3-[3-(trifluoromethyl)phenyl], Registry No. 1100005-80-8, Feb. 3, 2009.
CAS Indexed Compounds, 2(1H)-Pyridinone, 5-bromo-1-[3-(1H-imidazol-1-yl)propyl], Registry No. 1482686-39-4, Nov. 28, 2013.
CAS Indexed Compounds, 2(1H)-Pyridinone, 5-bromo-1-[4-oxo-4-(2-thienyl)butyl], Registry No. 1458260-86-0, Oct. 15, 2013.
CAS Indexed Compounds, 4-Pyridinecarboxylic acid, 1,2-dihydro-1-[3-(1H-imidazol-1-yl)propyl]-2-Oxo, Registry No. 1548114-27-7, Feb. 18, 2014.
CAS Indexed Compounds, Registry No. 1480499-78-2, Nov. 25, 2013.
Dang, C., "Links Between Metabolism and Cancer", Genes Dev., 26(9):877-90, (2012).
Daye, D. et al., "Metabolic Reprogramming in Cancer: Unraveling the Role of Glutamine in Tumorigenesis", Semin Cell Dev Biol., 23(4):362-9, (2012).
Fung, M. et al., "Drug-Induced Amino Acid Deprivation as Strategy for Cancer Therapy", J Hematol Oncol., 10(1):144 pp. 1-18, (2017).

Golub, T. et al., "Molecular Classification of Cancer: Class Discovery and Class Prediction by Gene Expression Monitoring", Science, 286(5439):531-7, (1999).
Gorrini, C. et al., "Modulation of Oxidative Stress as an Anticancer Strategy", Nat Rev Drug Discov., 12(12):931-47, (2013).
Gross, M. et al., "Antitumor Activity of the Glutaminase Inhibitor CB-839 in Triple-Negative Breast Cancer", Mol Cancer Ther., 13(4):890-901, (2014).
Hays, J. et al., "A phase II Clinical Trial of Polyethylene Glycol-Conjugated L-Asparaginase in Patients with Advanced Ovarian Cancer: Early Closure for Safety", Mol Clin Oncol., 1(3):565-9, (2013).
Hensley, C. et al., "Glutamine and Cancer: Cell Biology, Physiology, and Clinical Opportunities", J Clin Invest., 123(9):3678-84, (2013).
Inami, Y. et al., "Persistent Activation of Nrf2 Through p62 in Hepatocellular Carcinoma Cells", J Cell Biol., 193(2):275-84, (2011).
International Application No. PCT/US2015/039134; International Preliminary Report on Patentability, dated Jan. 3, 2017; 06 pages.
International Application No. PCT/US2015/039134; International Search Report and Written Opinion of the International Searching Authority, dated Feb. 9, 2016; 10 pages.
International Application No. PCT/US2015/039143; International Preliminary Report on Patentability, dated Jan. 3, 2017; 06 pages.
International Application No. PCT/US2015/039143; International Search Report and Written Opinion of the International Searching Authority, dated Jan. 11, 2016; 10 pages.
International Application No. PCT/US2015/039150; International Preliminary Report on Patentability dated Jan. 3, 2017; 6 pages.
International Application No. PCT/US2015/039150; International Search Report and Written Opinion of the International Searching Authority, dated Dec. 4, 2015; 9 pages.
International Application No. PCT/US2015/039153; International Preliminary Report on Patentability, dated Jan. 3, 2017; 10 pages.
International Application No. PCT/US2015/039153; International Search Report and Written Opinion of the International Searching Authority, dated Jan. 7, 2016; 12 pages.
International Application No. PCT/US2016/040364; International Preliminary Report on Patentability, dated Jan. 2, 2018; 7 pages.
International Application No. PCT/US2016/040364; International Search Report and Written Opinion of the International Searching Authority, dated Jan. 5, 2017; 8 pages.
International Application No. PCT/US2016/068149; International Preliminary Report on Patentability, dated Jul. 6, 2018; 4 pages.
International Application No. PCT/US2016/068149; International Search Report and Written Opinion of the International Searching Authority, dated Mar. 27, 2017; 5 pages.
International Application No. PCT/US2018/056567; International Search Report and Written Opinion of the International Searching Authority, dated Dec. 31, 2018; 20 pages.
Katt, W. et al., "Glutaminase Regulation in Cancer Cells: A Druggable Chain of Events," Drug Discov Today, 19(4)450-7, (2014).
Kroemer, G. et al., "Tumor Cell Metabolism: Cancer's Achilles' Heel", Cancer Cell., 13(6):472-82, (2008).
Lala, P. et al., "Role of Nitric Oxide in Tumor Progression: Lessons From Experimental Tumors", Cancer Metastasis Rev., 17(1):91-106, (1998).
Li, Y. et al., "Sulforaphane Potentiates the Efficacy of 17-Allylamino 17-Demethoxygeldanamycin Against Pancreatic Cancer Through Enhanced Abrogation of Hsp90 Chaperone Function", Nutrition and Cancer, 63(7):1151-9, (2011).
Lin, C. et al., "Deficiency in Asparagine Synthetase Expression in Rectal Cancers Receiving Concurrent Chemoradiotherapy: Negative Prognostic Impact and Therapeutic Relevance", Tumour Biol., 35(7):6823-30, (2014).
Lorenzi, P. et al., "Asparagine Synthetase as a Causal, Predictive Biomarker for L-Asparaginase Activity in Ovarian Cancer Cells", Mol Cancer Ther., 5(11):2613-23, (2006).
Lorenzi, P. et al., "Asparagine Synthetase is a Predictive Biomarker of L-Asparaginase Activity in Ovarian Cancer Cell Lines", Mol Cancer Ther., 7(10):3123-8, (2008).
McMahon, G., "VEGF Receptor Signaling in Tumor Angiogenesis", The Oncologist, 5(Suppl 1):3-10, (2000).

(56) References Cited

OTHER PUBLICATIONS

Ni, M. et al., "Novel RGD Peptidomimetics Embedding 1, 2, 3-Triazole as Central Scaffold; Synthesis and αvβ3 Integrin Affinity", Lett Drug Design and Discov., 8(5):401-5, (2011).
Nikonorova, I. et al., "Obesity Challenges the Hepatoprotective Function of the Integrated Stress Response to Asparaginase Exposure in Mice", J Biol Chem., 292(16):6786-98, (2017).
Pinedo, H. et al., "Translational Research: The Role of VEGF in Tumor Angiogenesis", The Oncologist, 5(Suppl 1):1-2, (2000).
Robinson, M. et al., "Novel Mechanism of Inhibition of Rat Kidney-Type Glutaminase by Bis-2-(5-Phenylacetamido-1,2,4-Thiadiazol-2-yl)Ethyl Sulfide (BPTES)", Biochem J., 406(3):407-14, (2007).
Rotblat, B. et al., "NRF2 and p53: Januses in Cancer?", Oncotarget, 3(11):1272-83, (2012).
Shanware, N. et al., "Glutamine: Pleiotropic Roles in Tumor Growth and Stress Resistance", J Mol Med (Berl)., 89(3):229-36, (2011).
Shukla, K. et al., "Design, Synthesis, and Pharmacological Evaluation of Bis-2-(5-Phenylacetamido-1,2,4-Thiadiazol-2-yl)Ethyl Sulfide 3 (BPTES) Analogs as Glutaminase Inhibitors", J Med Chem., 55(23):10551-63, (2012).
Singh, A. et al., "Dysfunctional KEAP1-NRF2 Interaction in Non-Small-Cell Lung Cancer", PLoS Med., 3(10):e420, pp. 1-10, (2006).
Stanovnik, B. et al., "The Tautomerism of Heterocycles: Substituent Tautomerism of Six-Membered Ring Heterocycles", Advances in Heterocyclic Chemistry, 91:1-134, (2006).
Thangavelu, K. et al., "Structural Basis for the Allosteric Inhibitory Mechanism of Human Kidney-Type Glutaminase (KGA) and its Regulation by Raf-Mek-Erk Signaling in Cancer Cell Metabolism", Proc Natl Acad Sci USA, 109(20):7705-10, (2012).
U.S. Appl. No. 14/791,186; Examiner-Initiated Interview Summary, dated Dec. 6, 2016; 1 page.
U.S. Appl. No. 14/791,186; Final Office Action, dated Dec. 6, 2016; 31 pages.
U.S. Appl. No. 14/791,186; Non-Final Office Action, dated May 31, 2016; 13 pages.
U.S. Appl. No. 14/791,186; Notice of Allowability, dated May 11, 2017; 5 pages.
U.S. Appl. No. 14/791,186; Notice of Allowance, dated Mar. 15, 2017; 8 pages.
U.S. Appl. No. 14/791,284; Non-Final Office Action, dated Apr. 11, 2016; 9 pages.
U.S. Appl. No. 14/791,284; Notice of Allowability, dated Nov. 18, 2016; 4 pages.
U.S. Appl. No. 14/791,284; Notice of Allowance, dated Oct. 14, 2016; 9 pages.
U.S. Appl. No. 14/791,307; Non-Final Office Action, dated Jun. 21, 2017; 12 pages.
U.S. Appl. No. 15/199,100; Corrected Notice of Allowability, dated Jul. 30, 2018; 8 pages.
U.S. Appl. No. 15/199,100; Examiner-Initiated Interview Summary, dated Jul. 6, 2018; 1 page.
U.S. Appl. No. 15/199,100; Non-Final Office Action, for dated Sep. 13, 2017; 11 pages.
U.S. Appl. No. 15/199,100; Notice of Allowance, dated Jul. 6, 2018; 11 pages.
U.S. Appl. No. 15/387,560; Non-Final Office Action, dated Jan. 5, 2018; 10 pages.
U.S. Appl. No. 15/387,560; Notice of Allowance, dated Jul. 27, 2018; 5 pages.
U.S. Appl. No. 15/624,168; Non-Final Office Action, dated Jul. 13, 2018; 9 pages.
U.S. Appl. No. 15/624,168; Notice of Allowance, dated Feb. 14, 2019; 20 pages.
U.S. Appl. No. 16/412,050; Application as filed, dated May 14, 2019; 342 pages.
Van Den Heuvel, A. et al., "Analysis of Glutamine Dependency in Non-Small Cell Lung Cancer", Cancer Biol Ther., 13(12):1185-94, (2012).
Vander Heiden, M. et al., "Targeting Cancer Metabolism: A Therapeutic Window Opens", Nat Rev Drug Discov., 10(9):671-84, (2011).
Vander Heiden, M. et al., "Understanding the Warburg Effect: The Metabolic Requirements of Cell Proliferation", Science, 324(5930):1029-33, (2009).
Wang, J. et al., "Targeting Mitochondrial Glutaminase Activity Inhibits Oncogenic Transformation", Cancer Cell, 18(3):207-19, (2010).
Wise, D. et al., "Glutamine Addiction: A New Therapeutic Target in Cancer", Trends Biochem Sci., 35(8):427-33, (2010).
Zhang, D. et al., "Distinct Cysteine Residues in Keap1 are Required for Keap1-Dependent Ubiquitination of Nrf2 and for Stabilization of Nrf2 by Chemopreventive Agents and Oxidative Stress", Mol Cell Biol., 23(22):8137-51, (2003).
Zhang, P. et al., "Loss of Kelch-Like ECH-Associated Protein 1 Function in Prostate Cancer Cells Causes Chemoresistance and Radioresistance and Promotes Tumor Growth", Mol Cancer Ther., 9(2):336-47, (2010).
Huang, Q. et al., "Characterization of the Interactions of Potent Allosteric Inhibitors with Glutaminase C, a Key Enzyme in Cancer Cell Glutamine Metabolism", J Biol Chem., 293(10):3535-45, (2018).
U.S. Appl. No. 15/851,407; Non-Final Office Action, dated Jan. 27, 2020; 39 pages.
U.S. Appl. No. 16/152,901; Non-Final Office Action, dated Sep. 16, 2019; 15 pages.
U.S. Appl. No. 16/241,596; Non-Final Office Action, dated Jul. 23, 2019; 21 pages.
U.S. Appl. No. 16/412,050 ; Non-Final Office Action, dated Dec. 9, 2019; 30 pages.
Vippagunta, S. et al., "Crystalline Solids", Adv Drug Deliv Rev., 48(1):3-26, (2001).
CAS Registry No. 1355653-66-5 [Database Registry Chemical Abstracts Service, Columbus, Ohio, entry date Nov. 25, 2013]; p. 1.
International Application No. PCT/US2018/056567; International Search Report and Written Opinion of the International Searching Authority, dated Apr. 30, 2020; 17 pages.
Neidle, S. et al., "Failure Modes in Clinical Development", Cancer Drug Design & Discovery, pp. 427-31, (2008).
U.S. Appl. No. 16/152,901; Notice of Allowance, dated Apr. 1, 2020; 10 pages.
U.S. Appl. No. 16/241,596; Final Office Action, dated Mar. 5, 2020; 102 pages.
U.S. Appl. No. 16/412,050; Notice of Allowance, dated Apr. 10, 2020; 16 pages.

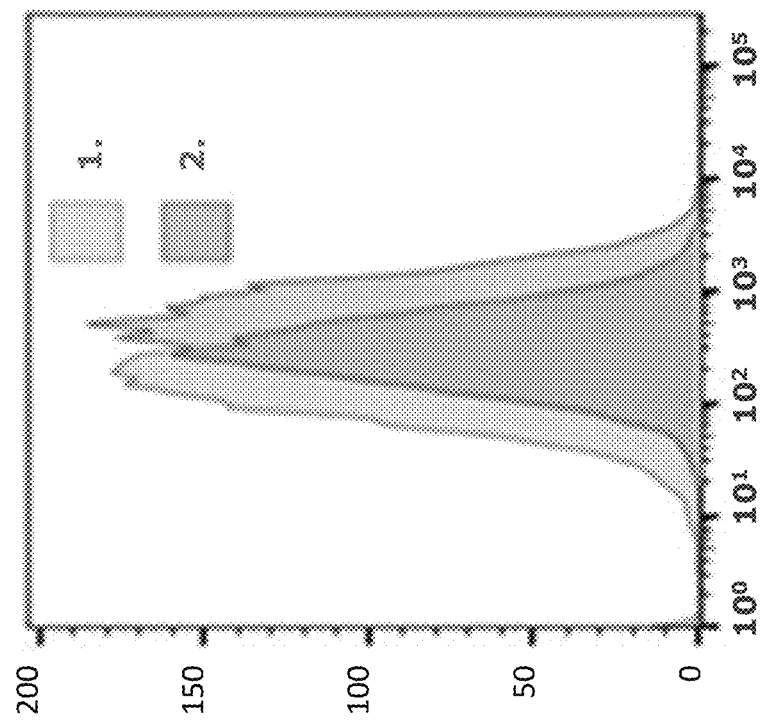
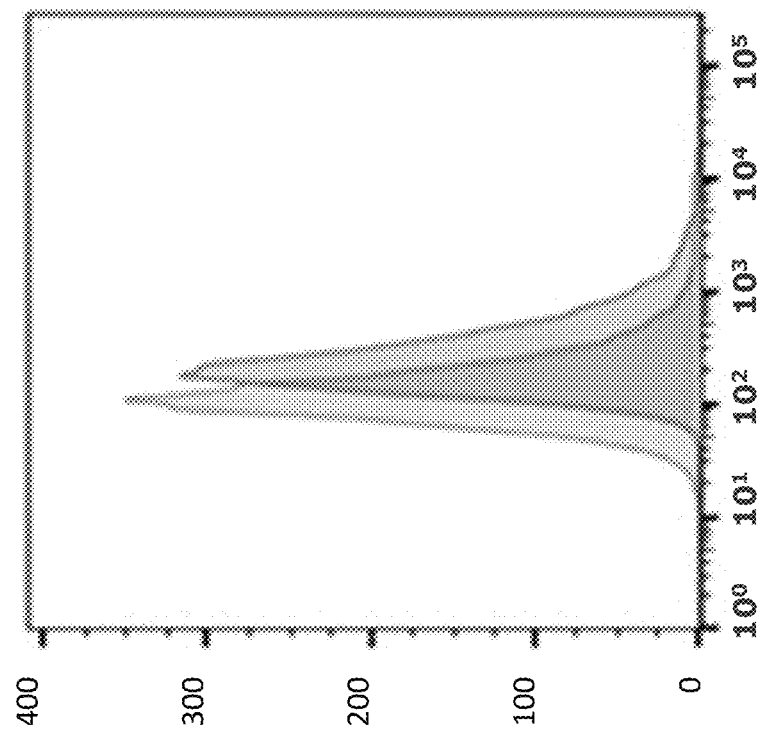

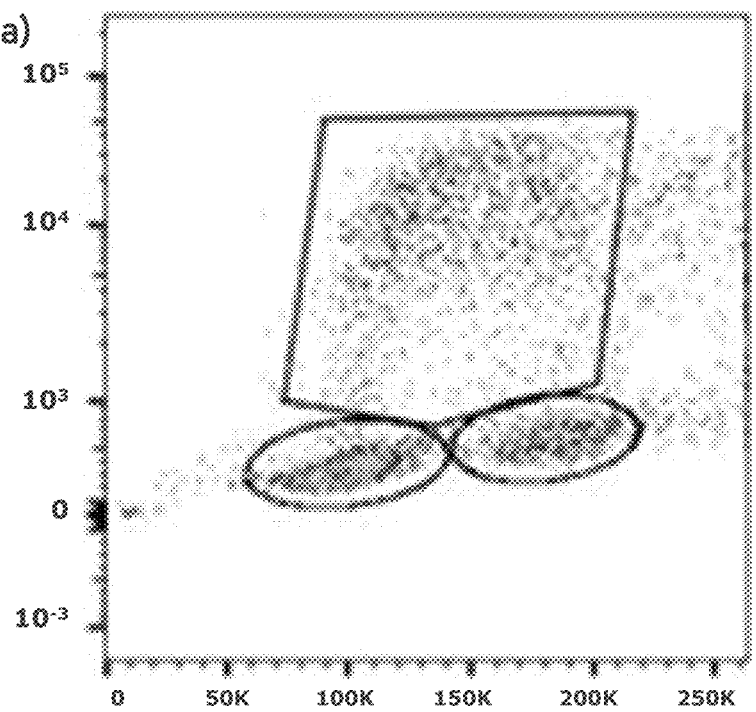
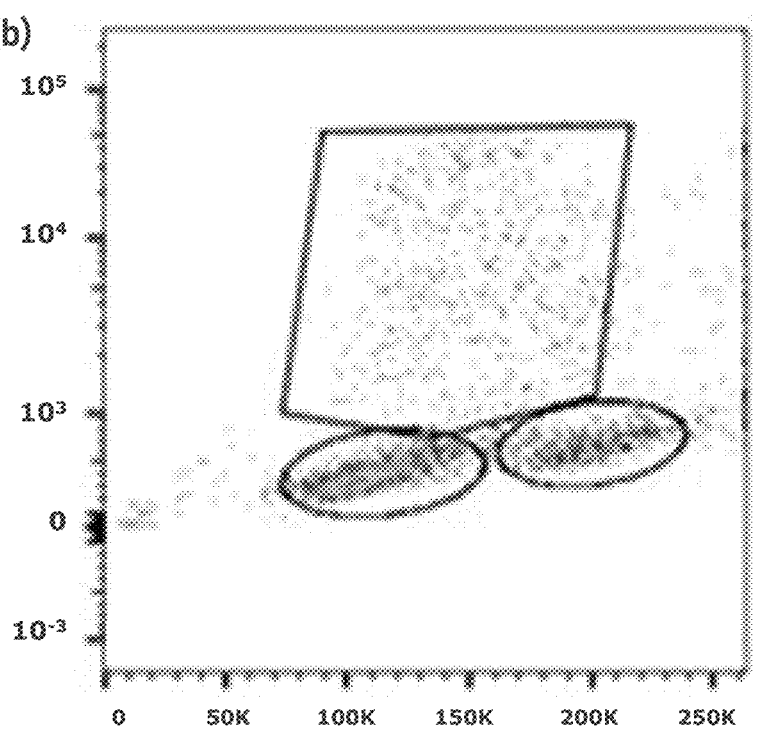

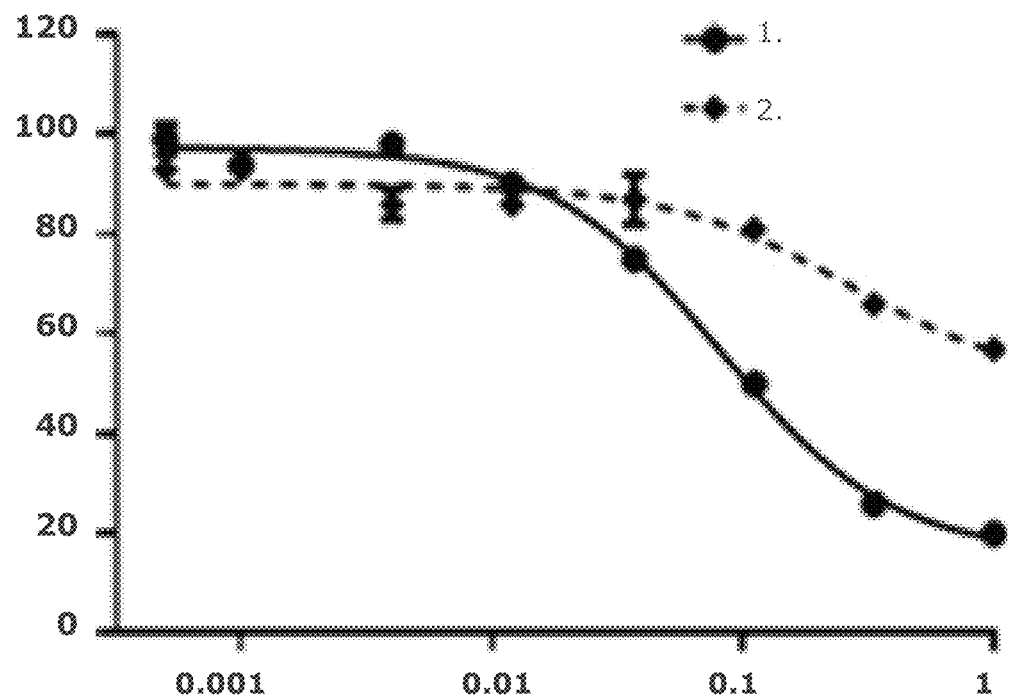
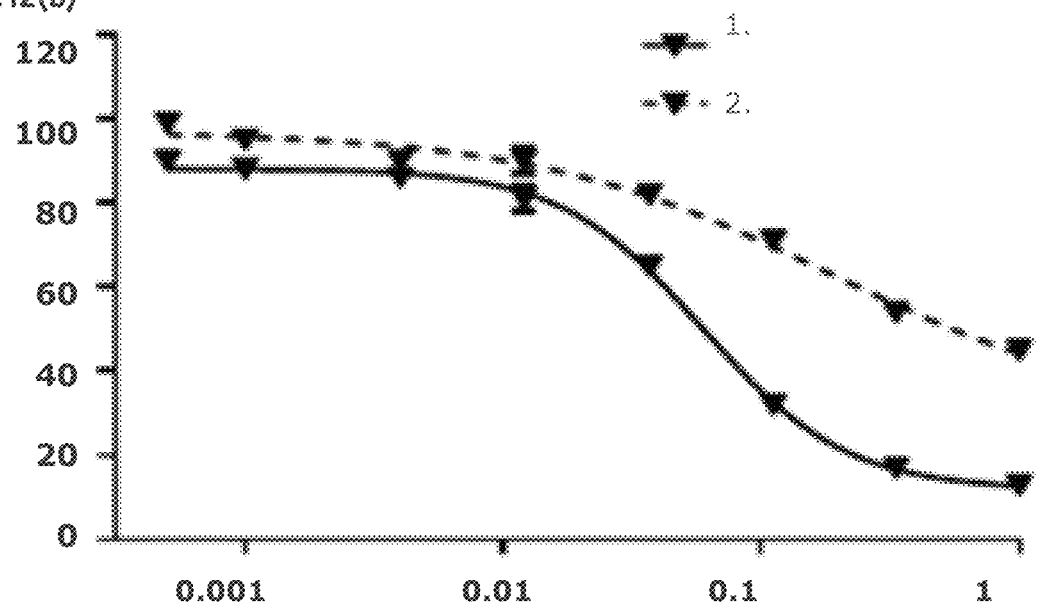

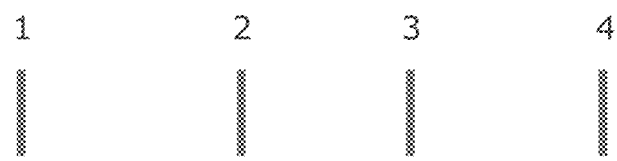
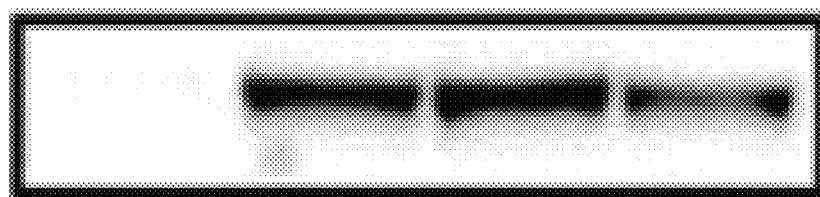
FIG.16(a)
FIG.16(b)
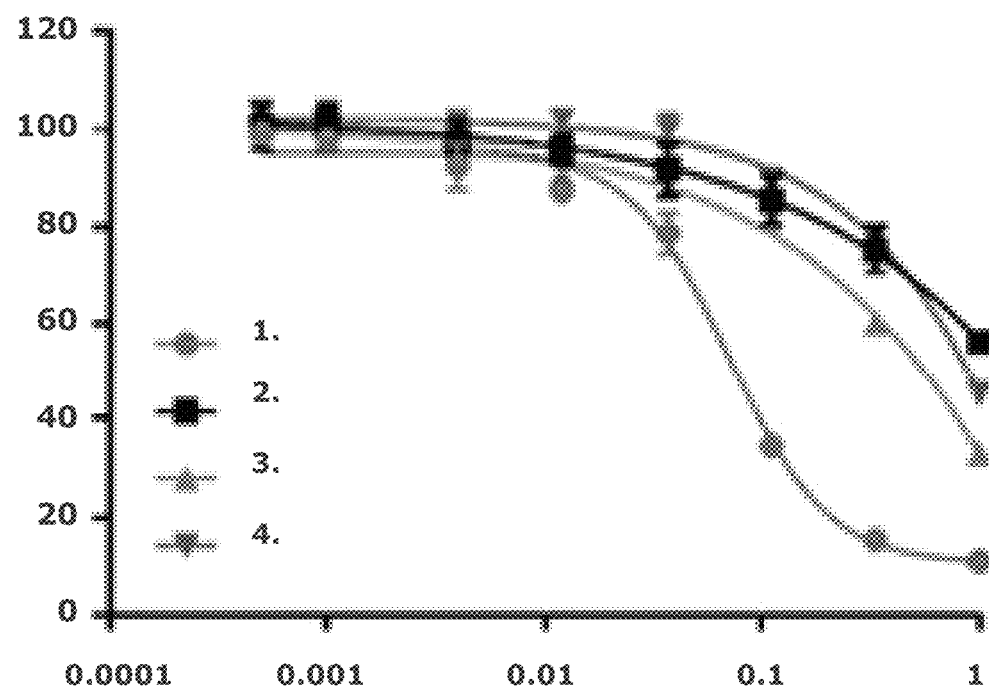
FIG.16(c)

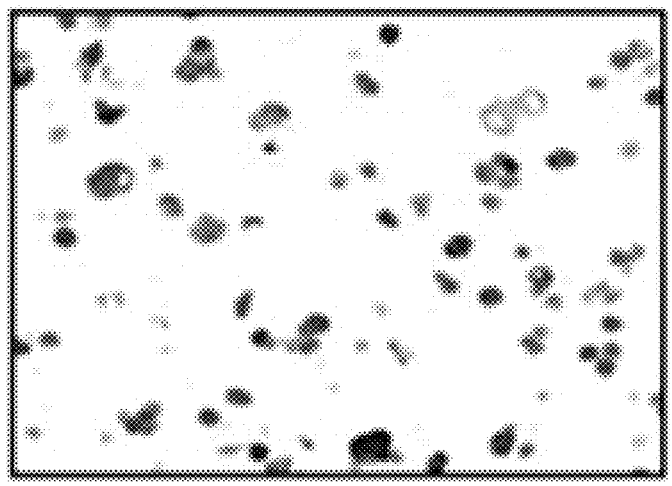
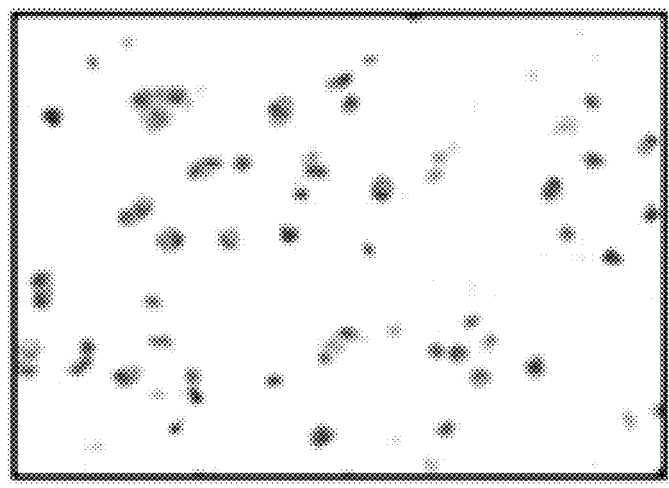

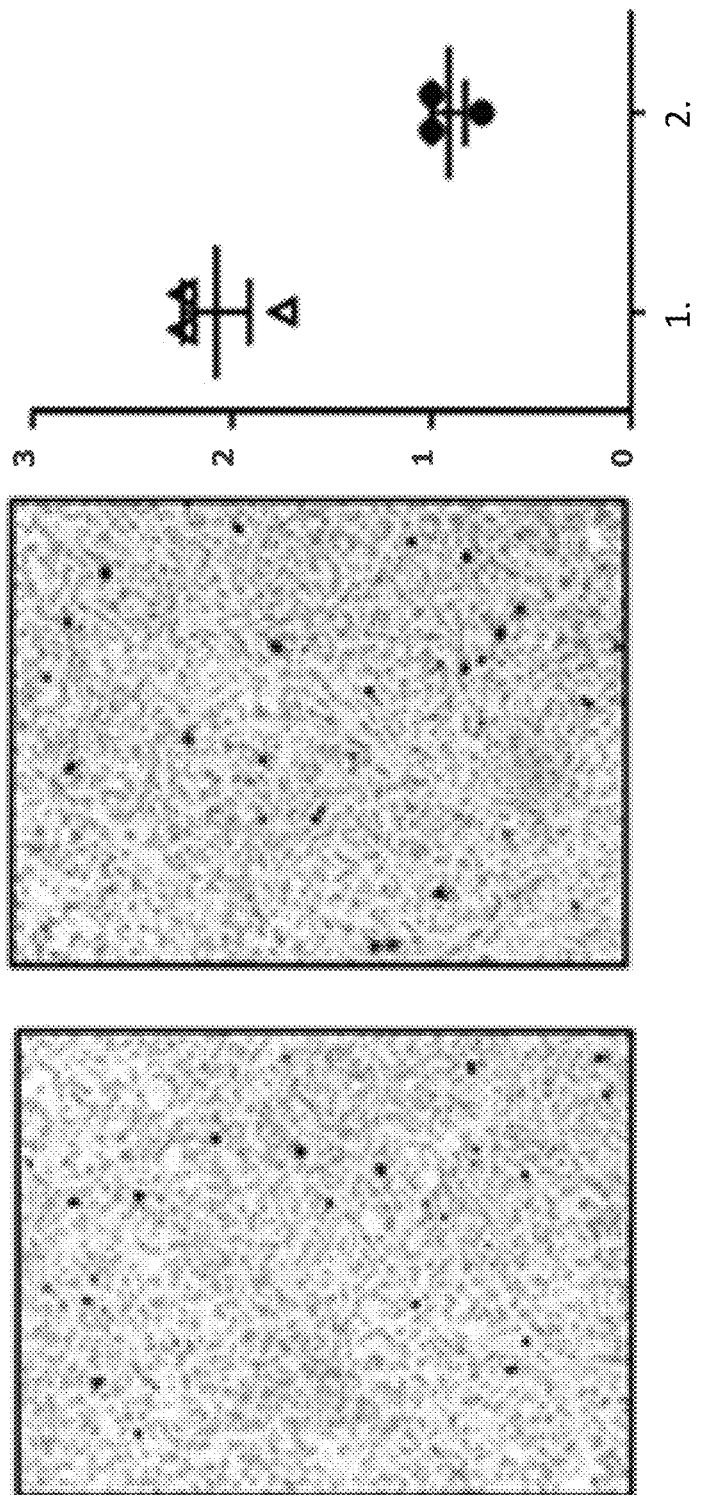

GLUTAMINASE INHIBITOR THERAPY

This application claims the benefit of priority of U.S. Provisional Application No. 62/573,906, filed Oct. 18, 2017, the disclosure of which is hereby incorporated by reference as if written herein in its entirety.

Metabolic deregulation is a hallmark of cancer as tumors exhibit an increased demand for nutrients and macromolecules to fuel their rapid proliferation. Glutamine (Gln), the most abundant amino acid in circulation, plays an essential role in providing cancer cells with biosynthetic intermediates required to support proliferation and survival. Specifically, tumor cells utilize glutaminolysis, or the enzymatic conversion of glutamine to glutamate, as a nutrient source for amino acid and nucleotide synthesis, and a carbon skeleton to fuel ATP and NADPH synthesis through the TCA cycle.

In addition to enabling cell growth and replication, glutamine metabolism plays a critical role in multiple metabolic events to generate energy and maintain cellular redox balance. Products of glutaminolysis are used in maintaining cellular redox homeostasis as glutamate can be converted into glutathione, the major intracellular antioxidant. Cancer cells require a constant source of biomass and macromolecules to support cell division and reducing agents to maintain redox homeostasis. While many of these building blocks are provided through aerobic glycolysis, many cancer cells have evolved a dependence on glutamine metabolism for growth and survival.

Glutamine metabolism, i.e., glutaminolysis is regulated by mitochondrial glutaminase (GLS), the rate limiting enzyme that catalyzes the conversion of glutamine to glutamate and ammonia. Mammalian cells contain two genes that encode glutaminase: the kidney-type (GLS-1) and liver-type (GLS-2) enzymes. Each has been detected in multiple tissue types, with GLS-1 being widely distributed throughout the body. GLS-1 is a phosphate-activated enzyme that exists in humans as two major splice variants, a long form (referred to as KGA) and a short form (GAC), which differ only in their C-terminal sequences. Both forms of GLS-1 are thought to bind to the inner membrane of the mitochondrion in mammalian cells, although at least one report suggests that glutaminase may exist in the intramembrane space, dissociated from the membrane. GLS is frequently overexpressed in human tumors and has been shown to be positively regulated by oncogenes such as Myc. Consistent with the observed dependence of cancer cell lines on glutamine metabolism, pharmacological inhibition of GLS offers the potential to target Gln addicted tumors. Such targeted treatment, however, is hampered by the lack of clinical biomarkers to identify sensitive patient populations.

Thus, there is a need for a means to identify markers and mechanisms that provide a method for evaluating a patient's successful treatment with glutaminase inhibitors as well as for methods of such treatment.

The present invention is based, in part, on the discovery of a mechanism whereby tumor cells with a specific metabolic dependence on the activity of glutaminase to generate intracellular pools of glutamate are uniquely sensitive to glutaminase inhibition. Conversely, cells which have alternative mechanisms for generating glutamate define a specific patient population that may be insensitive to glutaminase inhibitors.

In one embodiment of the invention, the invention comprises a method of treating cancer in a subject whose cancer cells express low levels of asparagine synthetase (ASNS), as defined by an Histophathology Score (H-score) of 0-100 (both inclusive) by immunohistochemical staining, comprising administering a glutaminase-1 (GLS-1) inhibitor to said subject.

In another embodiment of the invention, the invention comprises a method of treating a subject having a disorder, such as a cancer or tumor. The method comprises determining the concentration or expression of ASNS in said cancer or tumor of said subject; and administering a glutaminase-1 (GLS-1) inhibitor to said subject if the level of ASNS is quantified as an H-score of less than or equal to 100 by immunohistochemical staining. In another embodiment of the invention, the method comprises optionally obtaining a biological sample from a subject, determining that the concentration or expression of ASNS in said sample from said subject is low and administering a glutaminase-1 (GLS-1) inhibitor to said subject.

In yet another embodiment of the invention, the invention comprises a method of stratifying a subject for response to GLS inhibitor therapy. The method comprises determining that the concentration of ASNS or its expression levels in a tumor or in cancer cells of said subject are low and administering a glutaminase inhibitor to said subject.

The subject in need of treatment may be afflicted with a disorder or a condition, for example, cancer, including, but not limited to, bladder cancer, bone marrow cancer, breast cancer, cancer of the central nervous system, cervical cancer, colon cancer, endometrial cancer, cancer of the gastric system, head and neck cancer, kidney cancer, leukemia, liver cancer, lung cancer, lymphoma, muscle cancer, ovarian cancer, pancreatic cancer, prostate cancer, skin cancer, thyroid cancer, or a variant thereof. In some embodiments, the cancer is ovarian, skin, liver, prostate, breast, colon, lung, head and neck cancers or a lymphoma. In some embodiments, the cancer is ovarian cancer, for example, high-grade serous ovarian cancer (HGSOC). The GLS-1 inhibitor may, for example, be a selective inhibitor of GLS-1.

The next six figures show that GLS-dependence is driven by addiction to glutamine-dependent, glutathione-mediated redox maintenance in OVCA responder cell lines.

Figure 7:
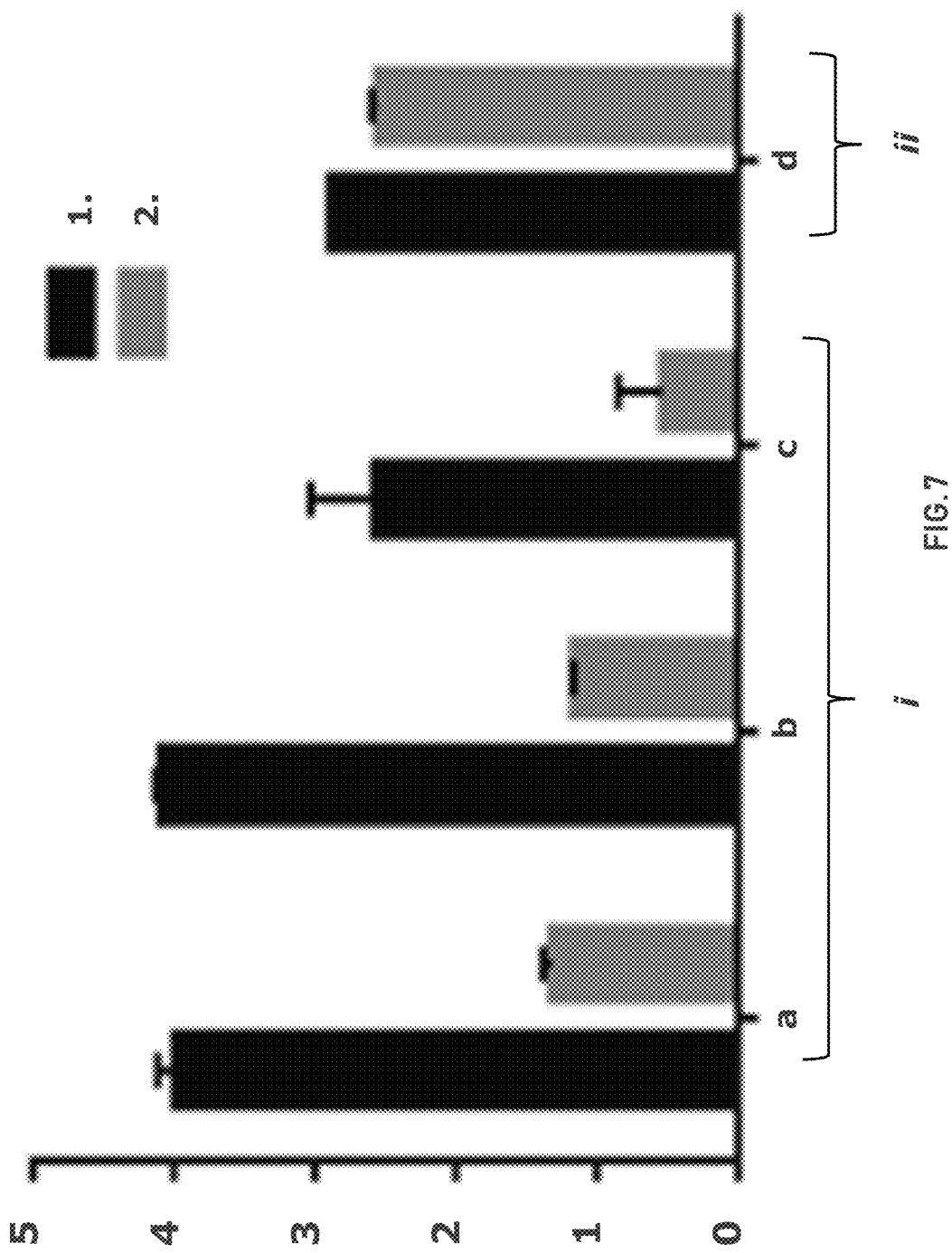

FIG. 7 shows that glutathione levels are decreased after treatment with compound 1 (2.) compared to DMSO (1.). Shown are the glutathione levels (uM) for responders (i) OVCAR420 (a); OVCAR429 (b); OVCAR8 (c); and a non-responder (ii) OVCAR4 (d).

FIG. 8(a) shows that the loss of glutathione (GSH) after treatment with compound 1, a GLS-1 inhibitor (GLS1i), leads to an accumulation of intracellular reactive oxygen species (ROS) in OVCAR420 cells.

FIG. 8(b) shows that the loss of glutathione (GSH) after treatment with compound 1, a GLS-1 inhibitor (GLS1i), leads to an accumulation of intracellular reactive oxygen species (ROS) in OVCAR429 cells.

Figure 9A:
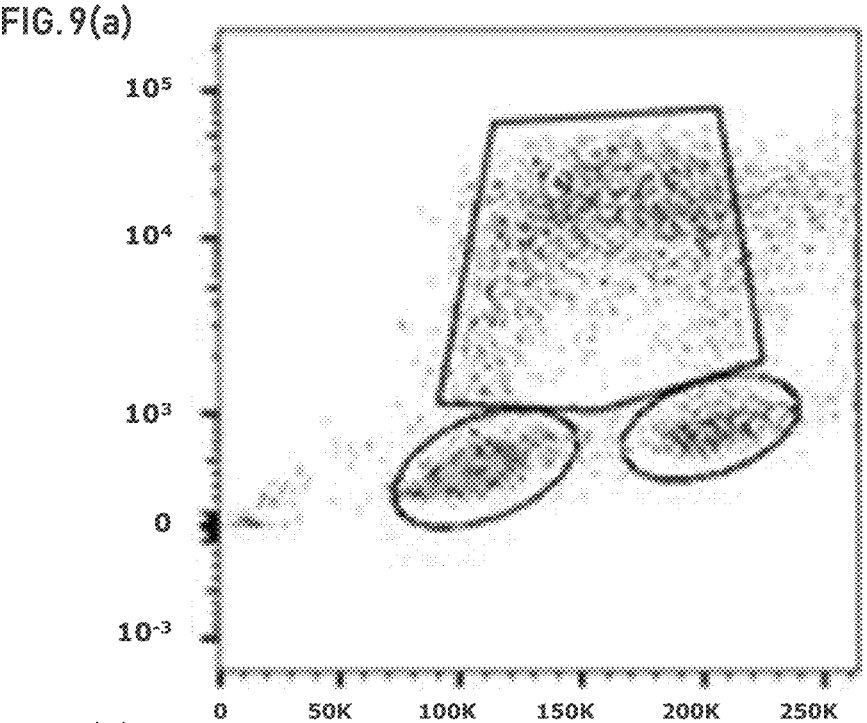

FIG. 9(a) shows a standard BrdU assay with OVCAR420 using DMSO control. x-axis=PI-A; y-axis=FITC-A.

Figure 9B:
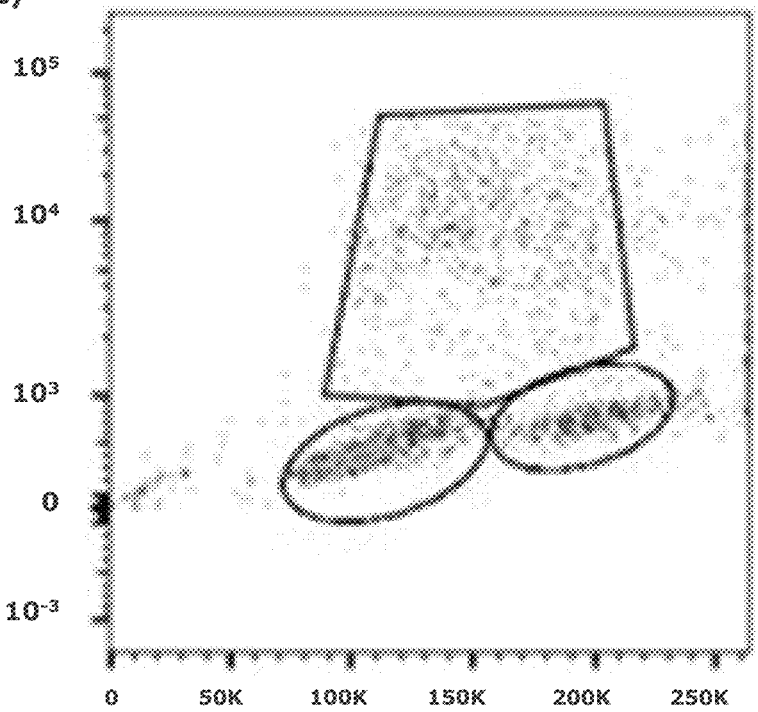

FIG. 9(b) shows a standard BrdU assay with OVCAR420 using GLS inhibitor. x-axis=PI-A; y-axis=FITC-A.

FIG. 10(a) shows a standard BrdU assay with OVCAR429 using DMSO control. x-axis=PI-A; y-axis=FITC-A.

FIG. 10(b) shows a standard BrdU assay with OVCAR429 using GLS inhibitor. x-axis=PI-A; y-axis=FITC-A.

Figure 11:
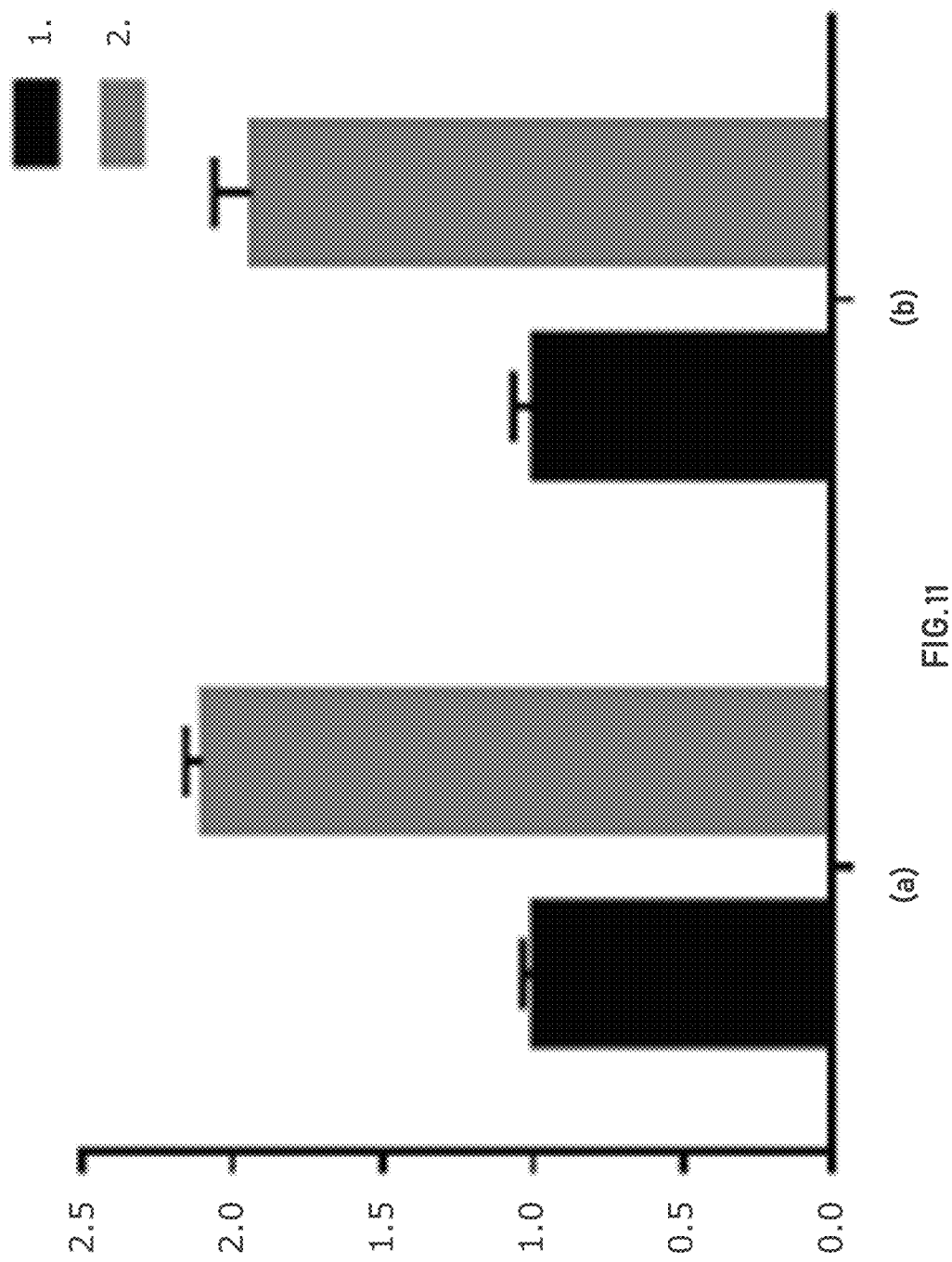

FIG. 11 shows that the GLS1i induces oxidative stress that leads to accumulation of DNA damage. y-axis is γH2AX foci, normalized to DMSO. (a): OVCAR8; (b) OVCAR420. In both cases, data are shown for DMSO (1.) and Compound 1 (2.).

FIG. 12(a) shows that application of exogenous GSH to responder cell line OVCAR420 rescues proliferation defects induced by compound 1. Viability upon application of cell-permeable GSH (1.) is shown, along with a control (2.) without GSH treatment.

FIG. 12(b) shows that application of exogenous GSH to responder cell line OVCAR429 rescues proliferation defects induced by compound 1. Viability upon application of cell-permeable GSH (1.) is shown, along with a control (2.) without GSH treatment.

The next four figures show that asparagine synthetase (ASNS) expression is a negative predictor of response after GLS-1 inhibition.

Figure 13:
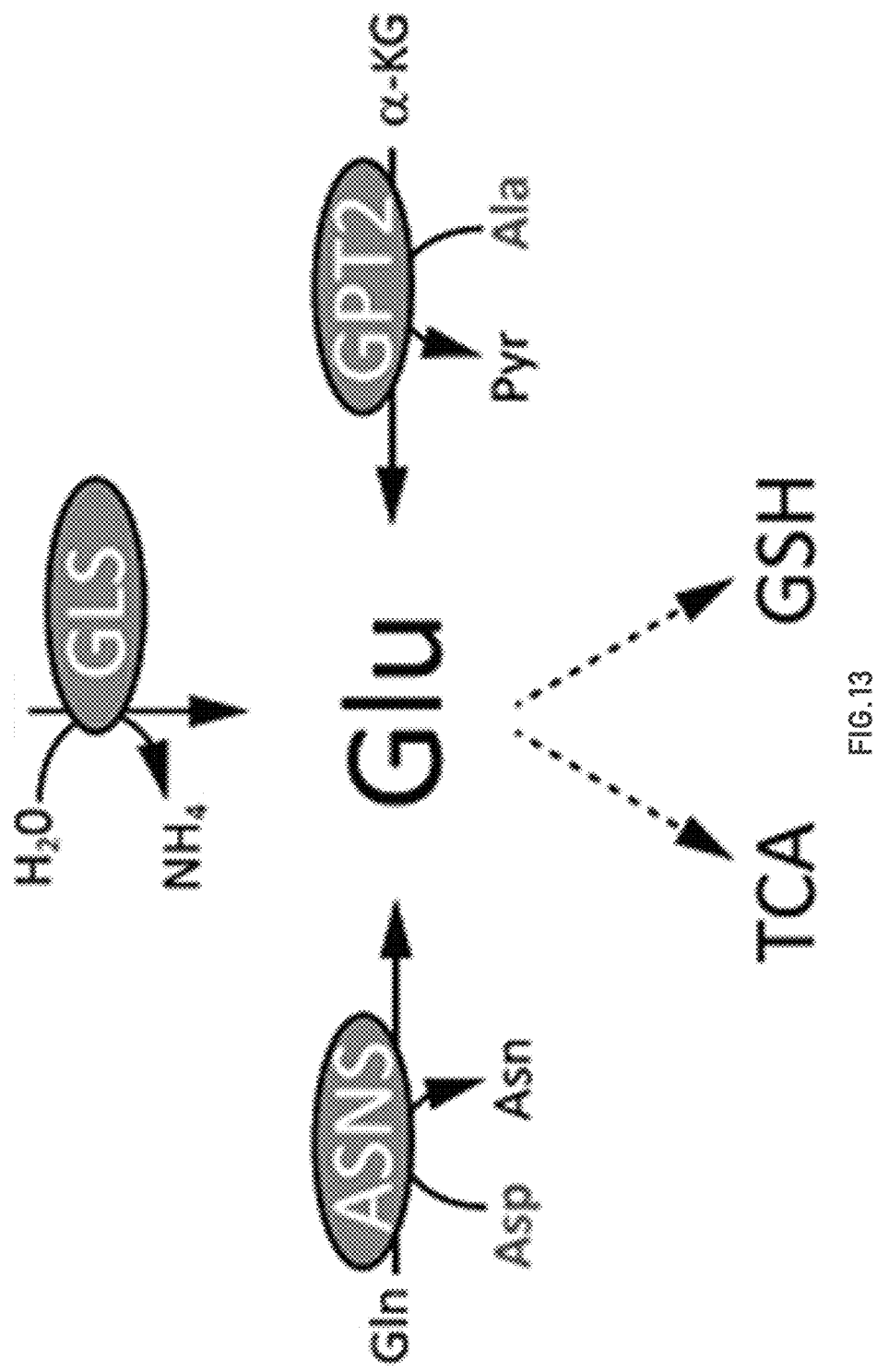

FIG. 13 shows key metabolic pathways that determine the production and fate of glutamine (GLU).

Figure 14:
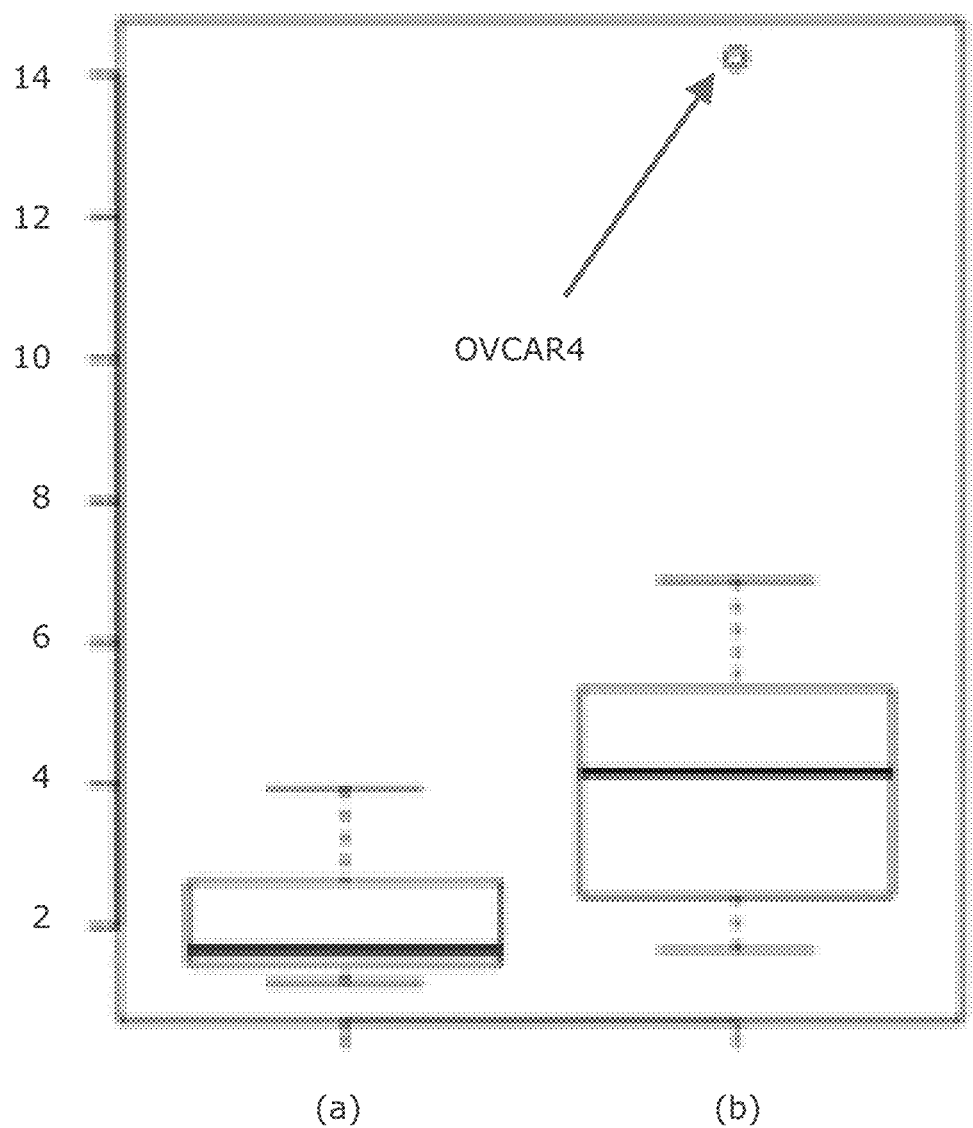

FIG. 14 shows the ASNS levels by reverse phase protein array (RPPA) expression analysis in responder (a) and non-responder (b) OVCA cell lines.

Figure 15:
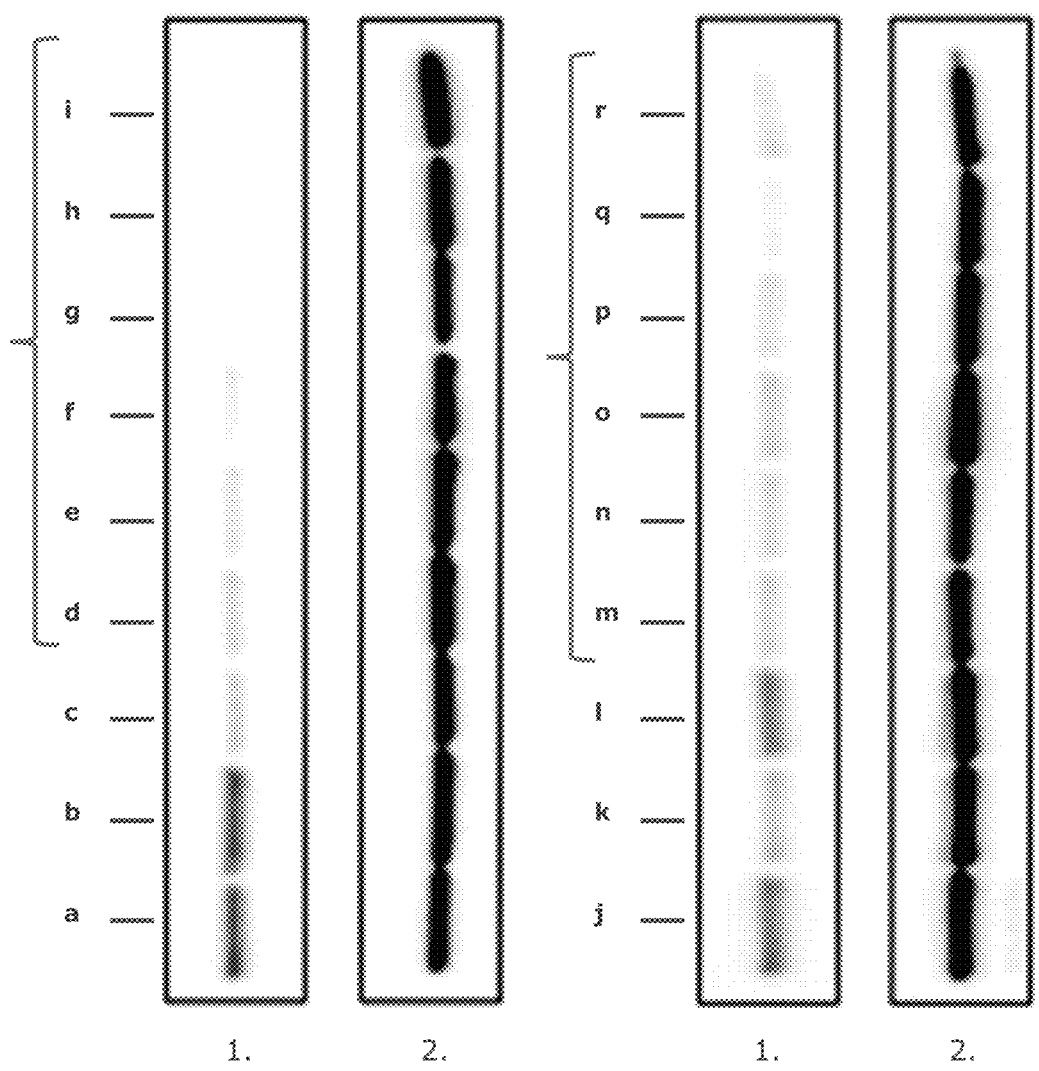

FIG. 15 shows the Western blot of ASNS expression across a panel of OVCA cell lines. ASNS (1.); HSP90 (2.). Responder cell lines are enclosed in brackets.

FIG. 16(a) shows western blot of ASNS for ASNS over-expression study. OV8 (1.); ASNS OE (2.); ASNS OE 1:10 (3.); ASNS OE (1:100).

FIG. 16(b) shows western blot of GAPDH for over-expression study. OV8 (1.); ASNS OE (2.); ASNS OE 1:10 (3.); ASNS OE (1:100).

FIG. 16(c) plots viability, normalized to DMSO, for OV8 (1.); OV8 ASNS OE (2.); OV8 ASNS OE 1:10 (3.); and OV8 ASNS OE 1:100 (4.).

The next three figures show that immuno-histochemical staining for ASNS confirms differential expression between responders and non-responders.

FIG. 17(a) shows ASNS western blot for ASNS knock-down study. NTC (1.) and ASNS KD (2.).

FIG. 17(b) shows Hsp90 western blot for ASNS knock-down study. NTC (1.) and ASNS KD (2.).

FIG. 17(c) (NTC) shows ASNS immunohistochemical (IHC) antibody validation.

FIG. 17(d) (KD) shows ASNS immunohistochemical (IHC) antibody validation.

Figure 18A:
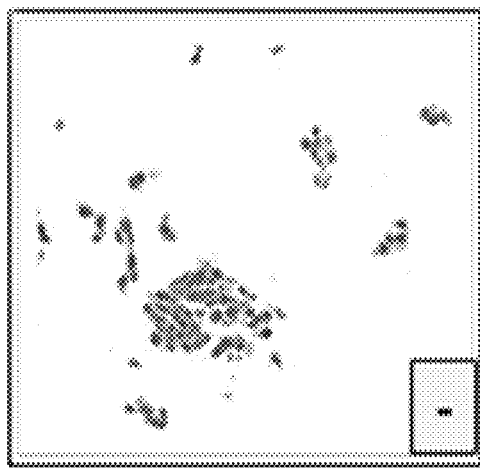

FIG. 18(a) shows IHC assay for responder OVCAR420.

Figure 18B:
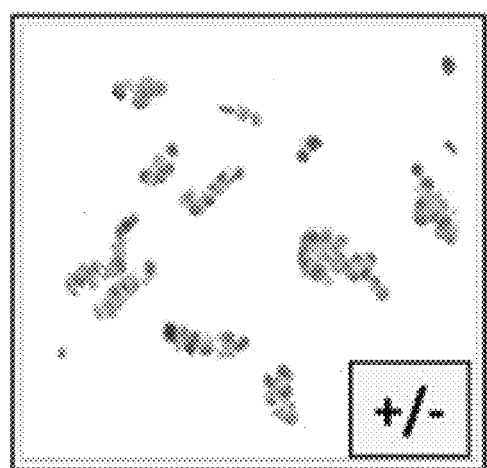

FIG. 18(b) shows IHC assay for responder OVCAR429.

Figure 18C:
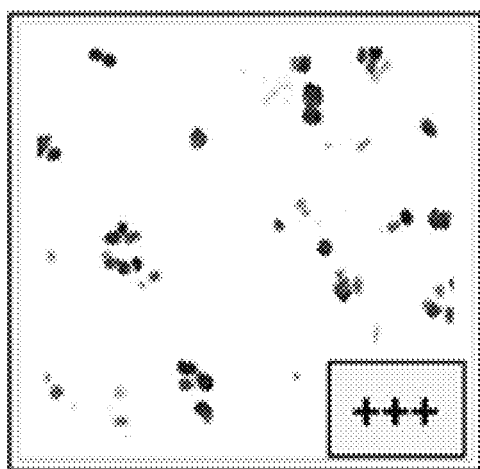

FIG. 18(c) shows IHC assay for non-responder OVCAR4.

Figure 18D:
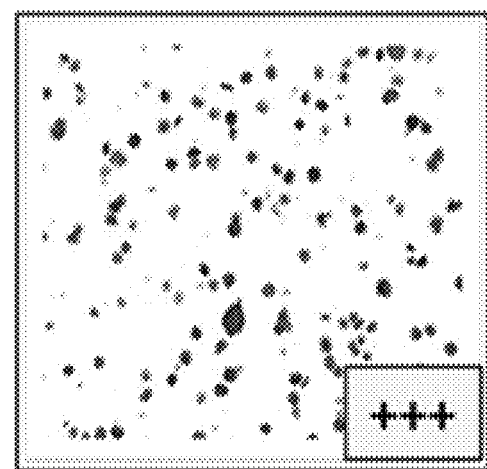

FIG. 18(d) shows IHC assay for non-responder A2780 (d).

Figure 19A:
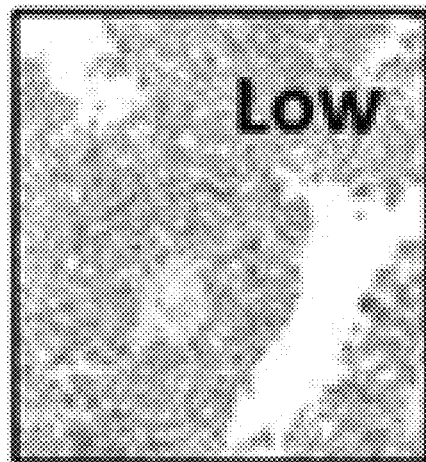

FIG. 19(a) shows tissue microarrays from ovarian cancer patients with low ASNS expressing TMA cores.

Figure 19B:
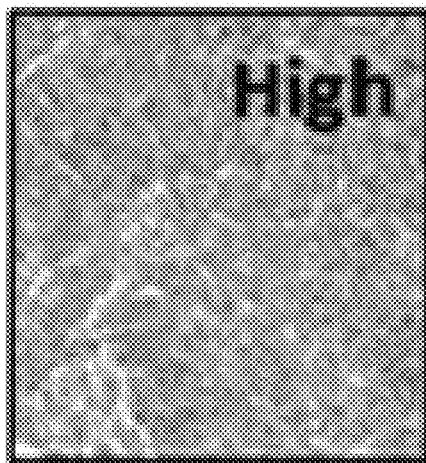

FIG. 19(b) shows tissue microarrays from ovarian cancer patients with high ASNS expressing TMA cores.

Figure 19C:
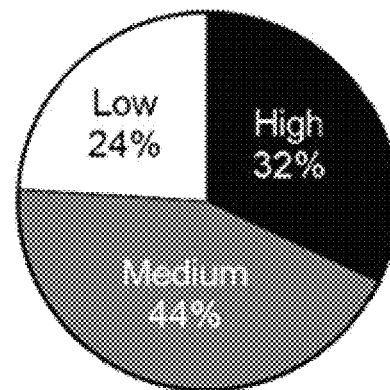

FIG. 19(c) shows provides quantification of patients with different levels of ASNS expression from ASNS scoring.

The next three figures show that glutaminase inhibition inhibits tumor growth in $ASNS_{low}$ models of ovarian cancer.

Figure 20A:
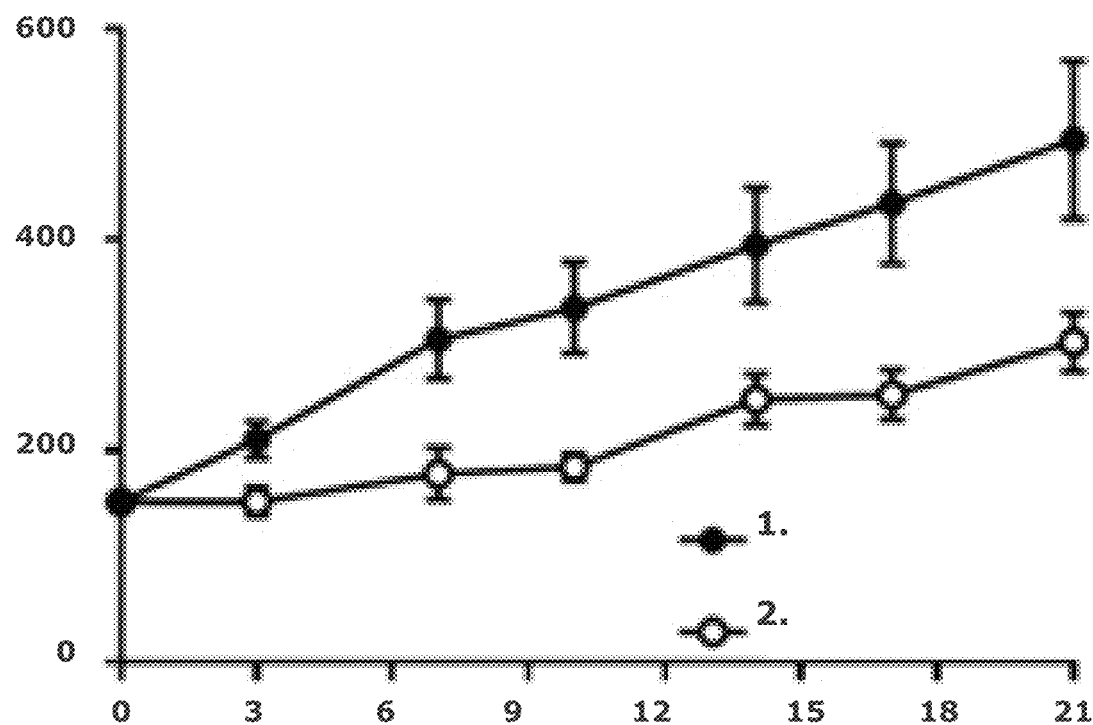

FIG. 20(a) shows that OVCAR-8 subcutaneous xeno-grafts are sensitive to GLS-1 inhibition. x-axis: day; y-axis=tumor volume ($mm^3$).

Figure 20B:
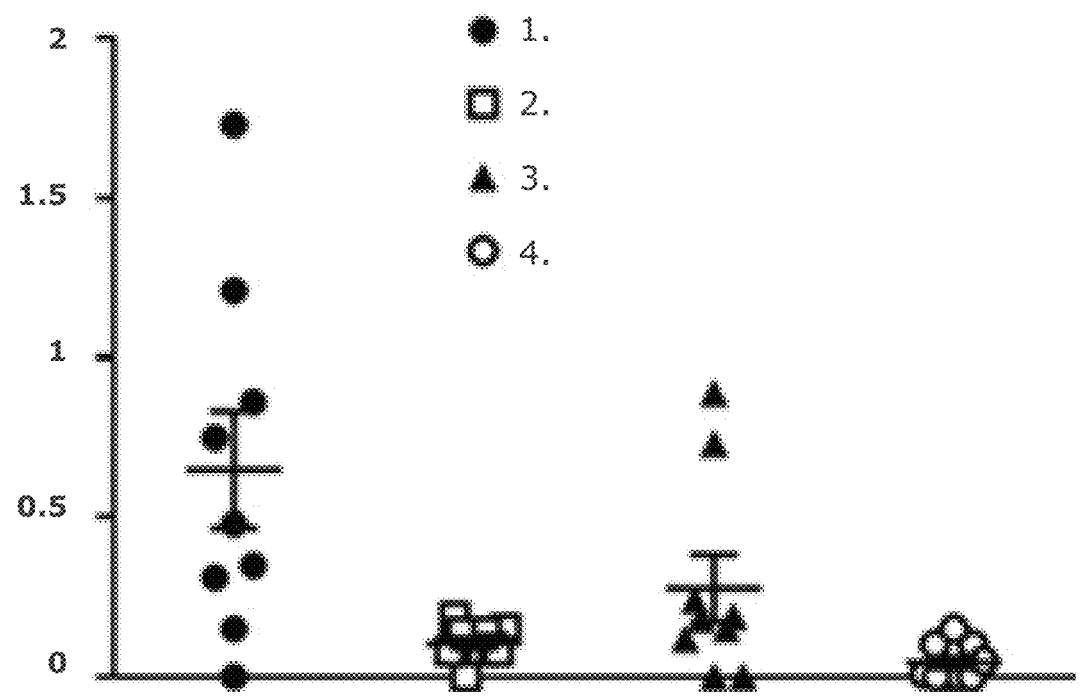

FIG. 20(b) shows that GLS-1 inhibition inhibits tumor progression in an orthotopic model of ovarian cancer. Vehicle (1.); Compound 2 100 mpk (2.); Paclitaxel 15 mpk (3.); and Compound 2+Paclitaxel (4.); y-axis=combined nodule weight (g).

Figure 21:
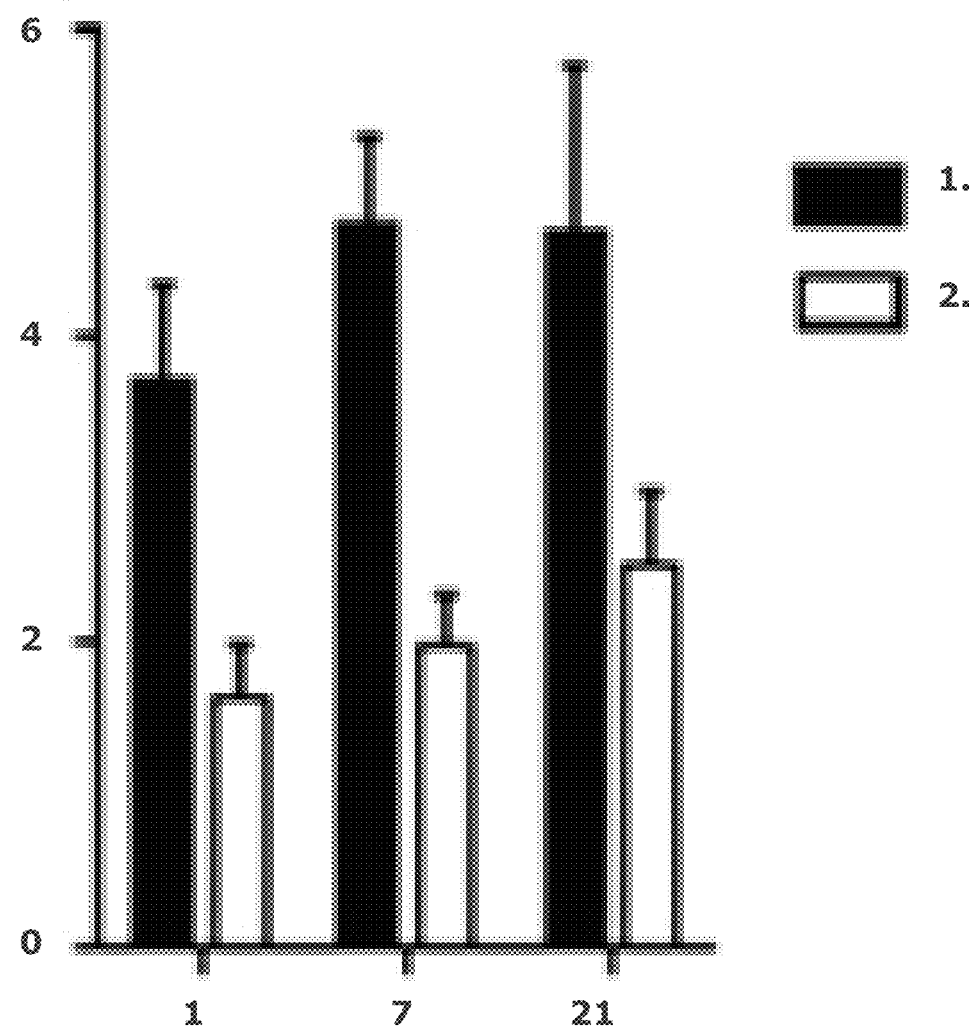

FIG. 21 shows that OVCAR-8 tumors demonstrate altered glutamine metabolism after GLS-1 inhibition. x-axis=day; y-axis=glutamate: glutamine ratio. Vehicle (1.) and Compound 2 (2.).

FIG. 22(a) shows phospho-histone H3 stain for Compound 1.

FIG. 22(b) shows phospho-histone H3 stain for vehicle.

FIG. 22(c) shows pathologist score for vehicle (1.) and Compound 1 (2.).

The next two figures show that glutaminase inhibition inhibits tumor growth in an $ASNS_{low}$ patient-derived xenograft (PDX) model of ovarian cancer.

Figure 23A:
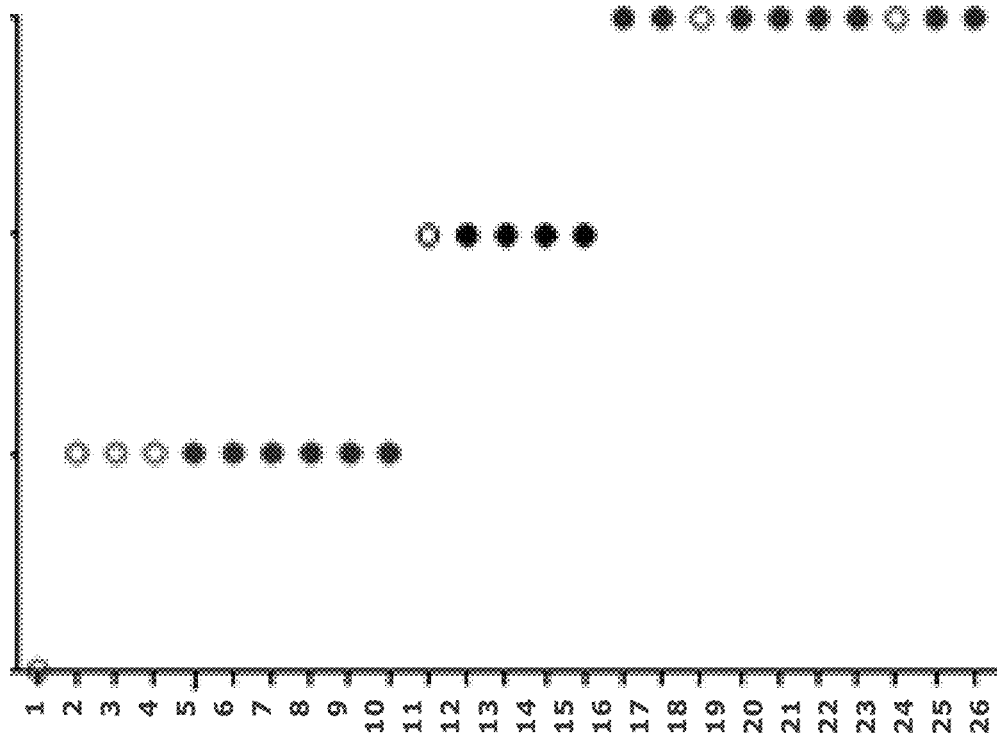

FIG. 23(a) shows scoring of patients samples using a traditional pathologist's scale of 0-3.

Figure 23B:
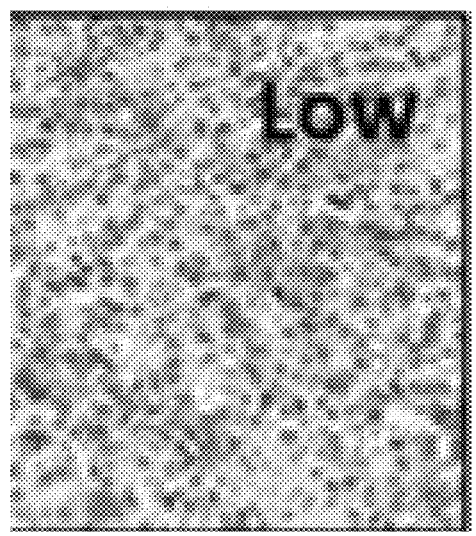

FIG. 23(b) shows example stains of TMA cores having low ASNS expression.

Figure 23C:
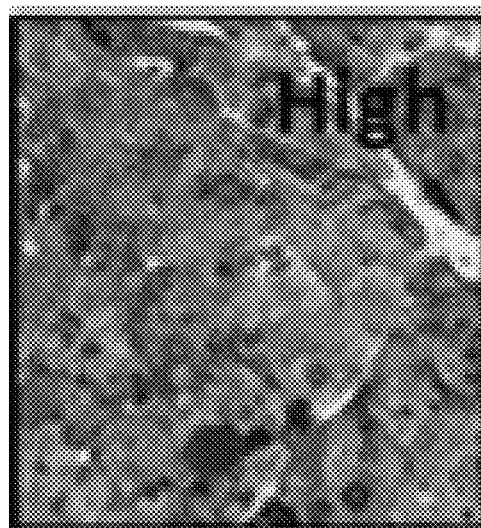

FIG. 23(c) shows example stains of TMA cores having ASNS expression.

Figure 24A:
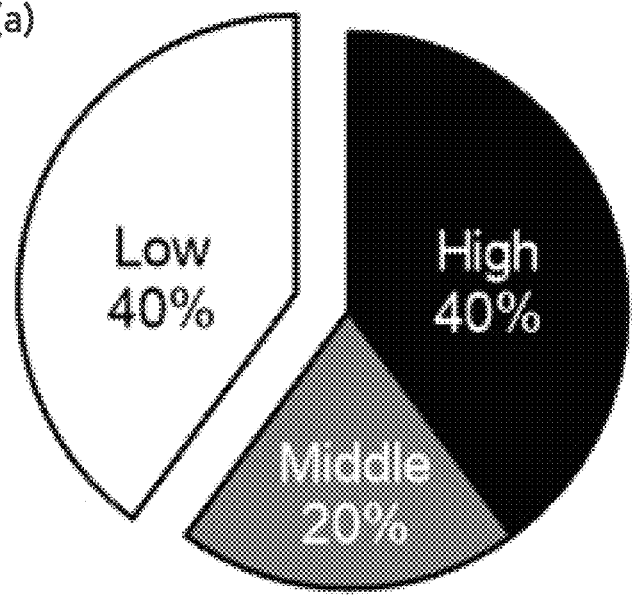

FIG. 24(a) shows a summary of scoring from TMA cores, which reveals 40% of patients with no or low ASNS expression, and another 20% with medium levels of ASNS expression. Both populations would be predicted to respond to GLS inhibition.

Figure 24B:
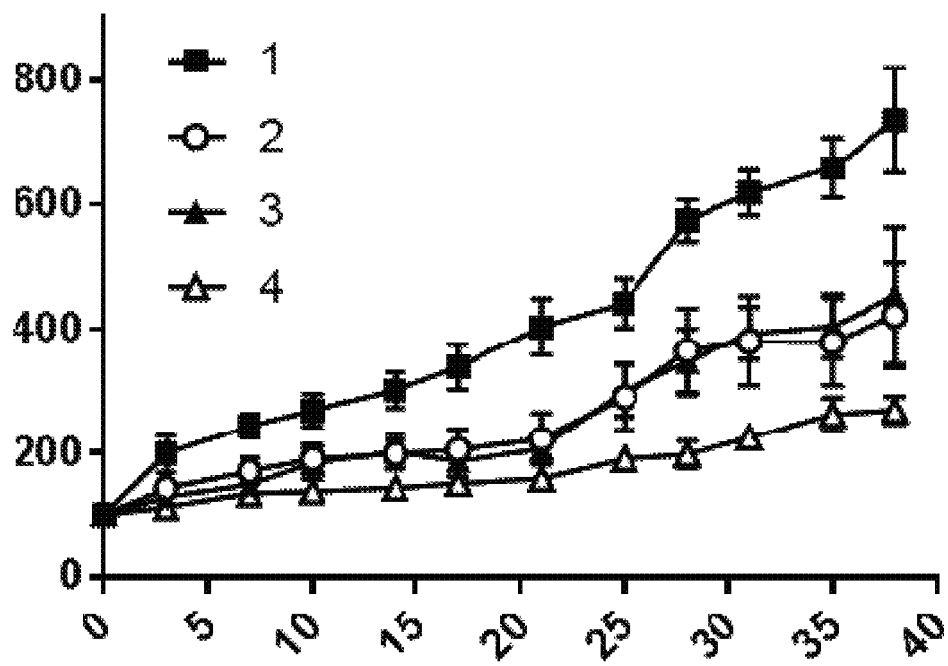

FIG. 24(b) shows that growth of an $ASNS_{low}$ PDX model is inhibited in vivo following treatment with GLSi. Vehicle (1.); Compound 2 100 mpk (2.); Paclitaxel 15 mpk (3.); and Compound 2+Paclitaxel (4.).

Figure 25A:
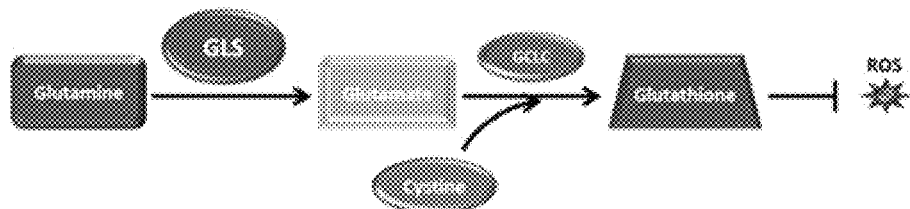

FIG. 25(a) shows production of glutathione and subsequent reduction of reactive oxygen species (ROS).

Figure 25B:
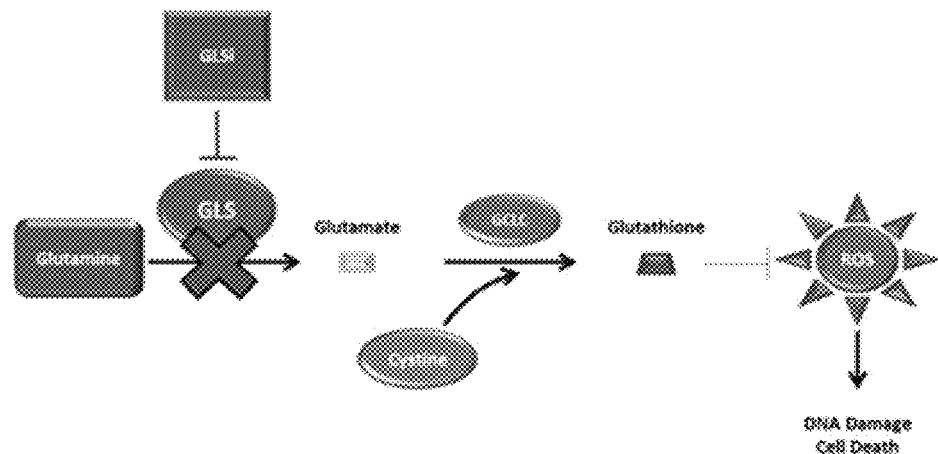

FIG. 25(b) shows that reduction of reactive oxygen species (ROS) levels can be reduced in responders by treatment with a GLS inhibitor, thus increasing ROS levels.

Figure 25C:
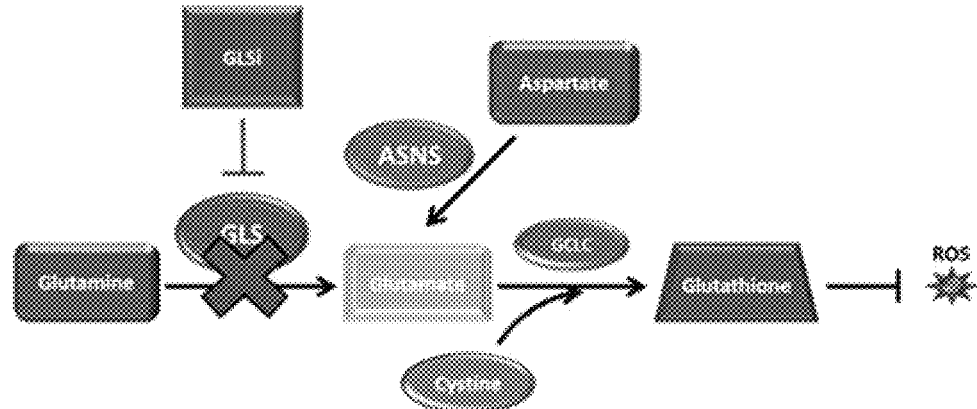

FIG. 25(c) shows that non-responders circumvent GLS inhibition by utilizing aspartate as an alternate feedstock for glutathione synthesis.

DETAILED DESCRIPTION

The present invention is based, in part, on the discovery of biomarkers and mechanisms that indicate responsiveness to glutaminase (GLS) inhibitor treatment. Specifically, a molecular mechanism has been identified that stratifies cancer patients for treatment and indicates responsiveness to GLS inhibition. In particular, the inventors have discovered that some cancer cells are sensitive to GLS inhibition. The inventors have also discovered that cells that express high levels of asparagine synthetase (ASNS) are resistant to inhibition of GLS.

Without being bound to any theory, it is believed that cells, for example, tumor cells, which are sensitive to GLS-1 inhibition display a dependence on reduced glutathione, the major endogenous antioxidant comprised of glycine, cysteine, and glutamine-derived glutamate. Inhibition of GLS-1 reduces the steady state levels of glutathione, thus shifting the redox balance of such cells. Consistent with this model, treatment of a subset of HGSOC cell lines with a potent GLS-1 inhibitor reduces intracellular levels of glutamate and glutathione and inhibits cell growth through a mechanism that involves reactive oxygen species (ROS)-induced DNA damage.

In contrast, HGSOC cell lines expressing high levels of ASNS, the enzyme that metabolizes aspartate to glutamate and asparagine, failed to respond to GLS-1 inhibitor treatment. These non-responder cells maintain glutamate and glutathione pools in the presence of GLS-1 inhibition through the activity of ASNS, and presumably utilize ASNS-derived glutamate to produce glutathione. Consequently, ASNS levels function as a negative indicator of response to GLS-1 inhibition, thus, serving as a patient stratification biomarker.

Nearly 21,000 new ovarian cancer patients are diagnosed each year, and approximately 14,000 deaths result from this disease in the United States alone. While surgical resection of these tumors is becoming more successful, when tumors are inoperable, or when resection is incomplete, there are no effective treatments. This invention provides a mechanism to identify, and methods of treatment of, metabolically distinct subsets of ovarian cancer patients that will respond to targeted GLS-1 inhibitor (GLS1i) therapy. Further, as ASNS expression levels indicate response to GLS-1 inhibition, the expression levels of this enzyme in cancerous cells serves as an invaluable marker for GLS1i therapy and the treatment of ovarian cancer patients.

Accordingly, in one aspect of the invention, the invention comprises a method of treating a tumor or a cancer in a subject. In one embodiment, the invention comprises a method of treating a tumor or a cancer in a subject wherein the tumor or cancer cells in said subject express low levels of asparagine synthetase (ASNS), comprising administering a glutaminase inhibitor to said subject.

In another embodiment of the invention, the invention comprises a method of treating a subject having a disorder, such as a cancer or tumor. The method comprises determining that the concentration or expression of ASNS in said cancer or tumor of said subject is low and administering a glutaminase inhibitor to said subject.

Methods and techniques of determining whether the concentration or expression of ASNS in the tumor or cancer cells of a subject are low or not are known to one of skill in the art and are also described herein. Any method known to one of skill in the art can be used, including, but not limited to, determining the Histopathology Score (H-score) of the tumor or cancer cells by immunohistochemical staining. An H-score of less than or equal to 100 indicates that the level of ASNS in the tumor or cancer cells of the subject are low.

In another embodiment of the invention, the invention comprises treating cancer in a subpopulation of subjects, the subpopulation being characterized by a low level of ASNS in the subjects, and administering a glutaminase inhibitor to the subjects in the subpopulation. In some embodiments, the level of ASNS in the subjects in the subpopulation is quantified as an H-score by immunohistochemical staining. In some embodiments, the H-score of subjects in the subpopulation is less than or equal to 150. In some embodiments, the H-score of subjects in the subpopulation is less than or equal to 125. In some embodiments, the H-score of subjects in the subpopulation is less than or equal to 100.

Embodiment 1

A method for treatment of a disorder in a subject characterized by a low level of expression or concentration of asparagine synthetase (ASNS), said treatment comprising administering one or more glutathione lowering agents to said subject.

Embodiment 2

A method for treatment of a disorder in a subpopulation of subjects, said subjects in said subpopulation being characterized by a low level of expression or concentration of ASNS, said treatment comprising administering one or more glutathione lowering agents to said subjects.

Embodiment 3

A method of stratifying a subject for response to GLS-1 inhibitor therapy, comprising determination of a low level of expression or concentration of ASNS in said subject, and administering one or more glutathione lowering agents to said subject.

Embodiment 4

A method comprising the treatment of a subject having a disorder in need of treatment, comprising determination of the expression or concentration or asparagine synthetase (ASNS) in the subject, and administering one or more glutathione lowering agents to said subject if said subject displays a low level of expression or concentration of ASNS.

Embodiment 5

The method of any one of Embodiments 1-4, further comprising obtaining a biological sample or samples from said subject or subjects.

Embodiment 6

The method of Embodiment 4, further comprising determining the level or concentration of ASNS from said biological sample or samples.

Embodiment 7

The method of any one of Embodiments 1-6, wherein said disorder is chosen from a cancer or a tumor.

Embodiment 8

The method of Embodiment 6, wherein said disorder is a cancer.

Embodiment 9

The method of Embodiment 8, wherein said cancer is chosen from Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma), Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, Low Malignant Potential Tumor and High Grade Serous Ovarian Cancer), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia and Wilms Tumor, or a variant thereof.

Embodiment 10

The method of Embodiment 8, wherein said cancer is chosen from high grade serous (HGSOC), epithelial, germ cell tumor, and low malignant potential tumor.

Embodiment 11

The method of Embodiment 8, wherein said cancer is chosen from ovarian, skin, liver, prostate, breast, colon, lung, head and neck cancers and lymphoma.

Embodiment 12

The method of Embodiment 11, wherein said cancer is ovarian cancer.

Embodiment 13

The method of Embodiment 12, wherein said ovarian cancer is high-grade serous ovarian cancer (HGSOC).

Embodiment 14

The method of Embodiment 13, wherein said ovarian cancer is nonresectable or relapsed HGSOC.

Embodiment 15

The method of Embodiment 7, wherein said disorder is a tumor or tumors.

Embodiment 16

The method of any one of Embodiments 1-15, wherein said low level of expression or concentration of ASNS is a low level of expression of ASNS.

Embodiment 17

The method of Embodiment 16, wherein said tumor or tumors of said subject or subjects is characterized by a low level of expression of ASNS.

Embodiment 18

The method of any one of Embodiments 1-15, wherein said low level of expression or concentration of ASNS is a low concentration of ASNS.

Embodiment 19

The method of Embodiment 16, wherein which said tumor or tumors of said subject or subjects is characterized by a low concentration of ASNS.

Embodiment 20

The method of either one of Embodiment 18 or 19, in which said concentration of ASNS is less than or equal to 150 by immunohistochemical staining.

Embodiment 21

The method of either one of Embodiment 18 or 19, in which said concentration of ASNS is less than or equal to 125 by immunohistochemical staining.

Embodiment 22

The method of either one of Embodiment 18 or 19, in which said concentration of ASNS is less than or equal to 100 by immunohistochemical staining.

Embodiment 23

The method of either one of Embodiment 18 or 19, in which said concentration of ASNS is less than or equal to 95 by immunohistochemical staining.

Embodiment 24

The method of either one of Embodiment 18 or 19, in which said concentration of ASNS is less than or equal to 90 by immunohistochemical staining.

Embodiment 25

The method of either one of Embodiment 18 or 19, in which said concentration of ASNS is less than or equal to 85 by immunohistochemical staining.

Embodiment 26

The method of either one of Embodiment 18 or 19, in which said concentration of ASNS is less than or equal to 80 by immunohistochemical staining.

Embodiment 27

The method of either one of Embodiment 18 or 19, in which said concentration of ASNS is less than or equal to 75 by immunohistochemical staining.

Embodiment 28

The method of either one of Embodiment 18 or 19, in which said concentration of ASNS is less than or equal to 70 by immunohistochemical staining.

Embodiment 29

The method of either one of Embodiment 18 or 19, in which said concentration of ASNS is less than or equal to 65 by immunohistochemical staining.

Embodiment 30

The method of either one of Embodiment 18 or 19, in which said concentration of ASNS is less than or equal to 60 by immunohistochemical staining.

Embodiment 31

The method of either one of Embodiment 18 or 19, in which said concentration of ASNS is less than or equal to 55 by immunohistochemical staining.

Embodiment 32

The method of either one of Embodiment 18 or 19, in which said concentration of ASNS is less than or equal to 50 by immunohistochemical staining.

Embodiment 33

The method of either one of Embodiment 18 or 19, in which said concentration of ASNS is less than or equal to 45 by immunohistochemical staining.

Embodiment 34

The method of either one of Embodiment 18 or 19, in which said concentration of ASNS is less than or equal to 40 by immunohistochemical staining.

Embodiment 35

The method of either one of Embodiment 18 or 19, in which said concentration of ASNS is less than or equal to 35 by immunohistochemical staining.

Embodiment 36

The method of either one of Embodiment 18 or 19, in which said concentration of ASNS is less than or equal to 30 by immunohistochemical staining.

Embodiment 37

The method of either one of Embodiment 18 or 19, in which said concentration of ASNS is less than or equal to 25 by immunohistochemical staining.

Embodiment 38

The method of either one of Embodiment 18 or 19, in which said concentration of ASNS is less than or equal to 20 by immunohistochemical staining.

Embodiment 39

The method of either one of Embodiment 18 or 19, in which said concentration of ASNS is less than or equal to 15 by immunohistochemical staining.

Embodiment 40

The method of either one of Embodiment 18 or 19, in which said concentration of ASNS is less than or equal to 10 by immunohistochemical staining.

Embodiment 41

The method of any one of Embodiments 1-40, wherein said one or more glutathione lowering agents comprises one or more compounds that inhibit glutathione production or activity.

Embodiment 42

The method of Embodiment 41, wherein said one or more glutathione lowering agents comprises one or more compounds that inhibit glutathione production.

Embodiment 43

The method of Embodiment 41, wherein said one or more glutathione lowering agents comprises one or more compounds that inhibit glutathione activity.

Embodiment 44

The method of any one of Embodiments 1-43, wherein said one or more glutathione lowering agents comprises one or more compounds that inhibits amino acid or glutathione transport.

Embodiment 45

The method of Embodiment 44, wherein said one or more glutathione lowering agents comprises one or more compounds that inhibits amino acid transport.

Embodiment 46

The method of Embodiment 44, wherein said one or more glutathione lowering agents comprises one or more compounds that inhibits glutathione transport.

Embodiment 47

The method of any one of Embodiments 1-46, wherein said one or more glutathione lowering agents comprises one or more glutaminase inhibitor.

Embodiment 48

The method of Embodiment 47, wherein said one or more glutaminase inhibitor comprises one or more GLS-1 inhibitors.

Embodiment 49

The method of Embodiment 48, wherein said one or more GLS-1 inhibitors comprises one or more selective GLS-1 inhibitors.

Embodiment 50

The method of Embodiment 48, wherein said one or more glutathione lowering agents comprises one or more GLS-1 inhibitors chosen from the group consisting of:
a) (S)-2-hydroxy-2-phenyl-N-(5-(4-(6-(2-(3-(trifluoromethoxy)phenyl)acetamido)pyridazin-3-yl)butyl)-1,3,4-thiadiazol-2-yl)acetamide,
b) N,N'-(5,5'-(2,2'-thiobis(ethane-2,1-diyl))bis(1,3,4-thiadiazole-5,2-diyl))bis(2-phenylacetamide), also known as BPTES,
c) 2-(pyridin-2-yl)-N-{5-[4-(6-{2-[3-(trifluoromethoxy)phenyl]acetamido}pyridazin-3-yl)butyl]-1,3,4-thiadiazol-2-yl}acetamide, also known as CB-839,
d) N,N'-(5,5'-(2,2'-sulfonylbis(ethane-2,1-diyl))bis(1,3,4-thiadiazole-5,2-diyl))bis(2-(pyridin-2-yl)acetamide),
e) N-methyl-1-{4-[6-(2-{4-[3-(trifluoromethoxy)phenyl]pyridin-2-yl}acetamido)pyridazin-3-yl]butyl}-1H-1,2,3-triazole-4-carboxamide,
f) 1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide,
g) 1-(2-fluoro-4-(6-(2-(4-(trifluoromethyl)pyridin-2-yl)acetamido)pyridazin-3-yl)butyl)-N-methyl-1H-1,2,3-triazole-4-carboxamide,
h) N-(pyridin-2-ylmethyl)-5-(3-(6-(2-(3-(trifluoromethoxy)phenyl)acetamido)pyridazin-3-yl)pyrrolidin-1-yl)-1,3,4-thiadiazole-2-carboxamide,
i) (R)-1-(2-fluoro-4-(6-(2-(4-(3-(trifluoromethoxy)phenyl)pyridin-2-yl)acetamido)-pyridazin-3-yl)butyl)-N-methyl-1H-1,2,3-triazole-4-carboxamide,
j) (R)-1-(2-fluoro-4-(6-(2-(4-(trifluoromethyl)pyridin-2-yl)acetamido)pyridazin-3-yl)butyl)-N-methyl-1H-1,2,3-triazole-4-carboxamide,
k) (R)-1-(2-fluoro-4-(6-(2-(6-methyl-4-(trifluoromethyl)pyridin-2-yl)acetamido)pyridazin-3-yl)butyl)-N-methyl-1H-1,2,3-triazole-4-carboxamide, l) (R)-1-(4-(6-(2-(4-(cyclopropyldifluoromethyl)pyridin-2-yl)acetamido)pyridazin-3-yl)-2-fluorobutyl)-N-methyl-1H-1,2,3-triazole-4-carboxamide, m) (R)-1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide, n) (R)-1-(2-fluoro-4-(6-(2-(1-(3-(trifluoromethoxy)phenyl)-1H-imidazol-4-yl)-acetamido)pyridazin-3-yl)butyl)-N-methyl-1H-1,2,3-triazole-4-carboxamide, o) 1-(4-(6-(2-(4-cyclobutoxypyridin-2-yl)acetamido)pyridazin-3-yl)butyl)-N-methyl-1H-1,2,3-triazole-4-carboxamide, p) 1-(4-(6-(2-(4-cyclobutoxypyridin-2-yl)acetamido)pyridazin-3-yl)-2-fluorobutyl)-N-methyl-1H-1,2,3-triazole-4-carboxamide, q) 1-(4-(6-(2-(4-(3,3-difluorocyclobutoxy)pyridin-2-yl)acetamido)pyridazin-3-yl)butyl)-N-methyl-1H-1,2,3-triazole-4-carboxamide, r) 1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide, s) (R)-1-(4-(6-(2-(4-cyclopropylpyridin-2-yl)acetamido)pyridazin-3-yl)-2-fluorobutyl)-N-methyl-1H-1,2,3-triazole-4-carboxamide, t) 5-(3-(6-(2-(pyridin-2-yl)acetamido)pyridazin-3-yl)pyrrolidin-1-yl)-N-((4-(trifluoromethyl)pyridin-2-yl)methyl)-1,3,4-thiadiazole-2-carboxamide, and u) N,N'-(5,5'-(cyclohexane-1,3-diyl)bis(1,3,4-thiadiazole-5,2-diyl))bis(2-phenylacetamide) (both or either of 1S,3S and 1R,2R enantiomers), or a salt and polymorph thereof.

Embodiment 51

The method of Embodiment 48, wherein said one or more glutathione lowering agents comprises two or more GLS-1 inhibitors chosen from the group consisting of:

a) (S)-2-hydroxy-2-phenyl-N-(5-(4-(6-(2-(3-(trifluoromethoxy)phenyl)acetamido)pyridazin-3-yl)butyl)-1,3,4-thiadiazol-2-yl)acetamide, b) N,N'-(5,5'-(2,2'-thiobis(ethane-2,1-diyl))bis(1,3,4-thiadiazole-5,2-diyl))bis(2-phenylacetamide), also known as BPTES, c) 2-(pyridin-2-yl)-N-{5-[4-(6-{2-[3-(trifluoromethoxy)phenyl]acetamido}pyridazin-3-yl)butyl]-1,3,4-thiadiazol-2-yl}acetamide, also known as CB-839, d) N,N'-(5,5'-(2,2'-sulfonylbis(ethane-2,1-diyl))bis(1,3,4-thiadiazole-5,2-diyl))bis(2-(pyridin-2-yl)acetamide), e) N-methyl-1-{4-[6-(2-{4-[3-(trifluoromethoxy)phenyl]pyridin-2-yl}acetamido)pyridazin-3-yl]butyl}-1H-1,2,3-triazole-4-carboxamide, f) 1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide, g) 1-(2-fluoro-4-(6-(2-(4-(trifluoromethyl)pyridin-2-yl)acetamido)pyridazin-3-yl)butyl)-N-methyl-1H-1,2,3-triazole-4-carboxamide, h) N-(pyridin-2-ylmethyl)-5-(3-(6-(2-(3-(trifluoromethoxy)phenyl)acetamido)pyridazin-3-yl)pyrrolidin-1-yl)-1,3,4-thiadiazole-2-carboxamide, i) (R)-1-(2-fluoro-4-(6-(2-(4-(3-(trifluoromethoxy)phenyl)pyridin-2-yl)acetamido)-pyridazin-3-yl)butyl)-N-methyl-1H-1,2,3-triazole-4-carboxamide, j) (R)-1-(2-fluoro-4-(6-(2-(4-(trifluoromethyl)pyridin-2-yl)acetamido)pyridazin-3-yl)butyl)-N-methyl-1H-1,2,3-triazole-4-carboxamide, k) (R)-1-(2-fluoro-4-(6-(2-(6-methyl-4-(trifluoromethyl)pyridin-2-yl)acetamido)pyridazin-3-yl)butyl)-N-methyl-1H-1,2,3-triazole-4-carboxamide, l) (R)-1-(4-(6-(2-(4-(cyclopropyldifluoromethyl)pyridin-2-yl)acetamido)pyridazin-3-yl)-2-fluorobutyl)-N-methyl-1H-1,2,3-triazole-4-carboxamide, m) (R)-1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide, n) (R)-1-(2-fluoro-4-(6-(2-(1-(3-(trifluoromethoxy)phenyl)-1H-imidazol-4-yl)-acetamido)pyridazin-3-yl)butyl)-N-methyl-1H-1,2,3-triazole-4-carboxamide, o) 1-(4-(6-(2-(4-cyclobutoxypyridin-2-yl)acetamido)pyridazin-3-yl)butyl)-N-methyl-1H-1,2,3-triazole-4-carboxamide, p) 1-(4-(6-(2-(4-cyclobutoxypyridin-2-yl)acetamido)pyridazin-3-yl)-2-fluorobutyl)-N-methyl-1H-1,2,3-triazole-4-carboxamide, q) 1-(4-(6-(2-(4-(3,3-difluorocyclobutoxy)pyridin-2-yl)acetamido)pyridazin-3-yl)butyl)-N-methyl-1H-1,2,3-triazole-4-carboxamide, r) 1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide, s) (R)-1-(4-(6-(2-(4-cyclopropylpyridin-2-yl)acetamido)pyridazin-3-yl)-2-fluorobutyl)-N-methyl-1H-1,2,3-triazole-4-carboxamide, t) 5-(3-(6-(2-(pyridin-2-yl)acetamido)pyridazin-3-yl)pyrrolidin-1-yl)-N-((4-(trifluoromethyl)pyridin-2-yl)methyl)-1,3,4-thiadiazole-2-carboxamide, and u) N,N'-(5,5'-(cyclohexane-1,3-diyl)bis(1,3,4-thiadiazole-5,2-diyl))bis(2-phenylacetamide) (both or either of 1S,3S and 1R,2R enantiomers), and/or salts and polymorphs thereof.

Embodiment 52

The method of Embodiment 48, wherein said one or more glutathione lowering agents comprises (S)-2-hydroxy-2-phenyl-N-(5-(4-(6-(2-(3-(trifluoromethoxy)phenyl)acetamido)pyridazin-3-yl)butyl)-1,3,4-thiadiazol-2-yl)acetamide, or a salt or polymorph thereof.

Embodiment 53

The method of Embodiment 48, wherein said one or more glutathione lowering agents comprises N,N'-(5,5'-(2,2'-thiobis(ethane-2,1-diyl))bis(1,3,4-thiadiazole-5,2-diyl))bis(2-phenylacetamide), or a salt or polymorph thereof.

Embodiment 54

The method of Embodiment 48, wherein said one or more glutathione lowering agents comprises (S)-2-hydroxy-2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide, or a salt or polymorph thereof.

Embodiment 55

The method of Embodiment 48, wherein said one or more glutathione lowering agents comprises N,N'-(5,5'-(2,2'-sulfonylbis(ethane-2,1-diyl))bis(1,3,4-thiadiazole-5,2-diyl))bis(2-(pyridin-2-yl)acetamide), or a salt or polymorph thereof.

Embodiment 56

The method of Embodiment 48, wherein said one or more glutathione lowering agents comprises N-methyl-1-{4-[6-

(2-{4-[3-(trifluoromethoxy)-phenyl]pyridin-2-yl}acetamido)pyridazin-3-yl]butyl}-1H-1,2,3-triazole-4-carboxamide, or a salt or polymorph thereof.

Embodiment 57

The method of Embodiment 48, wherein said one or more glutathione lowering agents comprises 1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide, or a salt or polymorph thereof.

Embodiment 58

The method of Embodiment 48, wherein said one or more glutathione lowering agents comprises 1-(2-fluoro-4-(6-(2-(4-(trifluoromethyl)pyridin-2-yl)acetamido)pyridazin-3-yl)butyl)-N-methyl-1H-1,2,3-triazole-4-carboxamide, or a salt or polymorph thereof.

Embodiment 59

The method of Embodiment 48, wherein said one or more glutathione lowering agents comprises N-(pyridin-2-ylmethyl)-5-(3-(6-(2-(3-(trifluoromethoxy)-phenyl)acetamido)pyridazin-3-yl)pyrrolidin-1-yl)-1,3,4-thiadiazole-2-carboxamide, or a salt or polymorph thereof.

Embodiment 60

The method of Embodiment 48, wherein said one or more glutathione lowering agents comprises (R)-1-(2-fluoro-4-(6-(2-(4-(3-(trifluoromethoxy)-phenyl)pyridin-2-yl)acetamido)pyridazin-3-yl)butyl)-N-methyl-1H-1,2,3-triazole-4-carboxamide, or a salt or polymorph thereof.

Embodiment 61

The method of Embodiment 48, wherein said one or more glutathione lowering agents comprises (R)-1-(2-fluoro-4-(6-(2-(4-(trifluoromethyl)pyridin-2-yl)acetamido)pyridazin-3-yl)butyl)-N-methyl-1H-1,2,3-triazole-4-carboxamide, or a salt or polymorph thereof.

Embodiment 62

The method of Embodiment 48, wherein said one or more glutathione lowering agents comprises (R)-1-(2-fluoro-4-(6-(2-(6-methyl-4-(trifluoromethyl)pyridin-2-yl)acetamido)pyridazin-3-yl)butyl)-N-methyl-1H-1,2,3-triazole-4-carboxamide, or a salt or polymorph thereof.

Embodiment 63

The method of Embodiment 48, wherein said one or more glutathione lowering agents comprises (R)-1-(4-(6-(2-(4-(cyclopropyldifluoromethyl)pyridin-2-yl)acetamido)pyridazin-3-yl)-2-fluorobutyl)-N-methyl-1H-1,2,3-triazole-4-carboxamide, or a salt or polymorph thereof.

Embodiment 64

The method of Embodiment 48, wherein said one or more glutathione lowering agents comprises (R)-1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide, or a salt or polymorph thereof.

Embodiment 65

The method of Embodiment 48, wherein said one or more glutathione lowering agents comprises (R)-1-(2-fluoro-4-(6-(2-(1-(3-(trifluoromethoxy)phenyl)-1H-imidazol-4-yl)acetamido)pyridazin-3-yl)butyl)-N-methyl-1H-1,2,3-triazole-4-carboxamide, or a salt or polymorph thereof.

Embodiment 66

The method of Embodiment 48, wherein said one or more glutathione lowering agents comprises 1-(4-(6-(2-(4-cyclobutoxypyridin-2-yl)acetamido)-pyridazin-3-yl)butyl)-N-methyl-1H-1,2,3-triazole-4-carboxamide, or a salt or polymorph thereof.

Embodiment 67

The method of Embodiment 48, wherein said one or more glutathione lowering agents comprises 1-(4-(6-(2-(4-cyclobutoxypyridin-2-yl)acetamido)-pyridazin-3-yl)-2-fluorobutyl)-N-methyl-1H-1,2,3-triazole-4-carboxamide, or a salt or polymorph thereof.

Embodiment 68

The method of Embodiment 48, wherein said one or more glutathione lowering agents comprises 1-(4-(6-(2-(4-(3,3-difluorocyclobutoxy)pyridin-2-yl)acetamido)pyridazin-3-yl)butyl)-N-methyl-1H-1,2,3-triazole-4-carboxamide, or a salt or polymorph thereof.

Embodiment 69

The method of Embodiment 48, wherein said one or more glutathione lowering agents comprises 1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide, or a salt or polymorph thereof.

Embodiment 70

The method of Embodiment 48, wherein said one or more glutathione lowering agents comprises (R)-1-(4-(6-(2-(4-cyclopropylpyridin-2-yl)acetamido)-pyridazin-3-yl)-2-fluorobutyl)-N-methyl-1H-1,2,3-triazole-4-carboxamide, or a salt or polymorph thereof.

Embodiment 71

The method of Embodiment 48, wherein said one or more glutathione lowering agents comprises 5-(3-(6-(2-(pyridin-2-yl)acetamido)pyridazin-3-yl)pyrrolidin-1-yl)-N-((4-(trifluoromethyl)pyridin-2-yl)methyl)-1,3,4-thiadiazole-2-carboxamide, or a salt or polymorph thereof.

Embodiment 72

The method of Embodiment 48, wherein said one or more glutathione lowering agents comprises N,N'-(5,5'-(cyclohexane-1,3-diyl)bis(1,3,4-thiadiazole-5,2-diyl))bis(2-phenylacetamide), or a salt or polymorph thereof.

Embodiment 73

The method of Embodiment 48, wherein said one or more glutathione lowering agents comprises N,N'-(5,5'-((1S,3S)- cyclohexane-1,3-diyl)bis(1,3,4-thiadiazole-5,2-diyl))bis(2-phenylacetamide), or a salt or polymorph thereof.

Embodiment 74

The method of Embodiment 48, wherein said one or more glutathione lowering agents comprises N,N'-(5,5'-((1R,3R)-cyclohexane-1,3-diyl)bis(1,3,4-thiadiazole-5,2-diyl))bis(2-phenylacetamide), or a salt or polymorph thereof.

Embodiment 75

The method of Embodiment 48, wherein said one or more glutathione lowering agents comprises Compound 1:

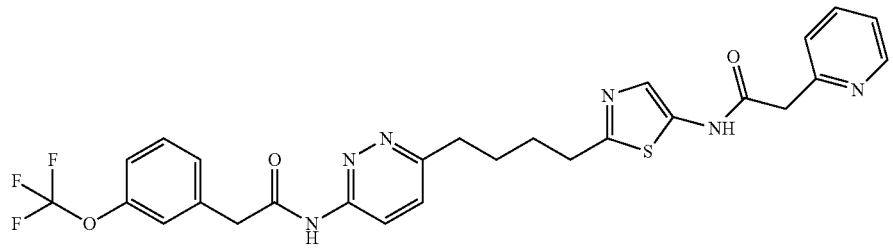 [SMILES: O=C(Cc1cccc(OC(F)(F)F)c1)Nc1ccc(CCCCc2ncc(NC(=O)Cc3ccccn3)s2)nn1]

also known as 2-(pyridin-2-yl)-N-{5-[4-(6-{2-[3-(trifluoromethoxy)phenyl]acetamido}-pyridazin-3-yl)butyl]-1,3,4-thiadiazol-2-yl}acetamide (CB-839).

Embodiment 76

The method of Embodiment 48, wherein said one or more glutathione lowering agents comprises Compound 2:

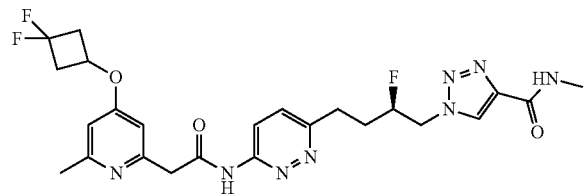 [SMILES: CNC(=O)c1cn(C[C@H](F)CCc2ccc(NC(=O)Cc3cc(OC4CC(F)(F)C4)cc(C)n3)nn2)nn1]

also known as (R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide.

Embodiment 77

The method of Embodiment 48, wherein said one or more glutathione lowering agents comprises a compound of Formula I:

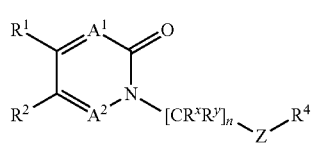

(I)

or a salt thereof, wherein:

n is chosen from 3, 4, and 5;

each $R^x$ and $R^y$ is independently chosen from alkyl, cyano, H, and halo, wherein two $R^x$ groups together with the atoms to which they are attached optionally form a cycloalkyl ring;

$A^1$ and $A^2$ are independently chosen from C—H, C—F, and N;

$R^1$ and $R^4$ are independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^3)_2C(O)R^3$, $C(R^3)_2C(O)N(R^3)_2$, $C(R^3)_2N(R^3)_2$, $C(R^3)_2NR^3C(O)R^3$, $C(R^3)_2NR^3C(O)OR^3$, $C(R^3)_2NR^3C(O)N(R^3)_2$, $C(R^3)_2NR^3S(O)R^3$, $C(R^3)_2NR^3S(O)_2R^3$, $N(R^3)_2$, $NR^3C(O)R^3$, $NR^3C(O)OR^3$, $NR^3C(O)N(R^3)_2$, $NR^3S(O)R^3$, $NR^3S(O)_2R^3$, $C(O)N(R^3)_2$, $S(O)N(R^3)_2$, $S(O)_2N(R^3)_2$, $C(O)R^3$, $SR^3$, $S(O)R^3$, and $S(O)_2R^3$, wherein each $R^1$ and $R^4$ may be optionally substituted with between 0 and 3 $R^z$ groups;

$R^2$ is chosen from alkyl, heterocycloalkyl, cyano, cycloalkyl, H, halo, and haloalkyl, wherein $R^1$ and $R^2$ together with the atoms to which they are attached optionally form an form an aryl, cycloalkyl, heteroaryl, or heterocycloalkyl ring, which may be optionally substituted with between 0 and 3 $R^z$ groups;

each $R^3$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^3$ may be optionally substituted with between 0 and 3 $R^z$ groups, wherein two $R^3$ groups together with the atoms to which they are attached optionally form an aryl, cycloalkyl, heteroaryl, or heterocycloalkyl ring, which may be optionally substituted with between 0 and 3 $R^z$ groups;

each $R^z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^6)_2$, $NR^6C(O)C(R^6)_3$, $NR^6C(O)OC(R^6)_3$, $NR^6C(O)N(R^6)_2$, $NR^6S(O)C(R^6)_3$, $NR^6S(O)_2C(R^6)_3$, $C(O)N(R^6)_2$, $S(O)N(R^6)_2$, $S(O)_2N(R^6)_2$, $C(O)C(R^6)_3$, $SC(R^6)_3$, $S(O)C(R^6)_3$, and $S(O)_2C(R^6)_3$;

each $R^6$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein two $R^6$ groups together with the atoms to which they are attached optionally form an aryl, cycloalkyl, heteroaryl, or heterocycloalkyl ring, which may be optionally substituted with between 0 and 3 $R^x$ groups; and Z is heteroaryl, which may be optionally substituted.

Embodiment 78

The method of Embodiment 77, wherein:
Z is

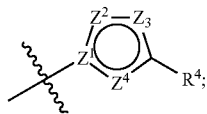

$Z^1$ is chosen from C and N; and $Z^2$, $Z^3$, and $Z^4$ are independently chosen from N, O, S, and CH, wherein at least one of $Z^1$, $Z^2$, $Z^3$, and $Z^4$ is chosen from N, O, and S.

Embodiment 79

The method of Embodiment 77, wherein:
Z is

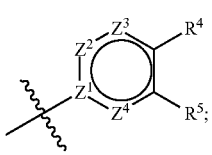

$Z^1$ is chosen from C and N;

$Z^2$ is chosen from N, CH, and C(O);

$Z^3$, and $Z^4$ are independently chosen from N and CH, wherein at least one of $Z^1$, $Z^2$, $Z^3$, and $Z^4$ is N; and $R^5$ is chosen from alkyl, heterocycloalkyl, cyano, cycloalkyl, H, halo, and haloalkyl, wherein $R^4$ and $R^5$ together with the atoms to which they are attached optionally form an aryl, cycloalkyl, heteroaryl, or heterocycloalkyl ring, which may be optionally substituted with between 0 and 3 $R^z$ groups.

Embodiment 80

The method of Embodiment 48, wherein said one or more glutathione lowering agents comprises a compound of Formula II:

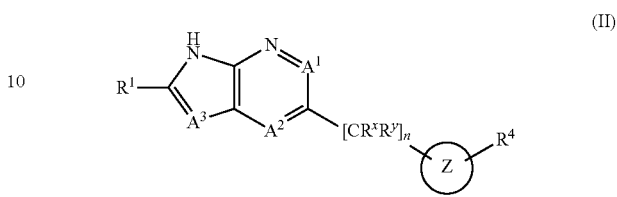

or a salt thereof, wherein:
n is chosen from 3, 4, and 5;
each $R^x$ and $R^y$ is independently chosen from alkyl, cyano, H, and halo, wherein two $R^x$ groups together with the atoms to which they are attached optionally form a cycloalkyl ring;
$A^1$ and $A^2$ are independently chosen from N and CH;
$A^3$ is chosen from N and $CR^2$;
$R^1$ is chosen from alkenyl, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, $C(O)N(R^3)_2$, and $C(O)C(R^3)_3$, wherein $R^1$ may be optionally substituted with between 0 and 3 $R^z$ groups;
$R^2$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(O)N(R^3)_2$, $C(O)C(R^3)_3$, C(O)OH, $C(O)OC(R^3)_3$, wherein $R^1$ and $R^2$ together with the atoms to which they are attached optionally form an form an aryl, cycloalkyl, heteroaryl, or heterocycloalkyl ring, which may be optionally substituted with between 0 and 3 $R^z$ groups;
each $R^3$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^3$ may be optionally substituted with between 0 and 3 $R^z$ groups, wherein two $R^3$ groups together with the atoms to which they are attached optionally form an aryl, cycloalkyl, heteroaryl, or heterocycloalkyl ring, which may be optionally substituted with between 0 and 3 $R^z$ groups;
$R^4$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $N(R^3)_2$, $NR^3C(O)C(R^3)_3$, $NR^3C(O)OC(R^3)_3$, $NR^3C(O)N(R^3)_2$, $NR^3S(O)C(R^3)_3$, $NR^3S(O)_2C(R^3)_3$, $C(O)N(R^3)_2$, $S(O)N(R^3)_2$, $S(O)_2N(R^3)_2$, $C(O)C(R^3)_3$, $SC(R^3)_3$, $S(O)C(R^3)_3$, and $S(O)_2C(R^3)_3$, wherein $R^4$ may be optionally substituted with between 0 and 3 $R^z$ groups;
each $R^z$ group is independently chosen from alkenyl, alkoxy, alkyl, aryl, arylalkyl, cyano, cycloalkyl, cycloalkylalkyl, halo, haloalkyl, heteroaryl, heteroarylalkyl, heterocycloalkyl, heterocycloalkylalkyl, hydroxyl, oxo, $N(R^6)_2$, $NR^6C(O)C(R^6)_3$, $NR^6C(O)OC(R^6)_3$, $NR^6C(O)N(R^6)_2$, $NR^6S(O)C(R^6)_3$, $NR^6S(O)_2C(R^6)_3$, $C(O)N(R^6)_2$, $S(O)N(R^6)_2$, $S(O)_2N(R^6)_2$, $C(O)C(R^6)_3$, $SC(R^6)_3$, $S(O)C(R^6)_3$, and $S(O)_2C(R^6)_3$;
each $R^6$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein two $R^6$ groups together with the atoms to which they are attached optionally form an aryl, cycloalkyl, heteroaryl, or heterocycloalkyl ring, which may be optionally substituted with between 0 and 3 $R^x$ groups; and
Z is heteroaryl, which may be optionally substituted.

Embodiment 81

The method of Embodiment 80, wherein:
Z is $$\text{(ring with } Z^1, Z^2, Z^3, Z^4 \text{ and } R^4\text{)}$$

$Z^1$ is chosen from C and N; and
$Z^2$, $Z^3$, and $Z^4$ are independently chosen from N, O, S, and CH, wherein at least one of $Z^1$, $Z^2$, $Z^3$, and $Z^4$ is chosen from N, O, and S.

Embodiment 82

The method of Embodiment 80, wherein:
Z is $$\text{(ring with } Z^1, Z^2, Z^3, Z^4, R^4 \text{ and } R^5\text{)}$$

$Z^1$ is chosen from C and N;
$Z^2$ is chosen from N, CH, and C(O);
$Z^3$, and $Z^4$ are independently chosen from N and CH, wherein at least one of $Z^1$, $Z^2$, $Z^3$, and $Z^4$ is N; and
$R^5$ is chosen from alkyl, heterocycloalkyl, cyano, cycloalkyl, H, halo, and haloalkyl, wherein $R^4$ and $R^5$ together with the atoms to which they are attached optionally form an aryl, cycloalkyl, heteroaryl, or heterocycloalkyl ring, which may be optionally substituted with between 0 and 3 $R^z$ groups.

Embodiment 83

The method of Embodiment 48, wherein said one or more glutathione lowering agents comprises a compound of Formula III:

(III)

$$\text{(structure with } R^1, R^2, N, O, A^1, A^2, A^3, A^4, [CR^xR^y]_n, Z, R^3\text{)}$$

or a salt thereof, wherein:
n is chosen from 3, 4, and 5;
each $R^X$ and $R^Y$ is independently chosen from alkyl, cyano, H, and halo, or two $R^X$ groups together with the atoms to which they are attached optionally form a cycloalkyl ring;
$A^1$ is chosen from C and N;
$A^2$, $A^3$, and $A^4$ are independently chosen from N, O, S, and CH, wherein at least one of $A^1$, $A^2$, $A^3$, and $A^4$ is chosen from N, O, and S;

$R^1$ and $R^2$ are each independently chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ and $R^2$ each may be optionally substituted with one to three $R^Z$ groups, wherein $R^1$ and $R^2$ together with the atoms to which they are attached optionally form an heteroaryl, or heterocycloalkyl ring, which may be optionally substituted with one to three $R^Z$ groups;

$R^3$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^4)_2C(O)R^4$, $C(R^4)_2C(O)N(R^4)_2$, $C(R^4)_2$ $N(R^4)_2$, $C(R^4)_2NR^4C(O)R^4$, $C(R^4)_2NR^4C(O)OR^4$, $C(R^4)_2NR^4C(O)N(R^4)_2$, $C(R^4)_2NR^4S(O)R^4$, $C(R^4)_2NR^4S(O)_2R^4$, $N(R^4)_2$, $NR^4C(O)R^4$, $NR^4C(O)OR^4$, $NR^4C(O)N(R^4)_2$, $NR^4S(O)R^4$, $NR^4S(O)_2R^4$, $C(O)N(R^4)_2$, $S(O)N(R^4)_2$, $S(O)_2N(R^4)_2$, $C(O)R^4$, $SR^4$, $S(O)R^4$, and $S(O)_2R^4$;

wherein each $R^3$ may be optionally substituted with one to three $R^Z$ groups;

each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^4$ may be optionally substituted with one to three $R^Z$ groups, wherein two $R^4$ groups together with the atoms to which they are attached optionally form an heteroaryl, or heterocycloalkyl ring, which may be optionally substituted with one to three $R^Z$ groups;

each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$;

each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups; and Z is a monocyclic heteroaryl, which may be optionally substituted.

Embodiment 84

The method of Embodiment 83, wherein:
Z is

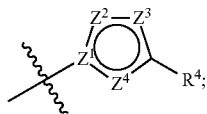

$Z^1$ is chosen from C and N; and
$Z^2$, $Z^3$, and $Z^4$ are independently chosen from N, O, S, and CH, wherein at least one of $Z^1$, $Z^2$, $Z^3$, and $Z^4$ is chosen from N, O, and S.

Embodiment 85

The method of Embodiment 83, wherein:
Z is

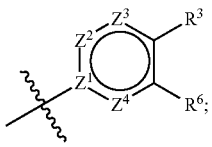

$Z^1$ is C;
$Z^2$ is chosen from N and CH;
$Z^3$, and $Z^4$ are independently chosen from N and CH, wherein at least one of $Z^1$, $Z^2$, $Z^3$, and $Z^4$ is N; and
$R^6$ is chosen from, alkyl, cyano, cycloalkyl, H, halo, haloalkyl, and heterocycloalkyl, wherein $R^3$ and $R^6$ groups together with the atoms to which they are attached optionally form an aryl, cycloalkyl, heteroaryl, or heterocycloalkyl ring, which may be optionally substituted with one to three $R^Z$ groups.

Embodiment 86

The method of Embodiment 48, wherein said one or more glutathione lowering agents comprises a compound of Formula IIIc:

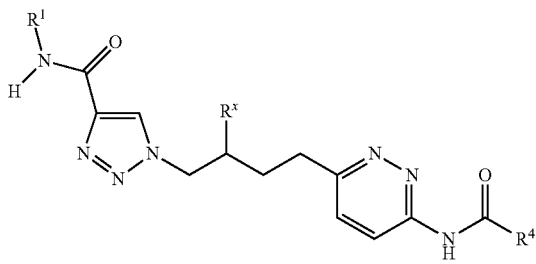

or a salt thereof, wherein:
$R^x$ is chosen from fluoro and H;
$R^1$ is chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ may be optionally substituted with one to three $R^Z$ groups;
each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein $R^4$ may be optionally substituted with one to three $R^Z$ groups;
each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; and
each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups.

Embodiment 87

The method of Embodiment 86, wherein $R^1$ is methyl.

Embodiment 88

The method of Embodiment 48, wherein said one or more glutathione lowering agents comprises a compound of Formula IIIc-1:

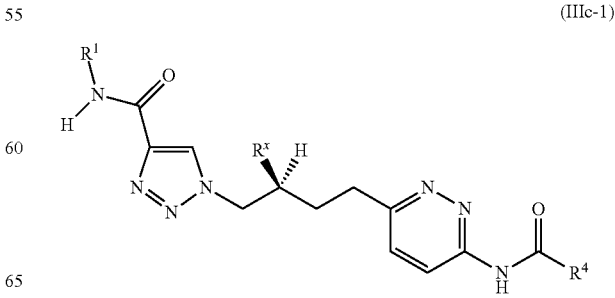

or a salt thereof, wherein:

$R^X$ is chosen from fluoro and H;

$R^1$ is chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ may be optionally substituted with one to three $R^Z$ groups;

each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein $R^4$ may be optionally substituted with one to three $R^Z$ groups;

each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; and each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups.

Embodiment 89

The method of Embodiment 48, wherein said one or more glutathione lowering agents comprises a compound of Formula IIIc-2:

(IIIc-2)

or a salt thereof, wherein:

$R^X$ is chosen from fluoro and H;

$R^1$ is chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ may be optionally substituted with one to three $R^Z$ groups;

each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein $R^4$ may be optionally substituted with one to three $R^Z$ groups;

each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; and each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups.

Embodiment 90

The method of Embodiment 48, wherein said one or more glutathione lowering agents comprises a compound of Formula IIId:

(IIId)

or a salt thereof, wherein:

R$^X$ is chosen from fluoro and H;

each of R$^{Z1}$ and R$^{Z2}$ is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, and oxo.

Embodiment 91

The method of Embodiment 90, wherein:

R$^X$ is chosen from fluoro and H; and each of R$^{Z1}$ and R$^{Z2}$ is independently chosen from alkyl, cycloalkyl, cycloalkylhaloalkyl, cycloalkyloxy, H, haloalkoxy, haloalkoxyaryl, haloalkyl, halocycloalkyloxy, heterocycloalkyl, and heterocycloalkyloxy.

Embodiment 92

The method of Embodiment 90, wherein:

R$^X$ is chosen from fluoro and H; and each of R$^{Z1}$ and R$^{Z2}$ is independently chosen from H,

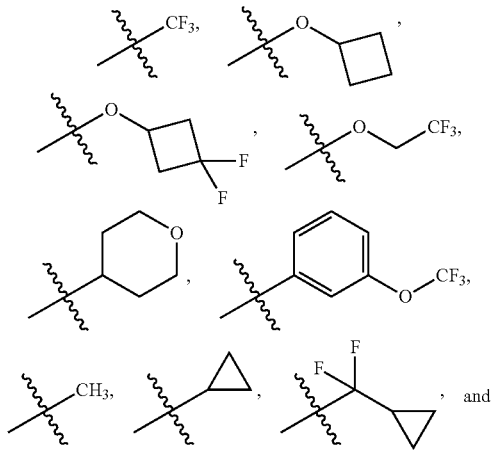

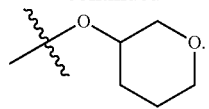

Embodiment 93

The method of Embodiment 48, wherein said one or more glutathione lowering agents comprises a compound of Formula IIIe:

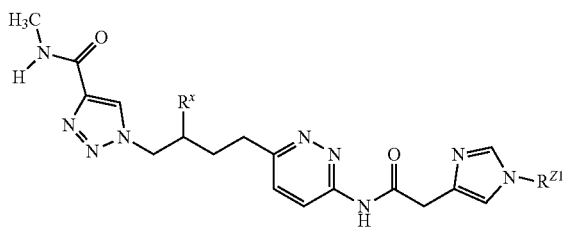

(IIIe)

or a salt thereof, wherein:

R$^X$ is chosen from fluoro and H;

R$^{Z1}$ is chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, and oxo.

Embodiment 94

The method of any one of Embodiments 48-50 and 52-93, wherein said one or more glutathione lowering agents comprises exactly one GLS-1 inhibitor.

Provided below are exemplary embodiments of the disclosure.

Embodiment M-1

A method of treating cancer in a subject whose cancer cells express low levels of asparagine synthetase (ASNS), as

Embodiment M-1 defined by an Histophathology Score (H-score) of less than or equal to 100 by immunohistochemical staining, comprising administering a glutaminase-1 (GLS-1) inhibitor to said subject.

Embodiment M-2

A method of treating a subject having a cancer or a tumor in need of treatment comprising:
(a) determining the concentration or expression of ASNS in said cancer or tumor of said subject; and
(b) administering a glutaminase-1 (GLS-1) inhibitor to said subject if the level of ASNS is quantified as an H-score of less than or equal to 100 by immunohistochemical staining.

Embodiment M-3

The method of Embodiment M-2, wherein the tumor is cancerous.

Embodiment M-4

The method of Embodiment M-1 or Embodiment M-3, wherein the cancer is: bladder cancer, bone marrow cancer, breast cancer, cancer of the central nervous system, cervical cancer, colon cancer, endometrial cancer, cancer of the gastric system, head and neck cancer, kidney cancer, leukemia, liver cancer, lung cancer, lymphoma, muscle cancer, ovarian cancer, pancreatic cancer, prostate cancer, skin cancer, thyroid cancer, or a variant thereof.

Embodiment M-5

The method of Embodiment M-4, wherein the cancer is ovarian, skin, liver, prostate, breast, colon, lung, head and neck cancers or a lymphoma.

Embodiment M-6

The method of Embodiment M-4, wherein the cancer is ovarian cancer.

Embodiment M-7

The method of Embodiment M-6, wherein the ovarian cancer is high-grade serous ovarian cancer (HGSOC).

Embodiment M-8

The method of Embodiment M-7, wherein the ovarian cancer is nonresectable or relapsed HGSOC.

Embodiment M-9

The method of Embodiment M-1 or Embodiment M-2, wherein the GLS-1 inhibitor is a selective inhibitor of GLS-1.

Embodiment M-10

The method of Embodiment M-1 or Embodiment M-2, wherein the GLS-1 inhibitor binds an allosteric pocket on the solvent exposed region of the GLS-1 dimer in the binding pocket present in the vicinity of Leu321, Phe322, Leu323, and Tyr394 from both monomers.

Embodiment M-11

The method of Embodiment M-1 or Embodiment M-2, wherein the GLS-1 inhibitor is selected from the list of compounds provided in Table 1.

Embodiment M-12

The method of Embodiment M-1 or Embodiment M-2, wherein the GLS-1 inhibitor is compound 1 or compound 2.

Embodiment M-13

The method of claim Embodiment M-1 or Embodiment M-2, wherein the subject is human.

Embodiment M-14

The method of claim Embodiment M-1 or Embodiment M-3, further comprising administering another pharmaceutically active compound.

Embodiment M-15

The method of claim Embodiment M-14, wherein the other pharmaceutically active compound is an anti-cancer agent.

Embodiment M-16

The method of claim Embodiment M-15, wherein the anti-cancer agent is chosen from a platinum-based agent, a taxane-based agent, an immunotherapy, an immuno-oncotherapy, and a targeted therapy.

Embodiment M-17

The method of claim Embodiment M-15, wherein the targeted therapy is an inhibitor of MEK kinase, HSP90, CDK4, or the mTOR pathway.

Embodiment M-18

The method of claim Embodiment M-1 or Embodiment M-3, wherein the method further comprises administering non-chemical methods of cancer treatment.

Embodiment M-19

The method of Embodiment M-18, wherein the method further comprises administering radiation therapy.

Embodiment M-20

The method of Embodiment M-18, wherein the method further comprises administering surgery, thermoablation, focused ultrasound therapy, cryotherapy, or any combination thereof.

Also provided herein is a GLS-1 inhibitor or a compound that inhibits glutathione production for use as a medicament in the treatment of a disorder, for example, a tumor or cancer, in need of treatment, in a subject in whose tumors or cancer cells the concentration or expression level of ASNS is low. In one embodiment, the tumor is cancerous and the concentration or expression level of ASNS in the tumor of the subject is low.

The cancer may be any one of the types of cancers provided below. In one embodiment, the cancer is ovarian, skin, liver, prostate, breast, colon, lung, head and neck cancers or a lymphoma. In another embodiment, the cancer is ovarian cancer, for example HGSOC, Epithelial, Germ Cell Tumor, and Low Malignant Potential Tumor.

Also provided herein is a GLS-1 inhibitor or a compound that inhibits glutathione production for treatment of a disorder in need of treatment, in a subject in whose tumor or cancer cells the concentration or expression level of ASNS is low.

Also provided herein is a GLS-1 inhibitor or a compound that inhibits glutathione production for use in the manufacture of a medicament for the treatment of a disorder in need of treatment, in a subject in whose tumor or cancer cells the concentration or expression level of ASNS is low.

In certain embodiments, the disorder is a cancer. The cancer may be any cancer now known, or later discovered, including, but not limited to, Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma), Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, Low Malignant Potential Tumor and High Grade Serous Ovarian Cancer), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia and Wilms Tumor, or a variant thereof.

In certain embodiments, the cancer is ovarian, skin, liver, prostate, breast, colon, lung, head and neck cancers, a lymphoma, or a variant thereof.

In certain embodiments, the cancer is ovarian cancer.

In certain embodiments, the cancer is high-grade serous ovarian cancer (HGSOC).

In certain embodiments, the cancer is nonresectable or relapsed HGSOC.

In some embodiments of the invention, the invention comprises a method of treating a tumor or a cancer in a subject whose tumor or cancer cells express low levels of ASNS comprising administering a glutaminase inhibitor to said subject. In one embodiment, the level of ASNS as measured by immunohistochemistry is quantified with an H-score of less than or equal to 100. The cancer may be any of the cancers listed above. In one embodiment, the cancer is ovarian, skin, liver, prostate, breast, colon, lung, head and neck cancers or a lymphoma. In another embodiment, the cancer is ovarian cancer, for example, high-grade serous ovarian cancer (HGSOC). In yet another embodiment, the cancer is nonresectable or relapsed HGSOC.

As provided above, the inventors have discovered that cells, for example, cancer or tumor cells, that express high levels of ASNS are resistant to inhibition of GLS-1. Inhibition of GLS-1 reduces the steady state levels of glutathione, thus shifting the redox balance of the cells. This inhibits cell growth through a mechanism that involves reactive oxygen species (ROS)-induced DNA damage. Asparagine synthetase or ASNS or aspartate-ammonia ligase is a chiefly cytoplasmic enzyme that generates asparagine from aspartate, while converting glutamine to glutamate. Attempts to reduce cellular levels of glutamate (and ultimately glutathione) by GLS-1 inhibitors would have little, or no, overall effect if the reduction is countered through the activity of ASNS, and ASNS-derived glutamate to produce glutathione.

In order for cells, such as cancer or tumor cells, to respond to treatment with a GLS-1 inhibitor (GLS1i), the levels of ASNS must be below certain levels. In one embodiment, the level of ASNS is quantified by immunohistochemistry and calculated as an H-score. An H-score of 0-100 (inclusive) or less than or equal to 100 would indicate response to GLS inhibition.

Calculation of a Histophathology Score or H-score is known to one of skill in the art. In one embodiment, expression of ASNS protein in tumor cells is detected or measured, for example, using microscopy and immunohistochemistry (IHC) and the H-score is determined therefrom. Based on the intensity of staining, the sample is, for example, scored at 4 different levels, on a scale of 0 to 3+, for ASNS protein expression.

As used herein the term "H-score" is used to mean an immunohistology score for ASNS expression in a tumor sample. In an attempt to accurately describe the extent of immunohistochemical staining of a tumor, the degree of IHC staining, if any, in each sub-cellular compartment in tumor cells is captured for ASNS. As further described below, the degree or intensity of staining is classified into 4 levels that are assigned a score from 0 (no staining) to 3+(greatest degree or most intense staining).

This algorithm includes capturing the percentage of tumor cells stained at each intensity level. A semi-quantitative intensity scale ranging from 0 for no staining, to 3+ for the most intense staining, is used. All of this information is used to calculate the H-Score. This score is more representative of the staining of the entire tumor on the section. Although given sections may share the same simple intensity score, there is a difference between a 3+ case with only 10% of the cells staining as compared to a 3+ case where greater than 90% of the cells are staining. This difference is easily picked up using the H-Score method. An H-Score is typically calculated for staining of each sub-cellular compartment for both normal and tumor cells using the following formula; H-Score=(% cells at 0)*0+(% cells at 1+)*1+(% cells at 2+)*2+.(% cells at 3+)*3. Thus, this score produces a continuous variable that ranges from 0 to 300. An H-score of 0-100 would be considered 1+, an H-score of 101-200 would be scored 2+, and an H-score of 201-300 scored 3+.

In some embodiments, the tumor or cancer express low levels of ASNS, as determined by the H-score. In one embodiment, the H-score is 0-150 (both inclusive). In another embodiment, the H-score is less than or equal to 150. In another embodiment, the H-score is 0-125 (both inclusive). In another embodiment, the H-score is less than or equal to 125. In some embodiments, the H-score is 0-100 (both inclusive). In some embodiments, the H-score is less than or equal to 100. In some embodiments, the H-score is less than 100.

In some embodiments, the H-score is less than or equal to 95. In some embodiments, the H-score is less than or equal to 90. In some embodiments, the H-score is less than or equal to 85. In some embodiments, the H-score is less than or equal to 80. In some embodiments, the H-score is less than or equal to 75. In some embodiments, the H score is less than or equal to 70. In some embodiments, the H-score is less than or equal to 65. In some embodiments, the H-score is less than or equal to 60. In some embodiments, the H-score is less than or equal to 55. In some embodiments, the H-score is less than or equal to 50. In some embodiments, the H-score is less than or equal to 45. In some embodiments, the H-score is less than or equal to 40. In some embodiments, the H-score is less than or equal to 35. In some embodiments, the H-score is less than or equal to 30. In some embodiments, the H-score is less than or equal to 25. In some embodiments, the H-score is less than or equal to 20. In some embodiments, the H-score is less than or equal to 15. In some embodiments, the H-score is less than or equal to 10.

In certain embodiments, the GLS1i is a selective inhibitor of GLS-1.

In certain embodiments, the GLS1i binds an allosteric pocket on the solvent exposed region of the GLS-1 dimer in the binding pocket present in the vicinity of Leu321, Phe322, Leu323, and Tyr394 from both monomers.

In certain embodiments, the GLS1i is compound 1. In certain embodiments, the GLS1i is compound 2. In certain embodiments, the GLS-1 inhibitor is selected from the list of compounds provided in Table 1 below. In certain embodiments, the compound is chosen from any combination of the compounds provided in Table 1, or a salt or polymorph thereof. For example, in certain embodiments, the GLS1i is chosen from any two, three, four, five, six, seven, eight, none or ten of the compounds provided in Table 1, or a salt or polymorph thereof.

In certain embodiments, the subject is human.

In certain embodiments, methods disclosed herein further comprise administering another pharmaceutically active compound. In certain embodiments, the disorder to be treated is a cancer and the other pharmaceutically active compound is an anti-cancer agent. In certain embodiments, the anti-cancer agent is a chosen from a platinum-based agent, a taxane-based agent, an immunotherapy, an immune-oa targeted therapy. In certain embodiments, the targeted therapy is an inhibitor of MEK kinase, HSP90, CDK4, or the mTOR pathway.

In certain embodiments, methods disclosed herein further comprise administering non-chemical methods of cancer treatment. In certain embodiments, the method further comprises administering radiation therapy. In certain embodiments, the method further comprises administering surgery, thermoablation, focused ultrasound therapy, cryotherapy, or any combination thereof.

In certain embodiments, methods disclosed herein administer the active agent (e.g., a compound that inhibits glutathione production, glutaminase-1 inhibitor, or selective GLS1i) as a pharmaceutical composition comprising a pharmaceutically acceptable excipient or carrier. In certain embodiments, the pharmaceutical composition is formulated for oral administration. In certain embodiments, pharmaceutical composition is formulated as a tablet or capsule. In certain embodiments, the pharmaceutical composition is formulated for parenteral administration.

Also provided are embodiments wherein any embodiment disclosed herein, may be combined with any one or more of these embodiments to form a new compound or class of compounds, or pharmaceutical composition comprising it, or method of use employing it, provided the combination is not mutually exclusive. For example, a combination embodiment wherein the subject is human and the disorder in need of treatment is cancer is valid because the recited limitations are not mutually exclusive.

Abbreviations and Definitions

To facilitate understanding of the disclosure, a number of terms and abbreviations as used herein are defined below as follows:

When introducing elements of the present disclosure or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e., A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein in relation to a numerical value x means x±10%.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The terms "GLS-1 inhibitor" and "GLS1i" are used interchangeably herein to refer to a compound that exhibits an $IC_{50}$ with respect to GLS-1 activity of no more than about 100 µM and more typically not more than about 50 µM, as measured in the GLS-1 enzyme assay described generally herein below. $IC_{50}$ is that concentration of inhibitor that reduces the activity of an enzyme (e.g., GLS-1) to half-maximal level. Certain compounds disclosed herein have been discovered to exhibit inhibition against GLS-1. In certain embodiments, compounds will exhibit an $IC_{50}$ with respect to GLS-1 of no more than about 10 µM; in further embodiments, compounds will exhibit an $IC_{50}$ with respect to GLS-1 of no more than about 5 µM; in yet further embodiments, compounds will exhibit an $IC_{50}$ with respect to GLS-1 of not more than about 1 µM; in yet further embodiments, compounds will exhibit an $IC_{50}$ with respect to GLS-1 of not more than about 200 nM, as measured in the GLS-1 enzymatic assay described herein.

The terms "inhibitor selective for GLS-1" and a "selective inhibitor of GLS-1" are used interchangeably herein and refer to inhibitors that are about 100 times more selective for GLS-1 than for GLS-2 as measured in any assay known to one of skill in the art that measures the activity of the enzyme. An example of such an assay includes, but is not limited to, the GLS-1 enzyme assay (GLS-1 Enzymatic Activity Assay) described below.

The term "glutathione lowering agent" is used herein to refer to a compound that reduces glutathione levels. In certain embodiments, the glutathione lowering agent inhibits amino acid or glutathione transport. In certain embodiments, the glutathione lowering agent inhibits amino acid or glutathione activity. In certain embodiments, the compound is a glutaminase inhibitor. In certain embodiments, the glutathione lowering agent is a GLS-1 inhibitor.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prevention, prophylaxis, attenuation, amelioration and therapy. Treatment may also include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The terms "subject" and "patient" are used interchangeably herein to mean all mammals including humans. Examples of subjects include, but are not limited to, humans, monkeys, dogs, cats, horses, cows, goats, sheep, pigs, and rabbits. In one embodiment, the patient is a human.

The terms "affected with a disease or disorder," "afflicted with a disease or disorder," and "having a disease or disorder" are used interchangeably herein and refer to a subject or patient with any disease, disorder, syndrome or condition. No increased or decreased level of severity of the disorder is implied by the use of one the terms as compared to the other.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl will comprise from 1 to 10 carbon atoms. In further embodiments, the alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH2-). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl" as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term "aryloxy" as used herein, alone or in combination, refers to an aryl group attached to the parent molecular moiety through an oxy.

The terms "benzo" and "benz," as used herein, alone or in combination, refer to the divalent radical C6H4=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF2-), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each the heteroatom may be independently selected from the group consisting of nitrogen, oxygen, and sulfur In certain embodiments, the hetercycloalkyl will comprise from 1 to 4 heteroatoms as ring members. In further embodiments, the hetercycloalkyl will comprise from 1 to 2 heteroatoms as ring members. In certain embodiments, the hetercycloalkyl will comprise from 3 to 8 ring members in each ring. In further embodiments, the hetercycloalkyl will comprise from 3 to 7 ring members in each ring. In yet further embodiments, the hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS-group, where R is as defined herein.

The term "nitro," as used herein, alone or in combination, refers to —NO2.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO3H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)2—.

The term "N-sulfonamido" refers to a RS(=O)2NR'— group with R and R' as defined herein.

The term "S-sulfonamido" refers to a —S(=O)2NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X3CS(O)2NR— group with X is a halogen and R as defined herein.

The term "trihalomethanesulfonyl" refers to a X3C-S(O)2— group where X is a halogen.

The term "trihalomethoxy" refers to a X3CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N3, SH, SCH₃, C(O)CH₃, CO₂CH₃, CO₂H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH₂CH₃), fully substituted (e.g., —CF₂CF₃), monosubstituted (e.g., —CH₂CH₂F) or substituted at a level anywhere in-between fully substituted and monosubstituted (e.g., —CH₂CF₃). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered part of larger substructure. A bond may be single, double, or triple unless otherwise specified. A dashed line between two atoms in a drawing of a molecule indicates that an additional bond may be present or absent at that position.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

Compounds

Examples of compounds useful in the methods of the invention are provided herein. In one embodiment, the compound is a compound that inhibits glutathione production or activity. In certain embodiments, the compound inhibits amino acid or glutathione transport. In some embodiments, the compound is a glutaminase inhibitor.

In certain embodiments, the compound is a GLS-1 inhibitor, for example, a selective inhibitor of GLS-1. It is known that GLS-1 forms a tetramer (PNAS 2012, 109, 7705). In certain embodiments, the GLS1i occupies an allosteric pocket on the solvent exposed region between two GLS-1 dimers. The GLS1i may, for example, bind GLS-1 in an allosteric pocket on the solvent exposed region of the GLS-1 dimer in the binding pocket present in the vicinity of amino acids Leu 321, Phe322, Leu323, and Tyr394 from both monomers. Without being bound by any theory, the inventors propose that key interactions are made within a hydrophobic cluster that comprises Leu321, Phe322, Leu323, and Tyr394 from both monomers which forms the allosteric pocket. Binding of the glutaminase inhibitor, for example, a GLS1i, induces a dramatic conformational change near the catalytic site rendering the enzyme inactive.

Compounds which inhibit GLS-1 are known in the art and disclosed herein. In certain embodiments, the compound is compound 1,

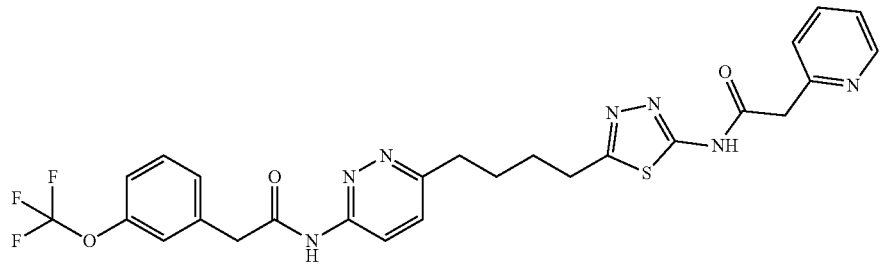 [SMILES: O=C(Cc1cccc(OC(F)(F)F)c1)Nc1ccc(CCCCc2nnc(NC(=O)Cc3ccccn3)s2)nn1]

also known as 2-(pyridin-2-yl)-N-{5-[4-(6-{2-[3-(trifluoromethoxy)phenyl]acetamido}pyridazin-3-yl)butyl]-1,3,4-thiadiazol-2-yl}acetamide (CB-839).

In certain embodiments, the compound is compound 2,

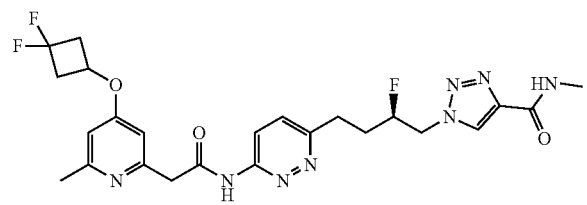 [SMILES: CNC(=O)c1cn(C[C@H](F)CCc2ccc(NC(=O)Cc3cc(OC4CC(F)(F)C4)cc(C)n3)nn2)nn1]

also known as (R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide.

In certain embodiments, the compound (and its molecular mass) is provided in Table 1 below, or a salt or polymorph thereof. In certain embodiments, the compound is chosen from any combination of the compounds provided in Table 1 below, or a salt or polymorph thereof. For example, in certain embodiments, the compound is chosen from any two, three, four, five, six, seven, eight, nine or ten of the compounds provided in Table 1 below, or a salt or polymorph thereof.

TABLE 1

| Compound | MS |
|---|---|
| (S)-2-hydroxy-2-phenyl-N-(5-(4-(6-(2-(3-(trifluoromethoxy)phenyl)acetamido)pyridazin-3-yl)butyl)-1,3,4-thiadiazol-2-yl)acetamide | 586 |
| N,N'-(5,5'-(2,2'-thiobis(ethane-2,1-diyl))bis(1,3,4-thiadiazole-5,2-diyl))bis(2-phenylacetamide), also known as BPTES | 524 |
| 2-(pyridin-2-yl)-N-{5-[4-(6-{2-[3-(trifluoromethoxy)phenyl]acetamido}pyridazin-3-yl)butyl]-1,3,4-thiadiazol-2-yl}acetamide, also known as CB-839 | 587 |
| N,N'-(5,5'-(2,2'-sulfonylbis(ethane-2,1-diyl))bis(1,3,4-thiadiazole-5,2-diyl))bis(2-(pyridin-2-yl)acetamide) | 558 |
| N-methyl-1-{4-[6-(2-{4-[3-(trifluoromethoxy)phenyl]pyridin-2-yl}acetamido)pyridazin-3-yl]butyl}-1H-1,2,3-triazole-4-carboxamide | 554 |
| 1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide | 563 |
| 1-(2-fluoro-4-(6-(2-(4-(trifluoromethyl)pyridin-2-yl)acetamido)pyridazin-3-yl)butyl)-N-methyl-1H-1,2,3-triazole-4-carboxamide | 480 |
| N-(pyridin-2-ylmethyl)-5-(3-(6-(2-(3-(trifluoromethoxy)phenyl)acetamido)pyridazin-3-yl)pyrrolidin-1-yl)-1,3,4-thiadiazole-2-carboxamide | 584 |
| (R)-1-(2-fluoro-4-(6-(2-(4-(3-(trifluoromethoxy)phenyl)pyridin-2-yl)acetamido)pyridazin-3-yl)butyl)-N-methyl-1H-1,2,3-triazole-4-carboxamide | 572 |
| (R)-1-(2-fluoro-4-(6-(2-(4-(trifluoromethyl)pyridin-2-yl)acetamido)pyridazin-3-yl)butyl)-N-methyl-1H-1,2,3-triazole-4-carboxamide | 480 |

TABLE 1-continued

| Compound | MS |
|---|---|
| (R)-1-(2-fluoro-4-(6-(2-(6-methyl-4-(trifluoromethyl)pyridin-2-yl)acetamido)pyridazin-3-yl)butyl)-N-methyl-1H-1,2,3-triazole-4-carboxamide | 494 |
| (R)-1-(4-(6-(2-(4-(cyclopropyldifluoromethyl)pyridin-2-yl)acetamido)pyridazin-3-yl)-2-fluorobutyl)-N-methyl-1H-1,2,3-triazole-4-carboxamide | 502 |
| (R)-1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide | 518 |
| (R)-1-(2-fluoro-4-(6-(2-(1-(3-(trifluoromethoxy)phenyl)-1H-imidazol-4-yl)acetamido)pyridazin-3-yl)butyl)-N-methyl-1H-1,2,3-triazole-4-carboxamide | 561 |
| 1-(4-(6-(2-(4-cyclobutoxypyridin-2-yl)acetamido)pyridazin-3-yl)butyl)-N-methyl-1H-1,2,3-triazole-4-carboxamide | 464 |
| 1-(4-(6-(2-(4-cyclobutoxypyridin-2-yl)acetamido)pyridazin-3-yl)-2-fluorobutyl)-N-methyl-1H-1,2,3-triazole-4-carboxamide | 482 |

TABLE 1-continued

| Compound | MS |
|---|---|
| 1-(4-(6-(2-(4-(3,3-difluorocyclobutoxy)pyridin-2-yl)acetamido)pyridazin-3-yl)butyl)-N-methyl-1H-1,2,3-triazole-4-carboxamide | 500 |
| 1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide | 518 |
| (R)-1-(4-(6-(2-(4-cyclopropylpyridin-2-yl)acetamido)pyridazin-3-yl)-2-fluorobutyl)-N-methyl-1H-1,2,3-triazole-4-carboxamide | 452 |
| 5-(3-(6-(2-(pyridin-2-yl)acetamido)pyridazin-3-yl)pyrrolidin-1-yl)-N-((4-(trifluoromethyl)pyridin-2-yl)methyl)-1,3,4-thiadiazole-2-carboxamide | 569 |
| N,N'-(5,5'-(cyclohexane-1,3-diyl)bis(1,3,4-thiadiazole-5,2-diyl))bis(2-phenylacetamide) (both or either of 1S,3S and 1R,2R enantiomers) | 518 |

In certain embodiments, the compound is (S)-2-hydroxy-2-phenyl-N-(5-(4-(6-(2-(3-(trifluoromethoxy)phenyl)acetamido)pyridazin-3-yl)butyl)-1,3,4-thiadiazol-2-yl)acetamide, or a salt or polymorph thereof. In certain embodiments, the compound is N,N'-(5,5'-(2,2'-thiobis(ethane-2,1-diyl))bis(1,3,4-thiadiazole-5,2-diyl))bis(2-phenylacetamide), or a salt or polymorph thereof. In certain embodiments, the compound is (S)-2-hydroxy-2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide, or a salt or polymorph thereof. In certain embodiments, the compound is N,N'-(5,5'-(2,2'-sulfonylbis(ethane-2,1-diyl))bis(1,3,4-thiadiazole-5,2-diyl))bis(2-(pyridin-2-yl)acetamide), or a salt or polymorph thereof. In certain embodiments, the compound is N-methyl-1-{4-[6-(2-{4-[3-(trifluoromethoxy)phenyl]pyridin-2-yl}acetamido)pyridazin-3-yl]butyl}-1H-1,2,3-triazole-4-carboxamide, or a salt or polymorph thereof. In certain embodiments, the compound is 1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide, or a salt or polymorph thereof. In certain embodiments, the compound is 1-(2-fluoro-4-(6-(2-(4-(trifluoromethyl)pyridin-2-yl)acetamido)pyridazin-3-yl)butyl)-N-methyl-1H-1,2,3-triazole-4-carboxamide, or a salt or polymorph thereof. In certain embodiments, the compound is N-(pyridin-2-ylmethyl)-5-(3-(6-(2-(3-(trifluoromethoxy)phenyl)acetamido)pyridazin-3-yl)pyrrolidin-1-yl)-1,3,4-thiadiazole-2-carboxamide, or a salt or polymorph thereof. In certain embodiments, the compound is (R)-1-(2-fluoro-4-(6-(2-(4-(3-(trifluoromethoxy)phenyl)pyridin-2-yl)acetamido)pyridazin-3-yl)butyl)-N-methyl-1H-1,2,3-triazole-4-carboxamide, or a salt or polymorph thereof. In certain embodiments, the compound is (R)-1-(2-fluoro-4-(6-(2-(4-(trifluoromethyl)pyridin-2-yl)acetamido)pyridazin-3-yl)butyl)-N-methyl-1H-1,2,3-triazole-4-carboxamide, or a salt or polymorph thereof. In certain embodiments, the compound is (R)-1-(2-fluoro-4-(6-(2-(6-methyl-4-(trifluoromethyl)pyridin-2-yl)acetamido)pyridazin-3-yl)butyl)-N-methyl-1H-1,2,3-triazole-4-carboxamide, or a salt or polymorph thereof. In certain embodiments, the compound is (R)-1-(4-(6-(2-(4-(cyclopropyldifluoromethyl)pyridin-2-yl)acetamido)pyridazin-3-yl)-2-fluorobutyl)-N-methyl-1H-1,2,3-triazole-4-carboxamide, or a salt or polymorph thereof. In certain embodiments, the compound is (R)-1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide, or a salt or polymorph thereof. In certain embodiments, the compound is (R)-1-(2-fluoro-4-(6-(2-(1-(3-(trifluoromethoxy)phenyl)-1H-imidazol-4-yl)acetamido)pyridazin-3-yl)butyl)-N-methyl-1H-1,2,3-triazole-4-carboxamide, or a salt or polymorph thereof. In certain embodiments, the compound is 1-(4-(6-(2-(4-cyclobutoxypyridin-2-yl)acetamido)pyridazin-3-yl)butyl)-N-methyl-1H-1,2,3-triazole-4-carboxamide, or a salt or polymorph thereof. In certain embodiments, the compound is 1-(4-(6-(2-(4-cyclobutoxypyridin-2-yl)acetamido)pyridazin-3-yl)-2-fluorobutyl)-N-methyl-1H-1,2,3-triazole-4-carboxamide, or a salt or polymorph thereof. In certain embodiments, the compound is 1-(4-(6-(2-(4-(3,3-difluorocyclobutoxy)pyridin-2-yl)acetamido)pyridazin-3-yl)butyl)-N-methyl-1H-1,2,3-triazole-4-carboxamide, or a salt or polymorph thereof. In certain embodiments, the compound is 1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide, or a salt or polymorph thereof. In certain embodiments, the compound is (R)-1-(4-(6-(2-(4-cyclopropylpyridin-2-yl)acetamido)pyridazin-3-yl)-2-fluorobutyl)-N-methyl-1H-1,2,3-triazole-4-carboxamide, or a salt or polymorph thereof. In certain embodiments, the compound is 5-(3-(6-(2-(pyridin-2-yl)acetamido)pyridazin-3-yl)pyrrolidin-1-yl)-N-((4-(trifluoromethyl)pyridin-2-yl)methyl)-1,3,4-thiadiazole-2-carboxamide, or a salt or polymorph thereof. In certain embodiments, the compound is N,N'-(5,5'-(cyclohexane-1,3-diyl)bis(1,3,4-thiadiazole-5,2-diyl))bis(2-phenylacetamide), or a salt or polymorph thereof. In certain embodiments, the compound is N,N'-(5,5'-((1S,3S)-cyclohexane-1,3-diyl)bis(1,3,4-thiadiazole-5,2-diyl))bis(2-phenylacetamide), or a salt or polymorph thereof. In certain embodiments, the compound is N,N'-(5,5'-((1R,3R)-cyclohexane-1,3-diyl)bis(1,3,4-thiadiazole-5,2-diyl))bis(2-phenylacetamide), or a salt or polymorph thereof.

Additional non-limiting examples of compounds useful in the methods of the invention include the following compounds and pharmaceutically acceptable salts thereof.

In certain embodiments, the GLS1i is disclosed in United States Patent Application Publication No. US2016/0002204 published Jan. 7, 2016.

In certain embodiments, the GLS-1 inhibitor is of Formula I:

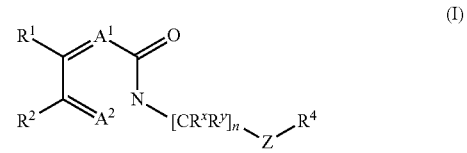

or a salt thereof, wherein:
n is chosen from 3, 4, and 5;
each $R^x$ and $R^y$ is independently chosen from alkyl, cyano, H, and halo, wherein two $R^x$ groups together with the atoms to which they are attached optionally form a cycloalkyl ring;
$A^1$ and $A^2$ are independently chosen from C—H, C—F, and N;
$R^1$ and $R^4$ are independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^3)_2C(O)R^3$, $C(R^3)_2C(O)N(R^3)_2$, $C(R^3)_2N(R^3)_2$, $C(R^3)_2NR^3C(O)R^3$, $C(R^3)_2NR^3C(O)OR^3$, $C(R^3)_2NR^3C(O)N(R^3)_2$, $C(R^3)_2NR^3S(O)R^3$, $C(R^3)_2NR^3S(O)_2R^3$, $N(R^3)_2$, $NR^3C(O)R^3$, $NR^3C(O)OR^3$, $NR^3C(O)N(R^3)_2$, $NR^3S(O)R^3$, $NR^3S(O)_2R^3$, $C(O)N(R^3)_2$, $S(O)N(R^3)_2$, $S(O)_2N(R^3)_2$, $C(O)R^3$, $SR^3$, $S(O)R^3$, and $S(O)_2R^3$, wherein each $R^1$ and $R^4$ may be optionally substituted with between 0 and 3 $R^z$ groups;

$R^2$ is chosen from alkyl, heterocycloalkyl, cyano, cycloalkyl, H, halo, and haloalkyl, wherein $R^1$ and $R^2$ together with the atoms to which they are attached optionally form an form an aryl, cycloalkyl, heteroaryl, or heterocycloalkyl ring, which may be optionally substituted with between 0 and 3 $R^z$ groups;

each $R^3$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^3$ may be optionally substituted with between 0 and 3 $R^z$ groups, wherein two $R^3$ groups together with the atoms to which they are attached optionally form an aryl, cycloalkyl, heteroaryl, or heterocycloalkyl ring, which may be optionally substituted with between 0 and 3 $R^z$ groups;

each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^6)_2$, $NR^6C(O)C(R^6)_3$, $NR^6C(O)OC(R^6)_3$, $NR^6C(O)N(R^6)_2$, $NR^6S(O)C(R^6)_3$, $NR^6S(O)_2C(R^6)_3$, $C(O)N(R^6)_2$, $S(O)N(R^6)_2$, $S(O)_2N(R^6)_2$, $C(O)C(R^6)_3$, $SC(R^6)_3$, $S(O)C(R^6)_3$, and $S(O)_2C(R^6)_3$;

each $R^6$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein two $R^6$ groups together with the atoms to which they are attached optionally form an aryl, cycloalkyl, heteroaryl, or heterocycloalkyl ring, which may be optionally substituted with between 0 and 3 $R^x$ groups; and Z is heteroaryl, which may be optionally substituted.

In certain embodiments, the GLS-1 inhibitor is of Formula Ia:

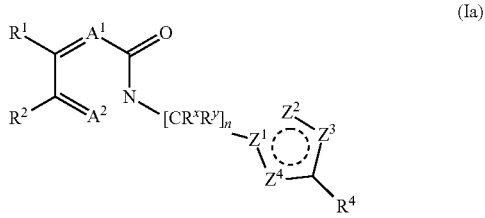

(Ia)

or a salt thereof, wherein:

n is chosen from 3, 4, and 5;

each $R^x$ and $R^y$ is independently chosen from alkyl, cyano, H, and halo, wherein two $R^x$ groups together with the atoms to which they are attached optionally form a cycloalkyl ring;

$A^1$ and $A^2$ are independently chosen from C—H, C—F, and N;

$Z^1$ is chosen from C and N;

$Z^2$, $Z^3$, and $Z^4$ are independently chosen from N, O, S, and CH, wherein at least one of $Z^1$, $Z^2$, $Z^3$, and $Z^4$ is chosen from N, O, and S;

$R^1$ and $R^4$ are independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^3)_2C(O)R^3$, $C(R^3)_2C(O)N(R^3)_2$, $C(R^3)_2N(R^3)_2$, $C(R^3)_2NR^3C(O)R^3$, $C(R^3)_2NR^3C(O)OR^3$, $C(R^3)_2NR^3C(O)N(R^3)_2$, $C(R^3)_2NR^3S(O)R^3$, $C(R^3)_2NR^3S(O)_2R^3$, $N(R^3)_2$, $NR^3C(O)R^3$, $NR^3C(O)OR^3$, $NR^3C(O)N(R^3)_2$, $NR^3S(O)R^3$, $NR^3S(O)_2R^3$, $C(O)N(R^3)_2$, $S(O)N(R^3)_2$, $S(O)_2N(R^3)_2$, $C(O)R^3$, $SR^3$, $S(O)R^3$, and $S(O)_2R^3$, wherein each $R^1$ and $R^4$ may be optionally substituted with between 0 and 3 $R^z$ groups;

$R^2$ is chosen from alkyl, heterocycloalkyl, cyano, cycloalkyl, H, halo, and haloalkyl, wherein $R^1$ and $R^2$ together with the atoms to which they are attached optionally form an form an aryl, cycloalkyl, heteroaryl, or heterocycloalkyl ring, which may be optionally substituted with between 0 and 3 $R^z$ groups;

each $R^3$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^3$ may be optionally substituted with between 0 and 3 $R^z$ groups, wherein two $R^3$ groups together with the atoms to which they are attached optionally form an aryl, cycloalkyl, heteroaryl, or heterocycloalkyl ring, which may be optionally substituted with between 0 and 3 $R^z$ groups;

each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^6)_2$, $NR^6C(O)C(R^6)_3$, $NR^6C(O)OC(R^6)_3$, $NR^6C(O)N$ $(R^6)_2$, $NR^6S(O)C(R^6)_3$, $NR^6S(O)_2C(R^6)_3$, $C(O)N(R^6)_2$, $S(O)N(R^6)_2$, $S(O)_2N(R^6)_2$, $C(O)C(R^6)_3$, $SC(R^6)_3$, $S(O)C(R^6)_3$, and $S(O)_2C(R^6)_3$; and each $R^6$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein two $R^6$ groups together with the atoms to which they are attached optionally form an aryl, cycloalkyl, heteroaryl, or heterocycloalkyl ring, which may be optionally substituted with between 0 and 3 $R^x$ groups.

In certain embodiments, the GLS-1 inhibitor is of Formula Ib:

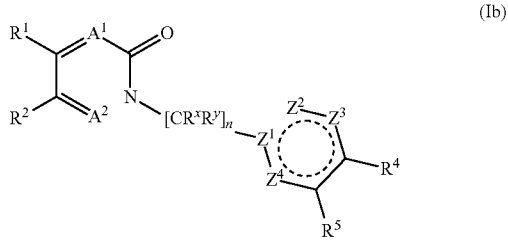

(Ib)

or a salt thereof, wherein:

n is chosen from 3, 4, and 5;

each $R^x$ and $R^y$ is independently chosen from alkyl, cyano, H, and halo, wherein two $R^x$ groups together with the atoms to which they are attached optionally form a cycloalkyl ring;

$A^1$ and $A^2$ are independently chosen from C—H, C—F, and N;

$Z^1$ is chosen from C and N;

$Z^2$ is chosen from N, CH, and C(O);

$Z^3$, and $Z^4$ are independently chosen from N and CH, wherein at least one of $Z^1$, $Z^2$, $Z^3$, and $Z^4$ is N;

$R^1$ and $R^4$ are independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^3)_2C(O)R^3$, $C(R^3)_2C(O)N(R^3)_2$, $C(R^3)_2N(R^3)_2$, $C(R^3)_2NR^3C(O)R^3$, $C(R^3)_2NR^3C(O)OR^3$, $C(R^3)_2NR^3C(O)N(R^3)_2$, $C(R^3)_2NR^3S(O)R^3$, $C(R^3)_2NR^3S(O)_2R^3$, $N(R^3)_2$, $NR^3C(O)R^3$, $NR^3C(O)OR^3$, $NR^3C(O)N(R^3)_2$, $NR^3S(O)R^3$, $NR^3S(O)_2R^3$, $C(O)N(R^3)_2$, $S(O)N(R^3)_2$, $S(O)_2N(R^3)_2$, $C(O)R^3$, $SR^3$, $S(O)R^3$, and $S(O)_2R^3$, wherein each $R^1$ and $R^4$ may be optionally substituted with between 0 and 3 $R^z$ groups;

$R^2$ and $R^5$ are chosen from alkyl, heterocycloalkyl, cyano, cycloalkyl, H, halo, and haloalkyl, wherein $R^1$ and $R^2$ together with the atoms to which they are attached optionally form an form an aryl, cycloalkyl, heteroaryl, or heterocycloalkyl ring, which may be optionally substituted with between 0 and 3 $R^z$ groups, wherein $R^4$ and $R^5$ together with the atoms to which they are attached optionally form an aryl, cycloalkyl, heteroaryl, or heterocycloalkyl ring, which may be optionally substituted with between 0 and 3 $R^z$ groups;

each $R^3$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^3$ may be optionally substituted with between 0 and 3 $R^z$ groups, wherein two $R^3$ groups together with the atoms to which they are attached optionally form an aryl, cycloalkyl, heteroaryl, or heterocycloalkyl ring, which may be optionally substituted with between 0 and 3 $R^z$ groups;

each $R^z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^6)_2$, $NR^6C(O)C(R^6)_3$, $NR^6C(O)OC(R^6)_3$, $NR^6C(O)N(R^6)_2$, $NR^6S(O)C(R^6)_3$, $NR^6S(O)_2C(R^6)_3$, $C(O)N(R^6)_2$, $S(O)N(R^6)_2$, $S(O)_2N(R^6)_2$, $C(O)C(R^6)_3$, $SC(R^6)_3$, $S(O)C(R^6)_3$, and $S(O)_2C(R^6)_3$; and each $R^6$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein two $R^6$ groups together with the atoms to which they are attached optionally form an aryl, cycloalkyl, heteroaryl, or heterocycloalkyl ring, which may be optionally substituted with between 0 and 3 $R^x$ groups.

In certain embodiments, the GLS1i is disclosed in United States Patent Application Publication No. US 2016/0002248, published Jan. 7, 2016.

In certain embodiments, the GLS-1 inhibitor is of Formula II:

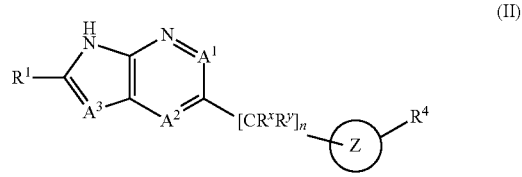

(II)

or a salt thereof, wherein:

n is chosen from 3, 4, and 5;

each $R^x$ and $R^y$ is independently chosen from alkyl, cyano, H, and halo, wherein two $R^x$ groups together with the atoms to which they are attached optionally form a cycloalkyl ring;

$A^1$ and $A^2$ are independently chosen from N and CH;

$A^3$ is chosen from N and $CR^2$;

$R^1$ is chosen from alkenyl, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, $C(O)N(R^3)_2$, and $C(O)C(R^3)_3$, wherein $R^1$ may be optionally substituted with between 0 and 3 $R^z$ groups;

R² is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, C(O)N(R³)₂, C(O)C(R³)₃, C(O)OH, C(O)OC(R³)₃, wherein R¹ and R² together with the atoms to which they are attached optionally form an form an aryl, cycloalkyl, heteroaryl, or heterocycloalkyl ring, which may be optionally substituted with between 0 and 3 R$^z$ groups;

each R³ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each R³ may be optionally substituted with between 0 and 3 R$^z$ groups, wherein two R³ groups together with the atoms to which they are attached optionally form an aryl, cycloalkyl, heteroaryl, or heterocycloalkyl ring, which may be optionally substituted with between 0 and 3 R$^z$ groups;

R⁴ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, N(R³)₂, NR³C(O)C(R³)₃, NR³C(O)OC(R³)₃, NR³C(O)N(R³)₂, NR³S(O)C(R³)₃, NR³S(O)₂C(R³)₃, C(O)N(R³)₂, S(O)N(R³)₂, S(O)₂N(R³)₂, C(O)C(R³)₃, SC(R³)₃, S(O)C(R³)₃, and S(O)₂C(R³)₃, wherein R⁴ may be optionally substituted with between 0 and 3 R$^z$ groups;

each R$^z$ group is independently chosen from alkenyl, alkoxy, alkyl, aryl, arylalkyl, cyano, cycloalkyl, cycloalkylalkyl, halo, haloalkyl, heteroaryl, heteroarylalkyl, heterocycloalkyl, heterocycloalkylalkyl, hydroxyl, oxo, N(R⁶)₂, NR⁶C(O)C(R⁶)₃, NR⁶C(O)OC(R⁶)₃, NR⁶C(O)N(R⁶)₂, NR⁶S(O)C(R⁶)₃, NR⁶S(O)₂C(R⁶)₃, C(O)N(R⁶)₂, S(O)N(R⁶)₂, S(O)₂N(R⁶)₂, C(O)C(R⁶)₃, SC(R⁶)₃, S(O)C(R⁶)₃, and S(O)₂C(R⁶)₃;

each R⁶ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein two R⁶ groups together with the atoms to which they are attached optionally form an aryl, cycloalkyl, heteroaryl, or heterocycloalkyl ring, which may be optionally substituted with between 0 and 3 R$^x$ groups; and Z is heteroaryl, which may be optionally substituted.

In certain embodiments, the GLS-1 inhibitor is of Formula IIa:

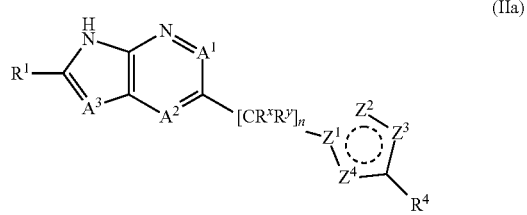

(IIa)

or a salt thereof, wherein:

n is chosen from 3, 4, and 5;

each R$^x$ and R$^y$ is independently chosen from alkyl, cyano, H, and halo, wherein two R$^x$ groups together with the atoms to which they are attached optionally form a cycloalkyl ring;

A¹ and A² are independently chosen from N and CH;

A³ is chosen from N and CR²;

Z¹ is chosen from C and N;

Z², Z³, and Z⁴ are independently chosen from N, O, S, and CH, wherein at least one of Z¹, Z², Z³, and Z⁴ is chosen from N, O, and S;

R¹ is chosen from alkenyl, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, C(O)N(R³)₂, and C(O)C(R³)₃, wherein R¹ may be optionally substituted with between 0 and 3 R$^z$ groups;

R² is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, C(O)N(R³)₂, C(O)C(R³)₃, C(O)OH, C(O)OC(R³)₃, wherein R¹ and R² together with the atoms to which they are attached optionally form an form an aryl, cycloalkyl, heteroaryl, or heterocycloalkyl ring, which may be optionally substituted with between 0 and 3 R$^z$ groups;

each R³ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each R³ may be optionally substituted with between 0 and 3 R$^z$ groups, wherein two R³ groups together with the atoms to which they are attached optionally form an aryl, cycloalkyl, heteroaryl, or heterocycloalkyl ring, which may be optionally substituted with between 0 and 3 R$^z$ groups;

R⁴ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, N(R³)₂, NR³C(O)C(R³)₃, NR³C(O)OC(R³)₃, NR³C(O)N(R³)₂, NR³S(O)C(R³)₃, NR³S(O)₂C(R³)₃, C(O)N(R³)₂, S(O)N(R³)₂, S(O)₂N(R³)₂, C(O)C(R³)₃, SC(R³)₃, S(O)C(R³)₃, and S(O)₂C(R³)₃, wherein R⁴ may be optionally substituted with between 0 and 3 R$^z$ groups;

each R$^z$ group is independently chosen from alkenyl, alkoxy, alkyl, aryl, arylalkyl, cyano, cycloalkyl, cycloalkylalkyl, halo, haloalkyl, heteroaryl, heteroarylalkyl, heterocycloalkyl, heterocycloalkylalkyl, hydroxyl, oxo, N(R⁶)₂, NR⁶C(O)C(R⁶)₃, NR⁶C(O)OC(R⁶)₃, NR⁶C(O)N(R⁶)₂, NR⁶S(O)C(R⁶)₃, NR⁶S(O)₂C(R⁶)₃, C(O)N(R⁶)₂, S(O)N(R⁶)₂, S(O)₂N(R⁶)₂, C(O)C(R⁶)₃, SC(R⁶)₃, S(O)C(R⁶)₃, and S(O)₂C(R⁶)₃; and each R⁶ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein two R⁶ groups together with the atoms to which they are attached optionally form an aryl, cycloalkyl, heteroaryl, or heterocycloalkyl ring, which may be optionally substituted with between 0 and 3 R$^x$ groups.

In certain embodiments, the GLS-1 inhibitor is of Formula IIb:

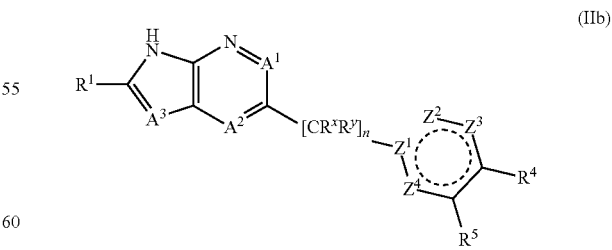

(IIb)

or a salt thereof, wherein:

n is chosen from 3, 4, and 5;

each R$^x$ and R$^y$ is independently chosen from alkyl, cyano, H, and halo, wherein two R$^x$ groups together with the atoms to which they are attached optionally form a cycloalkyl ring;

$A^1$ and $A^2$ are independently chosen from N and CH;

$A^3$ is chosen from N and $CR^2$;

$Z^1$ is chosen from C and N;

$Z^2$ is chosen from N, CH, and C(O);

$Z^3$, and $Z^4$ are independently chosen from N and CH, wherein at least one of $Z^1$, $Z^2$, $Z^3$, and $Z^4$ is N;

$R^1$ is chosen from alkenyl, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, $C(O)N(R^3)_2$, and $C(O)C(R^3)_3$, wherein $R^1$ may be optionally substituted with between 0 and 3 $R^z$ groups;

$R^2$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(O)N(R^3)_2$, $C(O)C(R^3)_3$, $C(O)OH$, $C(O)OC(R^3)_3$, wherein $R^1$ and $R^2$ together with the atoms to which they are attached optionally form an form an aryl, cycloalkyl, heteroaryl, or heterocycloalkyl ring, which may be optionally substituted with between 0 and 3 $R^z$ groups;

each $R^3$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^3$ may be optionally substituted with between 0 and 3 $R^z$ groups, wherein two $R^3$ groups together with the atoms to which they are attached optionally form an aryl, cycloalkyl, heteroaryl, or heterocycloalkyl ring, which may be optionally substituted with between 0 and 3 $R^z$ groups;

$R^4$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $N(R^3)_2$, $NR^3C(O)C(R^3)_3$, $NR^3C(O)OC(R^3)_3$, $NR^3C(O)N(R^3)_2$, $NR^3S(O)C(R^3)_3$, $NR^3S(O)_2C(R^3)_3$, $C(O)N(R^3)_2$, $S(O)N(R^3)_2$, $S(O)_2N(R^3)_2$, $C(O)C(R^3)_3$, $SC(R^3)_3$, $S(O)C(R^3)_3$, and $S(O)_2C(R^3)_3$, wherein $R^4$ may be optionally substituted with between 0 and 3 $R^z$ groups;

$R^5$ is chosen from alkyl, heterocycloalkyl, cyano, cycloalkyl, H, halo, and haloalkyl, wherein $R^4$ and $R^5$ together with the atoms to which they are attached optionally form an aryl, cycloalkyl, heteroaryl, or heterocycloalkyl ring, which may be optionally substituted with between 0 and 3 $R^z$ groups;

each $R^z$ group is independently chosen from alkenyl, alkoxy, alkyl, aryl, arylalkyl, cyano, cycloalkyl, cycloalkylalkyl, halo, haloalkyl, heteroaryl, heteroarylalkyl, heterocycloalkyl, heterocycloalkylalkyl, hydroxyl, oxo, $N(R^6)_2$, $NR^6C(O)C(R^6)_3$, $NR^6C(O)OC(R^6)_3$, $NR^6C(O)N(R^6)_2$, $NR^6S(O)C(R^6)_3$, $NR^6S(O)_2C(R^6)_3$, $C(O)N(R^6)_2$, $S(O)N(R^6)_2$, $S(O)_2N(R^6)_2$, $C(O)C(R^6)_3$, $SC(R^6)_3$, $S(O)C(R^6)_3$, and $S(O)_2C(R^6)_3$; and each $R^6$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein two $R^6$ groups together with the atoms to which they are attached optionally form an aryl, cycloalkyl, heteroaryl, or heterocycloalkyl ring, which may be optionally substituted with between 0 and 3 $R^x$ groups.

In certain embodiments, the GLS1i is disclosed in United States Patent Application Publication No. US 2016/0009704, published Jan. 14, 2016.

In certain embodiments, the GLS-1 inhibitor is of Formula III:

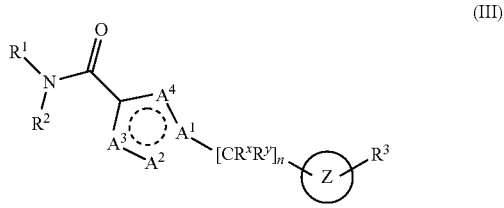

or a salt thereof, wherein:

n is chosen from 3, 4, and 5;

each $R^X$ and $R^Y$ is independently chosen from alkyl, cyano, H, and halo, or two $R^X$ groups together with the atoms to which they are attached optionally form a cycloalkyl ring;

$A^1$ is chosen from C and N;

$A^2$, $A^3$, and $A^4$ are independently chosen from N, O, S, and CH, wherein at least one of $A^1$, $A^2$, $A^3$, and $A^4$ is chosen from N, O, and S;

$R^1$ and $R^2$ are each independently chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ and $R^2$ each may be optionally substituted with one to three $R^Z$ groups, wherein $R^1$ and $R^2$ together with the atoms to which they are attached optionally form an heteroaryl, or heterocycloalkyl ring, which may be optionally substituted with one to three $R^Z$ groups;

$R^3$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^4)_2C(O)R^4$, $C(R^4)_2C(O)N(R^4)_2$, $C(R^4)_2 N(R^4)_2$, $C(R^4)_2NR^4C(O)R^4$, $C(R^4)_2NR^4C(O)OR^4$, $C(R^4)_2NR^4C(O)N(R^4)_2$, $C(R^4)_2NR^4S(O)R^4$, $C(R^4)_2NR^4S(O)_2R^4$, $N(R^4)_2$, $NR^4C(O)R^4$, $NR^4C(O)OR^4$, $NR^4C(O)N(R^4)_2$, $NR^4S(O)R^4$, $NR^4S(O)_2R^4$, $C(O)N(R^4)_2$, $S(O)N(R^4)_2$, $S(O)_2N(R^4)_2$, $C(O)R^4$, $SR^4$, $S(O)R^4$, and $S(O)_2R^4$;

wherein each $R^3$ may be optionally substituted with one to three $R^Z$ groups;

each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^4$ may be optionally substituted with one to three $R^Z$ groups, wherein two $R^4$ groups together with the atoms to which they are attached optionally form an heteroaryl, or heterocycloalkyl ring, which may be optionally substituted with one to three $R^Z$ groups;

each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$;

each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups; and Z is a monocyclic heteroaryl, which may be optionally substituted.

In certain embodiments, the GLS-1 inhibitor is of Formula IIIa:

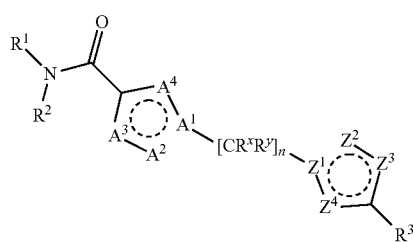

(IIIa)

or a salt thereof, wherein:
n is chosen from 3, 4, and 5;
each $R^X$ and $R^Y$ is independently chosen from alkyl, cyano, H, and halo, or two $R^X$ groups together with the atoms to which they are attached optionally form a cycloalkyl ring;
$A^1$ and $Z^1$ are independently chosen from C and N;
$A^2$, $A^3$, $A^4$, $Z^2$, $Z^3$, and $Z^4$ are independently chosen from N, O, S, and CH, wherein at least one of $A^1$, $A^2$, $A^3$, and $A^4$ and at least one of $Z^1$, $Z^2$, $Z^3$, and $Z^4$ is chosen from N, O, and S;
$R^1$ and $R^2$ are each independently chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ and $R^2$ each may be optionally substituted with one to three $R^Z$ groups, wherein $R^1$ and $R^2$ together with the atoms to which they are attached optionally form an heteroaryl, or heterocycloalkyl ring, which may be optionally substituted with one to three $R^Z$ groups;
$R^3$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkylalkyl, hydroxyl, $C(R^4)_2C(O)R^4$, $C(R^4)_2C(O)N(R^4)_2$, $C(R^4)_2N(R^4)_2$, $C(R^4)_2NR^4C(O)R^4$, $C(R^4)_2NR^4C(O)OR^4$, $C(R^4)_2NR^4C(O)N(R^4)_2$, $C(R^4)_2NR^4S(O)R^4$, $C(R^4)_2NR^4S(O)_2R^4$, $N(R^4)_2$, $NR^4C(O)R^4$, $NR^4C(O)OR^4$, $NR^4C(O)N(R^4)_2$, $NR^4S(O)R^4$, $NR^4S(O)_2R^4$, $C(O)N(R^4)_2$, $S(O)N(R^4)_2$, $S(O)_2N(R^4)_2$, $C(O)R^4$, $SR^4$, $S(O)R^4$, and $S(O)_2R^4$;

wherein each $R^3$ may be optionally substituted with one to three $R^Z$ groups;

each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^4$ may be optionally substituted with one to three $R^Z$ groups, wherein two $R^4$ groups together with the atoms to which they are attached optionally form an heteroaryl, or heterocycloalkyl ring, which may be optionally substituted with one to three $R^Z$ groups;

each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$;

each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups.

In certain embodiments, the GLS-1 inhibitor is of Formula IIIb:

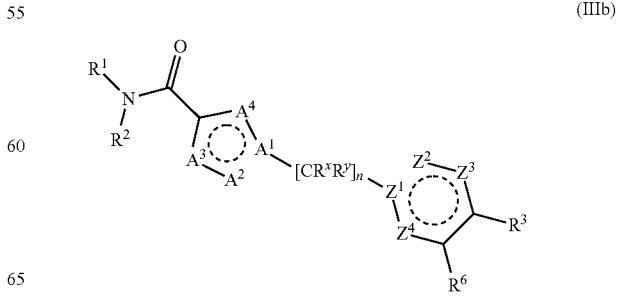

(IIIb)

or a salt thereof, wherein:

n is chosen from 3, 4, and 5;

each $R^X$ and $R^Y$ is independently chosen from alkyl, cyano, H, and halo, or two $R^X$ groups together with the atoms to which they are attached optionally form a cycloalkyl ring;

$A^1$ is chosen from C and N;

$A^2$, $A^3$, and $A^4$, are independently chosen from N, O, S, and CH, wherein at least one of $A^1$, $A^2$, $A^3$, and $A^4$ is chosen from N, O, and S;

$Z^1$ is C;

$Z^2$, $Z^3$ and $Z^4$ are independently chosen from N and CH, wherein at least one of $Z^1$, $Z^2$, $Z^3$, and $Z^4$ is N;

$R^1$ and $R^2$ are each independently chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ and $R^2$ each may be optionally substituted with one to three $R^Z$ groups, wherein $R^1$ and $R^2$ together with the atoms to which they are attached optionally form an heteroaryl, or heterocycloalkyl ring, which may be optionally substituted with one to three $R^Z$ groups;

$R^3$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^4)_2C(O)R^4$, $C(R^4)_2C(O)N(R^4)_2$, $C(R^4)_2$ $N(R^4)_2$, $C(R^4)_2NR^4C(O)R^4$, $C(R^4)_2NR^4C(O)OR^4$, $C(R^4)_2NR^4C(O)N(R^4)_2$, $C(R^4)_2NR^4S(O)R^4$, $C(R^4)_2NR^4S(O)_2R^4$, $N(R^4)_2$, $NR^4C(O)R^4$, $NR^4C(O)OR^4$, $NR^4C(O)N(R^4)_2$, $NR^4S(O)R^4$, $NR^4S(O)_2R^4$, $C(O)N(R^4)_2$, $S(O)N(R^4)_2$, $S(O)_2N(R^4)_2$, $C(O)R^4$, $SR^4$, $S(O)R^4$, and $S(O)_2R^4$;

wherein each $R^3$ may be optionally substituted with one to three $R^Z$ groups;

each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^4$ may be optionally substituted with one to three $R^Z$ groups, wherein two $R^4$ groups together with the atoms to which they are attached optionally form an heteroaryl, or heterocycloalkyl ring, which may be optionally substituted with one to three $R^Z$ groups;

each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$;

each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups; and $R^6$ is chosen from, alkyl, cyano, cycloalkyl, H, halo, haloalkyl, and heterocycloalkyl, wherein $R^3$ and $R^6$ groups together with the atoms to which they are attached optionally form an aryl, cycloalkyl, heteroaryl, or heterocycloalkyl ring, which may be optionally substituted with one to three $R^Z$ groups.

In certain embodiments, the GLS-1 inhibitor is of Formula IIIc:

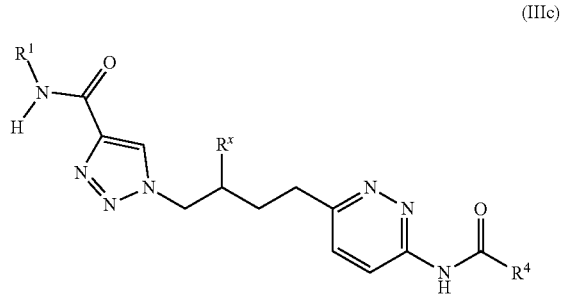

(IIIc)

or a salt thereof, wherein:

$R^X$ is chosen from fluoro and H;

$R^1$ is chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ may be optionally substituted with one to three $R^Z$ groups;

each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein $R^4$ may be optionally substituted with one to three $R^Z$ groups;

each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; and each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^x$ groups.

In certain embodiments, the GLS1i is of Formula IIIc as shown above, or a salt thereof, wherein $R^1$ is methyl.

In certain embodiments, the GLS-1 inhibitor is of Formula IIIc-1:

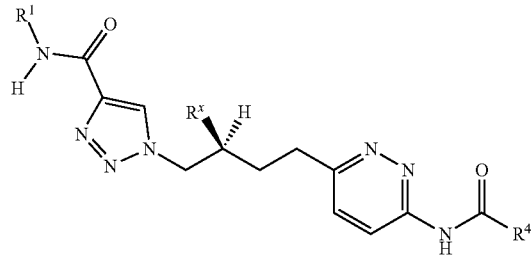

(IIIc-1)

or a salt thereof, wherein:

$R^x$ is chosen from fluoro and H;

$R^1$ is chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ may be optionally substituted with one to three $R^z$ groups;

each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein $R^4$ may be optionally substituted with one to three $R^z$ groups;

each $R^z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; and each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^x$ groups.

In certain embodiments, the GLS-1 inhibitor is of Formula IIIc-2:

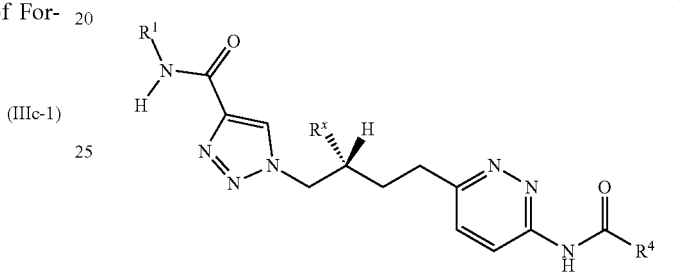

(IIIc-2)

or a salt thereof, wherein:

$R^x$ is chosen from fluoro and H;

$R^1$ is chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ may be optionally substituted with one to three $R^z$ groups;

each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein $R^4$ may be optionally substituted with one to three $R^z$ groups;

each $R^z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, N(R⁵)₂, NR⁵C(O)R⁵, NR⁵C(O)OR⁵, NR⁵C(O)N(R⁵)₂, NR⁵S(O)R⁵, NR⁵S(O)₂R⁵, C(O)N(R⁵)₂, S(O)N(R⁵)₂, S(O)₂N(R⁵)₂, C(O)R⁵, C(O)OR⁵, SR⁵, S(O)R⁵, and S(O)₂R⁵; and each R⁵ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two R⁵ groups together with the atoms to which they are attached optionally form an aryl, cycloalkyl, heteroaryl, or heterocycloalkyl ring, which may be optionally substituted with one to three Rˣ groups.

In certain embodiments, the GLS-1 inhibitor is of Formula IIId:

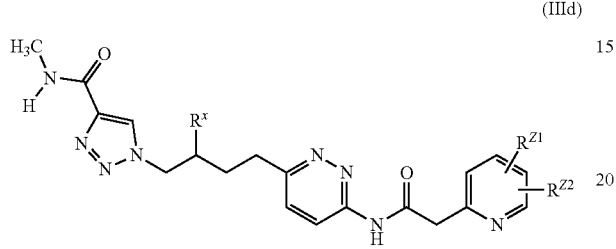

(IIId)

or a salt thereof, wherein:

Rˣ is chosen from fluoro and H;

each of R^{Z1} and R^{Z2} is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, and oxo.

In certain embodiments, the GLS-1 inhibitor is of Formula IIId as shown above, or a salt thereof, wherein:

Rˣ is chosen from fluoro and H; and each of R^{Z1} and R^{Z2} is independently chosen from alkyl, cycloalkyl, cycloalkylhaloalkyl, cycloalkyloxy, H, haloalkoxy, haloalkoxyaryl, haloalkyl, halocycloalkyloxy, heterocycloalkyl, and heterocycloalkyloxy.

In certain embodiments, the GLS-1 inhibitor is of Formula IIId as shown above, or a salt thereof, wherein:

Rˣ is chosen from fluoro and H; and each of R^{Z1} and R^{Z2} is independently chosen from H,

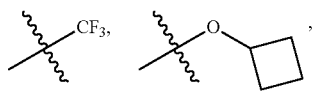

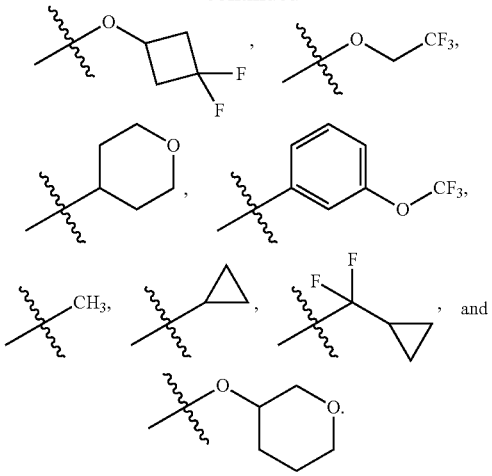

In certain embodiments, the GLS-1 inhibitor is of Formula IIIe:

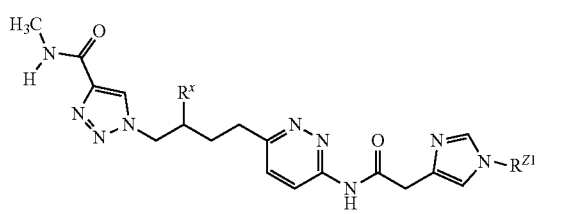

(IIIe)

or a salt thereof, wherein:

Rˣ is chosen from fluoro and H;

R^{Z1} is chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, and oxo.

In certain embodiments, the GLS-1 inhibitor is a compound or a salt thereof, wherein the compound is chosen from

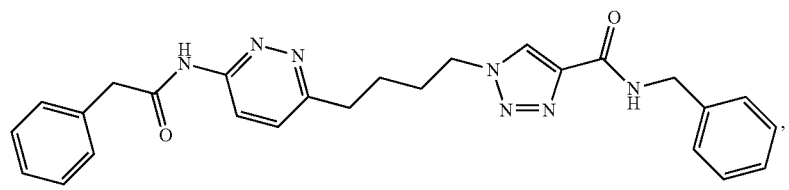
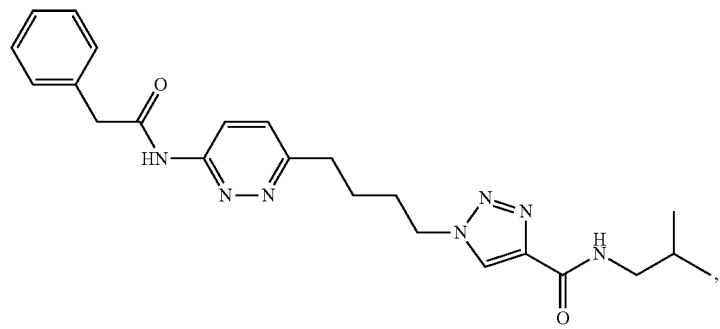
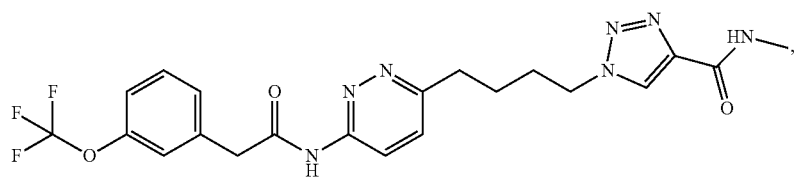
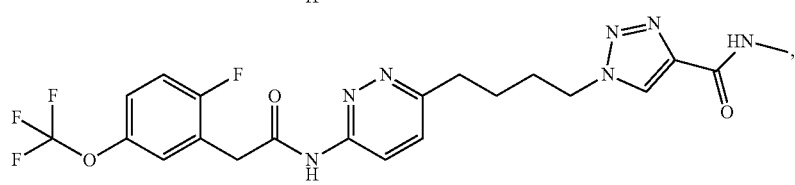
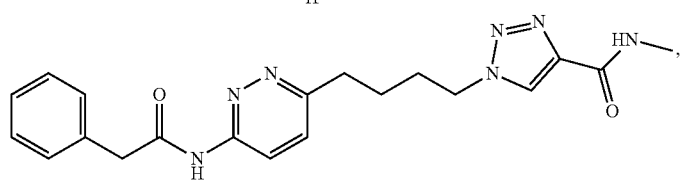
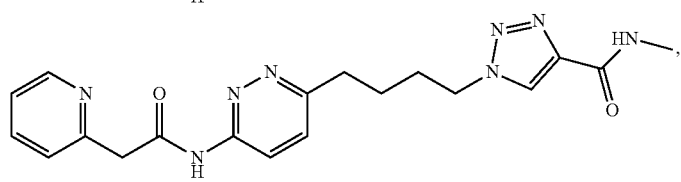
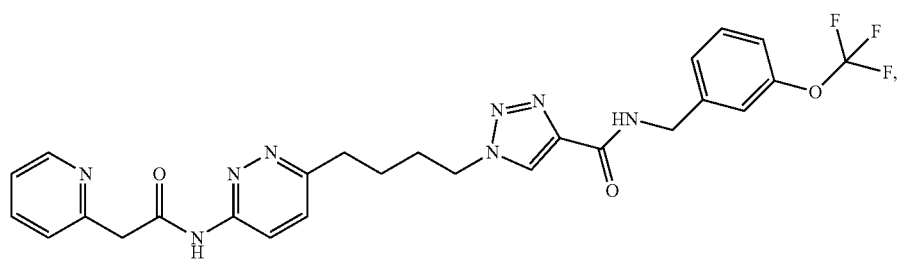
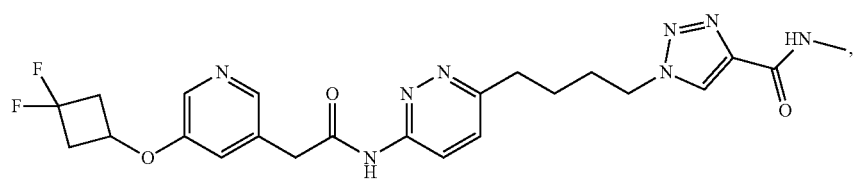

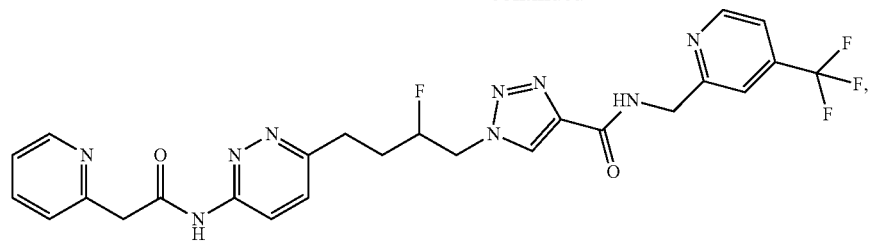
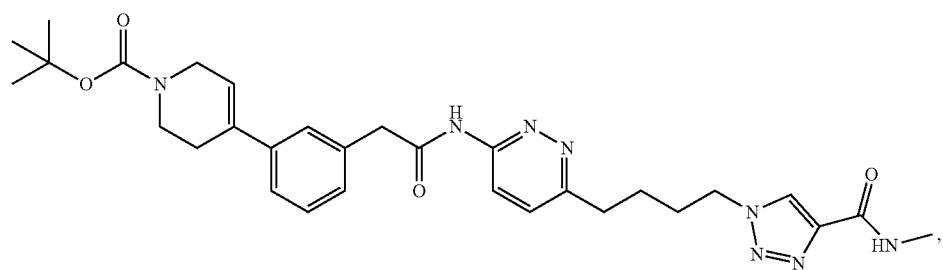
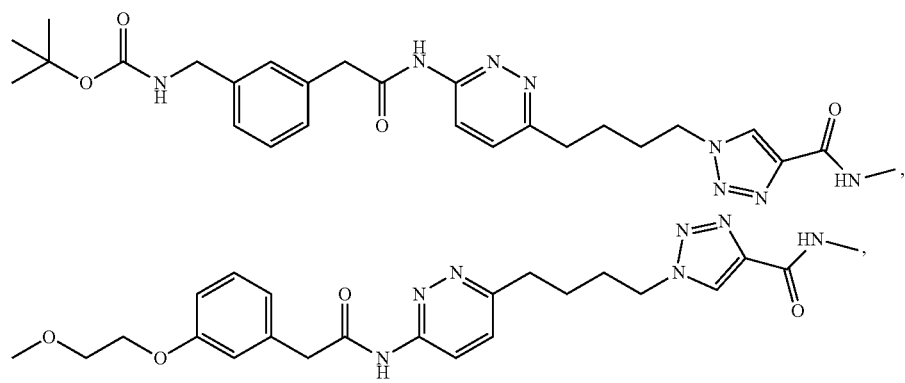
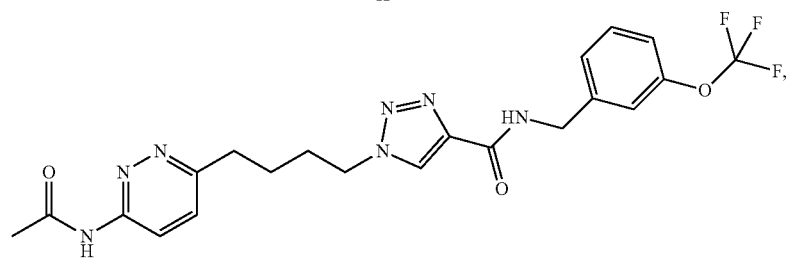
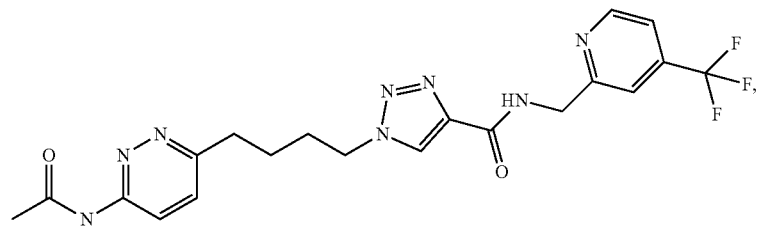
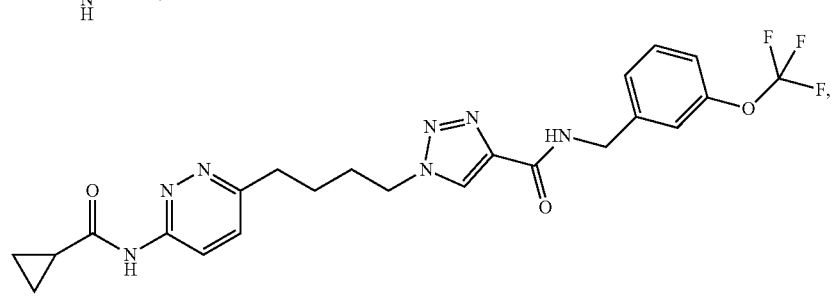

-continued
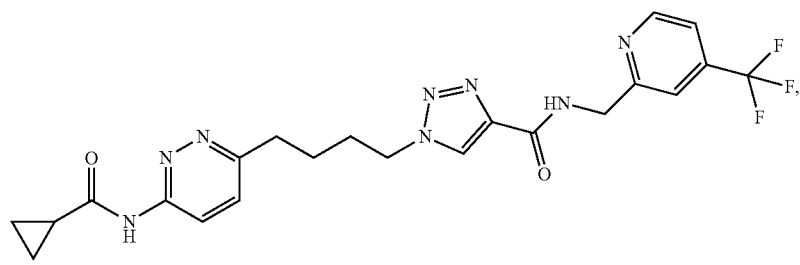
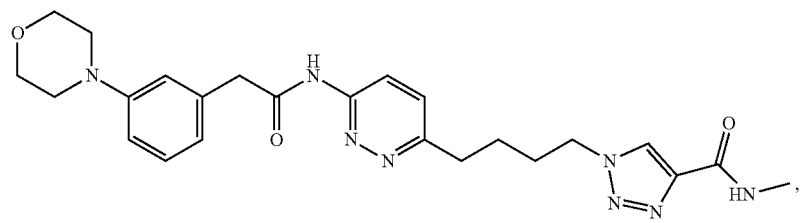
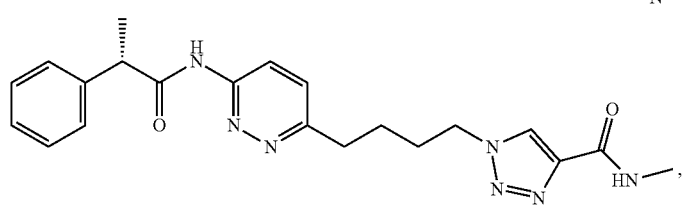
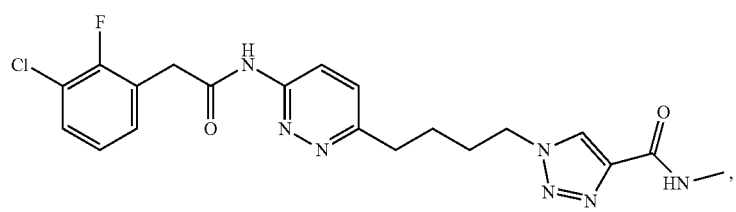
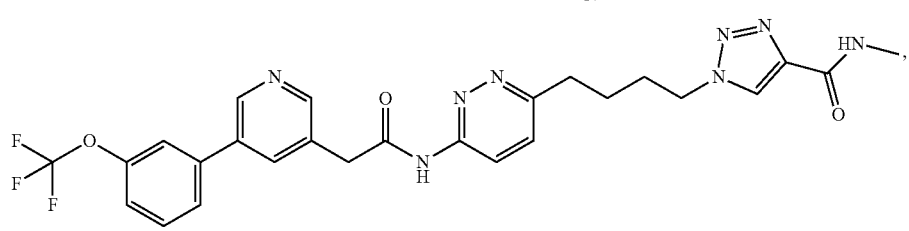
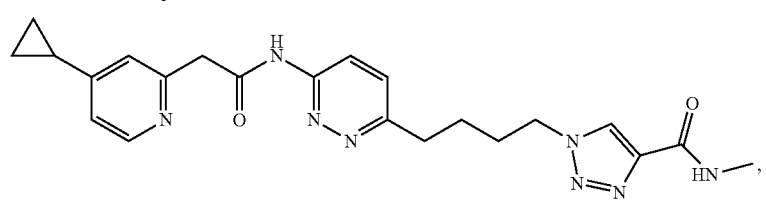
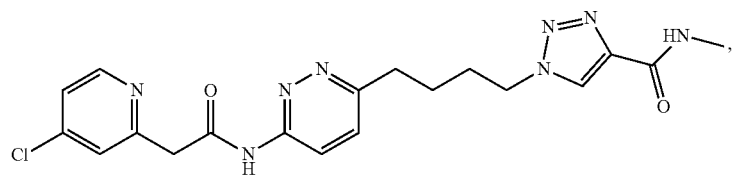
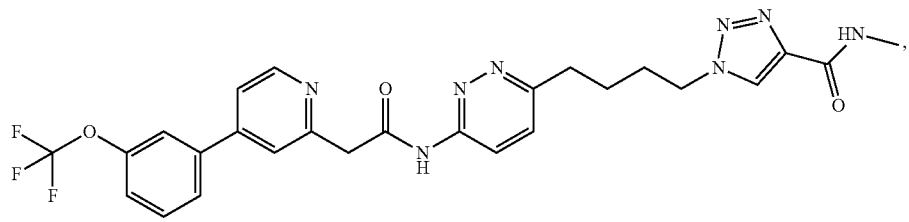

-continued
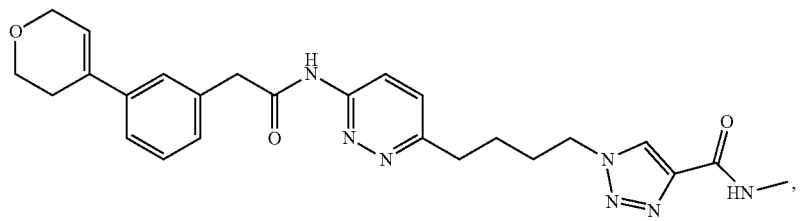
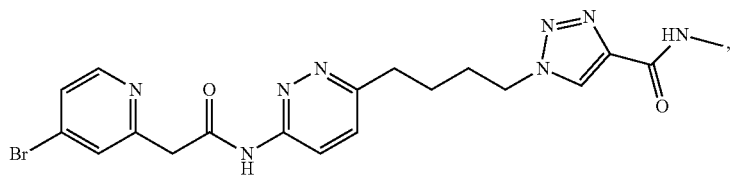
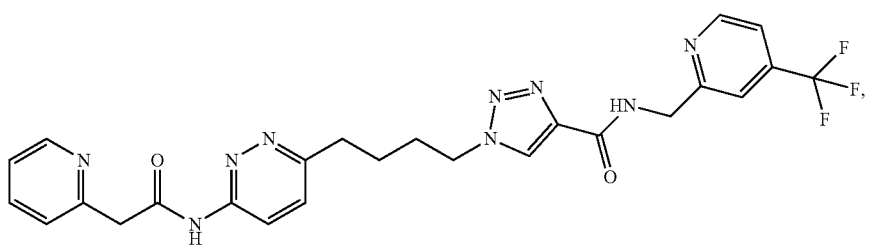
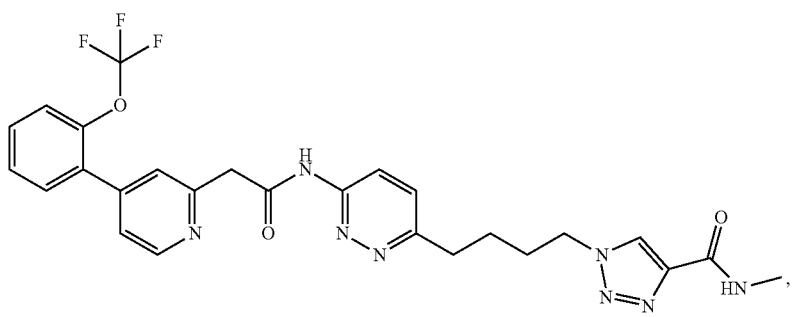
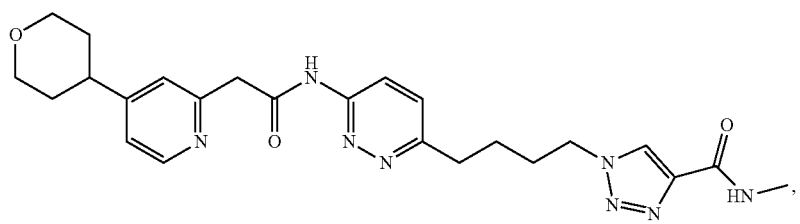
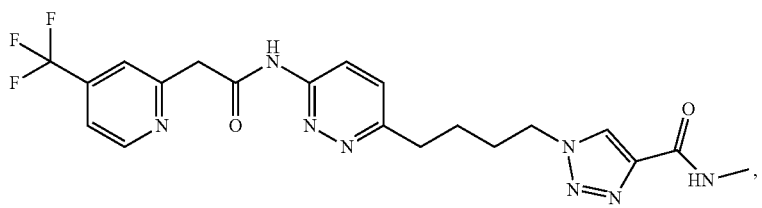
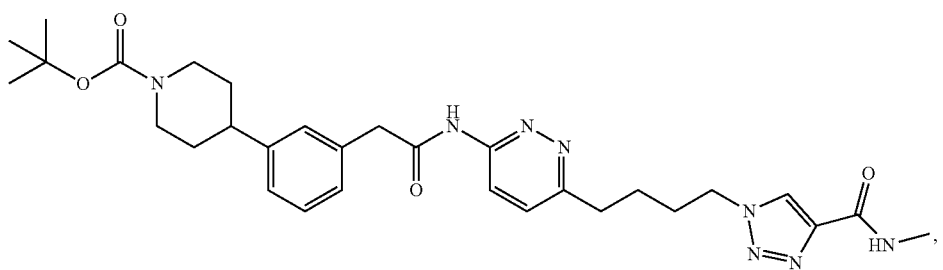

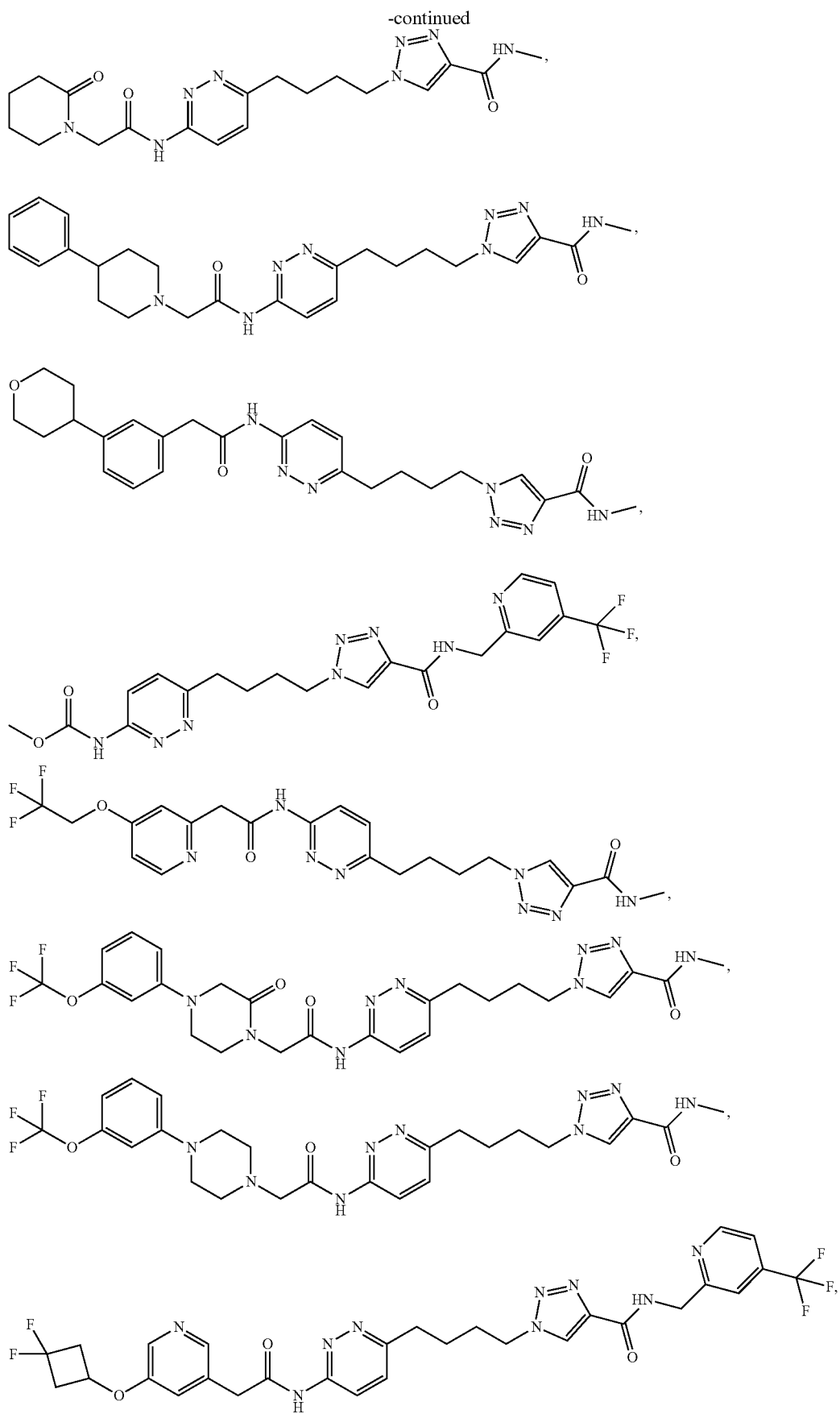

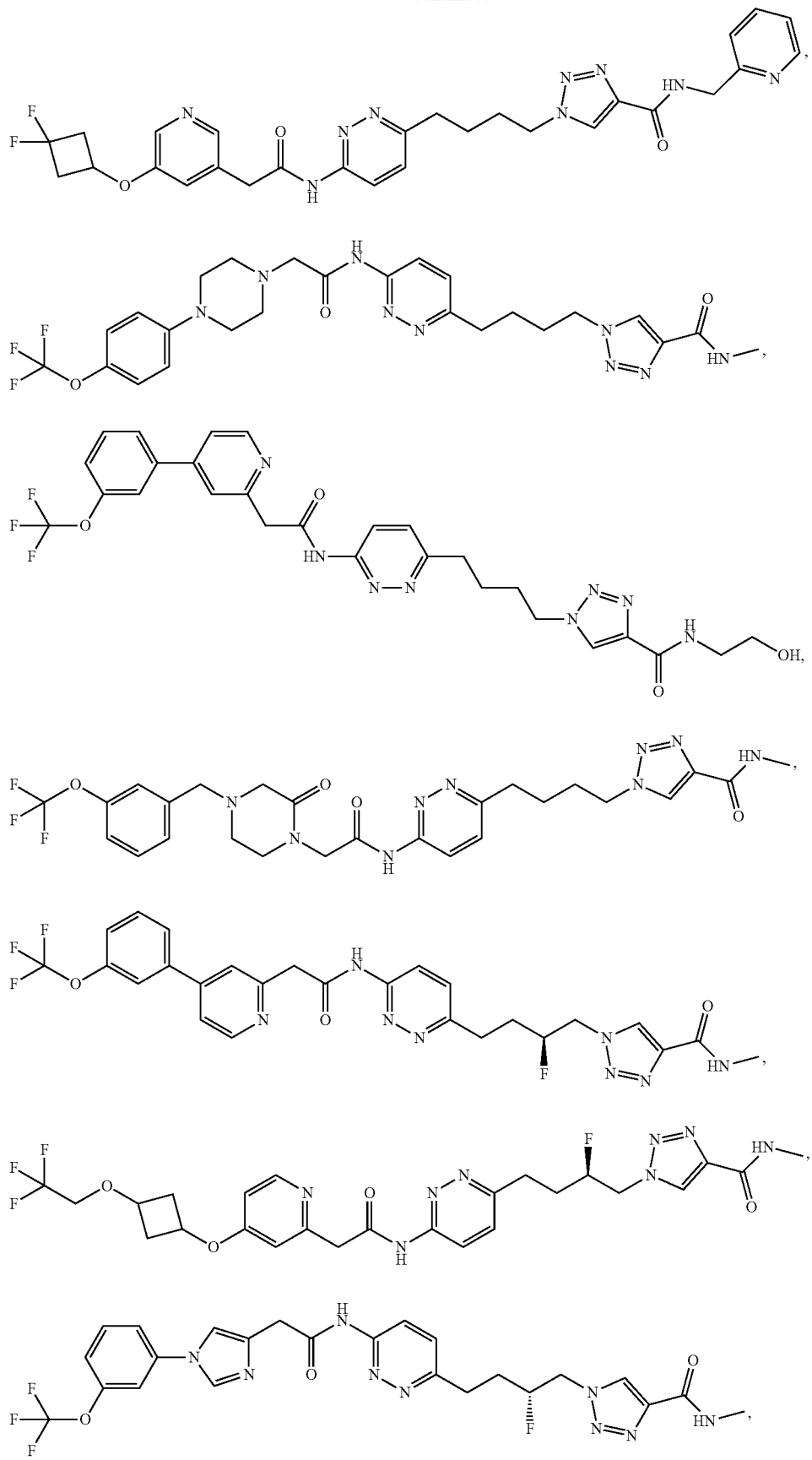

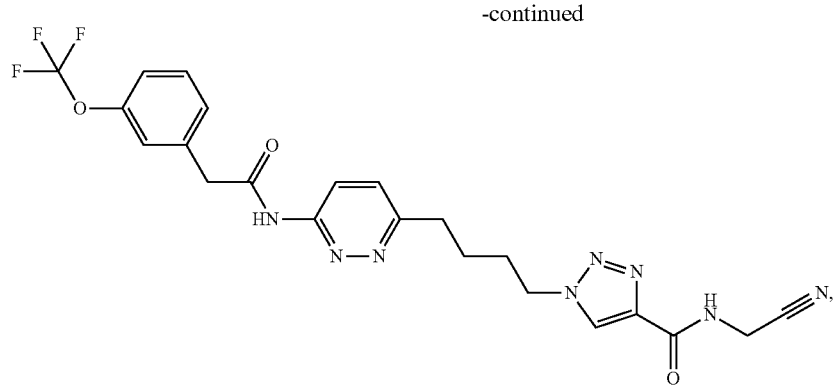
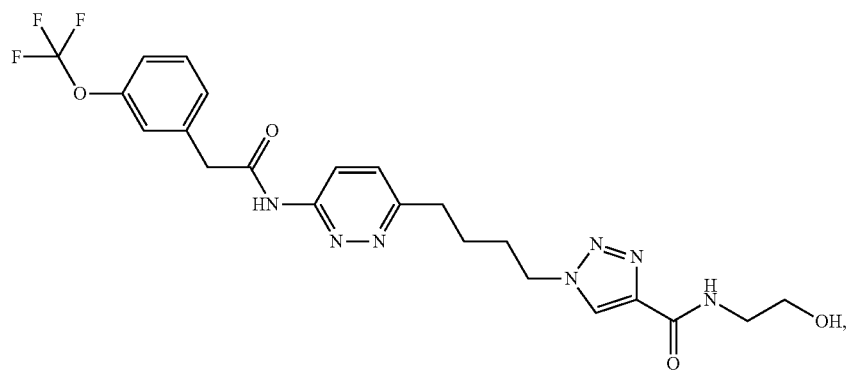
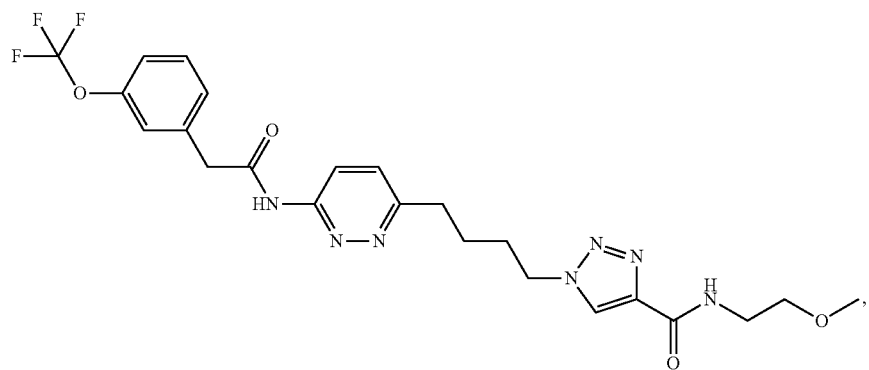
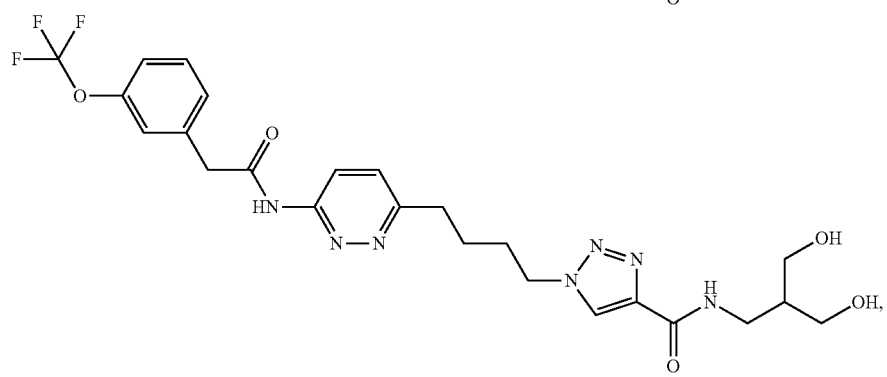
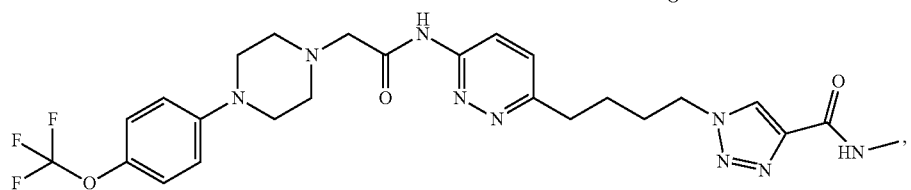

-continued
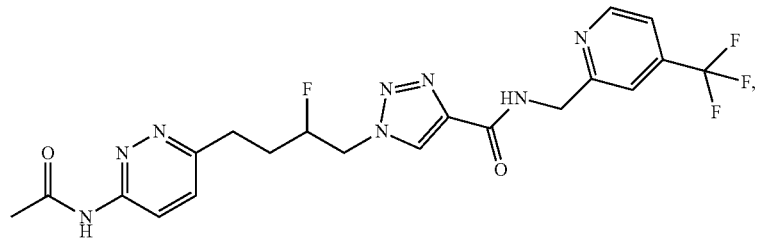
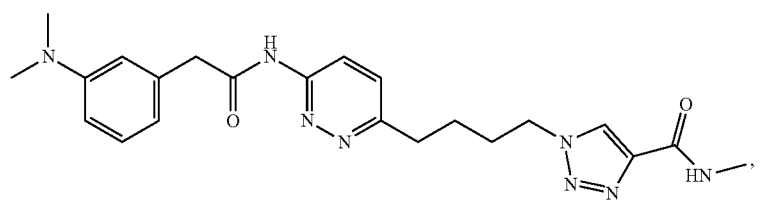
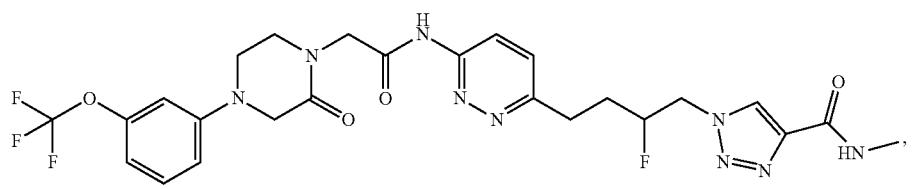
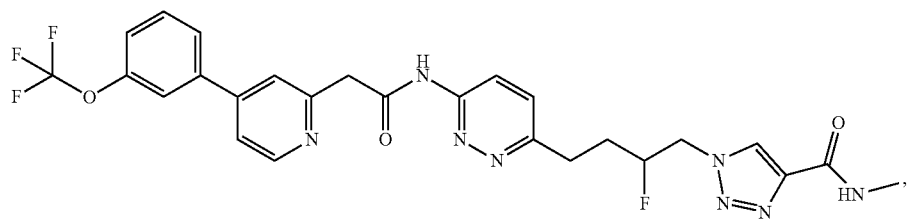
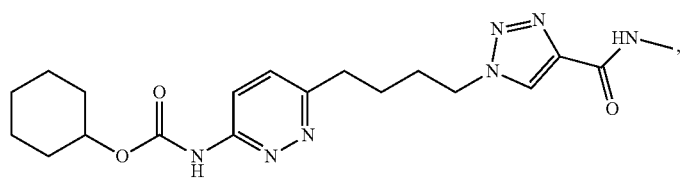
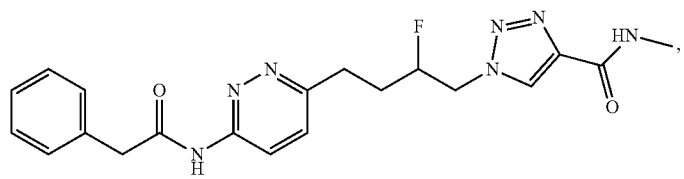
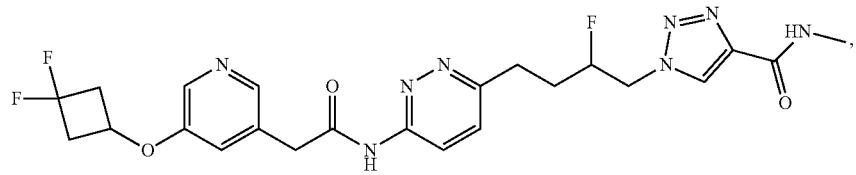
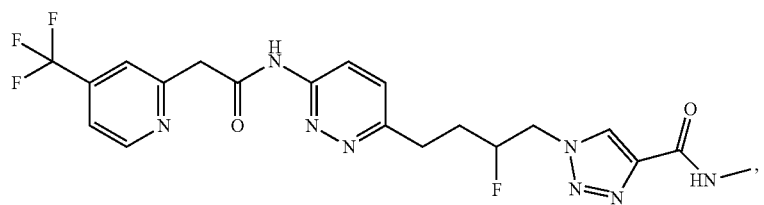

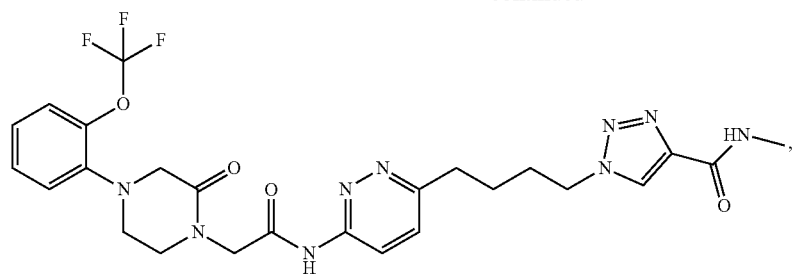
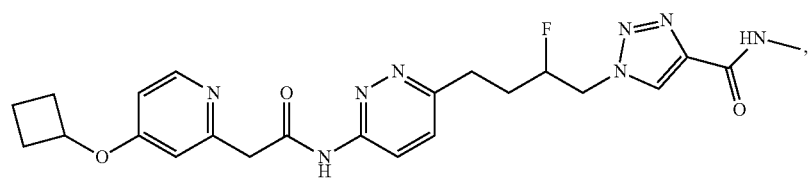
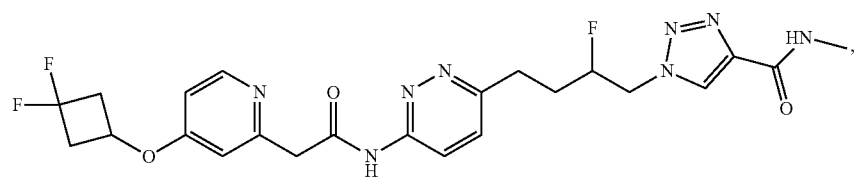
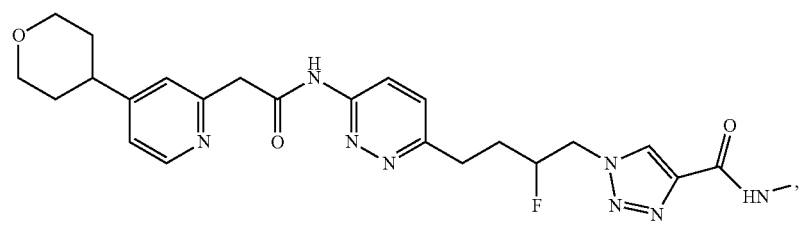
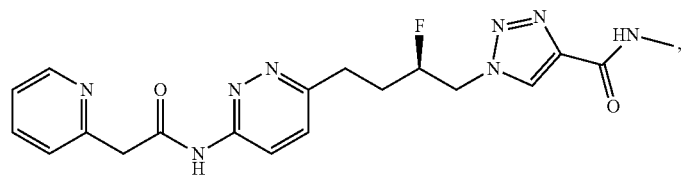
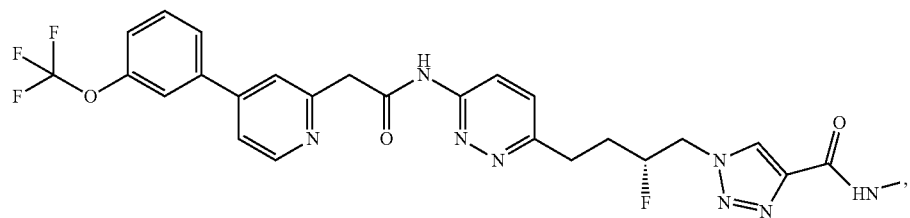
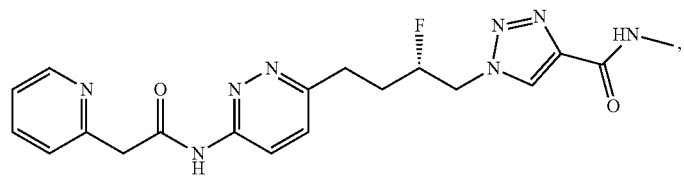
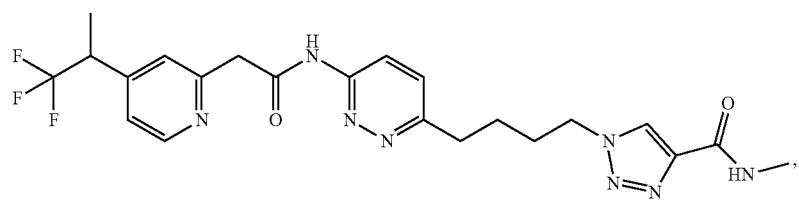

-continued
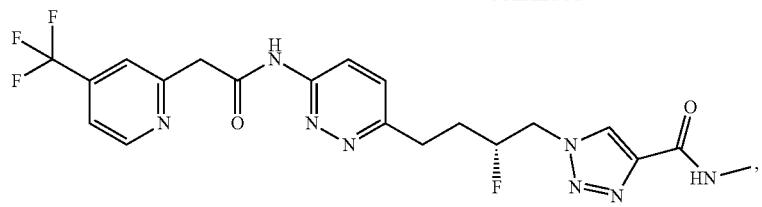
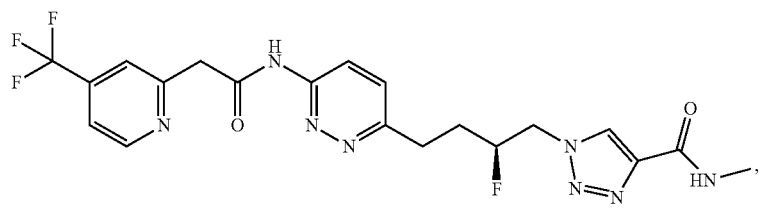
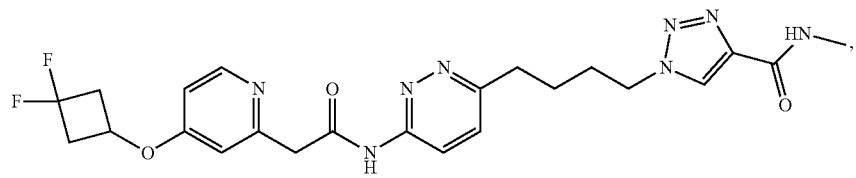
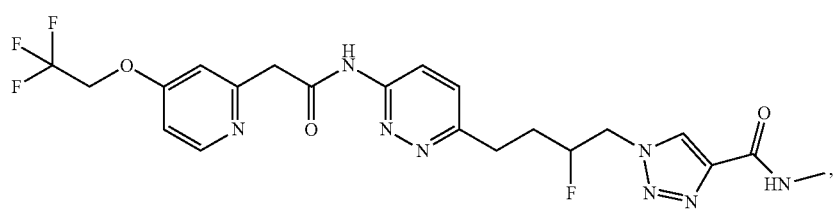
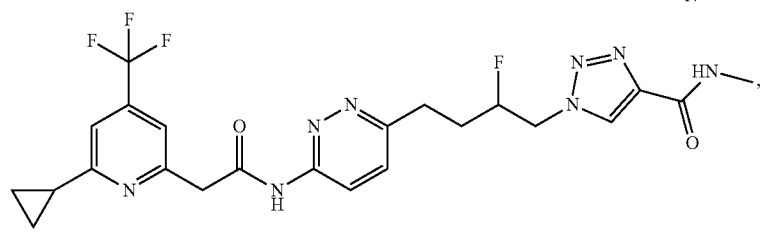
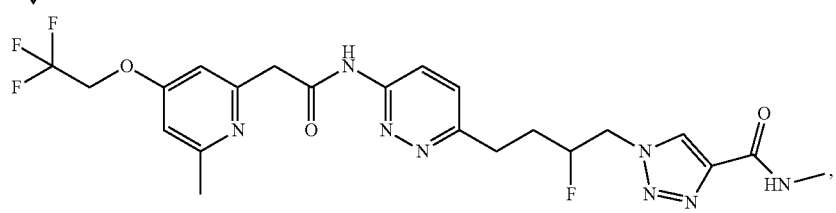
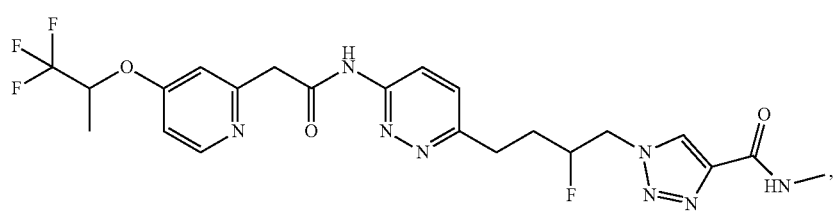
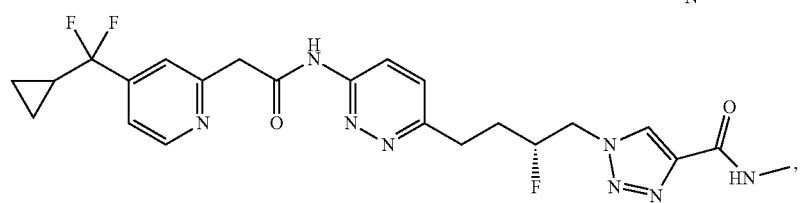

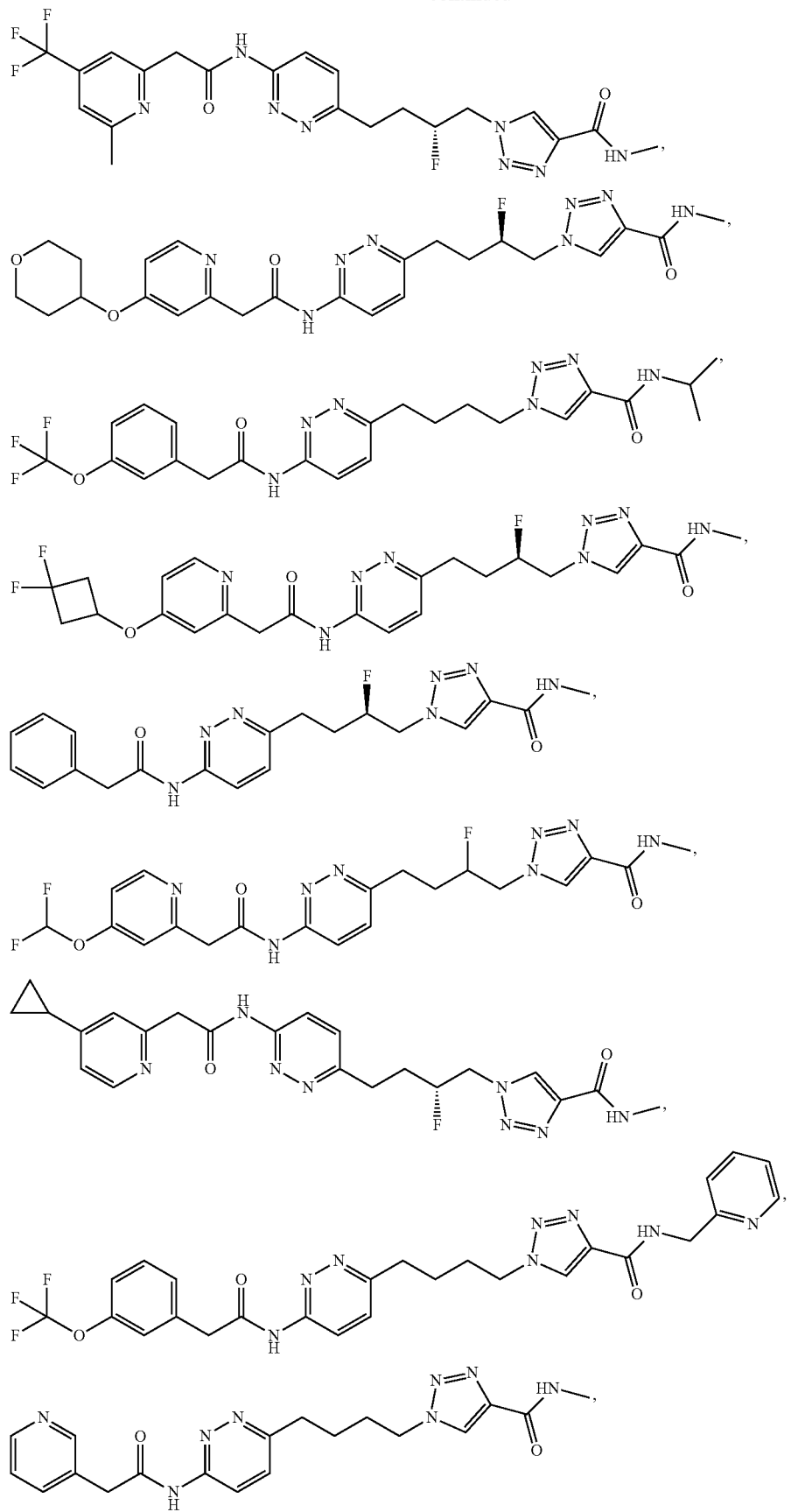

-continued
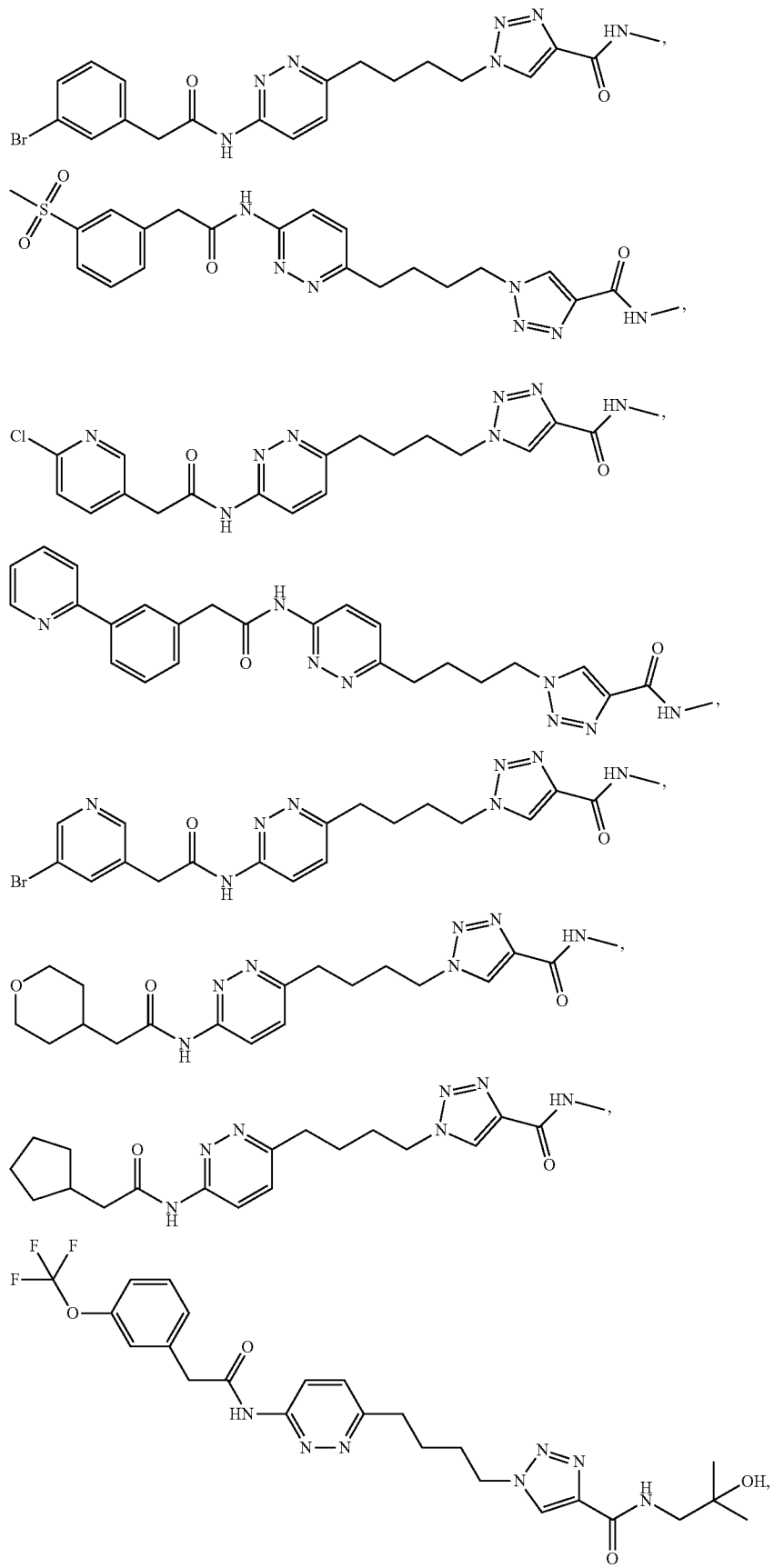

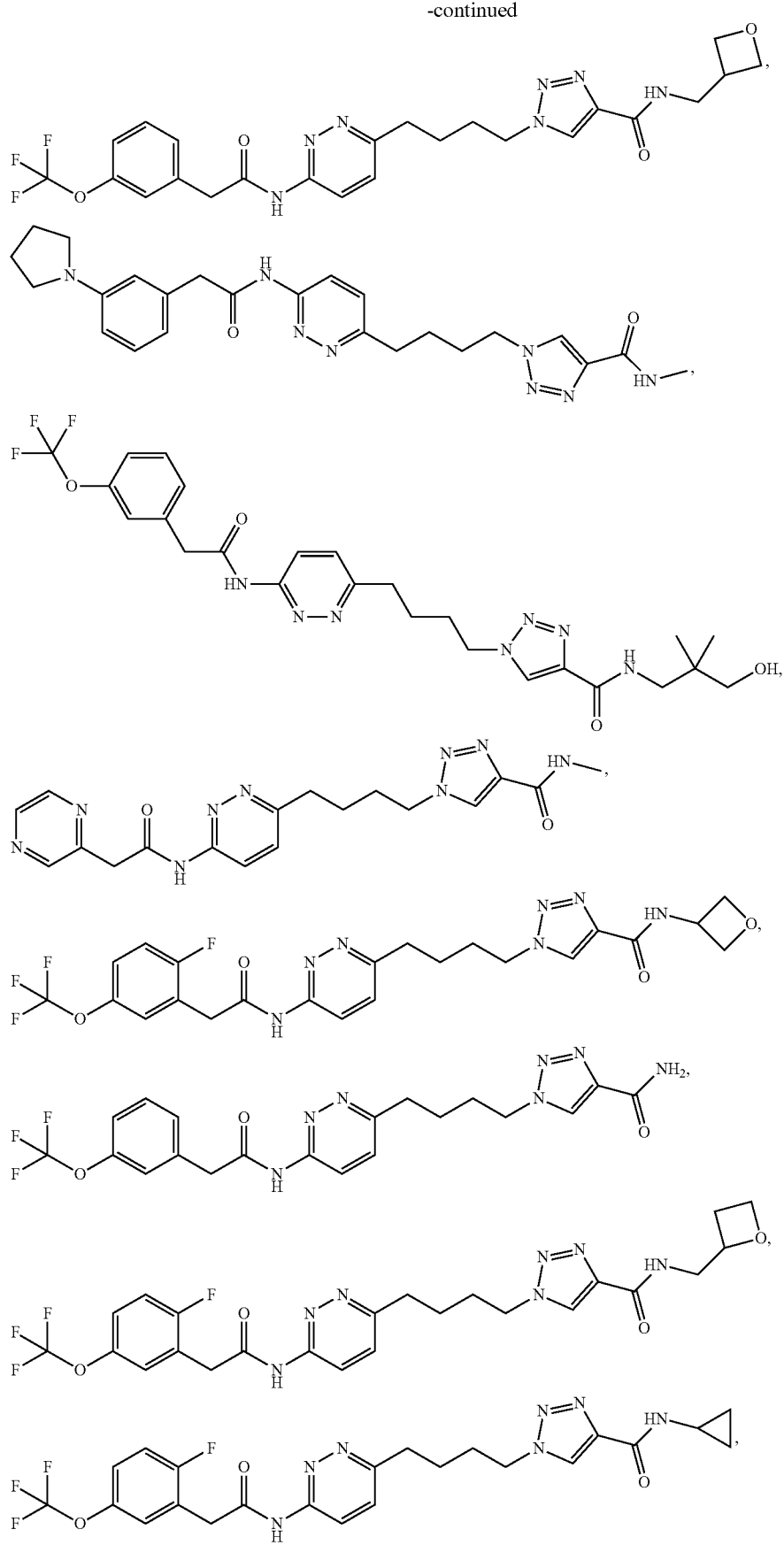

-continued
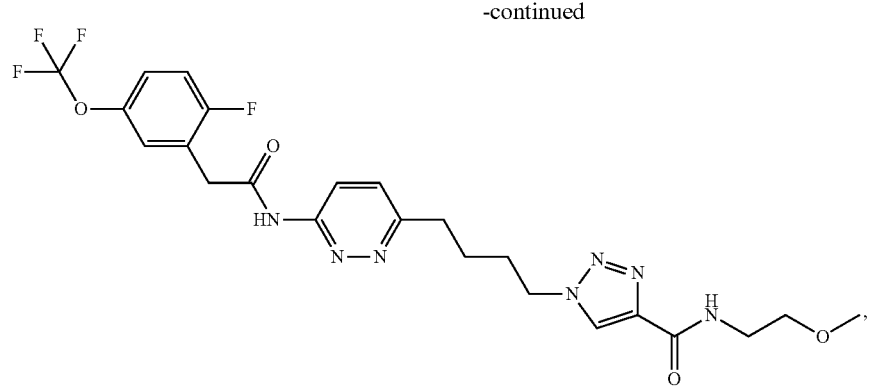
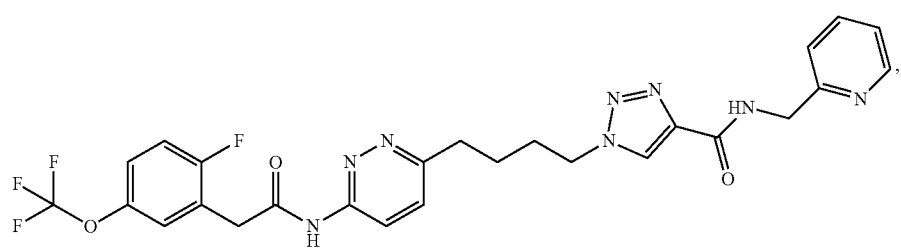
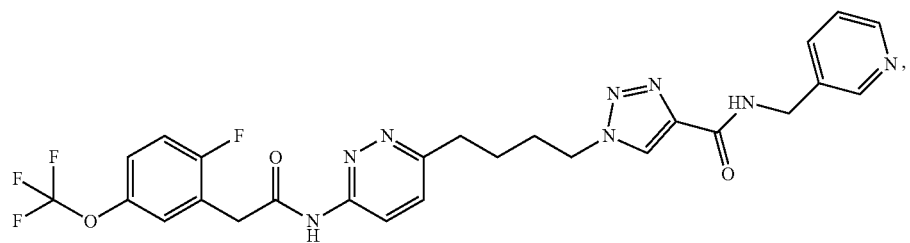
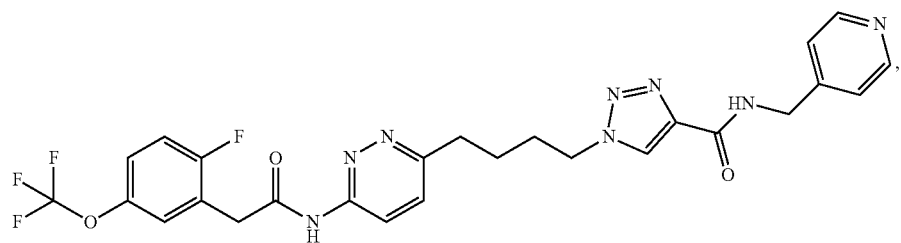
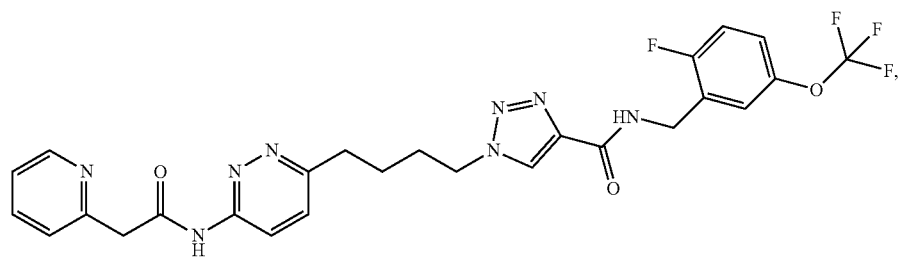
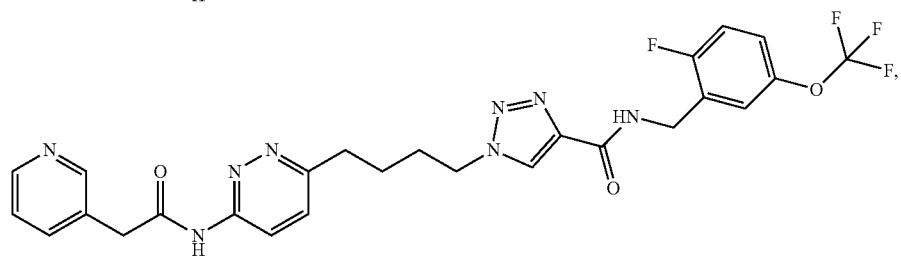

-continued
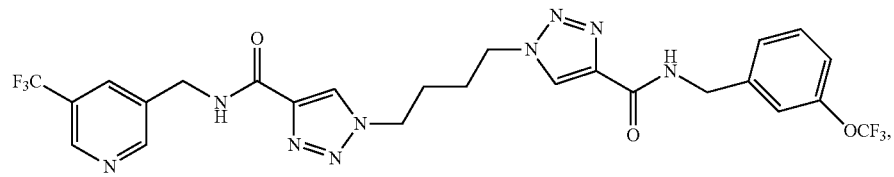
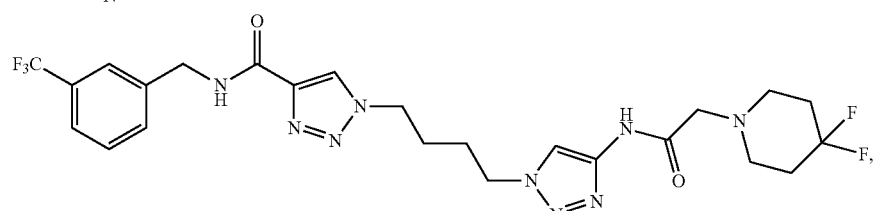
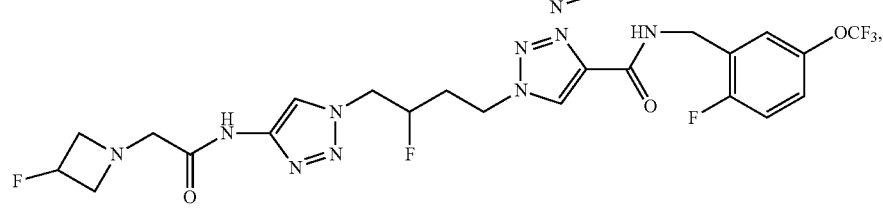
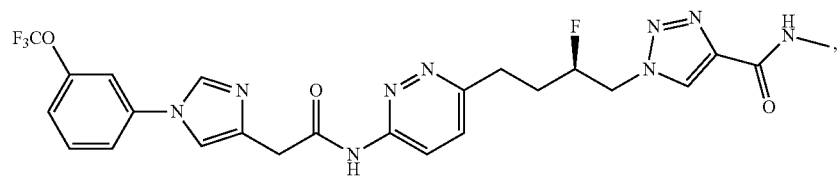
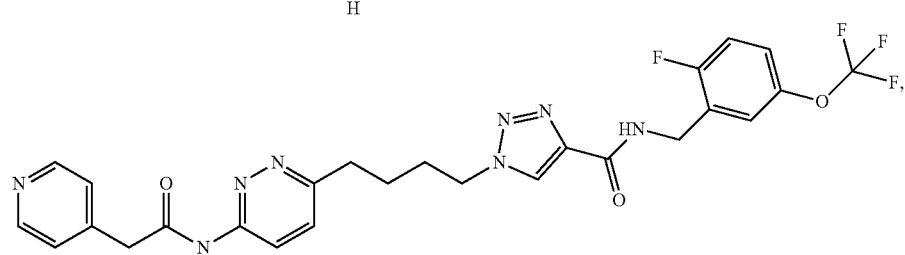
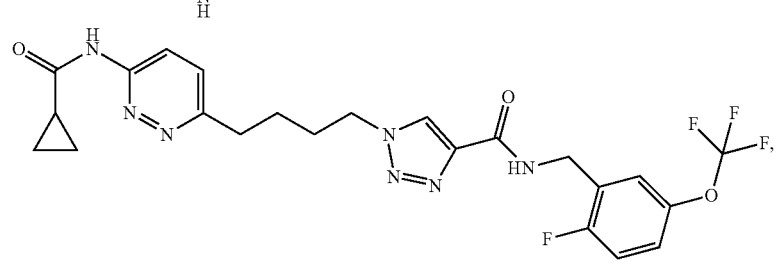
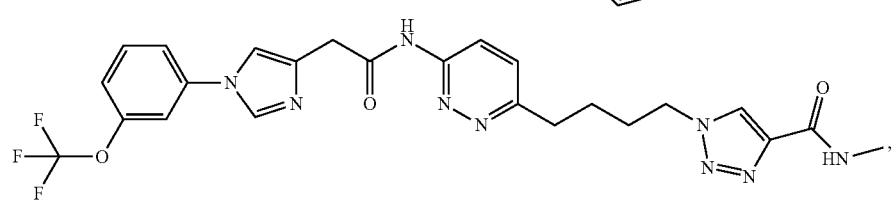
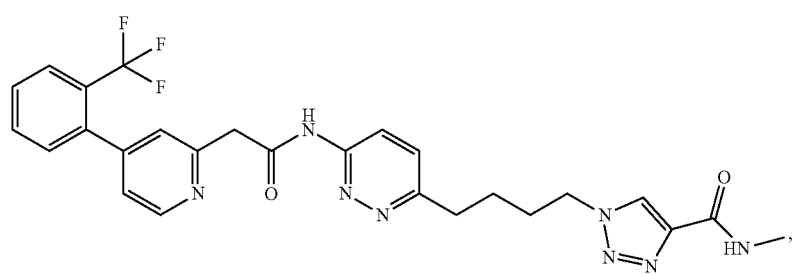

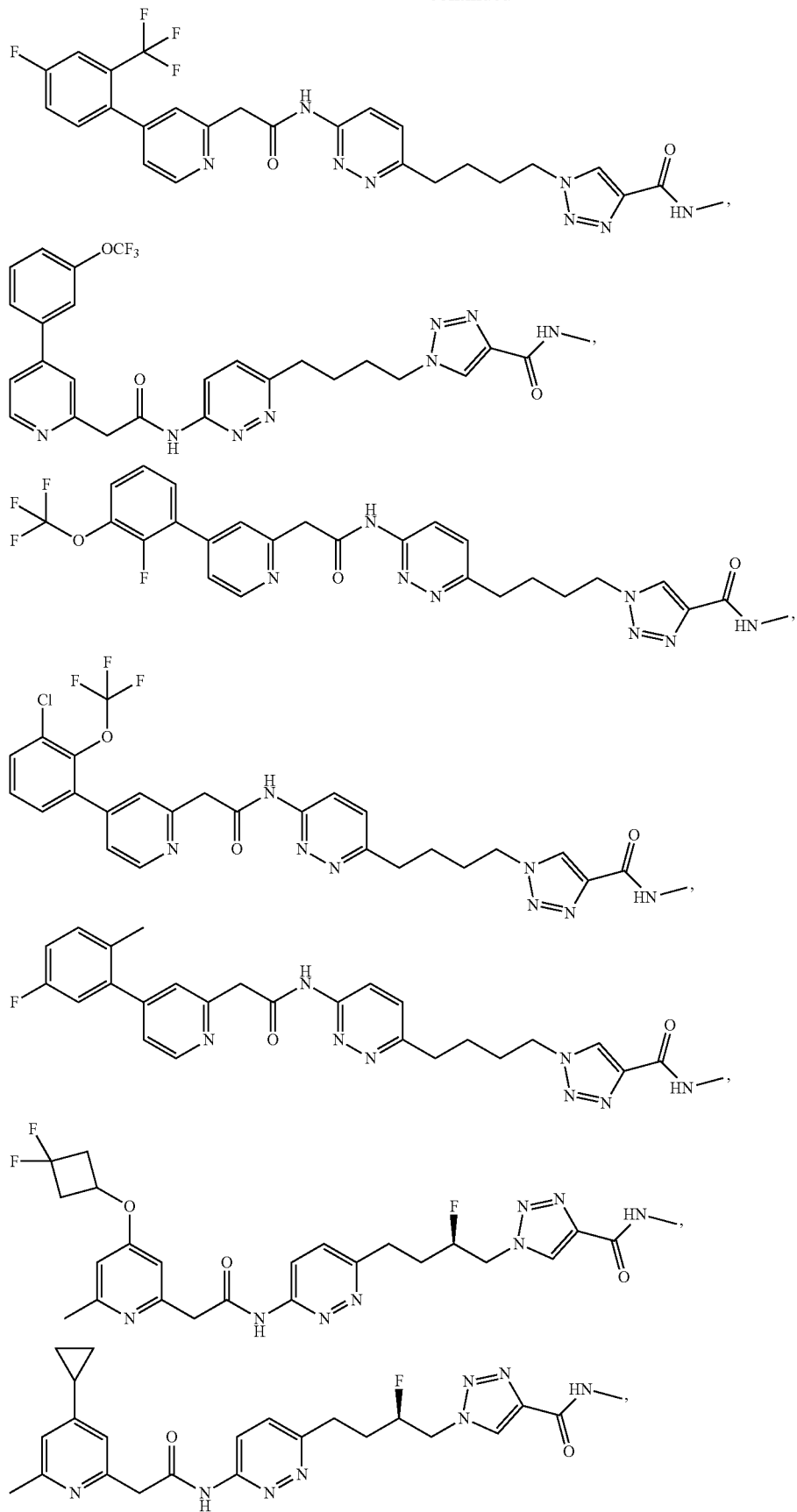

-continued
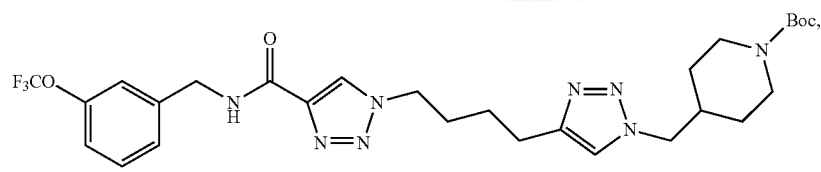
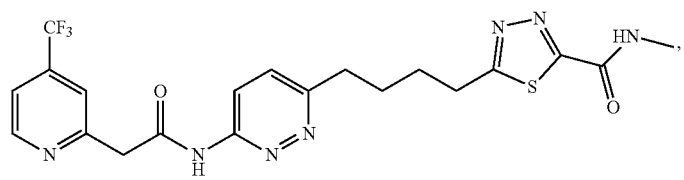
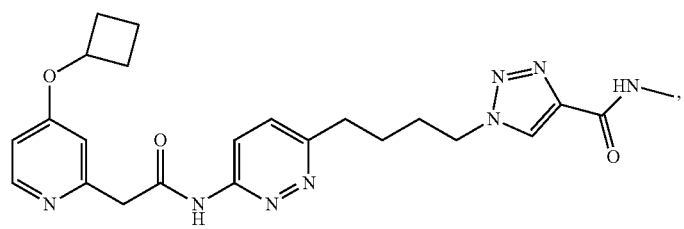
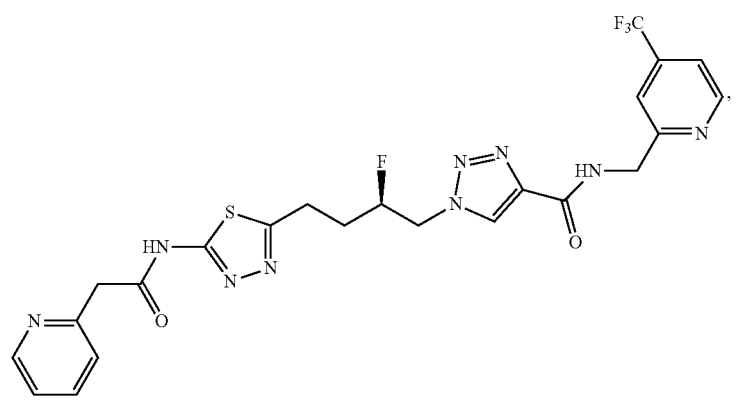
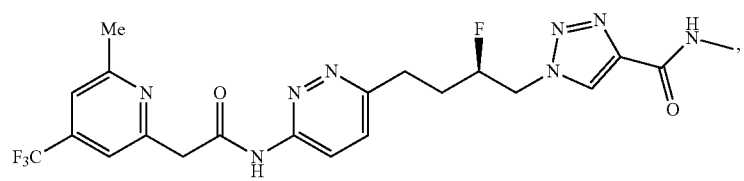
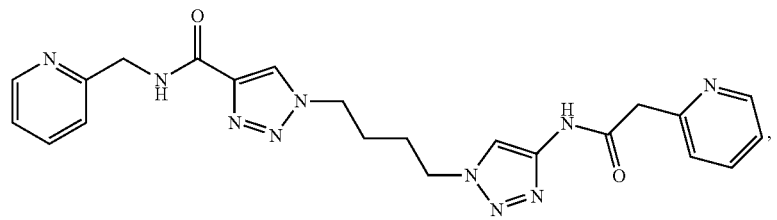

-continued
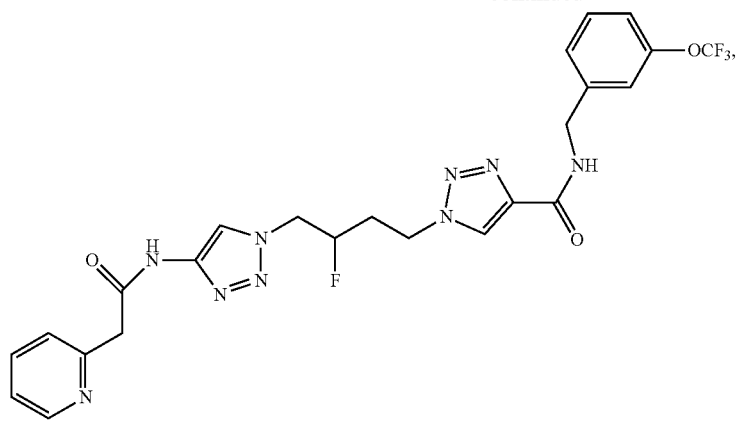
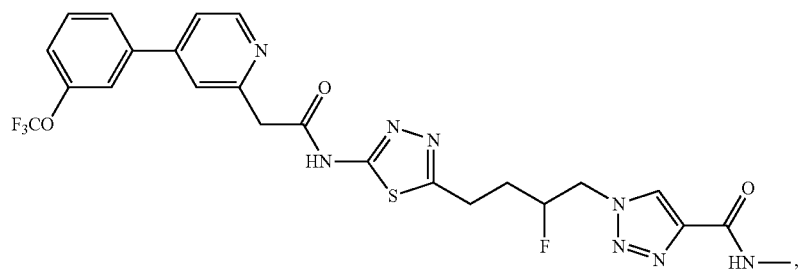
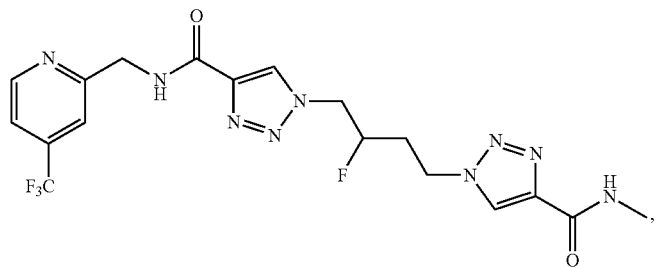
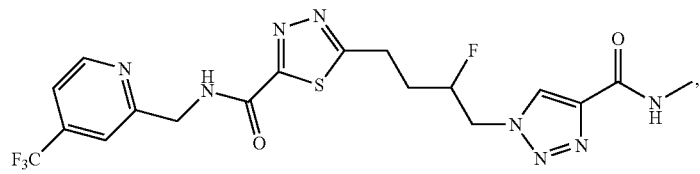
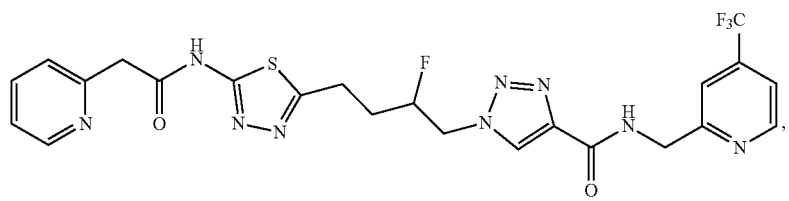
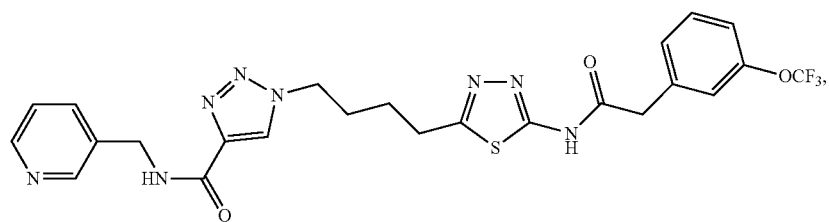

-continued
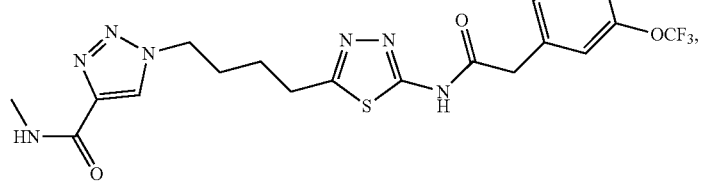
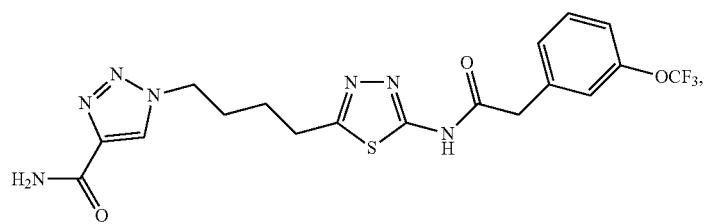
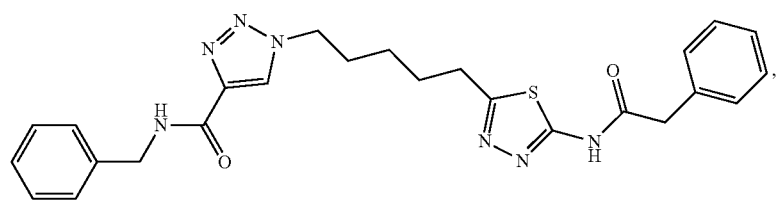
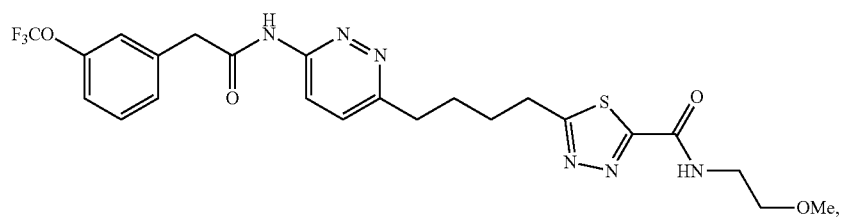
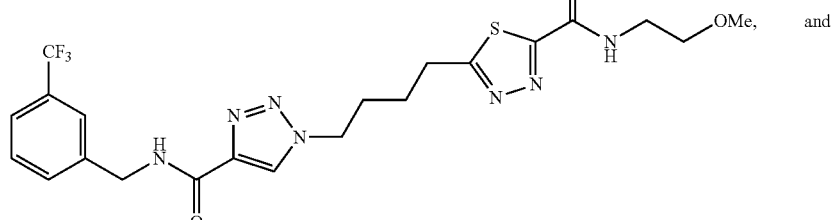
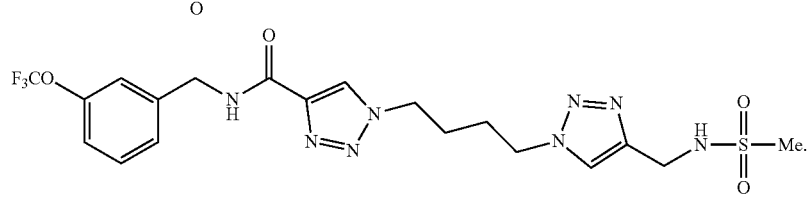

In certain embodiments, the GLS1i is one as disclosed in United States Patent Application Publication No. US 2017/0001996 filed Jan. 5, 2017.

In certain embodiments, the GLS-1 inhibitor is of Formula IV:

$$R^1 \underset{\substack{\displaystyle | \\ n}}{\overset{\displaystyle A}{\diagup}} N \underset{R^2}{\diagdown} Z \qquad (IV)$$

or a salt thereof, wherein:
n is chosen from 1 and 2;
$R^1$ is chosen from $NR^3C(O)R^3$, $NR^3C(O)OR^3$, $NR^3C(O)N(R^3)_2$, $C(O)N(R^3)_2$, and $N(R^3)_2$;
each $R^3$ is independently chosen from alkyl, aryl, arylalkyl, cycloalkyl, cycloalkylalkyl, H, haloalkyl, heteroaryl, heteroarylalkyl, heterocycloalkyl, heterocycloalkylalkyl, wherein each $R^3$ may be optionally substituted with one to three $R^x$ groups, wherein two $R^3$ groups together with the atoms to which they are attached optionally form an heteroaryl or heterocycloalkyl ring, which may be optionally substituted with one to three $R^x$ groups;
$R^2$ is chosen from $NR^4C(O)R^4$, $NR^4C(O)OR^4$, $NR^4C(O)N(R^4)_2$, $C(O)N(R^4)_2$ and $N(R^4)_2$;
each $R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups, wherein two $R^4$ groups together with the atoms to which they are attached optionally form an heteroaryl or heterocycloalkyl ring, which may be optionally substituted with one to three $R^x$ groups;
each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $C(O)N(R^5)_2$, and $C(O)R^5$;
each $R^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups;
$R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl;
A is a monocyclic heteroaryl, which may be optionally substituted with one to three $R^z$ groups; and
Z is a monocyclic heteroaryl, which may be optionally substituted with one to three $R^z$ groups.

In certain embodiments, the GLS1i is disclosed in United States Patent Application Publication No. US 2017/0001996, published Jan. 5, 2017.

In certain embodiments, the GLS-1 inhibitor is of Formula IVa:

$$R^1 \underset{\substack{\displaystyle | \\ n}}{\overset{\displaystyle A^1}{\diagup}} \underset{N}{\overset{N}{\diagdown}} \underset{Z^1}{\overset{Z^2}{\diagdown}} R^2 \qquad (IVa)$$

or a salt thereof, wherein:
n is chosen from 1 and 2;
$A^1$ is chosen from S and HC=CH;
$Z^1$ is chosen from S, CH, and HC=CH;
$Z^2$ is N when $Z^1$ is CH, and $Z^2$ is C when $Z^1$ is S or HC=CH;
$R^1$ is chosen from $NR^3C(O)R^3$, $NR^3C(O)OR^3$, $NR^3C(O)N(R^3)_2$, $C(O)N(R^3)_2$, and $N(R^3)_2$;
each $R^3$ is independently chosen from alkyl, aryl, arylalkyl, cycloalkyl, cycloalkylalkyl, H, haloalkyl, heteroaryl, heteroarylalkyl, heterocycloalkyl, heterocycloalkylalkyl, wherein each $R^3$ may be optionally substituted with one to three $R^x$ groups, wherein two $R^3$ groups together with the atoms to which they are attached optionally form an heteroaryl or heterocycloalkyl ring, which may be optionally substituted with one to three $R^x$ groups;
$R^2$ is chosen from $NR^4C(O)R^4$, $NR^4C(O)OR^4$, $NR^4C(O)N(R^4)_2$, $C(O)N(R^4)_2$ and $N(R^4)_2$;
each $R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups, wherein two $R^4$ groups together with the atoms to which they are attached optionally form an heteroaryl or heterocycloalkyl ring, which may be optionally substituted with one to three $R^x$ groups;
each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $C(O)N(R^5)_2$, and $C(O)R^5$;

each $R^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups; and $R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl.

In certain embodiments, the GLS-1 inhibitor is of Formula IVb:

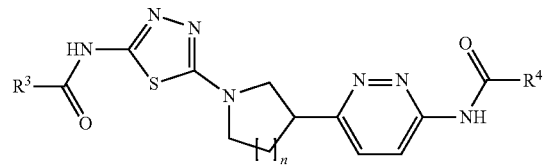

(IVb)

or a salt thereof, wherein:

n is chosen from 1 and 2;

$R^3$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^3$ may be optionally substituted with one to three $R^x$ groups;

$R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups;

each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $C(O)N(R^5)_2$, and $C(O)R^5$;

each $R^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups; and $R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl.

In certain embodiments, the GLS-1 inhibitor is of Formula IVc:

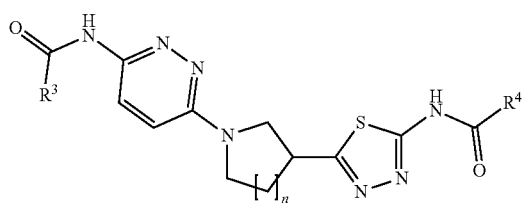

(IVc)

or a salt thereof, wherein:

n is chosen from 1 and 2;

$R^3$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^3$ may be optionally substituted with one to three $R^x$ groups;

$R^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each $R^4$ may be optionally substituted with one to three $R^x$ groups;

each $R^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, N(R$^5$)$_2$, NR$^5$C(O)R$^5$, NR$^5$C(O)OR$^5$, NR$^5$C(O)N(R$^5$)$_2$, C(O)N(R$^5$)$_2$, and C(O)R$^5$;

each R$^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three R$^z$ groups; and R$^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl.

In certain embodiments, the GLS-1 inhibitor is of Formula IVd:

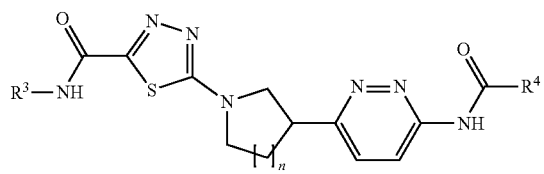

(IVd)

or a salt thereof, wherein:

n is chosen from 1 and 2;

R$^3$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each R$^3$ may be optionally substituted with one to three R$^x$ groups;

R$^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each R$^4$ may be optionally substituted with one to three R$^x$ groups;

each R$^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, N(R$^5$)$_2$, NR$^5$C(O)R$^5$, NR$^5$C(O)OR$^5$, NR$^5$C(O)N(R$^5$)$_2$, C(O)N(R$^5$)$_2$, and C(O)R$^5$;

each R$^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three R$^z$ groups; and R$^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl.

In certain embodiments, the GLS-1 inhibitor is of Formula IVe:

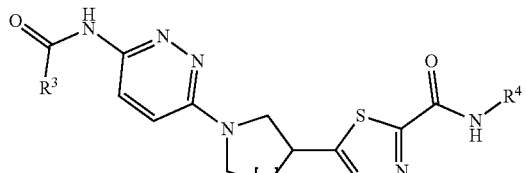

(IVe)

or a salt thereof, wherein:

n is chosen from 1 and 2;

R$^3$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each R$^3$ may be optionally substituted with one to three R$^x$ groups;

R$^4$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, wherein each R$^4$ may be optionally substituted with one to three R$^x$ groups;

each R$^x$ group is independently chosen from alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, N(R$^5$)$_2$, NR$^5$C(O)R$^5$, NR$^5$C(O)OR$^5$, NR$^5$C(O)N(R$^5$)$_2$, C(O)N(R$^5$)$_2$, and C(O)R$^5$;

each R$^5$ is independently chosen from alkyl, aryl, arylalkyl, cycloalkyl, cycloalkylalkyl, H, haloalkyl, heteroaryl, heteroarylalkyl, heterocycloalkyl, and heterocycloalkylalkyl, which may be optionally substituted with one to three $R^z$ groups; and $R^z$ is chosen from alkyl, aryl, arylalkyl, cyano, cycloalkyl, cycloalkylalkyl, H, halo, haloalkyl, heteroaryl, heteroarylalkyl, heterocycloalkyl, and heterocycloalkylalkyl.

In certain embodiments, the GLS1i is one as disclosed in US 2017/0174661, published Jun. 22, 2017.

In certain embodiments, the GLS1i is one as disclosed in WO2013/078123 or *Mol Cancer Ther* 2014; 13:890-901.

In certain embodiments, the GLS-1 inhibitor is of Formula A1,

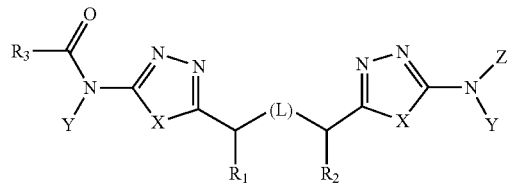

(A1)

or a pharmaceutically acceptable salt thereof, wherein:

L represents $CH_2SCH_2$, $CH_2CH_2$, $CH_2CH_2CH_2$, $CH_2$, $CH_2S$, $SCH_2$, $CH_2NHCH_2$, $CH=CH$, or cyclopropyl, preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;

X, independently for each occurrence, represents S, O or $CH=CH$, preferably S or $CH=CH$, wherein any hydrogen atom of a CH unit may be replaced by alkyl;

Y, independently for each occurrence, represents H or $CH_2O(CO)R_7$;

$R_7$, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or $R_3(CO)$;

$R_1$ and $R_2$ each independently represent H, alkyl, alkoxy or hydroxy;

$R_3$, independently for each occurrence, represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$;

$R_4$ and $R_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;

$R_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; and $R_8$, $R_9$ and $R_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H.

In certain embodiments, the GLS1i is one as disclosed in WO2014/078645.

In certain embodiments, the GLS-1 inhibitor is of Formula A2,

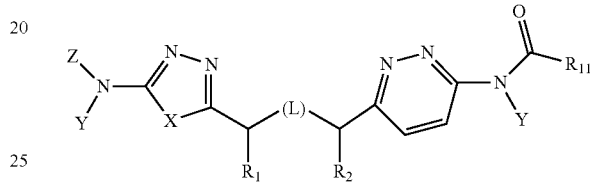

(A2)

or a pharmaceutically acceptable salt thereof, wherein:

L represents $CH_2SCH_2$, $CH_2CH_2$, $CH_2CH_2CH_2$, $CH_2$, $CH_2S$, $SCH_2$, $CH2NHCH_2$, $CH=CH$, or cyclopropyl, preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;

X represents S, O or $CH=CH$, preferably S or $CH=CH$, wherein any hydrogen atom of a CH unit may be replaced by alkyl;

Y, independently for each occurrence, represents H or $CH_2O(CO)R_7$;

$R_7$, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or $R_3(CO)$;

$R_1$ and $R_2$ each independently represent H, alkyl, alkoxy or hydroxy;

$R_3$ represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$;

$R_4$ and $R_5$ each independently for each occurrence represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;

$R_6$ represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;

R$_8$, R$_9$ and R$_{10}$ each independently for each occurrence represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or R$^8$ and R$^9$ together with the carbon to which they are attached, form a carbocyclic or heterocyclic ring system, wherein any free hydroxyl group may be acylated to form C(O)R$_7$, and wherein at least two of R$_8$, R$_9$ and R$_{10}$ are not H;

R$_{11}$ represents aryl, arylalkyl, aryloxy, aryloxyalkyl, heteroaryl, heteroarylalkyl, heteroaryloxy, or heteroaryloxyalkyl, wherein the aryl or heteroaryl ring is substituted with either —OCHF$_2$ or —OCF$_3$ and is optionally further substituted, or R$_{11}$ represents C(R$_{12}$)(R$_{13}$)(R$_{14}$), N(R$_4$)(R$_{14}$) or OR$_{14}$, wherein any free hydroxyl group may be acylated to form C(O)R$_7$;

R$_{12}$ and R$_{13}$ each independently respresent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R$_7$, and wherein both of R$^{12}$ and R$_{13}$ are not H; and R$_{14}$ represents aryl, arylalkyl, aryloxy, aryloxyalkyl, heteroaryl, heteroarylalkyl, heteroaryloxy, or heteroaryloxyalkyl, wherein the aryl or heteroaryl ring is substituted with either —OCHF$_2$ or —OCF$_3$ and is optionally further substituted.

In certain embodiments, the GLS1i is one as disclosed in WO2014/079011.

In certain embodiments, the GLS-1 inhibitor is of Formula A3,

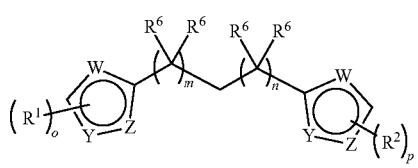

or a pharmaceutically acceptable salt thereof, wherein:

X is C$_3$-C$_7$ cycloalkylene;

each W, Y and Z is independently —S—, —CH=, —O—, —N=, or —NH—, provided that at least one of W, Y and Z is not —CH=;

each R$_1$ and R$_2$ is independently —NH$_2$, —N(R$_3$)—C(O)—R$_4$, —C(O)—N(R$_3$)—R$_4$, N(R$_3$)—C(O)—O—R$_4$, —N(R$_3$)—C(O)—N(R$_3$)—R$_4$ or —N(R$_3$)—C(O)—SR$_4$;

each R$_3$ is independently hydrogen, C$_{1-6}$ alkyl or aryl;

each R$_4$ is independently C$_{1-6}$ alkyl, aryl, heteroaryl, aralkyl, heteroaralkyl, cycloalkyl, cycloalkylalkyl, heterocyclylalkyl, or heterocyclyl, each of which is substituted with 0-3 occurrences of R$_5$;

each R$_5$ is independently C$_{1-6}$ alkyl, C$_{1-6}$ alkoxy, C$_{1-6}$ thioalkoxy, C$_{1-6}$ haloalkyl, C$_{3-7}$ cycloalkyl, C$_{3-7}$ cycloalkylalkyl, aryl, heteroaryl, aralkyl, heteroaralkyl, heterocyclylalkyl, heterocyclyl, cyano, halo, oxo, —OH, —OCF$_3$, —SO$_2$—C$_{1-6}$ alkyl, —NO$_2$, —N(R$_7$)—C(O)—C$_{1-6}$ alkyl, —N(R$_7$)$_2$, or two adjacent R$_5$ moieties, taken together with the atoms to which they are attached form a heterocyclyl;

each R$_6$ is independently hydrogen, fluoro, C$_{1-6}$ alkyl, —OH, —NH$_2$, —NH(CH$_3$), N(CH$_3$)$_2$, or C$_{1-6}$ alkoxy;

each R$_7$ is independently hydrogen or C$_{1-6}$ alkyl;

m is 0, 1, or 2;

n is 0, 1, or 2;

o is 1, 2 or 3; and p is 1, 2 or 3.

In certain embodiments, the GLS1i is one as disclosed in WO2014/081925A1 or US2014/0142081A1.

In certain embodiments, the GLS-1 inhibitor is of Formula A4,

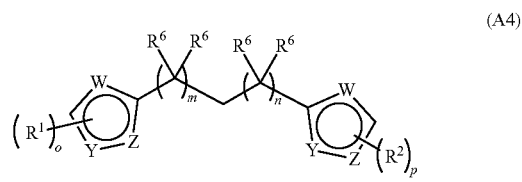

or a pharmaceutically acceptable salt thereof, wherein:

X is a bond —S— —S(O)—, —SO$_2$— —CH=CH— —NH— or —C(O)—;

each W, Y and Z is independently —S—, —CH=, —CH=CH—, —CH=CR1-, —CR1=CR1-, —O—, —N=, or —NH—, provided that (1) for each ring at least one of W, Y and Z is not-CH= and (2) when one of W is-S— and the Y in the same ring is N, then the Z in the same ring is not-CH=;

each R$_1$ and R$_2$ is independently C$_{1-6}$ alkylene-R$_4$, —N(R$_3$)—R$_4$, —N(R$_3$)—C(O)—R$_4$, C(O)—N(R$_3$)—R$_4$, —N(R$_3$)—C(O)—O—R$_4$, —N(R$_3$)—C(O)—N(R$_3$)—R$_4$, —O—C(O)—N(R$_3$)—R$_4$, —N(R$_3$)C(O)—C$_{1-6}$ alkylene-C(O)—R$_4$, —N(R$_3$)—C(O)—C$_{1-6}$ alkylene-N(R$_3$)—C(O)—R$_4$ or —N(R$_{3a}$)—C(O)CH2-N(R$_3$)—C(O)—R$_4$;

each R$_3$ and R$_{3a}$ is independently hydrogen, C$_{1-6}$ alkyl or aryl;

each R$_4$ is independently C$_{1-6}$ alkyl, C$_{1-6}$ alkenyl, aryl, heteroaryl, aralkyl, heteroaralkyl, heterocyclylalkyl, heterocyclyl, cycloalkyl or cycloalkylalkyl, each of which is substituted with 0-3 occurrences of R$_5$, or two adjacent R$_5$ moieties, taken together with the atoms to which they are attached form a heterocyclyl, heteroaryl, cycloalkyl or aryl;

each R$_5$ is independently oxo (=O), C$_{1-6}$ alkyl, C$_{1-6}$ haloalkyl, C$_{1-6}$ alkoxy, cyano, halo, —OH, —SH, —OCF$_3$, —SO$_2$C$_{1-6}$ alkyl, —NO$_2$, —N(R$_7$)—C(O)—C$_{1-6}$ alkyl, —N(R$_6$)$_2$, —O—C(O)C$_{1-6}$ alkyl, C$_{3-7}$ cycloalkyl, (C$_{3-7}$ cycloalkyl)alkyl, aryl, aryloxy, —C(O)-aryl, heteroaryl, aralkyl, heteroaralkyl, heterocyclylalkyl or heterocyclyl, wherein each aryl, heteroaryl or heterocyclyl is further substituted with 0-3 occurrences of R$_7$;

each R$_6$ is independently hydrogen, fluoro, OH or C$_{1-6}$ alkyl;

each R$_7$ is independently hydrogen, C$_{1-6}$ alkyl, —OH, —SH, cyano, halo, —CF$_3$, OCF$_3$, —SO$_2$—C$_{1-6}$ alkyl, —NO$_2$, —N(R$_7$)—C(O)—C$_{1-6}$ alkyl, —N(R$_6$)$_2$ or C$_{1-6}$ alkoxy;

m is 1, 2 or 3;

n is 1, 2 or 3; provided that when X is bond, the sum of m and n is from 3 to 6 and when X is —S—, —S(O)—, —SO$_2$, —CH=CH—, or —C(O)—, the sum of m and n is from 2 to 4;

o is 1, 2 or 3; and p is 1, 2 or 3.

Pharmaceutical Compositions

While it may be possible for the compounds disclosed herein to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Routes of Administration

Oral Administration

The compounds of the present invention may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Parenteral Administration

Compounds of the present invention may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present invention may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Rectal, Buccal, and Sublingual Administration

Suppositories for rectal administration of the compounds of the present invention can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Administration by Inhalation

For administration by inhalation, compounds may be conveniently delivered from an insufflator, nebulizer pressurized packs or other convenient means of delivering an aerosol spray or powder. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the invention may be prepared by any of the well-known techniques of pharmacy, such as effective formulation and administration procedures. Preferred unit dosage formulations are those containing an effective dose, as herein recited, or an appropriate fraction thereof, of the active ingredient. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

Methods of Treatment

The methods of the invention can be used to treat any subject in need of treatment. Examples of subjects or patients include, but are not limited to, humans, monkeys, deer, camel, pets and companion animals, including, but not limited to, dogs, cats, horses, rabbits, and guinea pigs; livestock, including, but not limited to, cows, buffalo, bison, mules, goats, sheep and pigs. In one embodiment, the subject is a human.

The methods of the invention provide for the administration of a glutaminase inhibitor or a compound that inhibits glutathione production for the treatment of several diseases and disorders. The glutaminase inhibitor may, for example, be a GLS-1 inhibitor or a selective inhibitor of GLS-1. In one embodiment, the glutaminase inhibitor is compound 1, compound 2 or a compound selected from Table 1.

In one embodiment the disorder is a cancer, including, but not limited to, bladder cancer, bone marrow cancer, breast cancer, cancer of the central nervous system, cervical cancer, colon cancer, endometrial cancer, cancer of the gastric system, head and neck cancer, kidney cancer, leukemia, liver cancer, lung cancer, lymphoma, muscle cancer, ovarian cancer, pancreatic cancer, prostate cancer, skin cancer, thyroid cancer, or a variant thereof. In another embodiment, the disorder is ovarian cancer, including, but not limited to, high-grade serous ovarian cancer (HGSOC) or nonresectable or relapsed HGSOC.

In one embodiment, provided herein is a method of treatment of a disease or disorder comprising the administration of a glutaminase inhibitor or a compound that inhibits glutathione production. Examples of diseases or disorders include, but are not limited to, cancers, as provided above. Examples of glutaminase inhibitors include, but are not limited to, GLS-1 inhibitors or a selective inhibitor of GLS-1 as provided above.

In another embodiment, provided herein is a glutaminase inhibitor or a compound that inhibits glutathione production for use as a medicament. For example, provided herein is a glutaminase inhibitor or a compound that inhibits glutathione production for use as a medicament in the treatment of a disease or disorder, including, but not limited to, the treatment of various cancers. In certain embodiments, the cancer is ovarian cancer, including, but not limited to, HGSOC or nonresectable or relapsed HGSOC. The glutaminase inhibitor may, for example, be a GLS-1 inhibitor or a selective inhibitor of GLS-1 as provided above.

In yet another embodiment, provided herein is the use of a glutaminase inhibitor or a compound that inhibits glutathione production for use in the manufacture of a medicament. For example, provided herein is the use of a glutaminase inhibitor or a compound that inhibits glutathione production for use in the manufacture of a medicament for the treatment of a disease or disorder, including, but not limited to, the treatment of various cancers. In certain embodiments, the cancer is ovarian cancer, including, but not limited to, HGSOC or nonresectable or relapsed HGSOC. The glutaminase inhibitor may, for example, be a GLS-1 inhibitor or a selective inhibitor of GLS-1. In one embodiment, the glutaminase inhibitor is compound 1, compound 2 or a compound selected from Table 1.

In some embodiments, the cancer is bladder cancer, bone marrow cancer, breast cancer, cancer of the central nervous system, cervical cancer, colon cancer, endometrial cancer, cancer of the gastric system, head and neck cancer, kidney cancer, leukemia, liver cancer, lung cancer, lymphoma, muscle cancer, ovarian cancer, pancreatic cancer, prostate cancer, skin cancer, thyroid cancer, or a variant thereof. In certain embodiments, the cancer is ovarian cancer, including, but not limited to, HGSOC.

In some embodiments, methods described herein are used to treat a disease or condition comprising administering to a subject in need thereof a therapeutically effective amount of a GLS-1 inhibitor or pharmaceutically acceptable salt thereof, wherein the condition is cancer which has developed resistance to chemotherapeutic drugs and/or ionizing radiation. In certain embodiments, the cancer is ovarian cancer, including, but not limited to, HGSOC or nonresectable or relapsed HGSOC. The glutaminase inhibitor may, for example, be a GLS-1 inhibitor or a selective inhibitor of GLS-1. In one embodiment, the glutaminase inhibitor is compound 1, compound 2 or a compound selected from Table 1.

Combinations and Combination Therapy

The compounds of the present invention can be used, alone or in combination with other pharmaceutically active compounds, to treat conditions such as those disclosed hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, provided herein is a glutaminase inhibitor or a compound that inhibits glutathione production for use as a medicament in combination with one or more additional pharmaceutically active compounds. In yet another embodiment, provided herein is the use of a glutaminase inhibitor or a compound that inhibits glutathione production and one or more additional pharmaceutically active compounds for the manufacturing of a medicament. For example, provided herein is the use of a glutaminase inhibitor or a compound that inhibits glutathione production and one or more additional pharmaceutically active compounds for the manufacturing of a medicament for the treatment of a disease or disorder, including, but not limited to, the treatment of various cancers.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is chosen from anti-cancer drugs, anti-proliferative drugs, and anti-inflammatory drugs. In certain embodiments, the anti-cancer agent is chosen from a platinum-based agent, a taxane-based agent, an immunotherapy, and a targeted therapy. In certain embodiments, the targeted therapy is an inhibitor of MEK kinase, HSP90, CDK4, or the mTOR pathway.

Glutaminase inhibitors, e.g., GLS-1 inhibitors, disclosed herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a glutaminase inhibitor compound, as disclosed herein, in combination with another therapeutic agent. By way of example only, the therapeutic effectiveness of a glutaminase inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a glutaminase inhibitor, e.g., a GLS-1 inhibitor, as disclosed herein) may be administered in any order, or simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, a glutaminase inhibitor, e.g., a GLS1i, is optionally used in combination with procedures that provide additional benefit to the patient. A glutaminase inhibitor and any additional therapies are optionally administered before, during, or after the occurrence of a disease or condition, and the timing of administering the composition containing a glutaminase inhibitor, e.g., a GLS1i, varies in some embodiments. Thus, for example, a glutaminase inhibitor is used as a prophylactic and is administered continuously to subjects with a propensity to develop conditions or diseases in order to prevent the occurrence of the disease or condition. A glutaminase inhibitor, e.g., a GLS1i, and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A glutaminase inhibitor, e.g., a GLS1i, disclosed herein can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in the treatment or attenuation of cancer and neoplastic diseases a glutaminase inhibitor may be optimally used together with one or more of the following non-limiting examples of anti-cancer agents, including, but not limited to:

1) inhibitors or modulators of a protein involved in one or more of the DNA damage repair (DDR) pathways such as:
   a. PARP1/2, including, but not limited to: olaparib, niraparib, rucaparib;
   b. checkpoint kinase 1 (CHK1), including, but not limited to: UCN-01, AZD7762, PF477736, SCH900776, MK-8776, LY2603618, V158411, and EXEL-9844;
   c. checkpoint kinase 2 (CHK2), including, but not limited to: PV1019, NSC 109555, and VRX0466617;
   d. dual CHK1/CHK2, including, but not limited to: XL-844, AZD7762, and PF-473336;
   e. WEE1, including, but not limited to: MK-1775 and PD0166285;
   f. ATM, including, but not limited to KU-55933,
   g. DNA-dependent protein kinase, including, but not limited to NU7441 and M3814; and
   h. Additional proteins involved in DDR;
2) Inhibitors or modulators of one or more immune checkpoints, including, but not limited to:
   a. PD-1 inhibitors such as nivolumab (OPDIVO), pembrolizumab (KEYTRUDA), pidilizumab (CT-011), and AMP-224 (AMPLIMMUNE);
   b. PD-L1 inhibitors such as Atezolizumab (TECENTRIQ), Avelumab (Bavencio), Durvalumab (Imfinzi), MPDL3280A (Tecentriq), BMS-936559, and MEDI4736;
   c. anti-CTLA-4 antibodies such as ipilimumab (YERVOY) and CP-675,206 (TREMELIMUMAB);
   d. inhibitors of T-cell immunoglobulin and mucin domain 3 (Tim-3);
   e. inhibitors of V-domain Ig suppressor of T cell activation (Vista);
   f. inhibitors of band T lymphocyte attenuator (BTLA);
   g. inhibitors of lymphocyte activation gene 3 (LAG3); and
   h. inhibitors of T cell immunoglobulin and immunoreceptor tyrosine-based inhibitory motif domain (TIGIT);
3) telomerase inhibitors or telomeric DNA binding compounds;
4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;
5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);
6) anti-metabolites, including, but not limited to: cladribine (LEUSTATIN), cytarbine, (ARA-C), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), and raltitrexed;
7) antimitotics, which are often plant alkaloids and terpenoids, or derivateves thereof including but limited to: taxanes such as docetaxel (TAXITERE), paclitaxel (ABRAXANE, TAXOL), *vinca* alkaloids such as vincristine (ONCOVIN), vinblastine, vindesine, and vinorelbine (NAVELBINE);
8) topoisomerase inhibitors, including, but not limited to: amsacrine, camptothecin (CTP), genisten, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VUMON), mitoxantrone (NOVANTRONE), and etoposide (EPOSIN);
9) DNA replication inhibitors, including, but not limited to: fludarabine (FLUDARA), aphidicolin, ganciclovir, and cidofovir;
10) ribonucleoside diphosphate reductase inhibitors, including, but not limited to: hydroxyurea;

11) transcription inhibitors, including, but not limited to: actinomycin D (dactinomycin, COSMEGEN) and plicamycin (mithramycin);
12) DNA cleaving agents, including, but not limited to: bleomycin (BLENOXANE), idarubicin,
13) cytotoxic antibiotics, including, but not limited to: actinomycin D (dactinomycin, COSMEGEN),
14) aromatase inhibitors, including, but not limited to: aminoglutethimide, anastrozole (ARIMIDEX), letrozole (FEMARA), vorozole (RIVIZOR), and exemestane (AROMASIN);
15) angiogenesis inhibitors, including, but not limited to: genistein, sunitinib (SUTENT), and bevacizumab (AVASTIN);
16) anti-steroids and anti-androgens, including, but not limited to: aminoglutethimide (CYTADREN), bicalutamide (CASODEX), cyproterone, flutamide (EULEXIN), nilutamide(NILANDRON);
17) tyrosine kinase inhibitors, including, but not limited to: imatinib (GLEEVEC), erlotinib (TARCEVA), lapatininb (TYKERB), sorafenib (NEXAVAR), and axitinib (INLYTA);
18) mTOR inhibitors, including, but not limited to: everolimus, temsirolimus (TORISEL), and sirolimus;
19) monoclonal antibodies, including, but not limited to: trastuzumab (HERCEPTIN) and rituximab (RITUXAN);
20) apoptosis inducers such as cordycepin;
21) protein synthesis inhibitors, including, but not limited to: clindamycin, chloramphenicol, streptomycin, anisomycin, and cycloheximide;
22) antidiabetics, including, but not limited to: metformin and phenformin;
23) antibiotics, including, but not limited to:
    a. tetracyclines, including, but not limited to: doxycycline;
    b. erythromycins, including, but not limited to: azithromycin;
    c. glycylglycines, including, but not limited to: tigecyline;
    d. antiparasitics, including, but not limted to: pyrvinium pamoate;
    e. beta-lactams, including, but not limited to the penicillins and cephalosporins;
    f. anthracycline antibiotics, including, but not limited to: daunorubicin and doxorubicin;
    g. other antibiotics, including, but not limited to: chloramphenicol, mitomycin C, and actinomycin;
24) antibody therapeutical agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and
25) other agents, such as *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon;
leucovorin; leuprolide (LUPRON); levamisole; lonidamine; mesna; metformin; mitotane (o,p'-DDD, LYSODREN); nocodazole; octreotide (SANDOSTATIN); perifosine;
porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone;

Where a subject is suffering from or at risk of suffering from an inflammatory condition, a glutaminase inhibitor, e.g., a GLS1i, compound disclosed herein is optionally used together with one or more agents or methods for treating an inflammatory condition in any combination. Therapeutic agents/treatments for treating an autoimmune and/or inflammatory condition include, but are not limited to any of the following examples:

1) corticosteroids, including but not limited to cortisone, dexamethasone, and methylprednisolone;
2) nonsteroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE);
3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN);
4) CD20 blockers, including but not limited to rituximab (RITUXAN);
5) Tumor Necrosis Factor (TNF) blockers, including but not limited to etanercept (ENBREL), infliximab (REMICADE) and adalimumab (HUMIRA);
6) interleukin-1 receptor antagonists, including but not limited to anakinra (KINERET);
7) interleukin-6 inhibitors, including but not limited to tocilizumab (ACTEMRA);
8) interleukin-17 inhibitors, including but not limited to AIN457;
9) Janus kinase inhibitors, including but not limited to tasocitinib; and
10) syk inhibitors, including but not limited to fostamatinib.

General Synthetic Methods for Preparing Compounds

Compounds useful in the methods of the present invention can be prepared using methods that are known to one of skill in the art. Starting materials used to prepare compounds of the present invention are commercially available or can be prepared using routine methods known in the art.

Biological Assays

The following are examples of biological assays useful with the methods of the invention. The assays provided herein are not limiting and other assays now known, or later discovered, by one of skill in the art can be used for the same purpose as the assays provided below.

Compounds disclosed herein are active as GLS-1 inhibitors. Certain compounds disclosed in Table 1 were synthesized and tested, and had IC50s of less than 100 nM.

Compounds disclosed herein are also active in inhibiting OVCAR8 cancer cell proliferation. Compounds disclosed in Table 1 were synthesized and tested, and had IC50s of less than 100 nM.

Glycerol Lysis Buffer Recipe

|  | Final Concentration |
|---|---|
| 2 ml 1M Tris-HCl pH 7.4 | 20 mM |
| 3 ml 5M NaCl | 150 mM |
| 15 ml 100% glycerol | 15% |
| 1 ml 100% Triton-X 100 | 1% |
| 79 ml Distilled Water | (100 ml total) |

To each 1 ml add before use: 100 ul 10% SDS, 5 µl 200 mM PMSF, 10 ul HALT Protease, 1 ul of Benzonase Cell Viability or Cell Proliferation Assay Cell Culture Media:

All cells were grown in RPMI-1640 (Gibco11875-119) with 2 mM Glutamine+10% FBS (Gibco16000-044) unless otherwise noted.

Cells were plated in black, 96-well Corning Costar 3603 at densities to allow for Log phase growth throughout the experiment (see table below) on Day 0. Cells were allowed to settle and attach overnight. Cells plated in triplicate for each concentration and control examined. On Day 1, media was removed from cells and replaced with RPMI-1640+10% Dialyzed FBS (Gibco26400-044) with indicated concentration of GLS-1 inhibitor (starting concentration 1 µM, diluted 1:3 to a final of 0.004 µM), 0.01% DMSO or 1 µM Staurosporine as indicated. Cells were incubated with compound or relevant controls for 72 hours. On Day 4, 72 hours after treatment, cells were analyzed by Cell Titer Glo (PromegaG7573) per manufacturer's instructions. Plates were read in luminescence mode on a PheraStarFS plate reader. Data was collected, replicates were averaged, standard deviations calculated and analyzed through nonlinear regression analysis with four (4) parameters to generate IC50s for each cell line tested.

| Cell Line | Cells Plated Per Well (96-well) |
|---|---|
| OVCAR8 | 2,500 |
| TOV21G | 2,000 |
| COV504 | 2,000 |
| ES-2 | 1,750 |
| MCAS | 1,000 |
| OV56 | 1,250 |
| OAW-42 | 4,000 |
| OVCAR429 | 1,250 |
| PA-1 | 1,000 |
| OVCAR432 | 1,000 |
| OVCAR420 | 2,000 |
| OVCAR433 | 1,250 |
| OVCAR5 | 1,000 |
| OV7 | 4,000 |
| SK-OV-3 | 1,250 |
| OV90 | 7,500 |
| OAW-28 | 4,000 |
| EFO27 | 1,250 |
| OV17R | 5,000 |
| IGROV1 | 2,000 |
| FUOV1 | 7,000 |
| EFO21 | 5,000 |
| OVCAR4 | 3,750 |
| A2780 | 4,000 |
| SW626 | 2,000 |

Analysis of Glutathione Levels:

Cells were plated in 96-well Corning Costar 3603 at 10,000 cells/well on Day 0. Cells were allowed to settle and attach overnight. Cells plated in triplicate for each concentration and control examined. On Day 1, media was removed from cells and replaced with RPMI-1640+10% Dialyzed FBS (Gibco26400-044) with indicated concentration of Compound 1 (starting concentration 1 uM, diluted 1:3 to a final of 0.004 uM), or 0.01% DMSO as indicated. Cells were incubated with compound or relevant controls for 24 hours. On Day 2, 24 hours after treatment, cells were analyzed by GSH-Glo (PromegaV6912) per manufacturer's instructions. Plates were read in luminescence mode on a PheraStarFS plate reader. Duplicate wells were plated and then stained with crystal violet in order to correct for differences in cell growth as described below.

GLS-1 Enzymatic Activity Assay

The following is a non-limiting example of an assay that may be used to evaluate the biological efficacy of compounds useful in the methods of the invention or to determine if a compound is a selective inhibitor of GLS-1.

The inhibition of purified recombinant human GAC by varying concentrations of inhibitors may be assessed via a dual-coupled enzymatic assay. The glutamate produced by the glutaminase reaction is used by glutamate oxidase to produce α-ketoglutarate, ammonia, and hydrogen peroxide. This hydrogen peroxide is subsequently used by horseradish peroxidase to produce resorufin in the presence of Amplex UltraRed. The assay buffer consisted of 50 mM HEPES (pH 7.4), 0.25 mM EDTA and 0.1 mM Triton X-100. GAC was incubated with potassium phosphate (10 minutes at room temperature) prior to incubation with inhibitor (10 minutes at room temperature). The final reaction conditions were as follows: 2 nM GAC, 50 mM potassium phosphate, 100 mU/mL glutamate oxidase (Sigma), 1 mM glutamine (Sigma), 100 mU/mL horseradish peroxidase (Sigma), 75 µM Amplex UltraRed (Life Technologies), and 1% (v/v) DMSO. The production of resorufin was monitored on a Perkin Elmer Envision plate reader (excitation 530 nm, emission 590 nm) either in a kinetics or endpoint mode (at 20 minutes). $IC_{50}$ values were calculated using a four-parameter logistic curve fit.

Target Engagement Assay

OVCA cells were plated in 96-well Corning Costar 3603 at 10,000 cells/well on Day 0. 24 h after plating, media was removed and replaced with media containing 1 µM Compound 1 or 0.01% DMSO (control). At 24 h, 100 µl of media was collected from each sample. Media was frozen at −80° C. after collection. One well for each condition was fixed and stained with crystal violet to normalize for cell number (see protocol below). All crystal violet samples were solubilized and used to normalize the collected data. Collected samples were analyzed for glutamine and glutamate content using the YSI2950 Bio-analyzer equipped with membranes that measure the relevant chemistries.

Crystal Violet Staining Protocol 500 mg crystal violet powder was combined with 35 ml 100% EtOH in sterile 50 ml tube until it dissolved. The mixture was transferred to a 1 L beaker, the tube washed out with $ddH_2O$, and $ddH_2O$ was added to the beaker to 500 ml final volume. The mixture was filter sterilized using a 0.45 µm filter. Media was removed and discarded (including wells without cells for background). 50 µL crystal violet stain+10% EtOH was added to the wells and stained for 10 min. The stain was removed from the wells and discarded into a waste container. Water was run in a large beaker or ice bucket and the plate was repeatedly rinsed in the water. The remaining liquid was shaken out into the sink. The plate was left upside down, uncovered for at least 5 hours to dry. Once completely dry, it was solubilized in 10% acetic acid by adding 100 µL to all stained wells. After 5 minutes, all wells were pipet mixed and after another 5 minutes read on Pherastar at OD 590 nm.

DNA Damage Staining and Quantification

OVCAR8 and OVCAR420 cells were seeded in 96-well Corning Costar 3603 plates and treated with 0.01% DMSO or 1 µM Compound 1 for 48 hours. Cells were then fixed using 4% Paraformaldehyde and permeabilized using 0.5% TritonX100. Fixed cells were stained with Anti-γH2AX, rabbit (Bethyl IHC-00059) (1:500) for 2 h at 37 C. The secondary antibody used was Alexa Fluor 546 donkey anti-rabbit (Invitrogen A10040) (1:150) simultaneously with Hoechst 33342, Trihydrochloride, Trihydrate (Invitrogen, H3570) (1:1000) for 1 h at 37 C. DNA damage was measured as a γH2AX signal per nucleus using PerkinElmer High Content Screening System Operetta with the Harmony software. First, nuclei were selected using Hoechst staining. Then, single cells were gated based on nucleus size and shape. Apoptotic and mitotic cells were excluded based on maximum Hoechst intensity in the nucleus. DNA damage foci were identified within the gated nuclei using the "find spots in Alexa 546 channel" analysis block. Finally, the total intensity of Alexa 546 within all "spots" in the nucleus, or the total number of spots in the nucleus, averaged per cell, was calculated.

Metabolomics Sample Preparation

OVCAR8 cells were plated at $3 \times 10^6$ cells per 10 cm dish and OVCAR429, IGROV1, and OVCAR4 were plated at $3.5 \times 10^6$ cells per 10 cm dish 24 hours (24 h) prior to treatment. Cells were treated on day zero (d.0) at time zero (t.0) with 0.01% DMSO, 1 µM, 100 nM, or 10 nM of Compound 1 for 24 h. On day 1 (d.1), 2 hours (2 h) prior to harvest, samples were washed with 5 mL media containing 10% dialyzed FBS. 10 mL of media was added to plates and plates were returned to the incubator for 2 h. Media was then aspirated from plates and 4 mL of 80% chilled MeOH (−80° C.) was immediately added. Plates were incubated at −80° C. for 15 minutes. Cells were then scraped with cell scraper to release cells while keeping plates on dry ice. The MeOH/cell lysate mixture was collected and transferred to conical tubes on dry ice. Tubes were centrifuged at full speed in 4° C. chilled centrifuge for 5 minutes. Supernatant was transferred to another set of conical tubes on dry ice by decanting. The remaining pellet was re-suspended in 500 µL of cold MeOH and the mixture was moved to a microcentrifuge tube. Microfuge tubes were spun at full speed for 5 minutes in 4° C. chilled microcentrifuge. Supernatant was transferred to conical tube with previously collected supernatant. This step was repeated 2 times. 1 mL of collected supernatant was transferred to pre-labeled sample/submission tubes and submit for drying by speedvac. Samples were then submitted to the Beth Israel Deaconess Medical Center Mass Spectrometry core facility for analysis by LC MS/MS using an Agilent SCIEX 5500 QTRAP to profile 258 metabolites (Yuan, M., et al. *Nature Protocols* 2012, 7(5) 872-81).

Metabolomics Sample Analysis

Differentially abundance analysis of metabolite levels was carried out using a moderated t-test function from Bioconductor's limma package (Smyth 2005). A normalization factor was applied to the metabolite peak data to account of variation in cell counts. The normalization factor was calculated by first defining a vector, Nmed, to be the median peak area for each metabolite across a set of samples. Next, for a sample i, a vector of fold-changes, FCi, is computed by dividing the metabolite peak areas by Nmed. The scaling factor for sample i was set as the median value of FCi. Significant changes in metabolite levels were defined an abundance change of a least 1.5 fold increase/decrease and t-test p-value $<=0.05$. The symbols were assigned according to the p-values with the following cutoffs: $+=p>0.005$ and $p<=0.05$, $*=p>0.00005$ and $p<=0.005$, $**=p<=0.00005$.

Gene Expression Analysis

Affymetrix U133 Plus2.0 microarrays were performed for each condition in triplicates. Robust multi-array average (RMA) method was used with default options (with background correction, quantile normalization, and log transformation) to normalize raw data from batches using R/Bioconductor's affy package (Irizarry et al 2003). Differentially expression analysis was carried out using a moderated t-test function from Bioconductor's limma package (Smyth 2005). A gene is called as differentially expressed if FDR corrected p-value is less than 0.05.

Analysis of Reactive Oxygen Species Production

One day prior to the experiment, OVCAR-8 and OVCAR420 cells were seeded in 6 well dishes (250,000 cells per well). The day of the experiment, cells were treated with 0.01% DMSO or 1 µM Compound 1 for 24 hours. The following day, an allocated well was treated with hydrogen peroxide for 20-30 minutes as a positive control for ROS generation. All wells were then stained with CM-H2DCFDA (5 µM, Life Technologies) for 30 minutes at 37° C., washed with 1×PBS, harvested by trypsinization, and re-suspended in 400 µl phenol-free RPMI medium. Cells were strained through a 40 µM cell strainer and analyzed using a flow cytometer (LSR Fortessa). Values displayed are fold changes compared to DMSO for mean fluorescence intensity of entire population.

EXAMPLES

Several embodiments of the present invention are provided in the following examples. The following examples are presented only by way of illustration and to assist one of ordinary skill in using the invention. The examples are not intended in any way to otherwise limit the scope of the invention.

Example 1. HGSOC Cell Lines are Differentially Sensitive to GLS Inhibition

To investigate the role of GLS in regulating HGSOC cell proliferation we first characterized a chemical probe designed to specifically inhibit GLS-1. We have confirmed that this tool compound (compound 1) is a potent inhibitor of GLS-1 ($IC_{50}$ 7.5 nM) in a coupled in vitro enzymatic assay (FIG. 1(*a*)). The inhibition of GAC by varying concentrations of compound 1 was assessed using a dual-coupled enzymatic assay (pH 7.4) containing 2 nM GAC, 50 mM potassium phosphate, 100 mU/mL glutamate oxidase, 1 mM glutamine, 100 mU/mL HRP and 75 µM Amplex Ultra Red. The production of resorufin was monitored on a Perkin Elmer Envision plate reader (excitation 530 nm, emission 590 nm) for 20 min.

In cells, the chemical probe inhibits the conversion of glutamine to glutamate; a measure of GLS-dependent activity (FIG. 1(*b*)-(*e*)). Target engagement can be measured after treatment with compound 1. As a measure of compound activity on GLS in cells, the conversion of glutamine to glutamate was measured in extracellular media samples treated with DMSO (control) or compound 1. Treatment of cells for 24 hours with compound 1 prevented the conversion of glutamine to glutamate (as measured by the ratio of glutamate to glutamine). This inhibition was evident by a decrease in the GLU:GLN ratio in cell lysates.

Figure 1A:
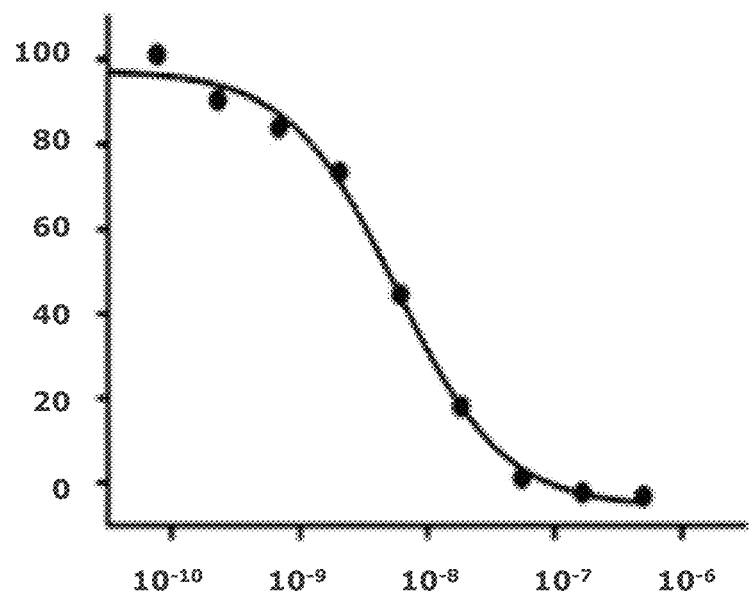
FIG. 1(a) shows the potent and specific inhibition of glutaminase-1 (GLS-1) by compound 1. x-axis=concentration of compound 1 (M); y-axis=activity (relative to control); $IC_{50}$=5.8 nm.
Figure 1B:
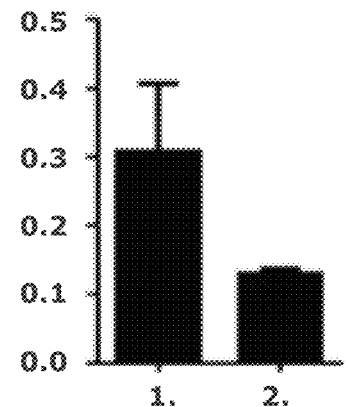
FIG. 1(b) shows that target engagement for OVCAR8 can be measured after treatment with compound 1. The glutamate: glutamine ratio is depicted for DMSO (1.) and Compound 1 (2.).
Figure 1C:
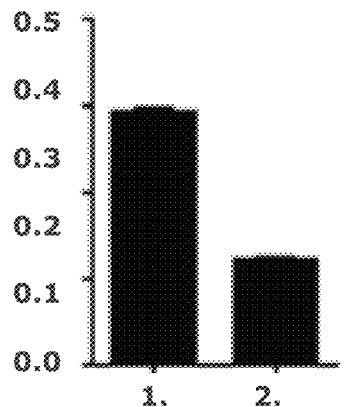
FIG. 1(c) shows that target engagement for OVCAR429 can be measured after treatment with compound 1. The glutamate: glutamine ratio is depicted for DMSO (1.) and Compound 1 (2.).
Figure 1D:
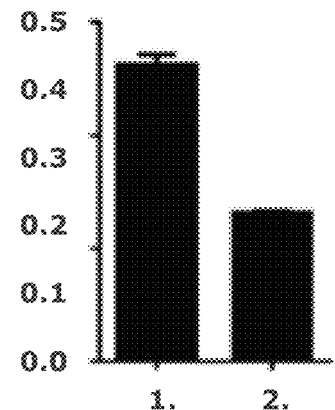
FIG. 1(d) shows that target engagement for IGROV1 can be measured after treatment with compound 1. The glutamate: glutamine ratio is depicted for DMSO (1.) and Compound 1 (2.).
Figure 1E:
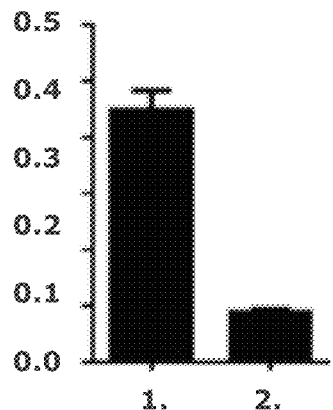
FIG. 1(e) shows that target engagement for OVCAR4 can be measured after treatment with compound 1. The glutamate: glutamine ratio is depicted for DMSO (1.) and Compound 1 (2.).
Figure 2A:
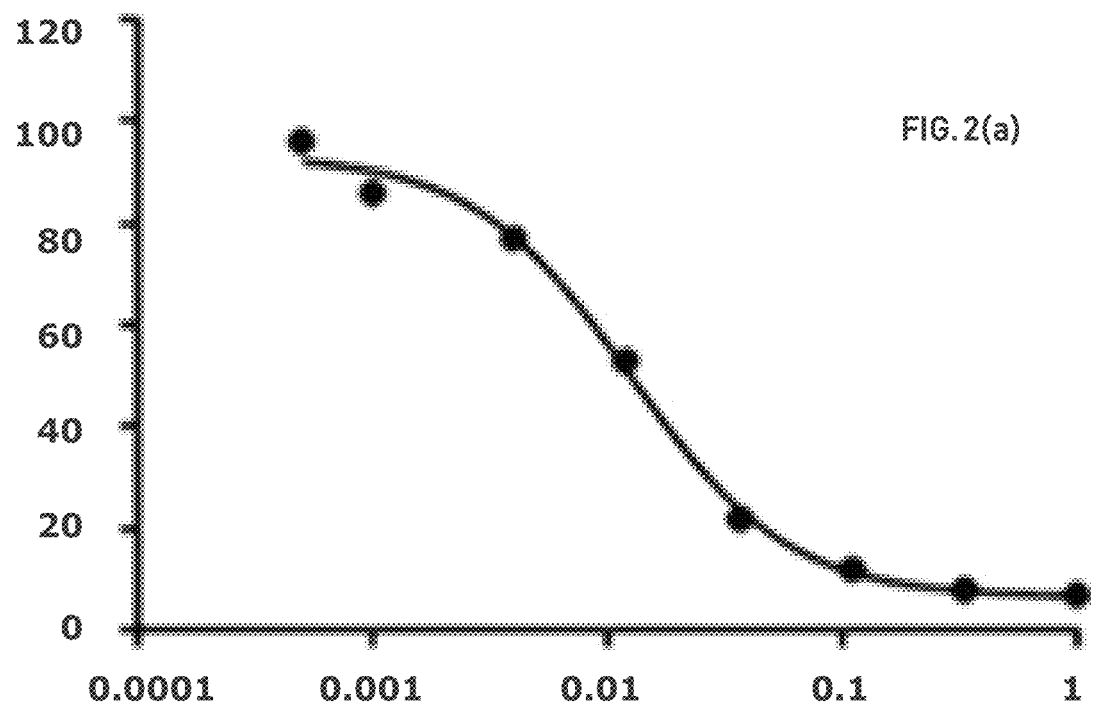
FIG. 2(a) shows that differential response to GLS-1 inhibition is observed in OVCA lines. Viability (relative to DMSO) of OVCAR8 is plotted as a function of Compound 1 concentration (uM). $IC_{50}$=0.013 uM.
Figure 2B:
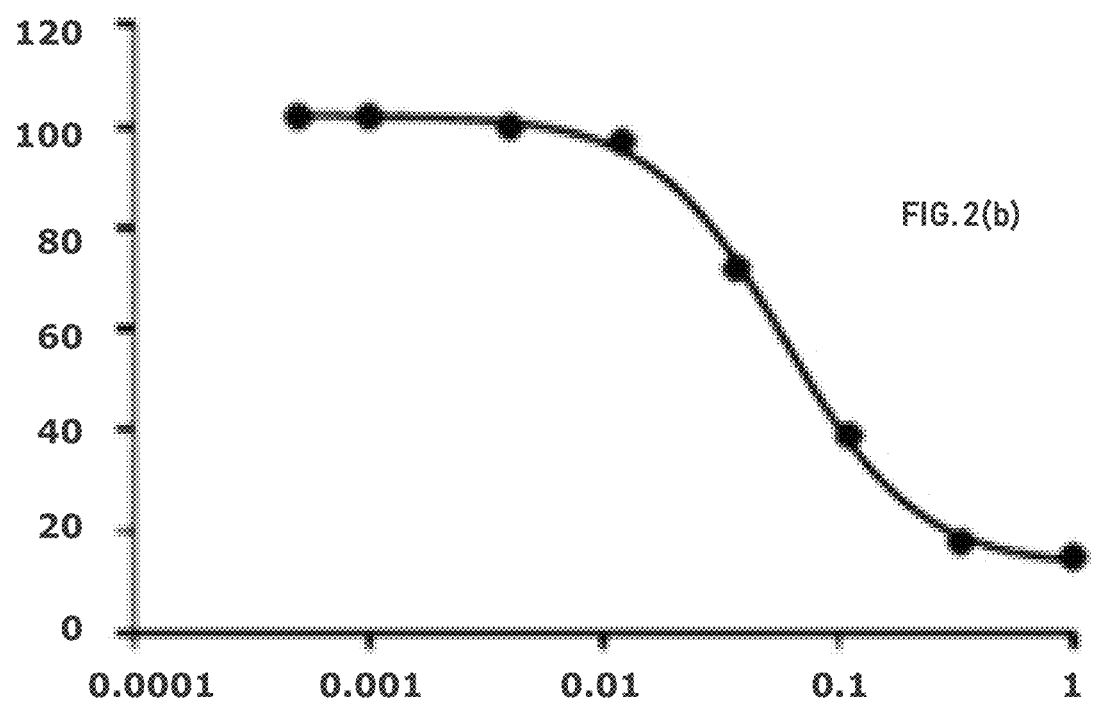
FIG. 2(b) shows that differential response to GLS-1 inhibition is observed in OVCA lines. Viability (relative to DMSO) of OVCAR429 is plotted as a function of Compound 1 concentration (uM). $IC_{50}$=0.059 uM.
Figure 3A:
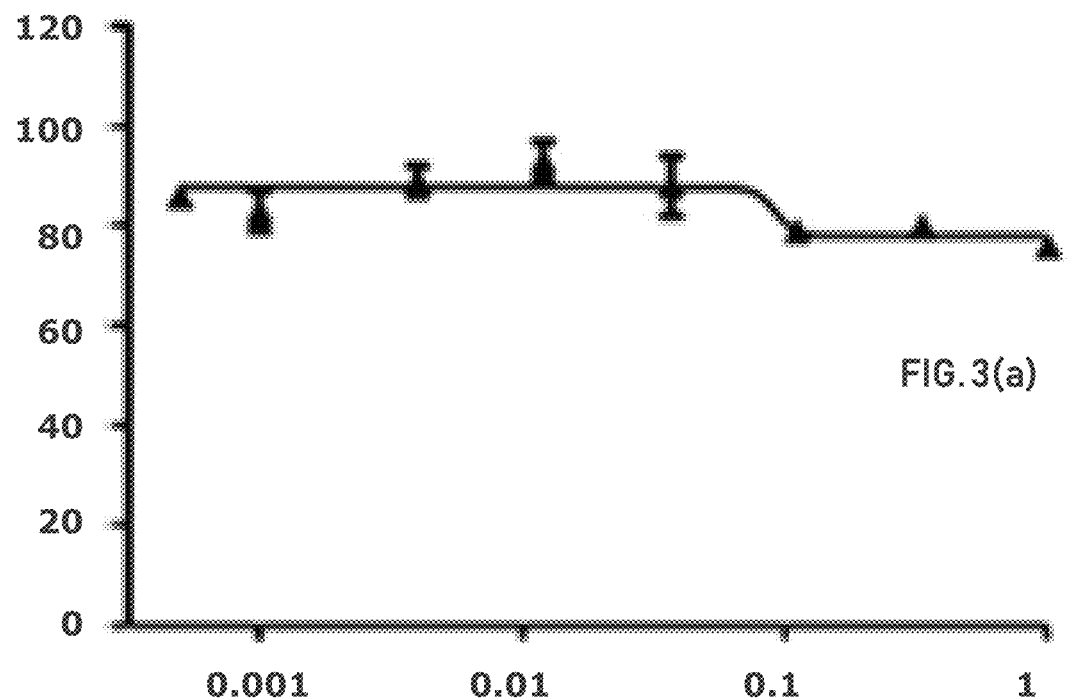
FIG. 3(a) shows that differential response to GLS-1 inhibition is observed in OVCA lines. Viability (relative to DMSO) of IGROV1 is plotted as a function of Compound 1 (uM).
Figure 3B:
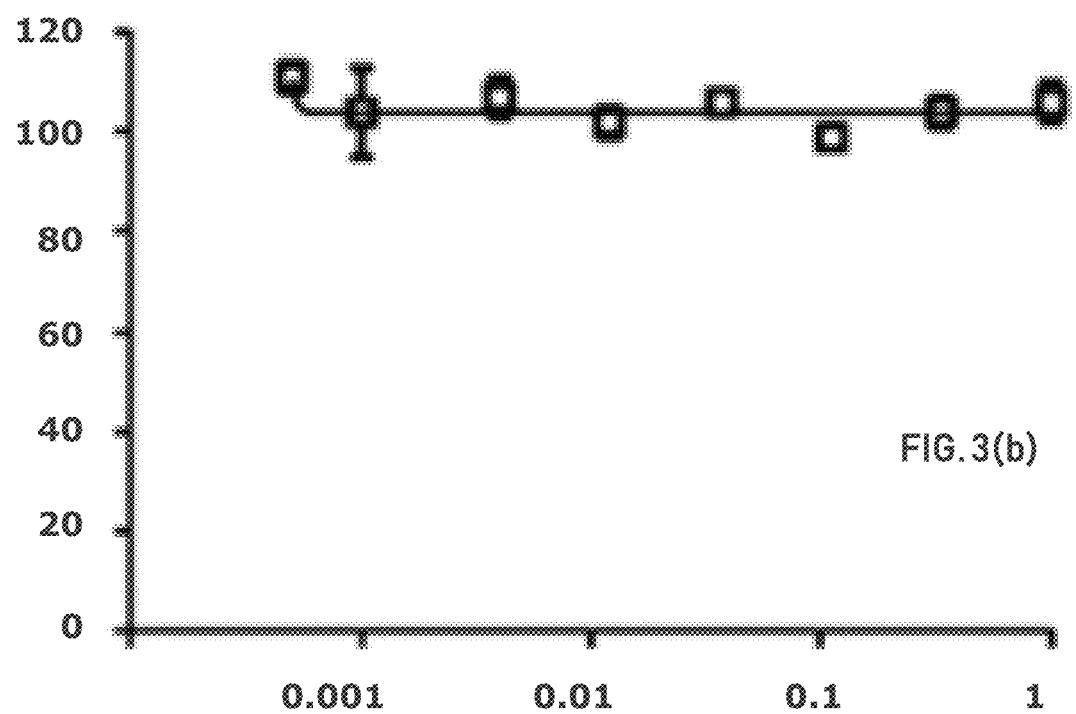
FIG. 3(b) shows that differential response to GLS-1 inhibition is observed in OVCA lines. Viability (relative to DMSO) of OVCAR4 is plotted as a function of Compound 1 concentration (uM).

Interestingly, while all cell lines tested showed a decrease in GLS activity, only some cells showed an anti-proliferative response after GLS1i treatment (FIG. 2(a)-(b)). Differential response to GLS-1 inhibition is observed in OVCA lines. OVCAR8, OVCAR429, OVCAR4, and IGROV1 cell lines were treated with compound 1 and 72 hour viability was analyzed. OVCAR8 and OVCAR429 show nM sensitivity to GLS1i, and OVCAR4 and IGROV1 cells are resistant to treatment with GLS1i.

Figure 4:
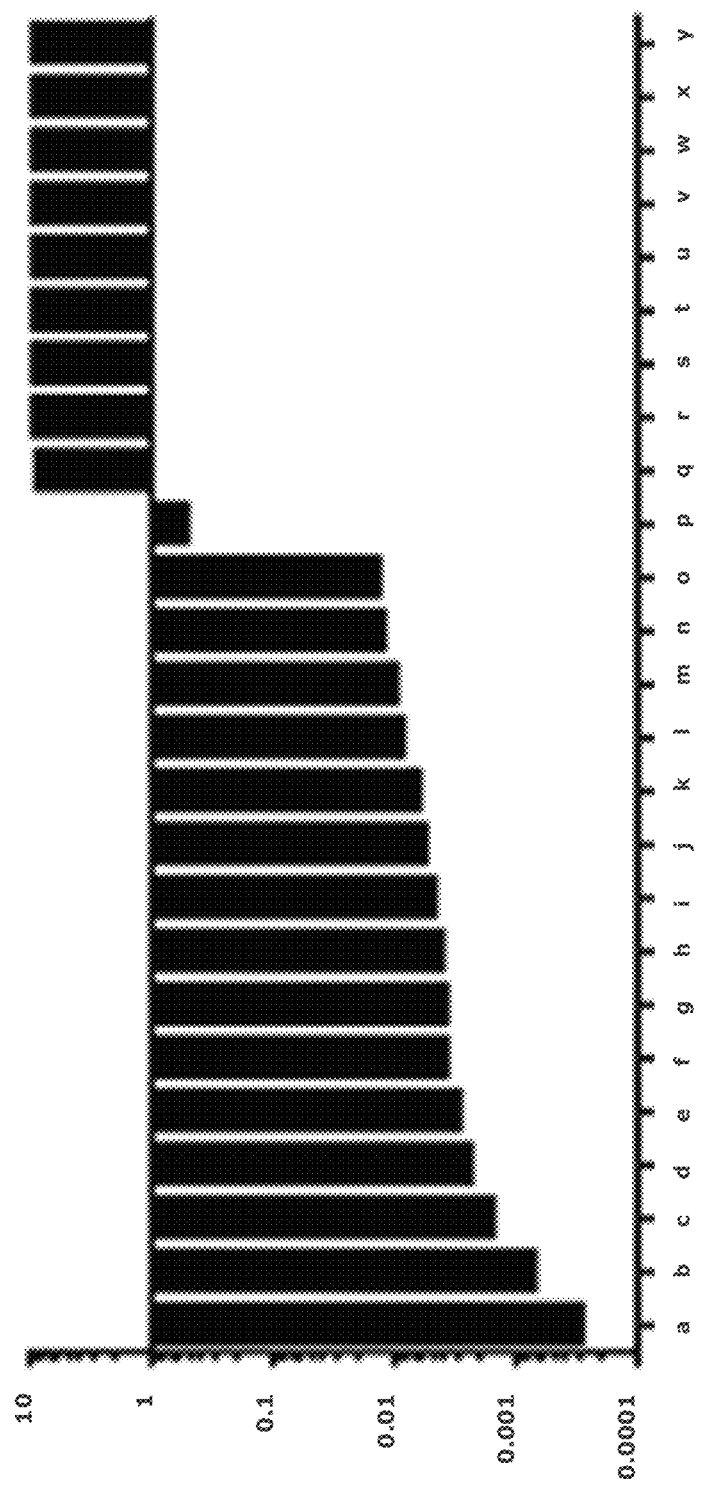
FIG. 4 shows a waterfall plot depicting differential response to GLS-1 inhibition in a broad panel of OVCA lines. IC50 (uM) at 72 h is plotted for several cell lines. A subset of OVCA lines show low nM sensitivity to GLSi while others do not show any response.

The potential therapeutic benefit of GLS-1 inhibition in HGSOC was also investigated. Through a cell screening campaign (conducted as described above in the Cell Viability or Cell Proliferation Assay), a subpopulation of HGSOC cell lines that are hypersensitive to GLS-1 inhibition ($IC_{50}$ 2D viability ≤50 nM in "responder"; >10 µM in "non-responder") was identified. FIG. 4 shows a waterfall plot depicting differential response to GLS-1 inhibition in broad panel of OVCA lines: (a) OVCAR8; (b) TOV21G; (c) COV504; (d) ES-2; (e) MCAS; (f) OV56; (g) OAW-42; (h) OVCAR429; (i) PA-1; (j) OVCAR432; (k) OVCAR420; (l) OVCAR433; (m) OVCAR5; (n) OV7; (o) SKOV3; (p) OV90; (q) OAW-28; (r) EF027; (s) OV17R; (t) IGROV-1; (u) FUOV-1; (v) EFO21; (w) OVCAR4; (x) A2780; (y) SW626. These cell lines were treated with GLS1i in a dose response and viability was analyzed after 72 hours. A subset of OVCA lines show low nM sensitivity to GLS1i while others do not show any response. Interestingly, nearly all lines (responders and non-responders) show an acute depletion of intracellular glutamate levels indicative of glutaminase inhibition. This suggests that a subset of HGSOC cell lines have a specific dependence on glutamine metabolism for survival.

Example 2. GLS Inhibition Alters Redox Balance in Responder Cell Lines

Figure 5:
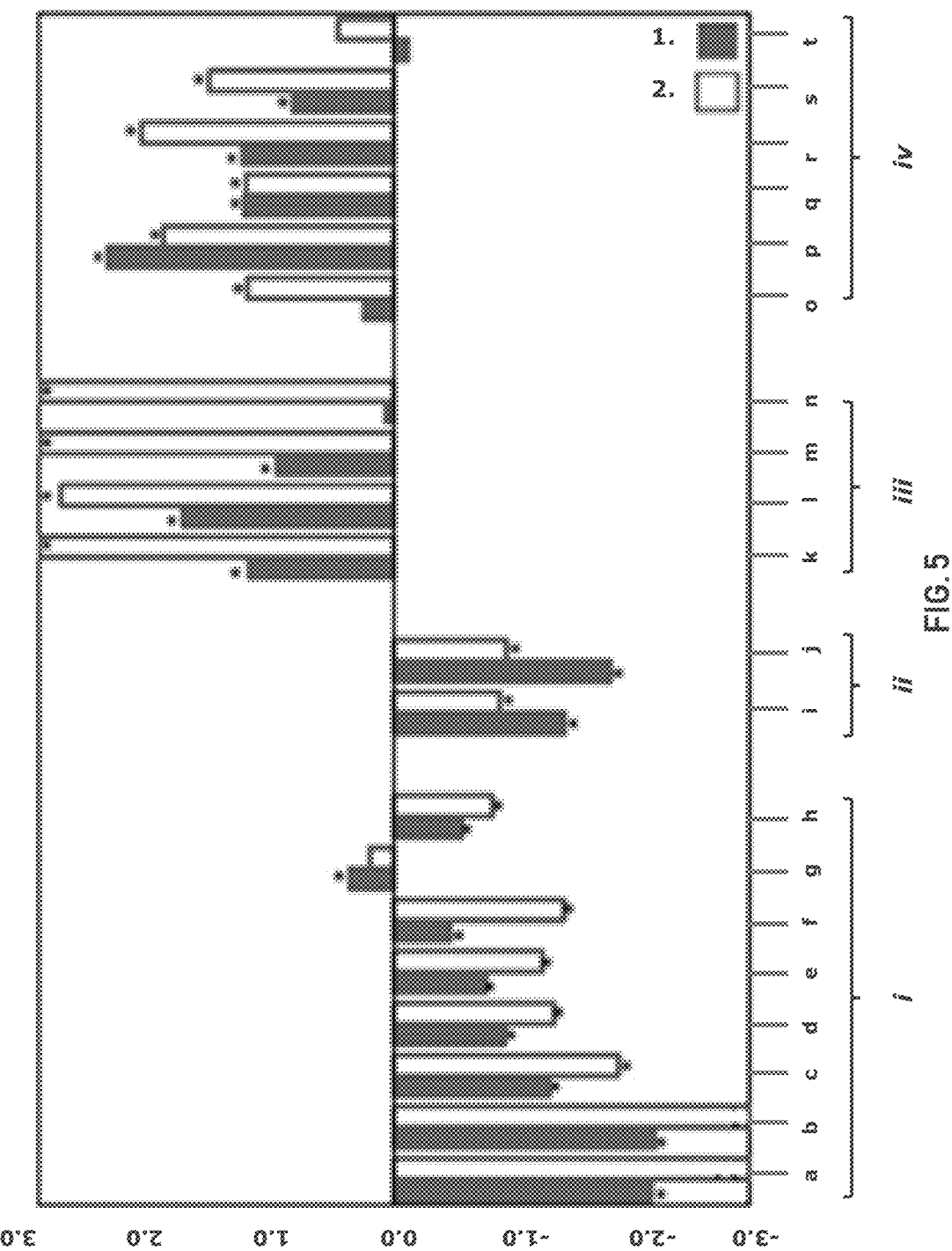
FIG. 5 shows that metabolic alterations result in an altered redox balance in response to treatment of OVCAR429 (1.) and OVCAR8 (2.) with compound 1. Metabolite fold change (log 2) is plotted for various metabolites involved in: TCA (i), glutamate synthesis (ii); purine (iii); and pentose phosphate (iv) pathways.
Figure 6:
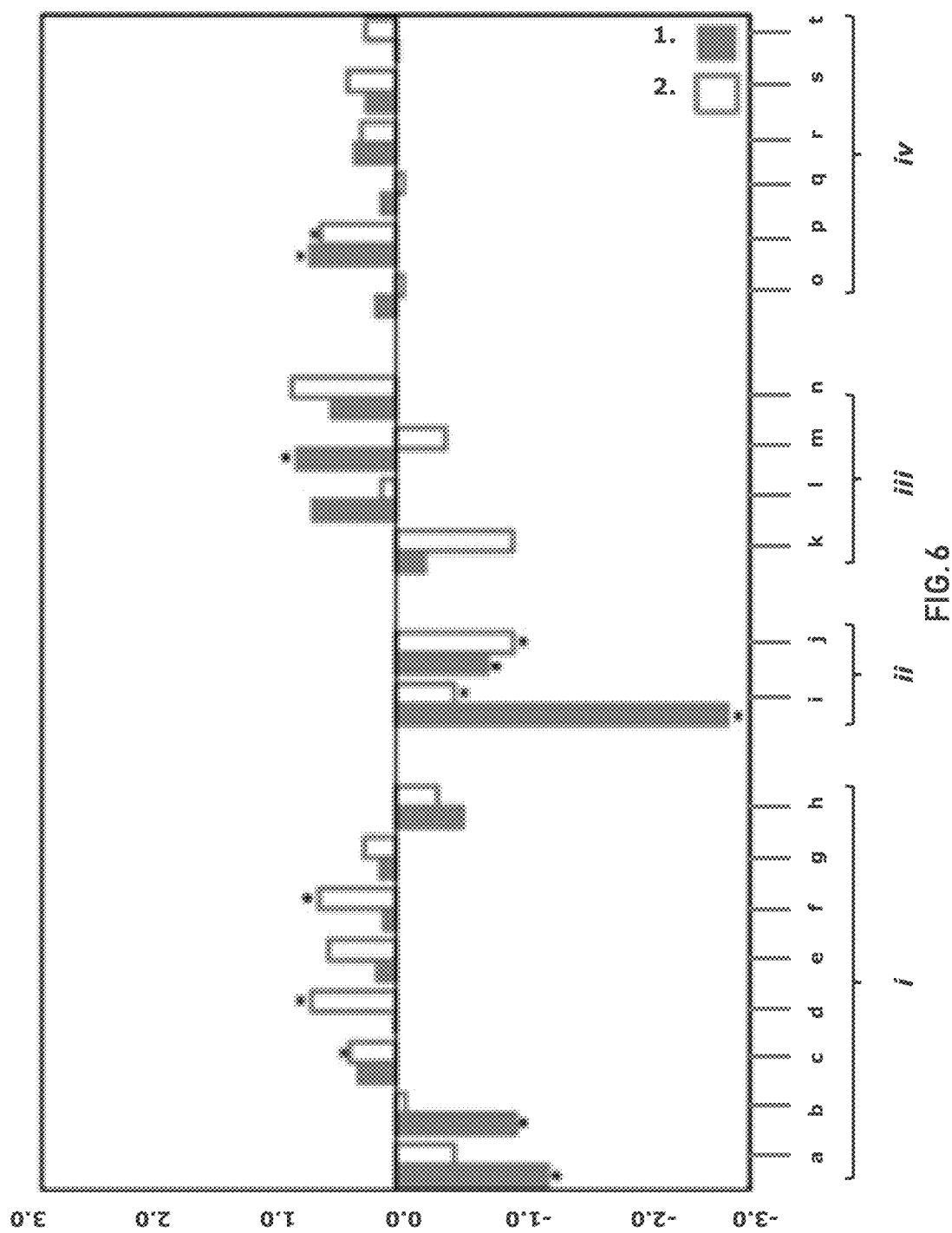
FIG. 6 shows that metabolic alterations result in an altered redox balance in response to treatment of OVCAR4 (1.) and IGROV1 (2.) with compound 1. Metabolite fold change (log 2) is plotted for various metabolites involved in: TCA (i), glutamate synthesis (ii); purine (iii); and pentose phosphate (iv) pathways.

To interrogate the role of glutaminase in the regulation of tumor metabolism, targeted liquid chromatography-tandem mass spectrometry (LC-MS/MS) metabolomic studies were performed to comprehensively characterize metabolic alterations following GLS-1 inhibition (FIGS. 5 and 6). Metabolites quantified are: (TCA) (a) fumarate; (b) maleate; (c) oxaloacetate; (d) citrate; (e) citrate-isocitrate; (f) isocitrate; (g) alpha-ketoglutarate; (h) succinate; (glutamate synthesis) (i) alanine; (j) aspartate; (purines) (k) AICA ribonucleotide (AICAR); (l) inosine monophosphate (IMP); (m) inosine; (n) hypoxanthine; (pentose phosphate) (o) ribose 5-phosphate (R5P); (p) sedoheptulose-7-phosphate (S7P); (q) sedoheptulose-1,7-bisphosphate (SBP); (r) glyceraldehyde 3-phosphate (GAP); (s) dihydroxyacetone phosphate (DHAP); (t) erythrose 4-phosphate (E4P). This analysis revealed that GLS-1 inhibition in "responder" cell lines induced significant metabolic changes involving multiple pathways, the most significant of which are intermediates in the TCA cycle.

Consistent with the role of glutamine in regulating intracellular redox balance, GLS-1 inhibition decreased the effective concentration of glutathione, and induced activity of the pentose phosphate and ribose salvage pathways. Interestingly, changes in these metabolic pathways were muted in "non-responder" HGSOC lines, confirming a differential addiction to glutamine. However, one common response across cell lines was activation of metabolic pathways designed to replenish glutamate pools in cells through aspartate and alanine metabolism, suggesting a possible compensatory mechanism sufficient for the survival of "non-responder" cell lines when challenged with GLS-1 inhibition.

OVCAR8, OVCAR429, OVCAR4, and IGROV1 cells treated with 1 µM compound 1 for 24 hours were subjected to global metabolic profiling after isolation of lysates by methanol extraction. Changes in metabolite levels reflected an accumulation of glutamine in cells after GLS-1 inhibition accompanied by a decrease in TCA cycle activity; likely due to decreased glutamine anaplerosis. Additionally, decreases in free nucleotide pools were seen. These decreased metabolic activities were accompanied by an increase in pentose phosphate pathway activity, presumably to attempt to maintain redox balance in the absence of glutathione derived from the GLS-dependent breakdown of glutamine to glutamate, and activation of a ribose salvage pathway in response to compound 1 treatment, suggesting that cells are attempting to maintain nucleotide and thiol pools in response to decreased glutaminolysis. It should be noted that these metabolic changes are muted or absent in non-responder lines treated with compound 1. Interestingly, several metabolites which serve as alternative starting points for glutamate synthesis were decreased across all samples. This is possibly an alternative mechanism to produce glutamate void of the glutamine to glutamate conversion by GLS.

Example 3. GLS Inhibition Induces ROS and DNA Damage in OVCA Cells

GLS-dependence is driven by addiction to glutamine-dependent, glutathione-mediated redox maintenance in OVCA responder cell lines. Metabolic profiling coupled with the differential sensitivity of HGSOC cell lines (see Metabolomics Sample Preparation and Analysis protocols described above) suggested an important role for glutamine-derived glutathione in regulating redox balance. Consistent with this hypothesis, GLS-1 inhibition induced a significant decrease in intracellular glutathione and a concurrent increase in reactive oxygen species (FIGS. 7 and 8) in responder lines. Glutathione levels are decreased after treatment with compound 1 in responder cell lines—GSH levels were analyzed in cell lines after treatment with compound 1. As seen in FIG. 7, GSH levels were significantly decreased in OVCAR420, OVCAR429, and OVCAR8 cells after 24 hours of treatment (1 µM). A representative non-responder line, OVCAR4, does not show a significant decrease in GSH levels after GLS-1 inhibition, suggesting that these cells have alternate mechanisms for maintaining redox balance.

As seen in FIG. 8, loss of GSH after GLS-1 inhibition leads to an accumulation of intracellular reactive oxygen species (ROS). Cells were analyzed for accumulation of intracellular ROS after 48 h treatment with compound 1 by staining with $CM-H_2DCFDA$ (an indicator of general oxidative stress) and analysis by flow cytometry. For each condition, calculation of mean fluorescence intensity allows for the comparison of ROS accumulation between control and treated samples. Shown are responder cells: (a) OVCAR420; (b) OVCAR429, with GFP-A on the x-axis, and count on the y-axis. Treatment of responder cells with compound 1 (1 µM) for 48 hours induces an accumulation of ROS that correlates with the depletion of the GSH pool from cells.

GLS-1 inhibition causes cell cycle arrest. Cells were analyzed for cell cycle state using a standard BrdU incorporation assay. As seen in FIGS. 9 and 10, after 24 hours of treatment with GLS ii, responder cell lines showed an accumulation of cells in G1, with a sever depletion of cells undergoing active DNA replication in S-phase.

GLS-1 inhibition induces oxidative stress that leads to accumulation of DNA damage. HGSOC cells treated with either DMSO or compound 1 for 48 hours were stained with Hoechst's Stain (nuclei) and an antibody to γH2AX (DNA damage) and then analyzed by high-content imaging. γH2AX foci were counted and quantified per nuclei. As seen in FIG. 11, quantification (bar plot shown) reveals that treatment with compound 1 induces DNA damage in multiple responder cell lines. Moreover, we observed an accumulation of γH2AX foci, a marker of DNA damage, and the likely cause of anti-proliferative effects observed upon GLS-1 inhibition (FIG. 11).

Application of exogenous GSH to responder cell lines rescues compound 1-induced proliferation defects. OVCAR420 and OVCAR429 cells were treated with compound 1 at the indicated doses in a 72 h growth assay. At the same time, a subset of the cells treated with compound 1 received applications of cell-permeable GSH (once at the time of compound 1 treatment, once 24 h post-treatment and once 48 h post-treatment). Application of exogenous GSH rescued a significant portion of cell growth that was inhibited after treatment with compound 1. GLS1i-induced inhibition of cell proliferation were rescued upon treatment with exogenous glutathione (FIG. 12). Of note, neither glutathione depletion, ROS induction, nor an accumulation of DNA damage was observed in non-responder cell lines. This suggests that a subpopulation of HGSOC is sensitive to GLS-1 inhibitors due to a dependence on glutamine-derived glutathione for maintenance of redox balance. Concurrently, the metabolic profiles of non-responder lines suggested alternative mechanisms for maintaining redox balance.

Example 4. High ASNS Expression Provides an Alternative Source of Glutamate and Confers Resistance to GLS Inhibition Next, molecular insight into the differential response to GLS inhibition was sought. Given the observed metabolic shift towards pathways involved in replenishing pools of glutamate, attention was focused on glutamate-producing enzymes (FIG. 13) which might enable non-responder lines to maintain glutamate pools in the absence of GLS activity and consequently prevent depletion of glutathione.

Enzymes including asparagine synthetase (ASNS) which converts aspartate to asparagine and glutamate, as well as glutamic pyruvate transaminase (GPT2) which converts alpha-ketoglutarate to pyruvate and glutamate were interrogated.

Differential expression of glutamate producing enzymes was observed in responder and non-responder cell lines. OVCAR8, OVCAR429, OVCAR4, OVCAR420, and IGROV1 cells treated with 1 µM of compound 1 for 24 hours were subjected to gene profiling after RNA isolation. Data analysis revealed that several glutamate producing enzymes such as asparagine synthetase (ASNS) and glutamic pyruvate transaminase (GPT2), had higher expression in OVCA non-responder cell lines compared to responder cell lines. This finding correlates with metabolomics profiling data that showed changes in metabolites that are involved in glutamate synthesis.

Data from cell line profiling using reverse phase protein array (RPPA) or western blotting showed increased expression of ASNS in non-responder cell lines compared to responder lines (FIGS. 14(a) and (b), respectively). FIG. 14 depicts RPPA protein expression analysis in OVCA cell lines. ASNS protein expression was compared across a subset of responder and non-responder cell lines. Higher ASNS levels were observed in non-responder cell lines (unpublished data).

FIG. 15 shows Western blot of ASNS expression across a panel of OVCA cell lines. Cell lines screened are (a) A2780; (b) OVCAR4; (c) SW626; (d) OV56; (e) OVCAR420; (f) SKOV3 (g) OVCAR5; (h) OVCAR8; (i) OCAR429; (j) OAW-28; (k) FUOV1; (l) OVCAR3; (m) OAW-42; (n) TOV21G; (o) COV504; (p) OVCAR433; (q) OVCAR432; (r) OV7. ASNS is differentially expressed in OVCA cell lines. Cells that do not respond to GLS1i have higher ASNS expression compared to responder cell lines. These increased levels of ASNS likely enable cells to cope with GLS-1 inhibition by circumventing the requirement for glutamine-derived glutamate to maintain glutathione pools. These tumors are able to maintain glutathione levels through aspartate-derived glutamate, and would consequently be insensitive to GLS-1 inhibition.

Indeed, over-expression of ASNS in OVCAR8 cells, which normally express little to no ASNS, confers resistance to GLS1i (FIG. 16). OVCAR8 cells which respond to GLS1i and express no ASNS (FIG. 15) were transduced with virus encoding an ASNS construct (ASNS OE—cells treated with non-diluted viral supernatant, ASNS OE 1:10 or ASNS OE 1:100—cells treated with diluted viral supernatant, 1:10 or 1:100, respectively) and analyzed by western blot (FIGS. 16(a) and (b)). Cells over-expressing ASNS display resistance to compound 1 in a 72 hour proliferation assay (FIG. 16(c)). Taken together, these data suggest that high ASNS expression may act as a negative predictor of response to GLS1i.

Example 5. Immuno-Histochemical Staining can Determine ASNS Levels and Act as a Predictor of Response Immuno-histochemical (IHC) staining for ASNS confirms differential expression between responders and non-responders. In order to interrogate the feasibility of detecting ASNS expression levels in tumors, an IHC assay for ASNS was established. OVCAR4 cells, which express high levels of ASNS (FIGS. 14 and 15) were treated with a pool of siRNA directed at ASNS. After conditions were established to provide a significant decrease in ASNS expression (FIG. 17), cytoblocks of these cells were prepared and analyzed by IHC with several antibodies. FIG. 17 shows the confirmation of the knockdown of ASNS protein. OVCAR4 cells were transiently transfected with ASNS siRNA and non-targeting control (NTC) for 7 hours. After 72 hours, cells were lysed and protein isolated. ASNS knock-down efficiency was analyzed by western blot. Results show a significant decrease in ASNS protein expression after ASNS siRNA transfection.

An ASNS expression assay was optimized (FIGS. 17 (c) and (d)) and analysis of a panel of responder and non-responder cell lines illustrates that high ASNS scores are a negative predicator of response in HGSOC cell lines (FIG. 18). FIGS. 17 (c) and (d) shows ASNS immunohistochemical antibody validation. An aliquot of transfected cells used in FIG. 17, were collected, fixed, and processed for immunohistochemical staining. Results show a significant decrease in ASNS expression after ASNS siRNA transfection.

FIG. 18 shows that an IHC assay for ASNS expression can stratify response to GLS-1 inhibition. OVCAR420, OVCAR429, OVCAR4, and A2780 (FIG. 18 (a)-(d), respectively) were cultured normally and collected. Cell pellets were coded for blinded analysis and fixed into cytoblocks. Samples were prepared and analyzed by a blinded pathologist and scored according to ASNS expression. OVCAR429 (compound 1 IC50=76 nM) and OVCAR 420 (compound 1 IC50=59 nM) received scores of − and −/+ respectively on a 4 point graded scale (−, +, ++, +++). Thus, these cell lines were correctly predicted to respond to GLS-1 inhibition. Conversely, OVCAR4 (no response to compound 1) and A2780 (no response to compound 1) both received a blinded score of +++, indicating high ASNS expression and predicting no response to GLS-1 inhibition.

FIG. 19 shows that the tissue microarrays from ovarian cancer patients illustrate actionable ASNS-low populations in patients who are refractory to frontline therapies. Tissue microarrays collected from 134 ovarian cancer patients who had undergone frontline therapies including platinum-based treatments (Cisplatin/Carbotaxol/etc.) were stained for expression of ASNS. Example stains of TMA cores are shown in the boxes illustrating low versus high ASNS expression. A summary of scoring from these cores reveals 24% of patients with no ASNS expression, and another 44% with medium levels of ASNS expression. Both populations would be predicted to respond to GLS-1 inhibition.

Example 6. Glutaminase Inhibition Inhibits Tumor Growth in $ASNS_{low}$ Models of Ovarian Cancer As seen in FIG. 20(a), OVCAR-8 subcutaneous xenografts are sensitive to GLS-1 inhibition. OVCAR-8 cells were implanted subcutaneously into athymic mice and allowed to grow into an established tumor. Animals were then treated with compound 2, for three weeks (100 mpk, twice a day) by oral gavage. Treatment with compound 2 resulted in a significant tumor growth inhibition after three weeks of dosing.

FIG. 20(b) shows that glutaminase inhibition inhibits tumor progression in an orthotopic model of ovarian cancer. SK-OV-3 cells were injected into the intraperitoneal cavity of athymic nude mice and allow to grow for 7 days. At day 7, animals were treated with the in vivo tool compound to inhibit GLS-1 and animals were monitored for clinical disease signs. At day 21, vehicle treated animals began to exhibit signs of disease burden and all groups were sacrificed and tumor nodule weight was analyzed. Single-agent-treatment with compound 2 showed a robust reduction in combined nodule weight per animal compared to vehicle or paclitaxel alone (a current standard of care agent). Additionally, the combination of compound 2 and paclitaxel showed some added benefit when compared to compound 2 treatment alone.

As seen in FIG. 21, OVCAR-8 tumors demonstrate altered glutamine metabolism after GLS-1 inhibition. OVCAR-8 tumors were dosed for 1, 7 or 21 days and then harvested from animals. Tumor lysates were analyzed by mass spec for the presence of glutamine and glutamate. Tumors treated with GLS1i showed decreased ratios of glutamate to glutamine over the course of the three week experiment, confirming on-target activity of tool compounds.

FIG. 22 shows that glutaminase inhibition decreases proliferation in vivo. SK-OV-3 cells were implanted subcutaneously into athymic nude mice and animals were treated with compound 1 for 3 days. Tumors were harvested and then stained for phospho-histone H3, a marker of cell proliferation. Representative images are shown, along with a blinded pathologist's score indicating that treatment with single-agent glutaminase inhibitor decrease proliferation in vivo.

Example 7. Inhibition of Glutaminolysis and Tumor Growth in the Patient Derived Tumor Models While ASNS expression levels stratify responder and non-responder cell lines, we asked whether or not this would be an actionable patient population in the clinic and if patient-derived pre-clinical models would respond to GLSi. Consequently, we measured the expression of ASNS in tumor tissue isolated from patient-derived xenograft models of HGSOC via IHC.

Tissue sections collected from 25 ovarian cancer patients who had undergone frontline therapies including platinum-based treatments (cisplatin/carbotaxol/etc.) were stained for expression of ASNS, evaluated by a trained pathologist and graded on a 4-point scale with longitudinal sections graded by H&E staining for ovarian cancer subtyping via histo-pathological features (FIG. 23(a)). The first model, scored as a 0, was not included in further study.

| 1 | OV15398 |
| 2 | OV15577 |
| 3 | OV5297 |
| 4 | OV5304 |
| 5 | OV5308 |
| 6 | OV5383 |
| 7 | OV5385 |
| 8 | OV5387 |
| 9 | OV5392 |
| 10 | OV15631 |
| 11 | OV15841 |
| 12 | OV5296 |
| 13 | OV5309 |
| 14 | OV5390 |
| 15 | OV13950 |
| 16 | OV13951 |
| 17 | OV14702 |
| 18 | OV14871 |
| 19 | OV14972 |
| 20 | OV15123 |
| 21 | OV15209 |
| 22 | OV15612 |
| 23 | OV15696 |
| 24 | OV5397 |

Of these 24 remaining models, approximately sections 40% were ASNS-low (FIG. 24(a)). One specific model, OV5392, was verified as high-grade serous subtype and selected for a follow-up in vivo study.

The anti-tumor effects of Compound 2 were tested in vivo in an $ASNS^{low}$ HGSOC patient-derived xenograft (PDX) model using human tumor tissue that was identified through immunohistochemistry to be $ASNS^{low}$ and characterized through histological phenotyping to be of a high-grade serous subtype, implanted in to NOD/SCID mice.

Compound 2 inhibits tumor growth of an $ASNS^{low}$ PDX xenograft as a single agent in NOD/SCID mice (FIG. 23(b)). In this experiment, Compound 2, administered orally at a dose of 100 mg/kg, BID for 39 days inhibited tumor growth (TGI=50%, p<0.0001 for tumor volumes after treatment with Compound 2 vs vehicle control). These data illustrate that Compound 2 is able to inhibit glutaminolysis and tumor growth in the patient derived tumor models, and may have significant additional benefit in combinations with standard of care chemotherapy.

Example 8. Glutaminase Inhibitors Exhibit Anti-Proliferative Effects on Cells with Low Levels of ASNS As seen in FIG. 25, tumor cells are able to cope with oxidative stress during conditions of rapid proliferation by maintaining high levels of glutathione (Tumor Cell, top panel). When GLS-1 is inhibited in a subset of these cells (Treated Tumor Cell-Responder, middle panel), intracellular pools of glutamate are drastically reduced, and thus, glutathione synthesis is inhibited. This response shifts the redox balance of tumor cells causing an increase in ROS accumulation and DNA damage leading to cell death. In certain cases, even though GLS-1 is inhibited, tumor cells with high ASNS expression are still able to produce intracellular glutamate by converting aspartate to glutamate and asparagine. Consequently, these tumor cells are able to maintain redox homeostasis (Treated Tumor Cell-Non-responder, bottom panel).

This demonstrates that ASNS is a negative indicator of response to GLS-1 inhibition (FIG. 25) and a clinical assay to examine ASNS expression in pre-treatment biopsies could be used to stratify patients for GLS-1 inhibitor treatment in the clinic.

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method of treating cancer in a subject whose cancer cells express low levels of asparagine synthetase (ASNS), as defined by an Histophathology Score (H-score) of less than or equal to 100 by immunohistochemical staining, comprising administering a glutathione lowering agent to said subject.

2. A method of treating a cancer or a tumor in a subject in need of treatment comprising:
   (a) determining the concentration or expression of ASNS in said cancer or tumor of said subject; and
   (b) administering a glutathione lowering agent to said subject if the level of ASNS is quantified as an H-score of less than or equal to 100 by immunohistochemical staining.

3. The method of claim 2, wherein the tumor is cancerous.

4. A method of treating cancer in a subpopulation of subjects, characterized in that the level of ASNS in the subjects in the subpopulation is quantified as an H-score of less than or equal to 100 by immunohistochemical staining, comprising administering a glutathione lowering agent to said subject.

5. The method of claim 4, wherein the glutathione lowering agent is a glutaminase (GLS) inhibitor.

6. The method of claim 5, wherein the GLS inhibitor is selective for glutaminase-1 (GLS-1).

7. The method of claim 6, wherein the cancer is chosen from bladder cancer, bone marrow cancer, breast cancer, cancer of the central nervous system, cervical cancer, colon cancer, endometrial cancer, cancer of the gastric system, head and neck cancer, kidney cancer, leukemia, liver cancer, lung cancer, lymphoma, muscle cancer, ovarian cancer, pancreatic cancer, prostate cancer, skin cancer, thyroid cancer, or a variant thereof.

8. The method of claim 7, wherein the cancer is chosen from ovarian, skin, liver, prostate, breast, colon, lung, head and neck cancers or a lymphoma.

9. The method of claim 8, wherein the cancer is ovarian cancer.

10. The method of claim 9, wherein the ovarian cancer is high-grade serous ovarian cancer (HGSOC).

11. The method of claim 10, wherein the ovarian cancer is nonresectable or relapsed HGSOC.

12. The method of claim 9, further comprising administering another pharmaceutically active compound.

13. The method of claim 12, wherein said another pharmaceutically active compound is chosen from carboplatin, cisplatin, paclitaxel, and docetaxel.

14. The method of claim 13, wherein said another pharmaceutically active compound is chosen from carboplatin and cisplatin.

15. The method of claim 13, wherein said another pharmaceutically active compound is chosen from paclitaxel and docetaxel.

16. The method of claim 15, wherein said another pharmaceutically active compound is paclitaxel.

17. The method of claim 6, wherein the GLS-1 inhibitor binds an allosteric pocket on the solvent-exposed region of the GLS-1 dimer in the binding pocket present in the vicinity of Leu321, Phe322, Leu323, and Tyr394 from both monomers.

18. The method of claim 6, wherein the GLS-1 inhibitor has Formula I:

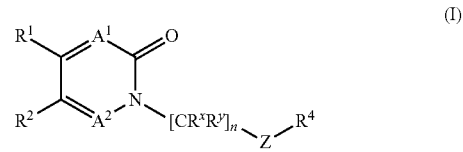

(I)

or a salt thereof, wherein:

n is chosen from 3, 4, and 5;

each $R^x$ and $R^y$ is independently chosen from alkyl, cyano, H, and halo, wherein two $R^x$ groups together with the atoms to which they are attached optionally form a cycloalkyl ring;

$A^1$ and $A^2$ are independently chosen from C—H, C—F, and N;

$R^1$ and $R^4$ are independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^3)_2C(O)R^3$, $C(R^3)_2C(O)N(R^3)_2$, $C(R^3)_2N(R^3)_2$, $C(R^3)_2NR^3C(O)R^3$, $C(R^3)_2NR^3C(O)OR^3$, $C(R^3)_2NR^3C(O)N(R^3)_2$, $C(R^3)_2NR^3S(O)R^3$, $C(R^3)_2NR^3S(O)_2R^3$, $N(R^3)_2$, $NR^3C(O)R^3$, $NR^3C(O)OR^3$, $NR^3C(O)N(R^3)_2$, $NR^3S(O)R^3$, $NR^3S(O)_2R^3$, $C(O)N(R^3)_2$, $S(O)N(R^3)_2$, $S(O)_2N(R^3)_2$, $C(O)R^3$, $SR^3$, $S(O)R^3$, and $S(O)_2R^3$, wherein each $R^1$ and $R^4$ may be optionally substituted with between 0 and 3 $R^z$ groups;

$R^2$ is chosen from alkyl, heterocycloalkyl, cyano, cycloalkyl, H, halo, and haloalkyl, wherein $R^1$ and $R^2$ together with the atoms to which they are attached optionally form an form an aryl, cycloalkyl, heteroaryl, or heterocycloalkyl ring, which may be optionally substituted with between 0 and 3 $R^z$ groups;

each $R^3$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^3$ may be optionally substituted with between 0 and 3 $R^z$ groups, wherein two $R^3$ groups together with the atoms to which they are attached optionally form an aryl, cycloalkyl, heteroaryl, or heterocycloalkyl ring, which may be optionally substituted with between 0 and 3 $R^z$ groups;

each $R^z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^6)_2$, $NR^6C(O)C(R^6)_3$, $NR^6C(O)OC(R^6)_3$, $NR^6C(O)N(R^6)_2$, $NR^6S(O)C(R^6)_3$, $NR^6S(O)_2C(R^6)_3$, $C(O)N(R^6)_2$, $S(O)N(R^6)_2$, $S(O)_2N(R^6)_2$, $C(O)C(R^6)_3$, $SC(R^6)_3$, $S(O)C(R^6)_3$, and $S(O)_2C(R^6)_3$;

each $R^6$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein two $R^6$ groups together with the atoms to which they are attached optionally form an aryl, cycloalkyl, heteroaryl, or heterocycloalkyl ring, which may be optionally substituted with between 0 and 3 $R^x$ groups; and Z is heteroaryl, which may be optionally substituted.

19. The method of claim 6, wherein the GLS-1 inhibitor has Formula II:

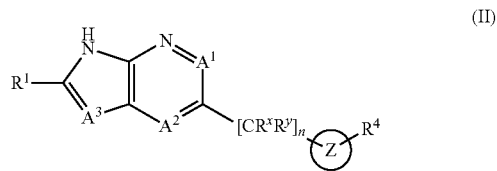

(II)

or a salt thereof, wherein:

n is chosen from 3, 4, and 5;

each $R^x$ and $R^y$ is independently chosen from alkyl, cyano, H, and halo, wherein two $R^x$ groups together with the atoms to which they are attached optionally form a cycloalkyl ring;

$A^1$ and $A^2$ are independently chosen from N and CH;

$A^3$ is chosen from N and $CR^2$;

$R^1$ is chosen from alkenyl, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, $C(O)N(R^3)_2$, and $C(O)C(R^3)_3$, wherein $R^1$ may be optionally substituted with between 0 and 3 $R^z$ groups, $R^2$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(O)N(R^3)_2$, $C(O)C(R^3)_3$, $C(O)OH$, $C(O)OC(R^3)_3$, wherein $R^1$ and $R^2$ together with the atoms to which they are attached optionally form an form an aryl, cycloalkyl, heteroaryl, or heterocycloalkyl ring, which may be optionally substituted with between 0 and 3 $R^z$ groups;

each $R^3$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^3$ may be optionally substituted with between 0 and 3 $R^z$ groups, wherein two $R^3$ groups together with the atoms to which they are attached optionally form an aryl, cycloalkyl, heteroaryl, or heterocycloalkyl ring, which may be optionally substituted with between 0 and 3 $R^z$ groups;

$R^4$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $N(R^3)_2$, $NR^3C(O)C(R^3)_3$, $NR^3C(O)OC(R^3)_3$, $NR^3C(O)N(R^3)_2$, $NR^3S(O)C(R^3)_3$, $NR^3S(O)_2C(R^3)_3$, $C(O)N(R^3)_2$, $S(O)N(R^3)_2$, $S(O)_2N(R^3)_2$, $C(O)C(R^3)_3$, $SC(R^3)_3$, $S(O)C(R^3)_3$, and $S(O)_2C(R^3)_3$, wherein $R^4$ may be optionally substituted with between 0 and 3 $R^z$ groups, each $R^z$ group is independently chosen from alkenyl, alkoxy, alkyl, aryl, arylalkyl, cyano, cycloalkyl, cycloalkylalkyl, halo, haloalkyl, heteroaryl, heteroarylalkyl, heterocycloalkyl, heterocycloalkylalkyl, hydroxyl, oxo, $N(R^6)_2$, $NR^6C(O)C(R^6)_3$, $NR^6C(O)OC(R^6)_3$, $NR^6C(O)N(R^6)_2$, $NR^6S(O)C(R^6)_3$, $NR^6S(O)_2C(R^6)_3$, $C(O)N(R^6)_2$, $S(O)N(R^6)_2$, $S(O)_2N(R^6)_2$, $C(O)C(R^6)_3$, $SC(R^6)_3$, $S(O)C(R^6)_3$, and $S(O)_2C(R^6)_3$;

each $R^6$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein two $R^6$ groups together with the atoms to which they are attached optionally form an aryl, cycloalkyl, heteroaryl, or heterocycloalkyl ring, which may be optionally substituted with between 0 and 3 $R^x$ groups; and Z is heteroaryl, which may be optionally substituted.

20. The method of claim 6, wherein the GLS-1 inhibitor has Formula IIIc:

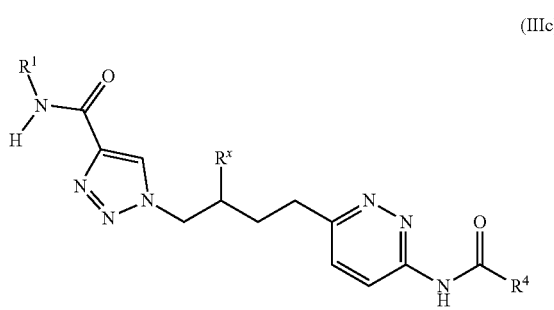

or a salt thereof, wherein:

$R^x$ is chosen from fluoro and H;

$R^1$ is chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ may be optionally substituted with one to three $R^z$ groups;

each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein $R^4$ may be optionally substituted with one to three $R^z$ groups;

each $R^z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; and each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^x$ groups.

21. The method of claim 6, wherein the GLS-1 inhibitor is selected from:

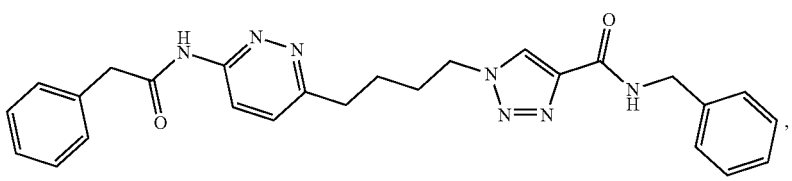

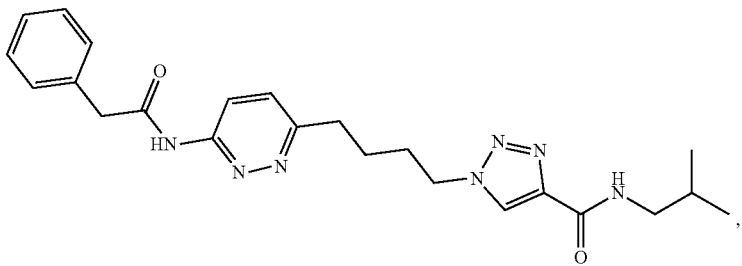

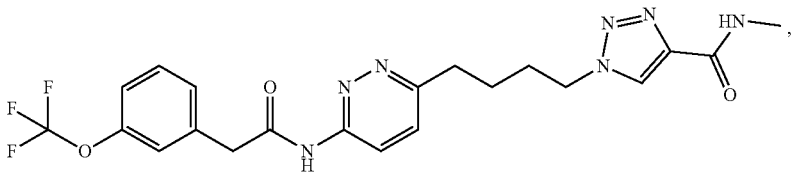

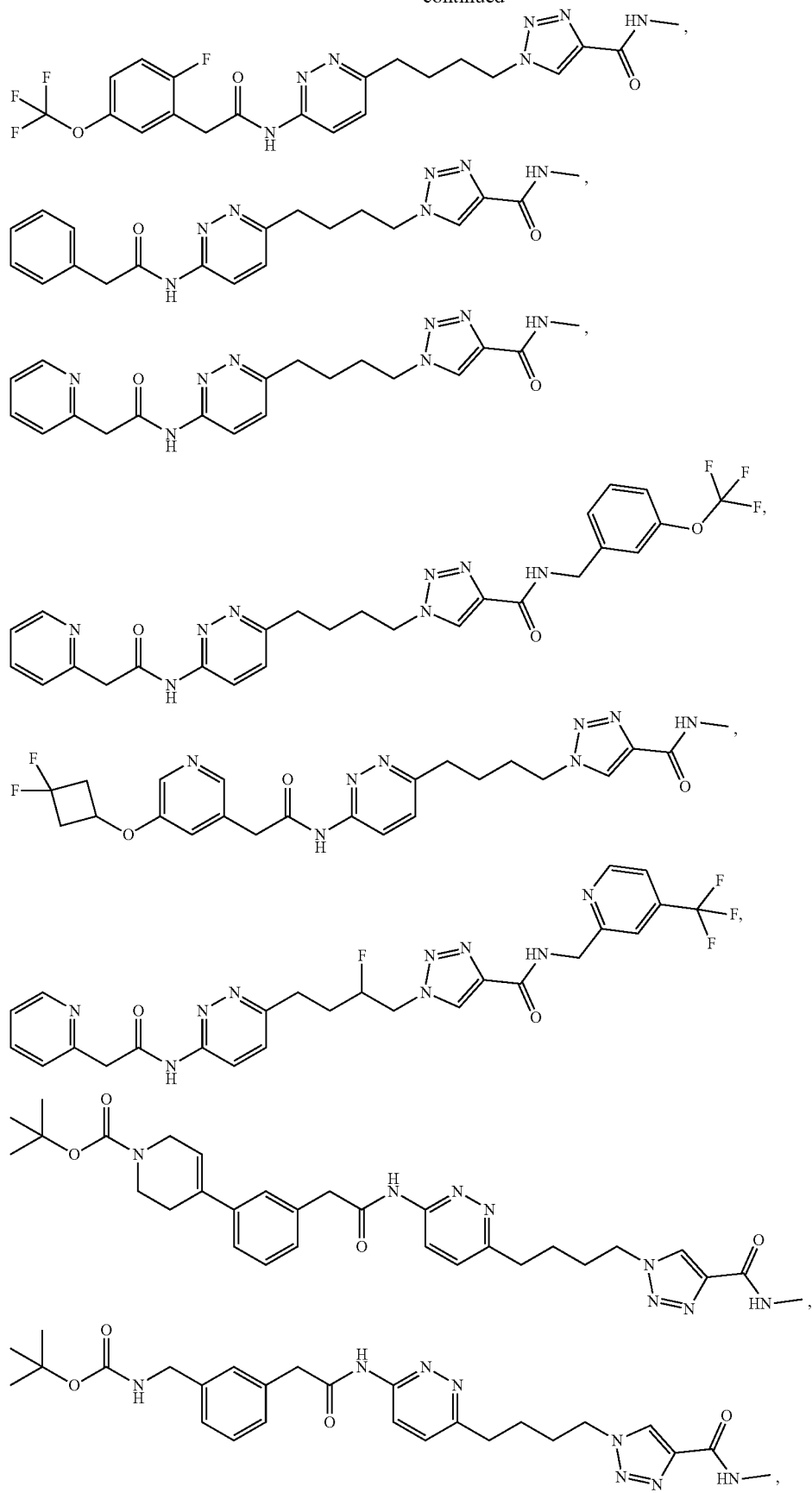

-continued
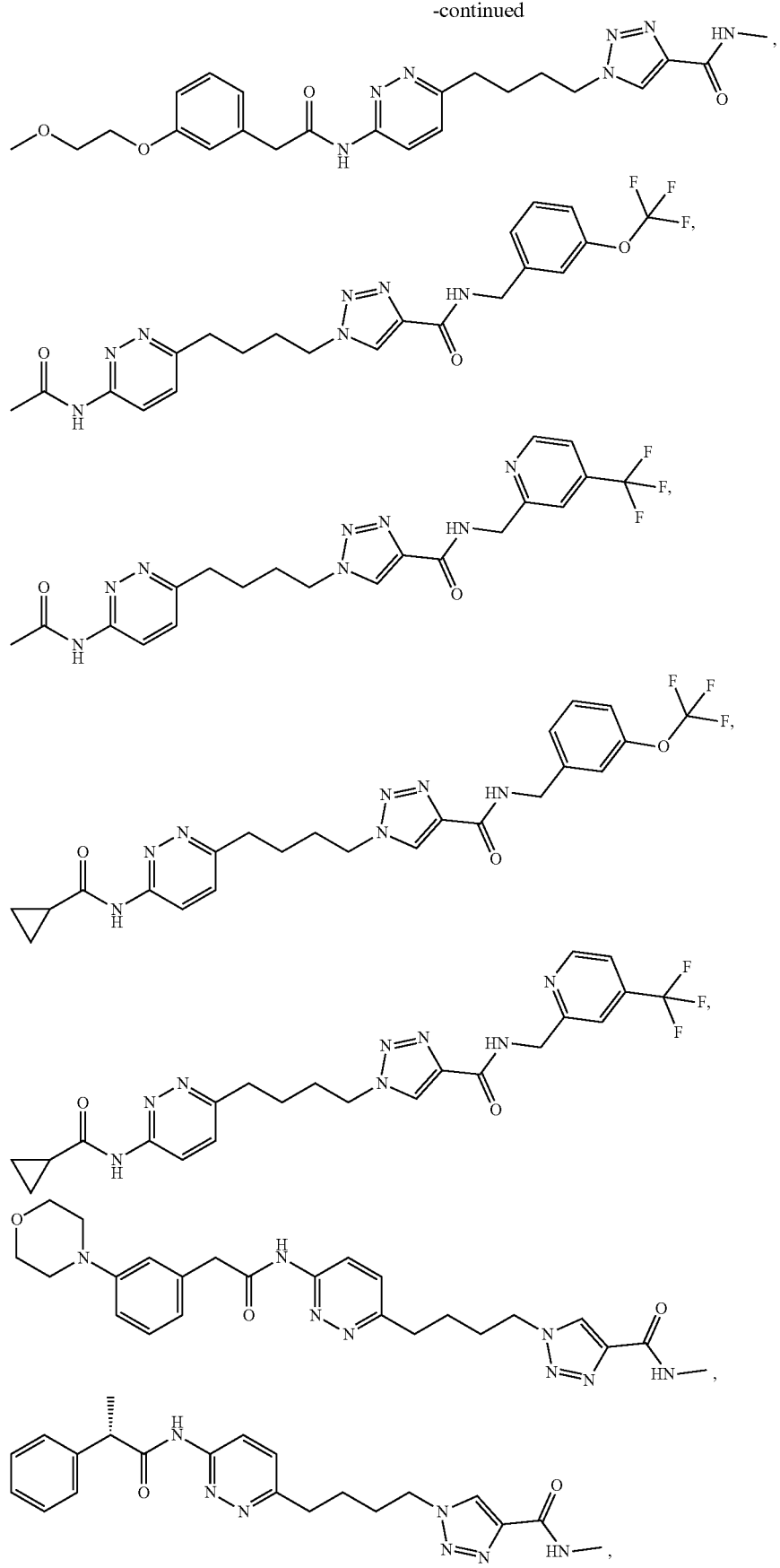

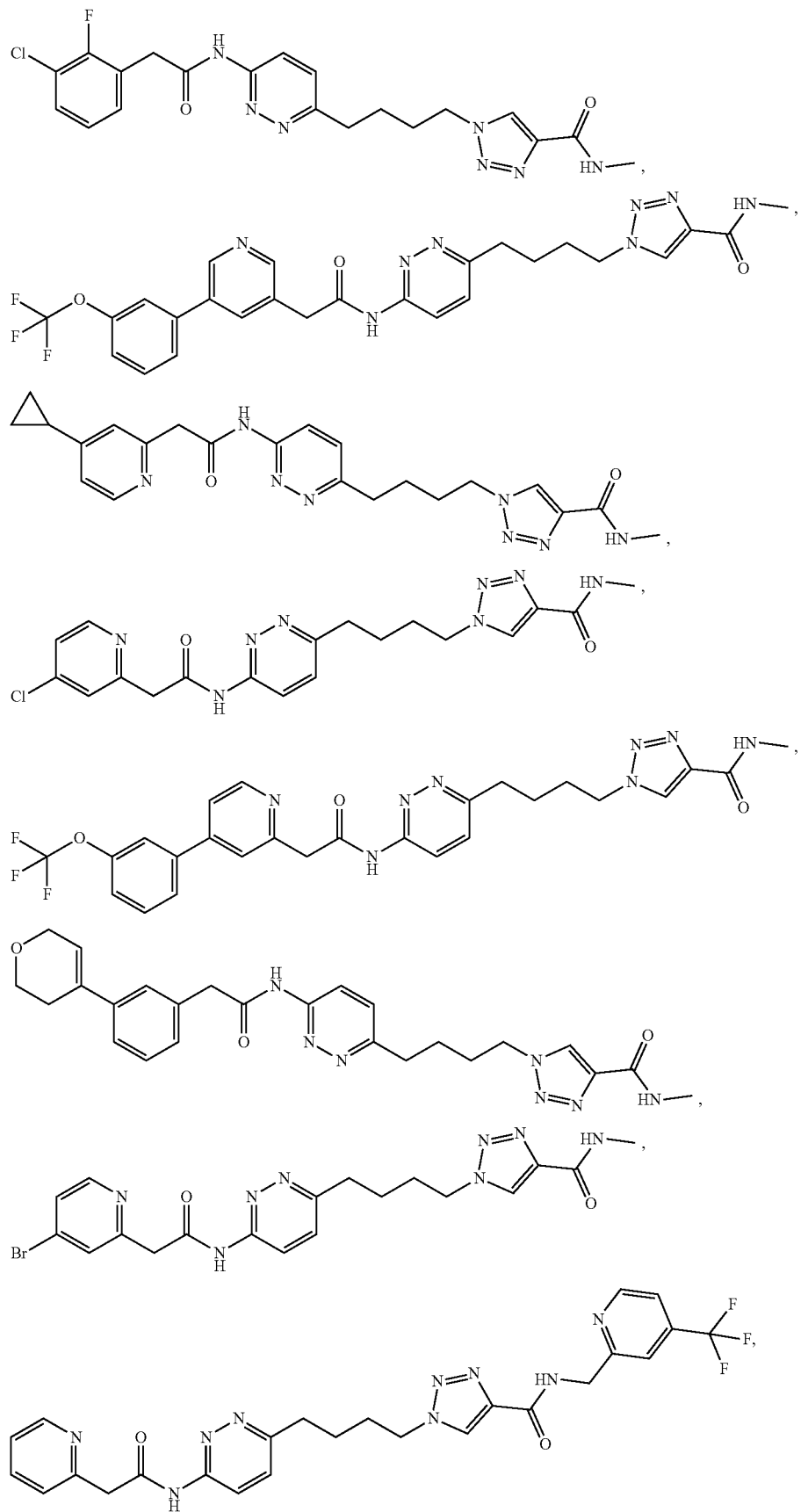

-continued
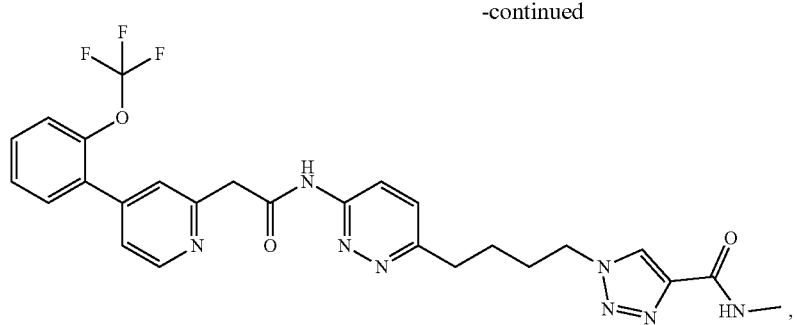
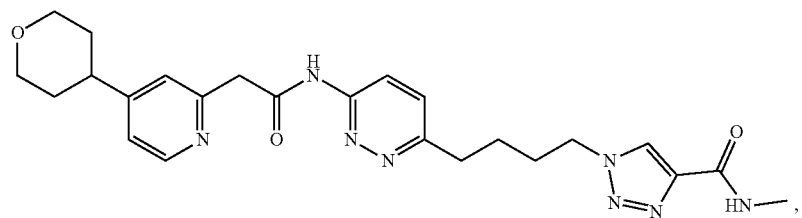
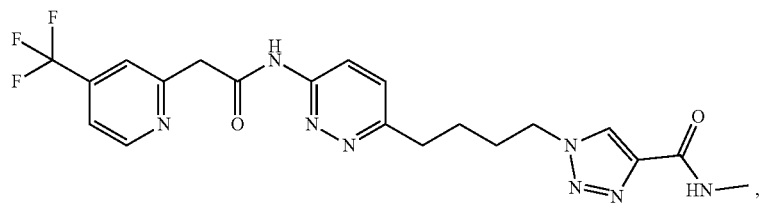
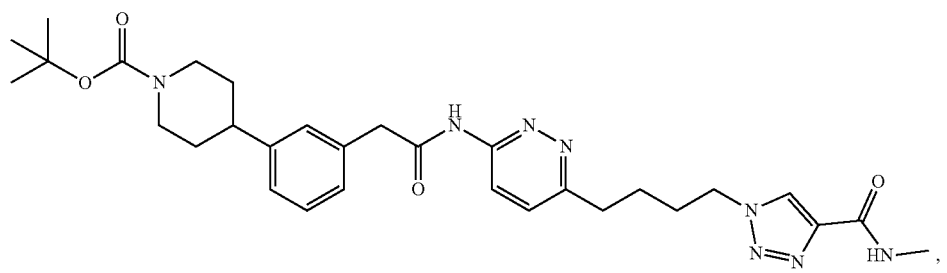
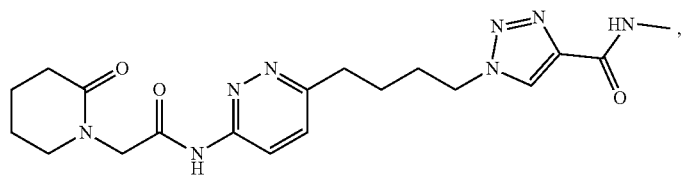
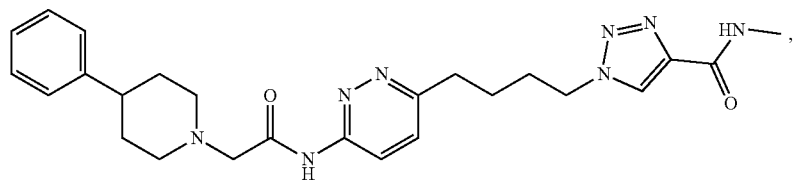
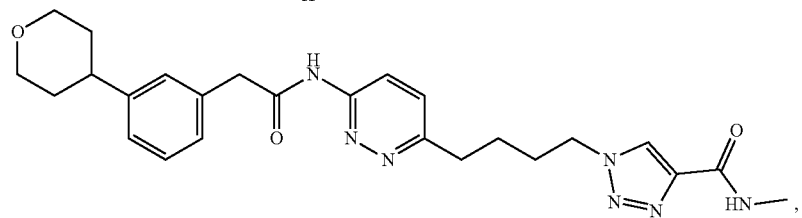

-continued
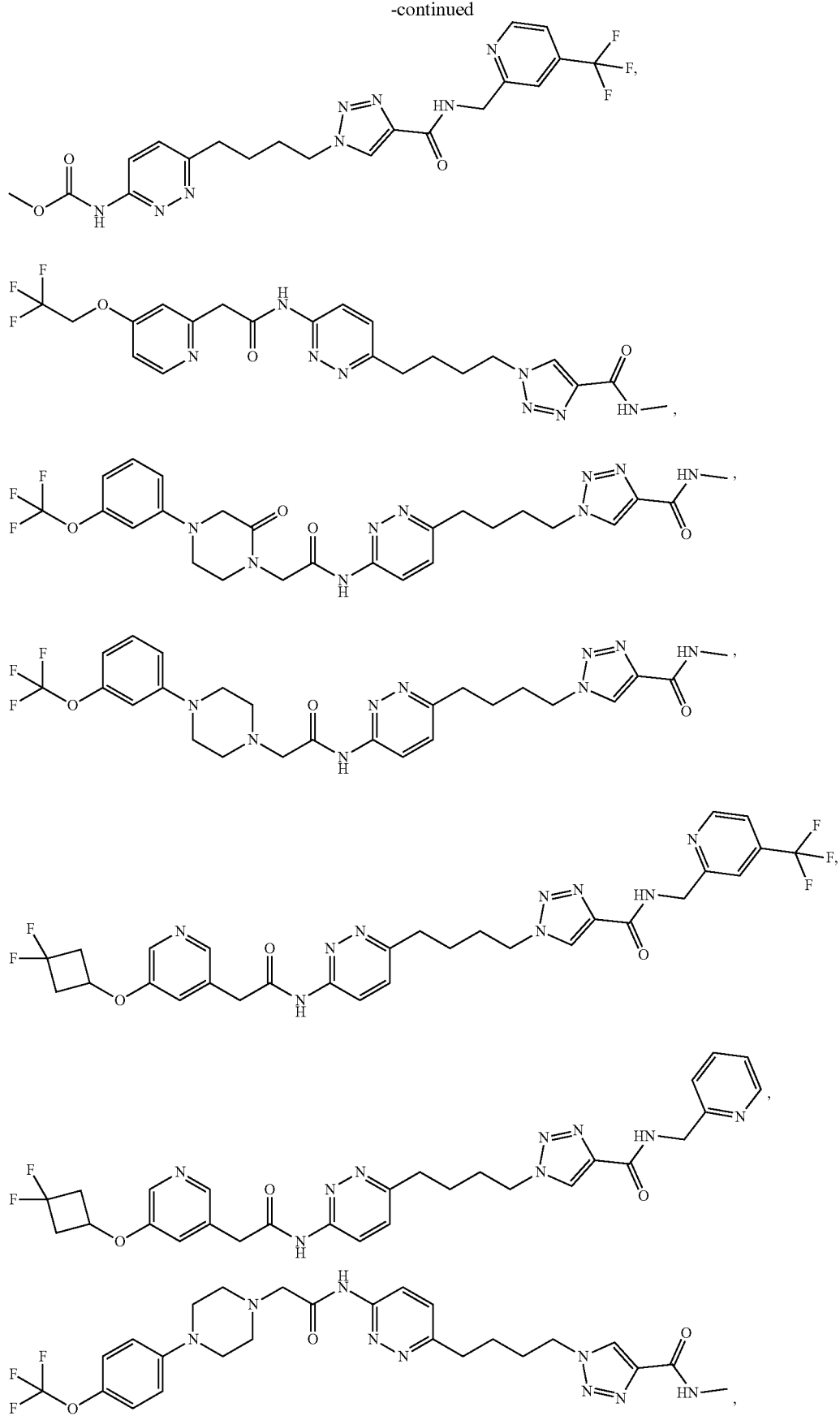

-continued
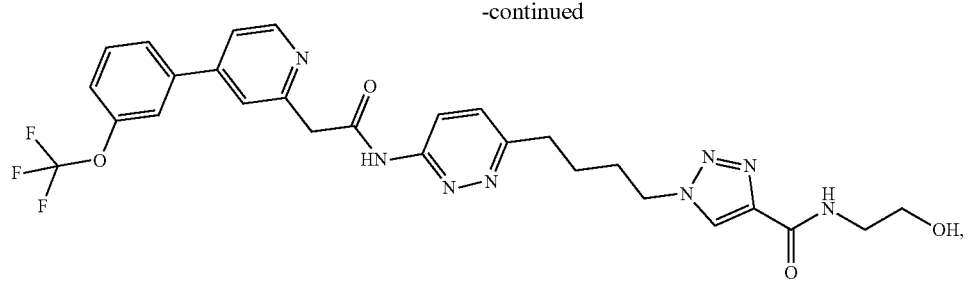
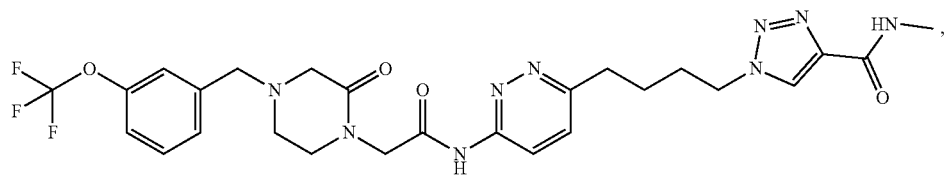
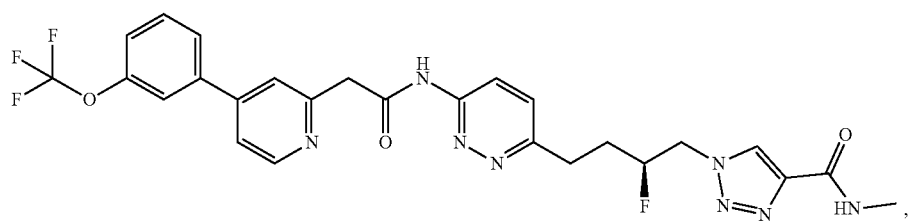
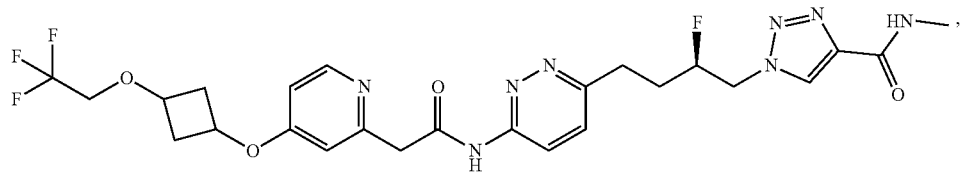
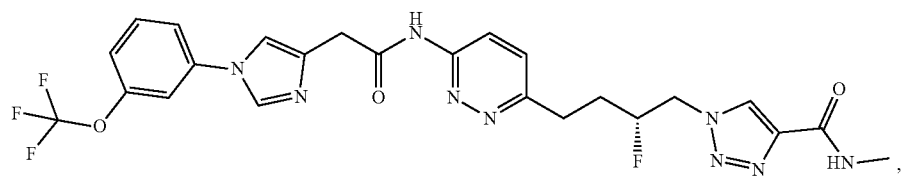
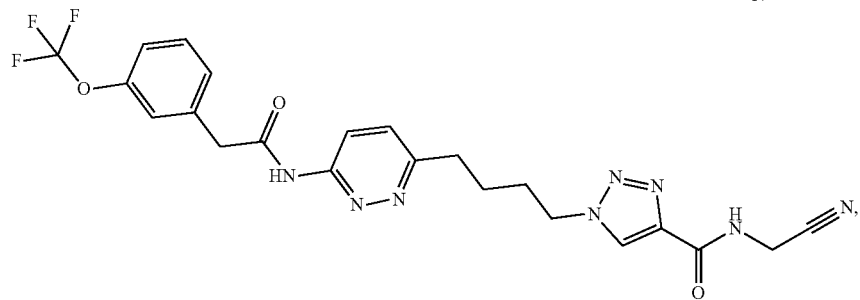
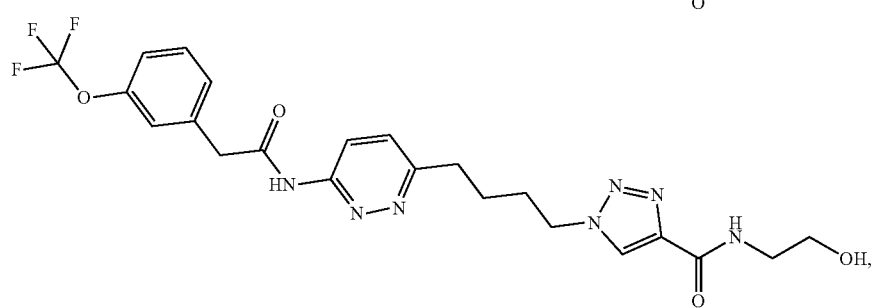

-continued
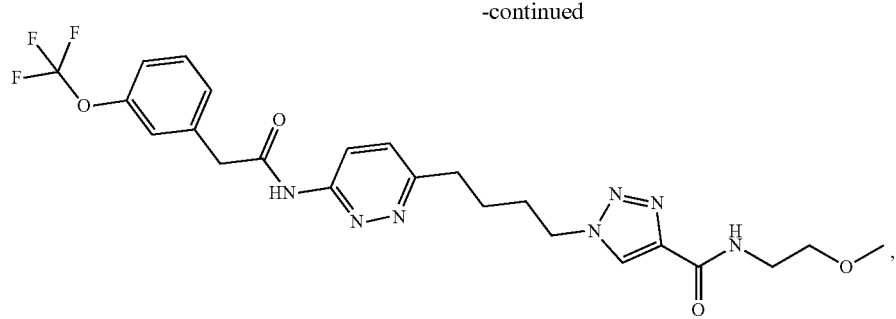
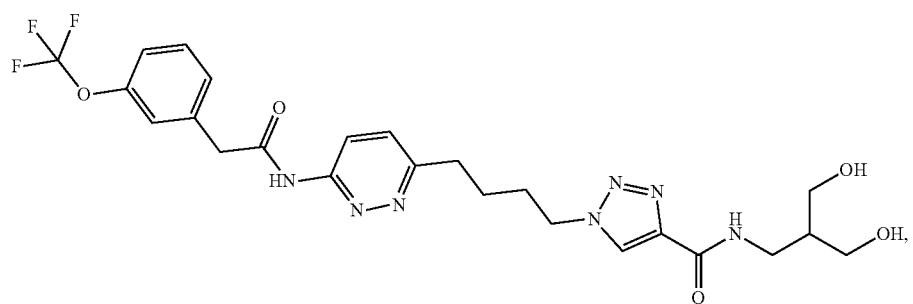
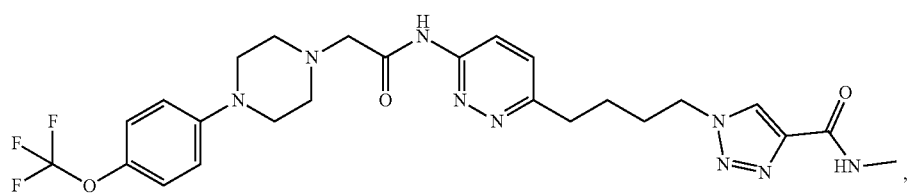
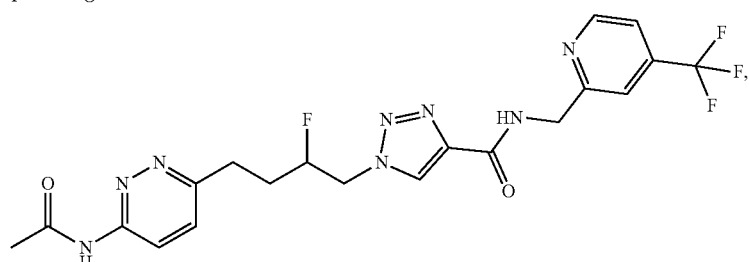
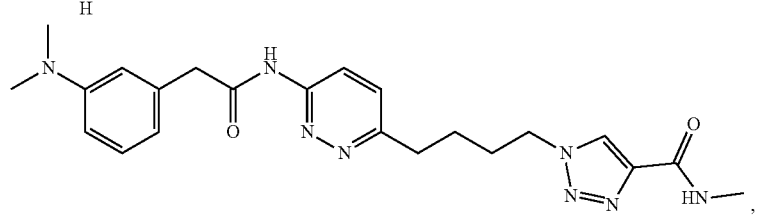
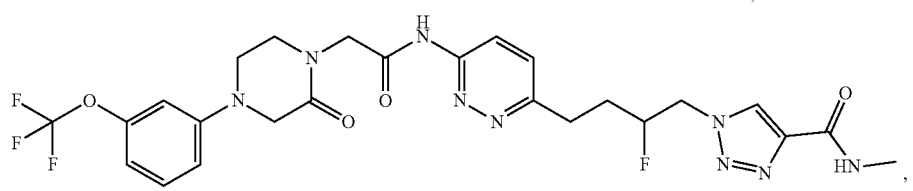
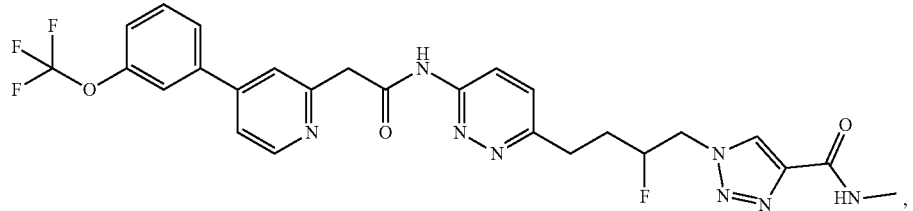

-continued
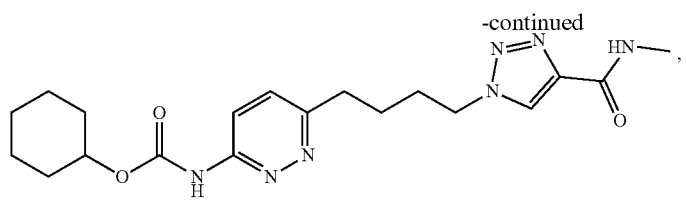
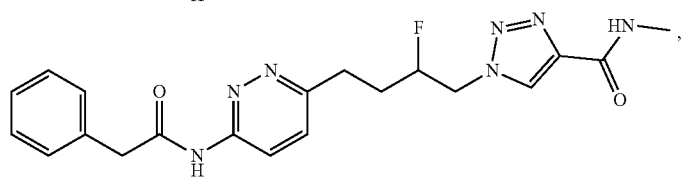
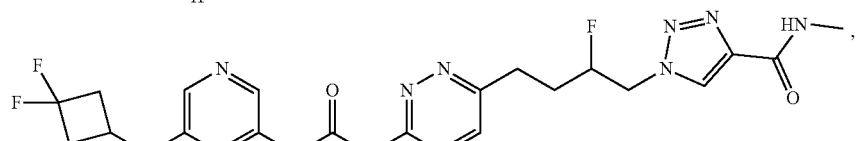
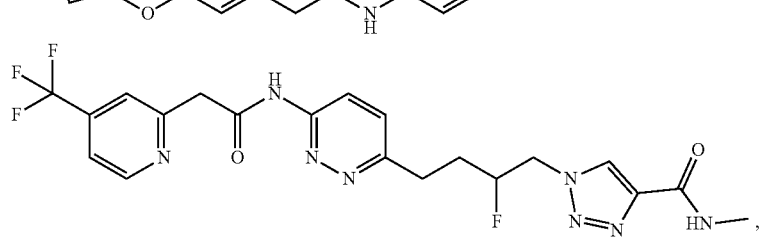
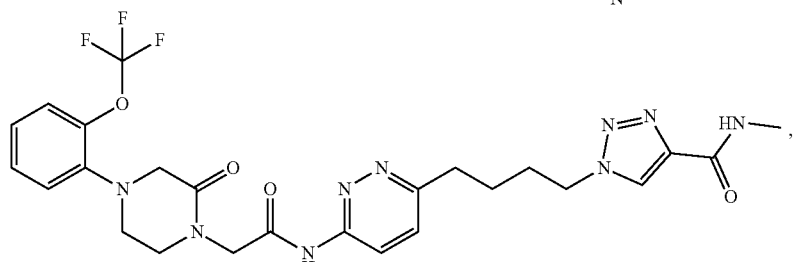
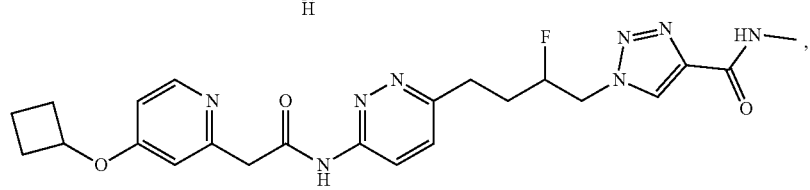
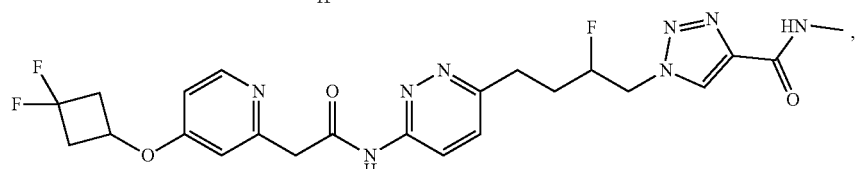
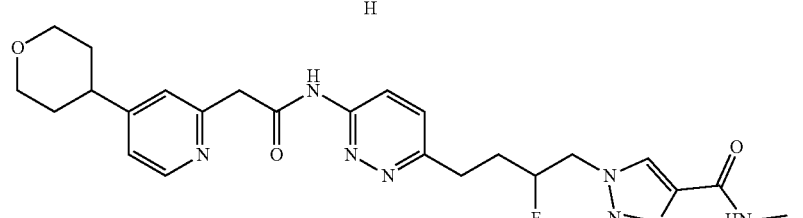
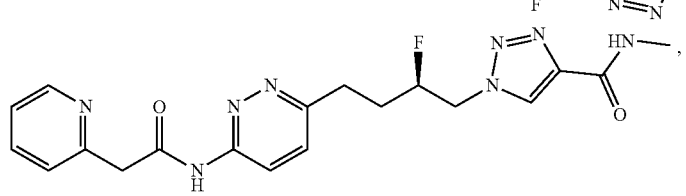

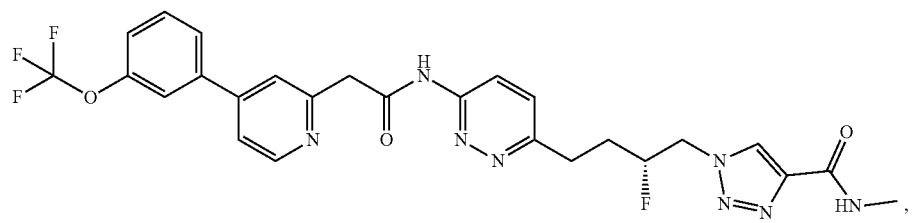
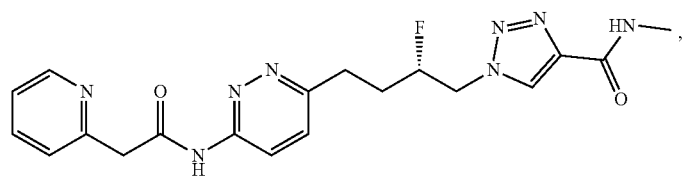
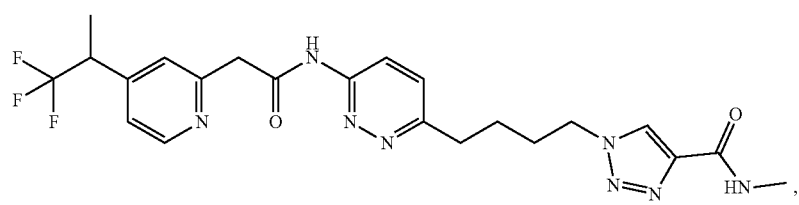
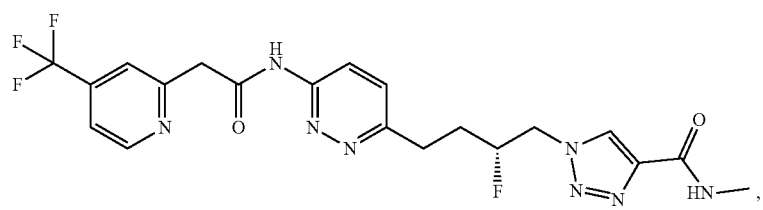
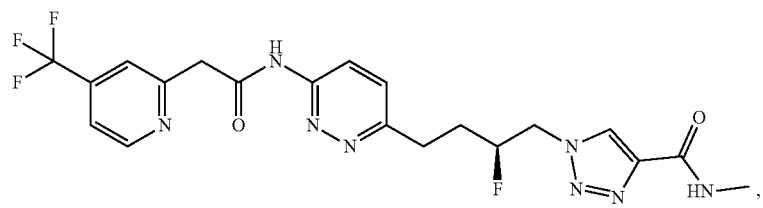
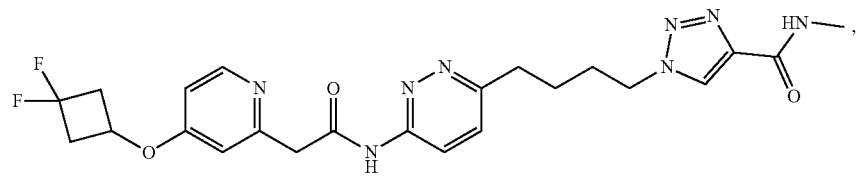
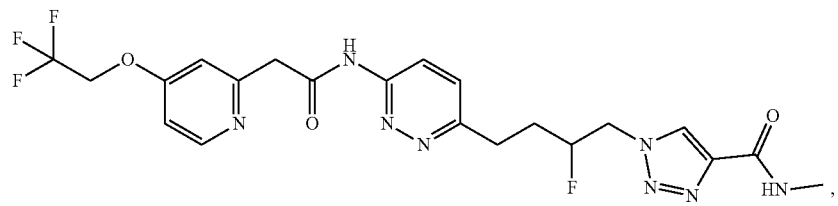
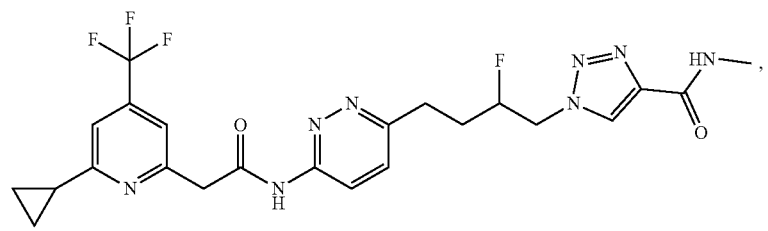

-continued
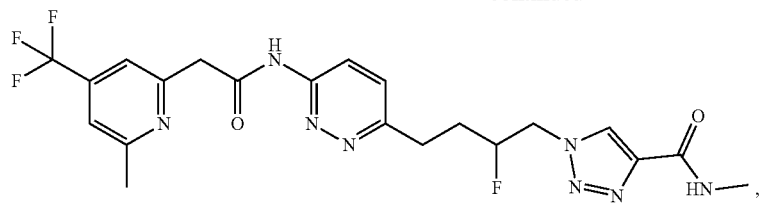
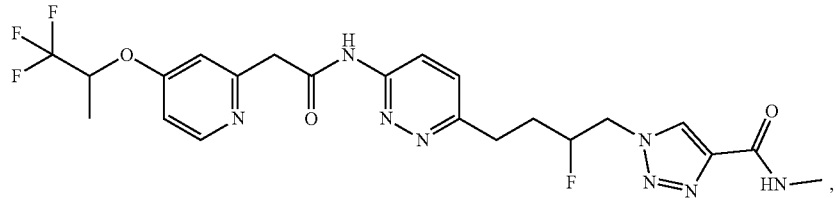
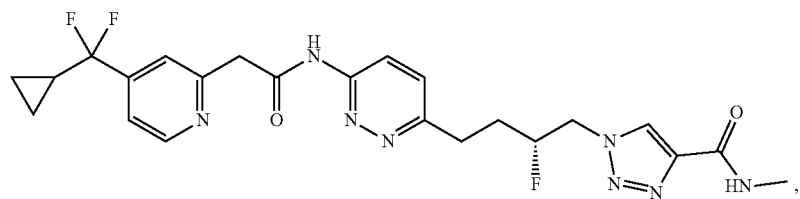
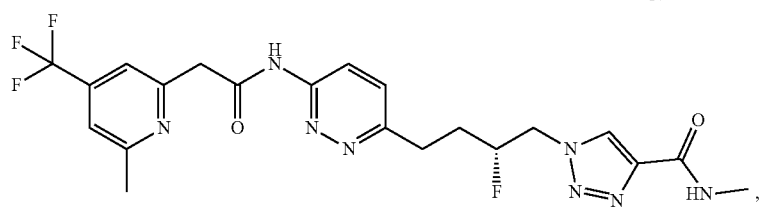
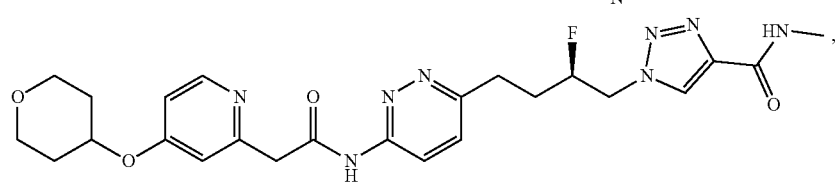
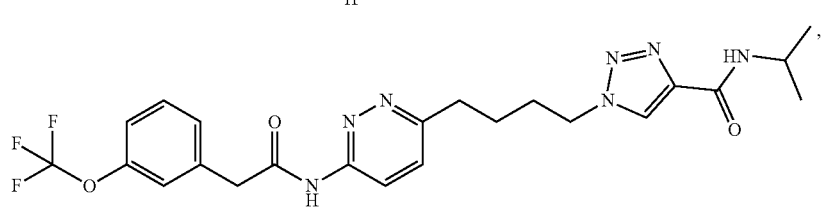
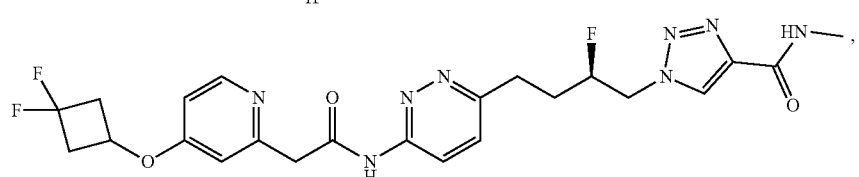
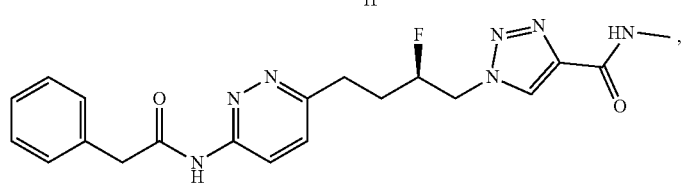
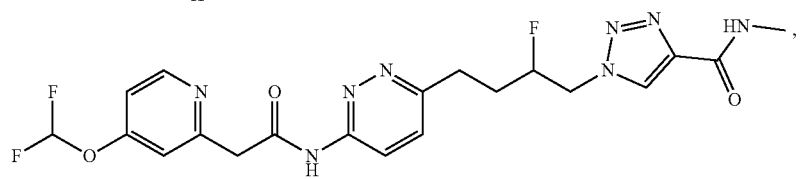

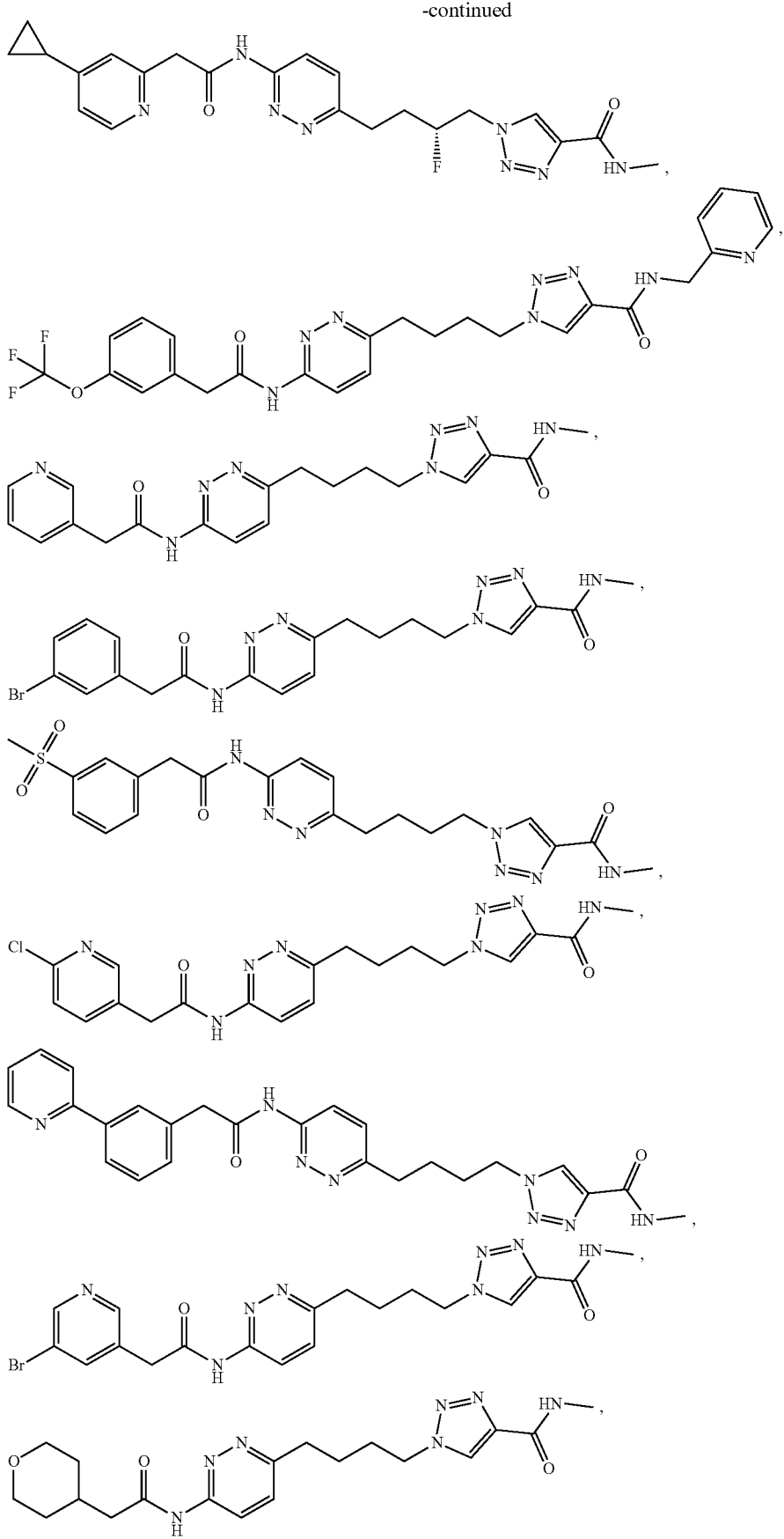

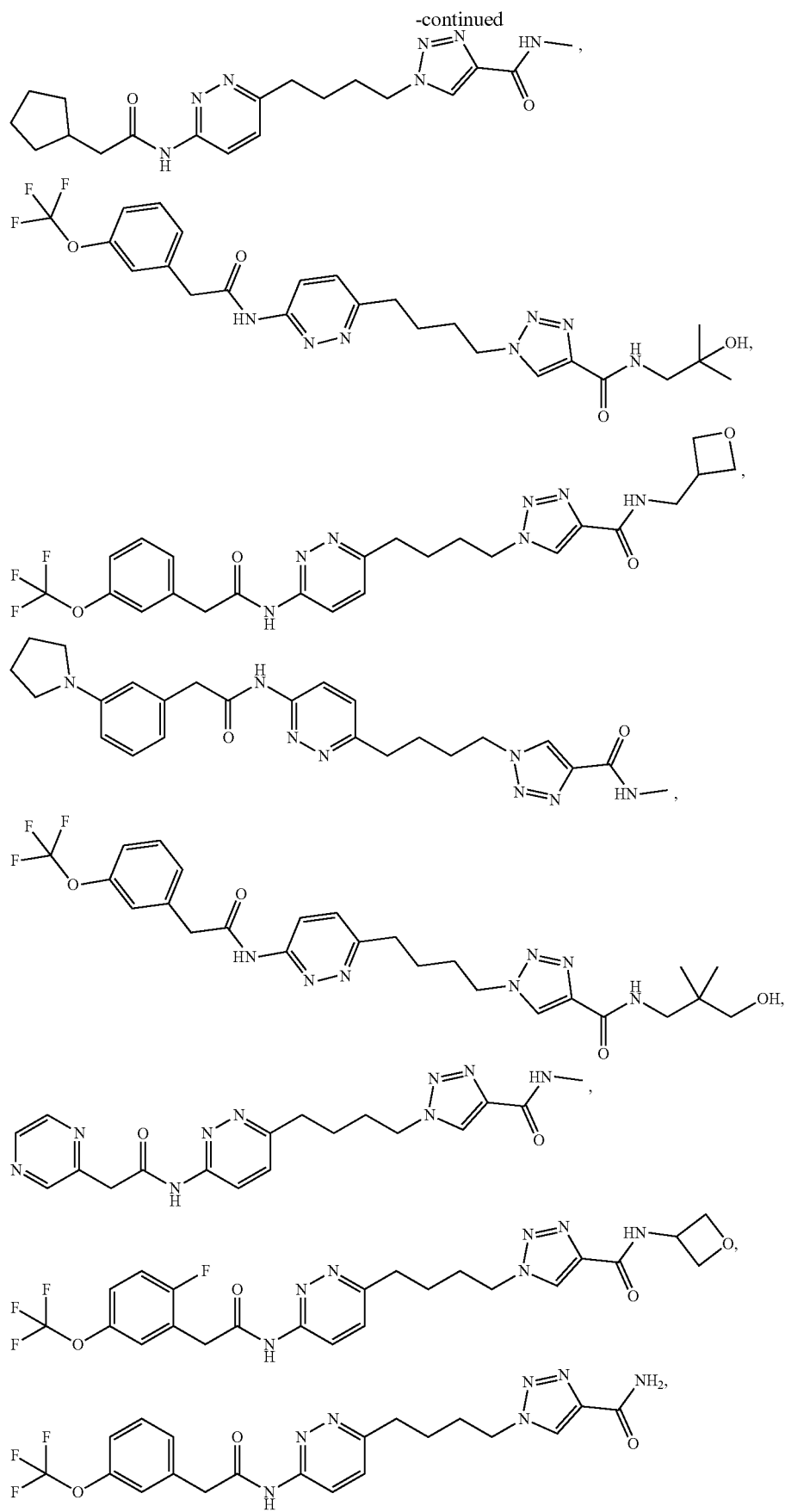

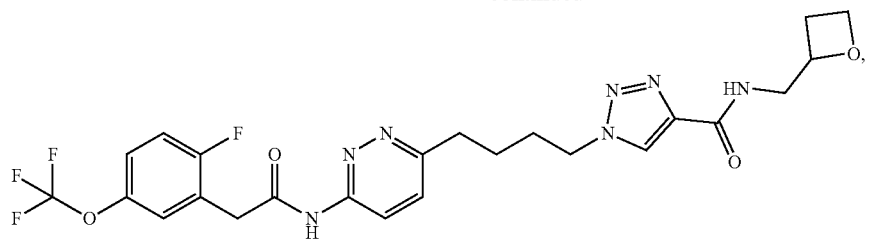
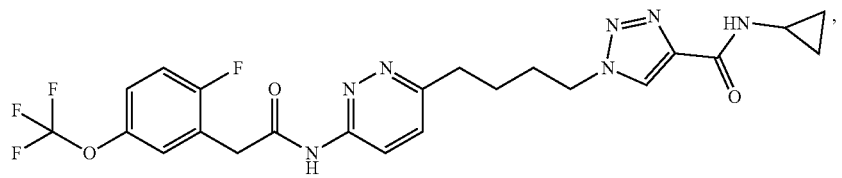
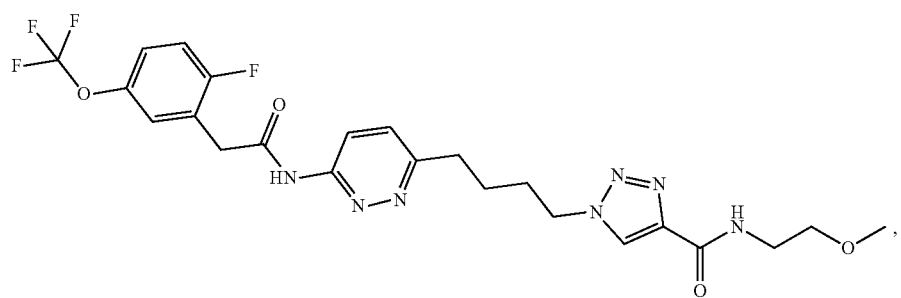
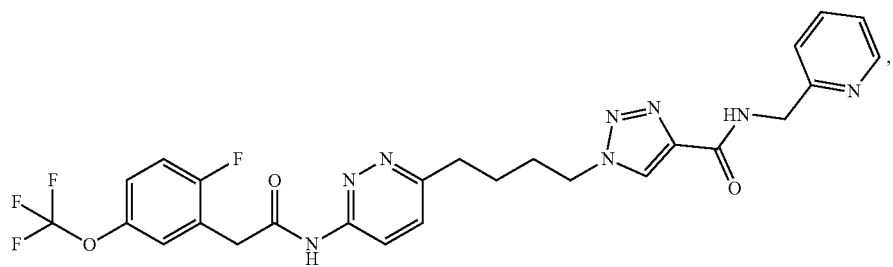
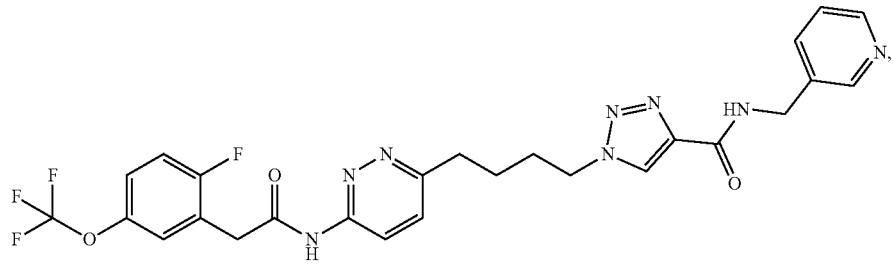
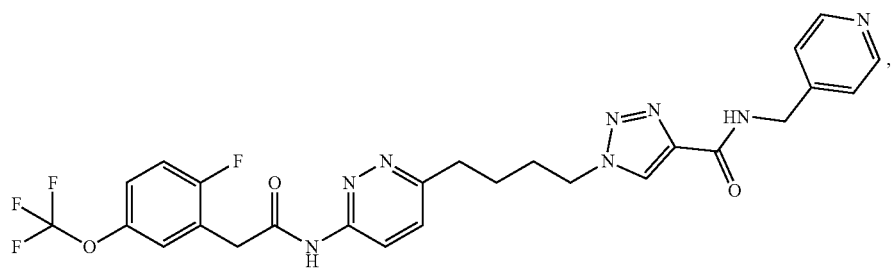

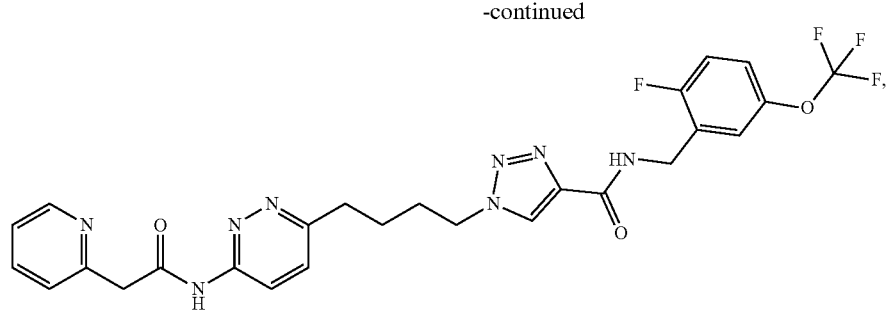
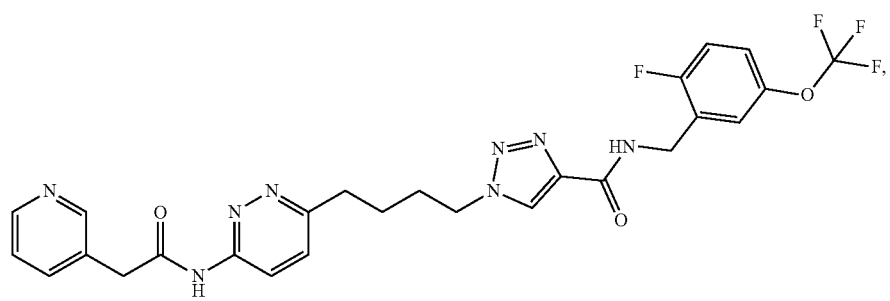
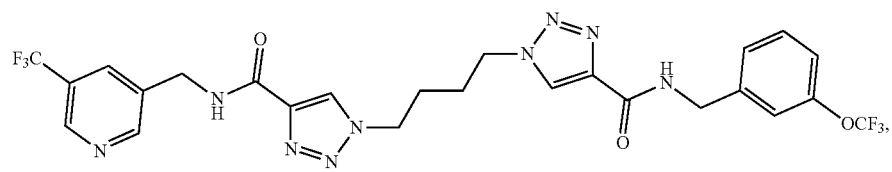
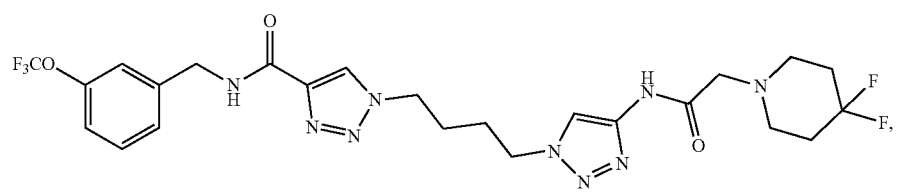
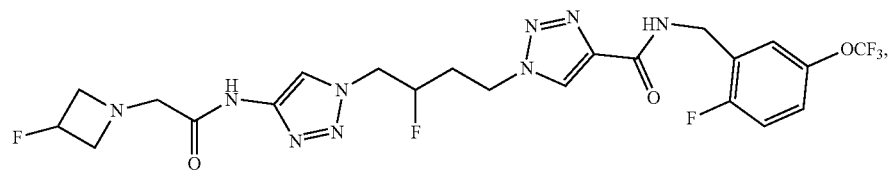
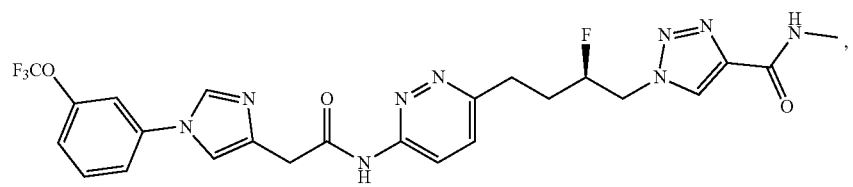
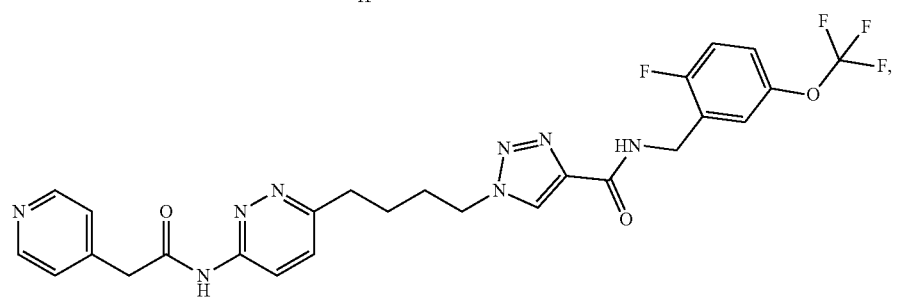

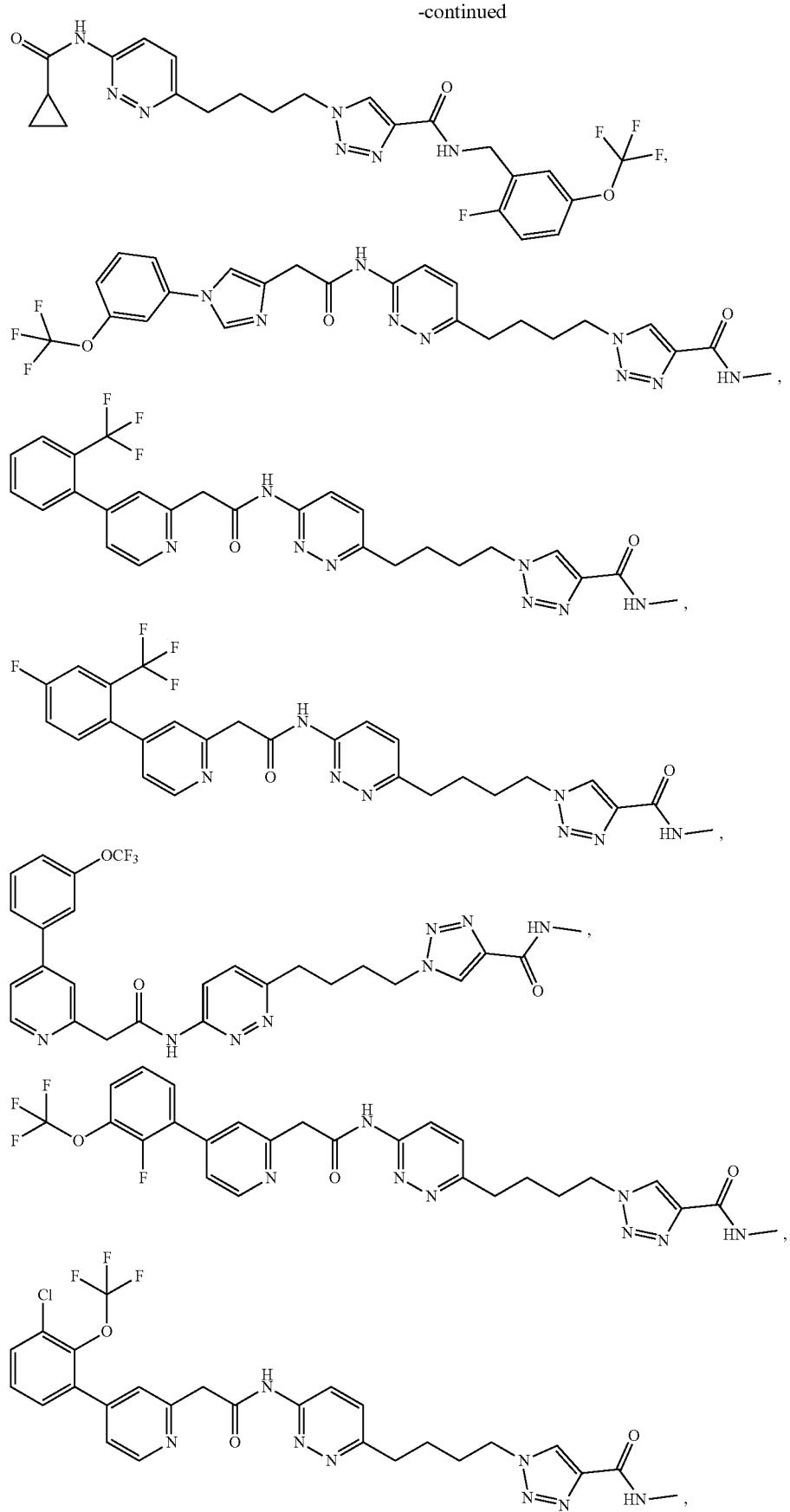

-continued
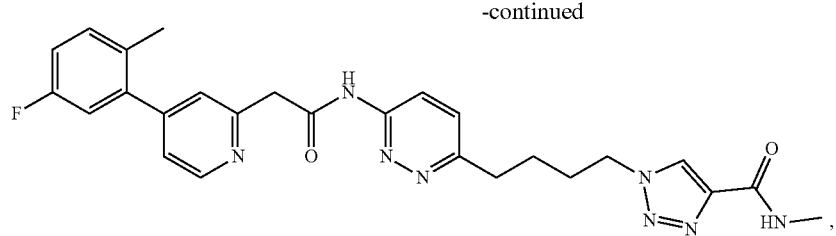
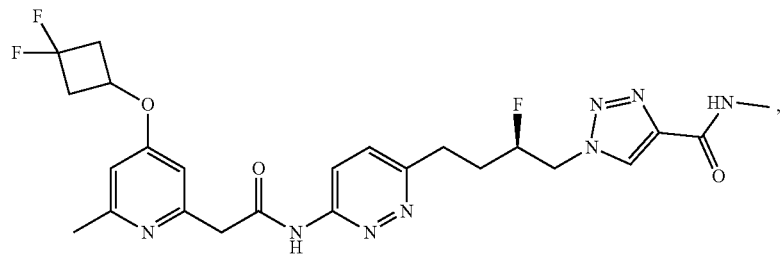
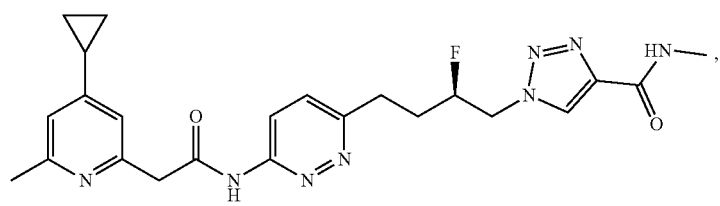
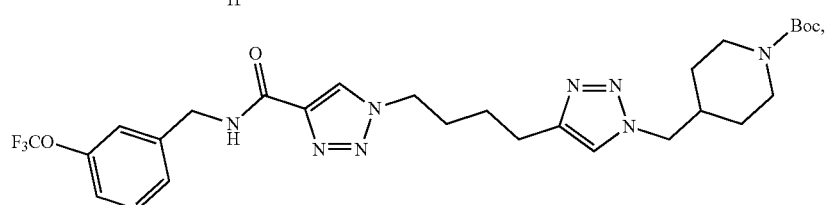
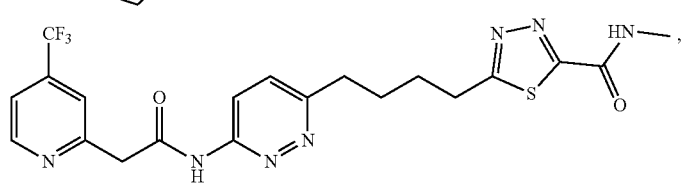
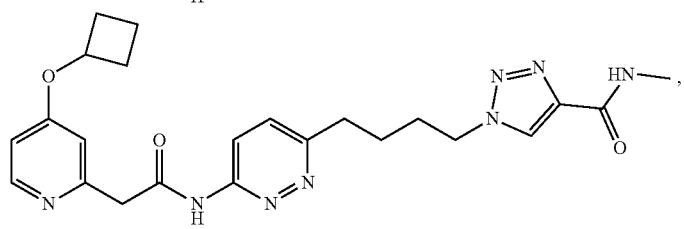
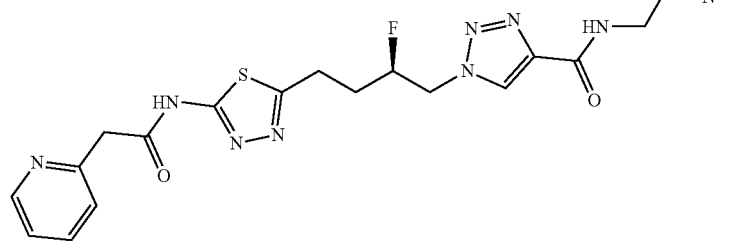

-continued
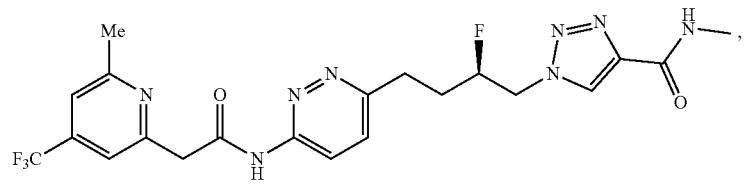
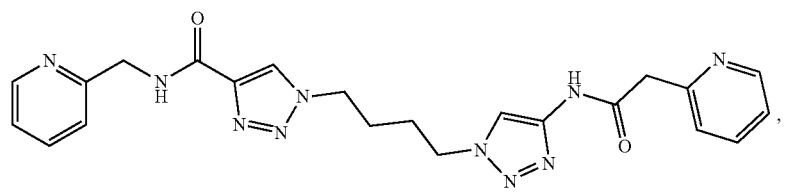
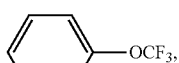
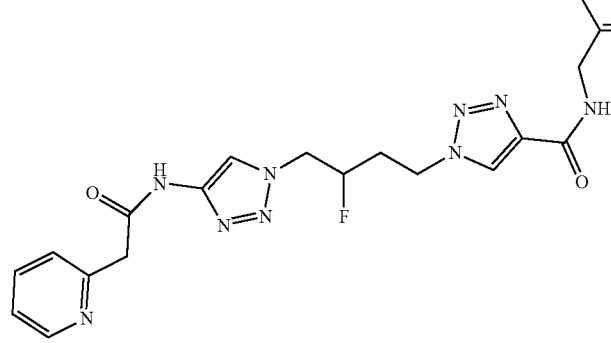
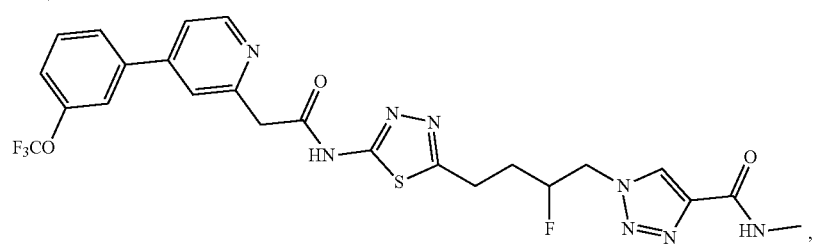
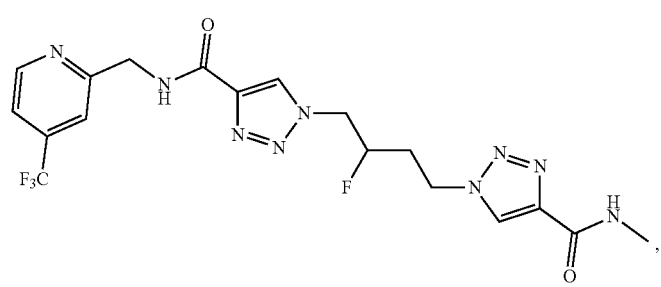
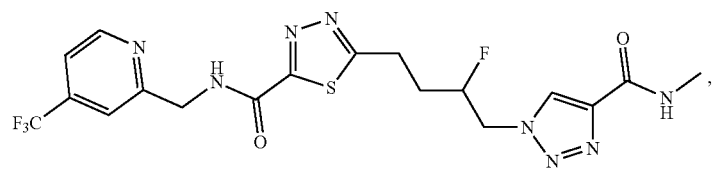
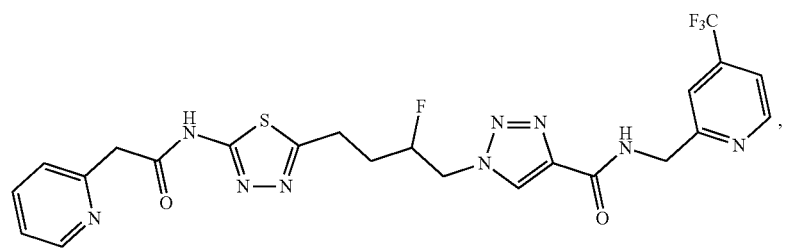

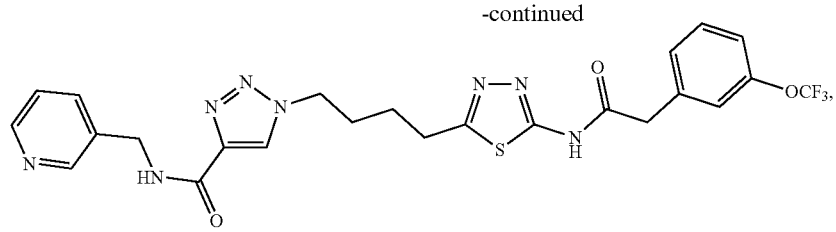
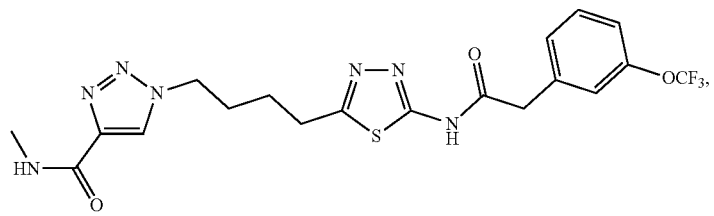
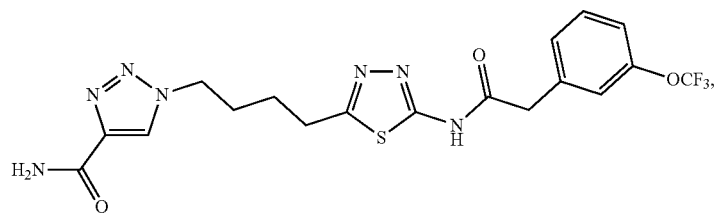
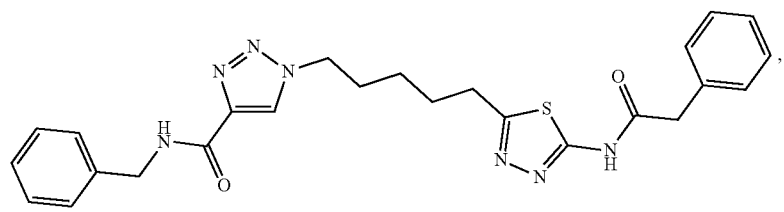
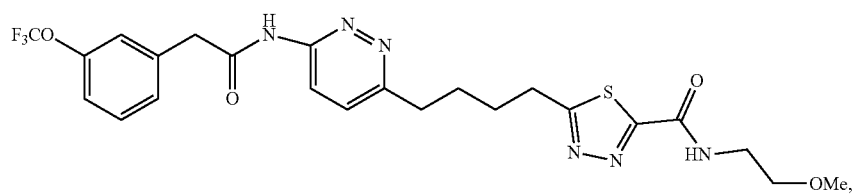
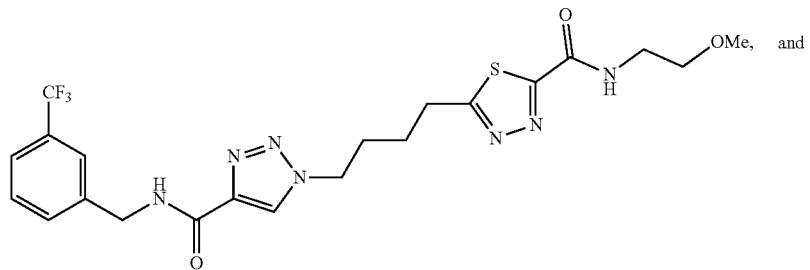
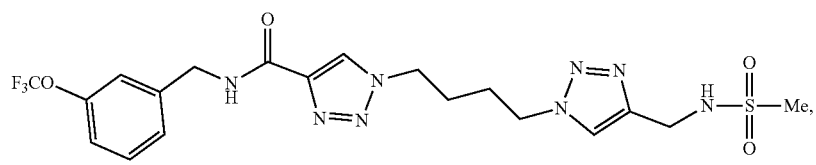
or a salt thereof.

22. The method of claim 6, wherein the GLS-1 inhibitor is selected from:
a) (S)-2-hydroxy-2-phenyl-N-(5-(4-(6-(2-(3-(trifluoromethoxy)phenyl)acetamido)pyridazin-3-yl)butyl)-1,3,4-thiadiazol-2-yl)acetamide,
b) N,N'-(5,5'-(2,2'-thiobis(ethane-2,1-diyl))bis(1,3,4-thiadiazole-5,2-diyl))bis(2-phenylacetamide), also known as BPTES,
c) 2-(pyridin-2-yl)-N-{5-[4-(6-{2-[3-(trifluoromethoxy)phenyl]acetamido}pyridazin-3-yl)butyl]-1,3,4-thiadiazol-2-yl}acetamide,
d) N,N'-(5,5'-(2,2'-sulfonylbis(ethane-2,1-diyl))bis(1,3,4-thiadiazole-5,2-diyl))bis(2-(pyridin-2-yl)acetamide), also known as CB-839,
e) N-methyl-1-{4-[6-(2-{4-[3-(trifluoromethoxy)phenyl]pyridin-2-yl}acetamido)pyridazin-3-yl]butyl}-1H-1,2,3-triazole-4-carboxamide,
f) 1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide,
g) 1-(2-fluoro-4-(6-(2-(4-(trifluoromethyl)pyridin-2-yl)acetamido)pyridazin-3-yl)butyl)-N-methyl-1H-1,2,3-triazole-4-carboxamide,
h) N-(pyridin-2-ylmethyl)-5-(3-(6-(2-(3-(trifluoromethoxy)phenyl)acetamido)pyridazin-3-yl)pyrrolidin-1-yl)-1,3,4-thiadiazole-2-carboxamide,
i) (R)-1-(2-fluoro-4-(6-(2-(4-(3-(trifluoromethoxy)phenyl)pyridin-2-yl)acetamido)-pyridazin-3-yl)butyl)-N-methyl-1H-1,2,3-triazole-4-carboxamide,
j) (R)-1-(2-fluoro-4-(6-(2-(4-(trifluoromethyl)pyridin-2-yl)acetamido)pyridazin-3-yl)butyl)-N-methyl-1H-1,2,3-triazole-4-carboxamide,
k) (R)-1-(2-fluoro-4-(6-(2-(6-methyl-4-(trifluoromethyl)pyridin-2-yl)acetamido)pyridazin-3-yl)butyl)-N-methyl-1H-1,2,3-triazole-4-carboxamide,
l) (R)-1-(4-(6-(2-(4-(cyclopropyldifluoromethyl)pyridin-2-yl)acetamido)pyridazin-3-yl)-2-fluorobutyl)-N-methyl-1H-1,2,3-triazole-4-carboxamide,
m) (R)-1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide,
n) (R)-1-(2-fluoro-4-(6-(2-(1-(3-(trifluoromethoxy)phenyl)-1H-imidazol-4-yl)-acetamido)pyridazin-3-yl)butyl)-N-methyl-1H-1,2,3-triazole-4-carboxamide,
o) 1-(4-(6-(2-(4-cyclobutoxypyridin-2-yl)acetamido)pyridazin-3-yl)butyl)-N-methyl-1H-1,2,3-triazole-4-carboxamide,
p) 1-(4-(6-(2-(4-cyclobutoxypyridin-2-yl)acetamido)pyridazin-3-yl)-2-fluorobutyl)-N-methyl-1H-1,2,3-triazole-4-carboxamide,
q) 1-(4-(6-(2-(4-(3,3-difluorocyclobutoxy)pyridin-2-yl)acetamido)pyridazin-3-yl)butyl)-N-methyl-1H-1,2,3-triazole-4-carboxamide,
r) 1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide,
s) (R)-1-(4-(6-(2-(4-cyclopropylpyridin-2-yl)acetamido)pyridazin-3-yl)-2-fluorobutyl)-N-methyl-1H-1,2,3-triazole-4-carboxamide,
t) 5-(3-(6-(2-(pyridin-2-yl)acetamido)pyridazin-3-yl)pyrrolidin-1-yl)-N-((4-(trifluoromethyl)pyridin-2-yl)methyl)-1,3,4-thiadiazole-2-carboxamide, and
u) N,N'-(5,5'-(cyclohexane-1,3-diyl)bis(1,3,4-thiadiazole-5,2-diyl))bis(2-phenylacetamide) (both or either of 1S,3S and 1R,2R enantiomers), or a salt and polymorph thereof.

23. The method of claim 6, wherein the GLS-1 inhibitor is chosen from:

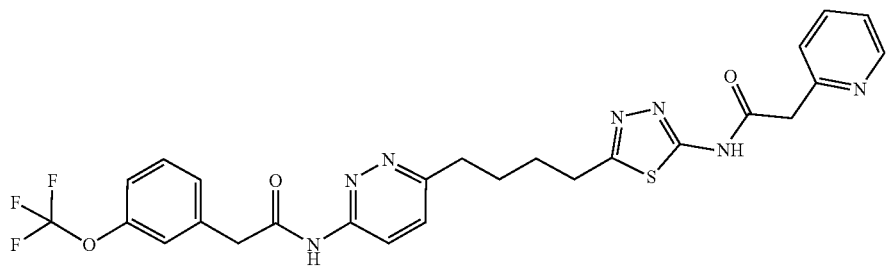 [SMILES: O=C(Cc1cccc(OC(F)(F)F)c1)Nc1ccc(CCCCc2nnc(NC(=O)Cc3ccccn3)s2)nn1]

and

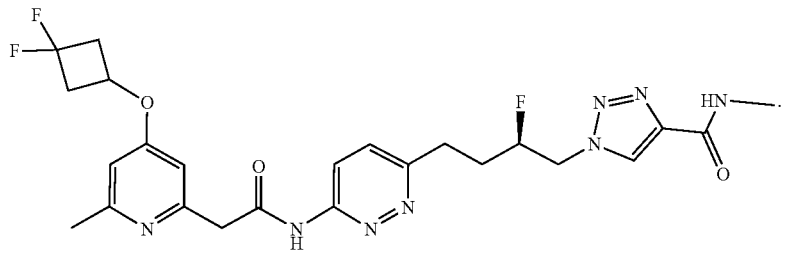 [SMILES: CNC(=O)c1cn(C[C@H](F)CCc2ccc(NC(=O)Cc3cc(OC4CC(F)(F)C4)cc(C)n3)nn2)nn1]

24. The method of claim 6, wherein the subject is human.

25. The method of claim 6, further comprising administering another pharmaceutically active compound.

26. The method of claim 25, wherein the other pharmaceutically active compound is an anti-cancer agent.

27. The method of claim 26, wherein the anti-cancer agent is chosen from a platinum-based agent, a taxane-based agent, an immunotherapy, an immuno-oncotherapy, and a targeted therapy.

28. The method of claim 27, wherein the targeted therapy is an inhibitor of MEK kinase, HSP90, CDK4, or the mTOR pathway.

29. The method of claim 28, wherein the method further comprises administering non-chemical methods of cancer treatment.

30. The method of claim 29, wherein the method further comprises administering radiation therapy.

31. The method of claim 29, wherein the method further comprises administering surgery, thermoablation, focused ultrasound therapy, cryotherapy, or any combination thereof.

32. The method of claim 6, wherein the GLS-1 inhibitor is

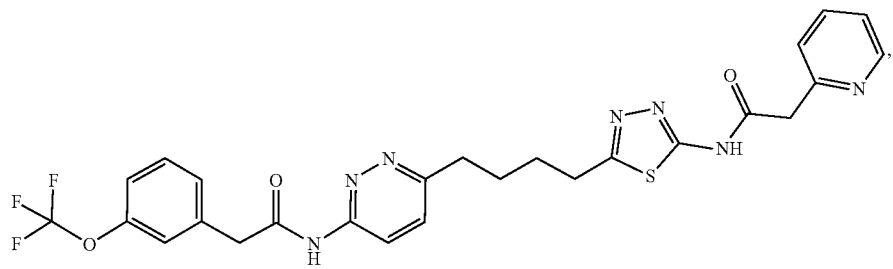 [SMILES: O=C(Cc1cccc(OC(F)(F)F)c1)Nc1ccc(CCCCc2nnc(NC(=O)Cc3ccccn3)s2)nn1]

or a salt thereof.

33. The method of claim 6, wherein the GLS-1 inhibitor is

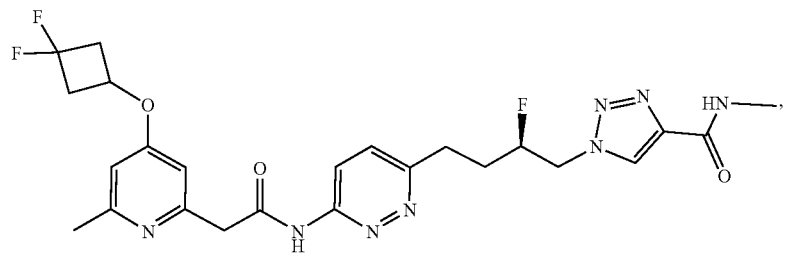 [SMILES: CNC(=O)c1cn(C[C@H](F)CCc2ccc(NC(=O)Cc3cc(OC4CC(F)(F)C4)cc(C)n3)nn2)nn1]

or a salt thereof.

34. The method of claim 6, wherein the GLS-1 inhibitor is

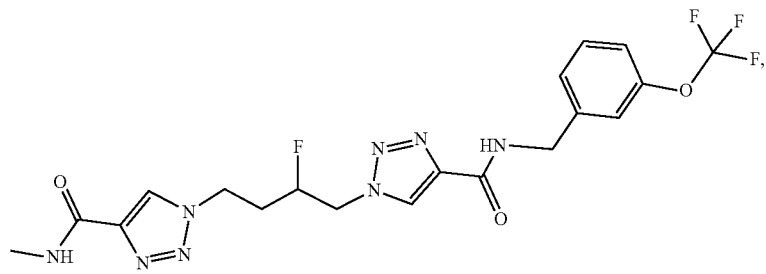 [SMILES: CNC(=O)c1cn(CCC(F)Cn2cc(C(=O)NCc3cccc(OC(F)(F)F)c3)nn2)nn1]

or a salt thereof.

35. The method of claim 6, wherein the GLS-1 inhibitor is
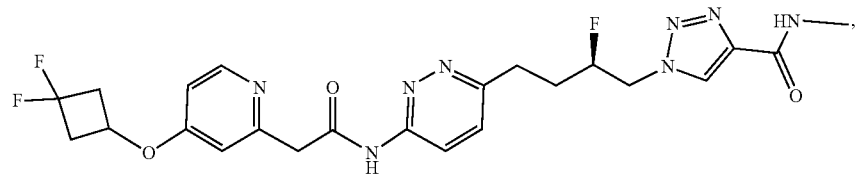 [SMILES: CNC(=O)c1cn(C[C@H](F)CCc2ccc(NC(=O)Cc3cc(OC4CC(F)(F)C4)ccn3)nn2)nn1]
or a salt thereof.